United States Patent
Dobbelaar et al.

(10) Patent No.: US 8,183,275 B2
(45) Date of Patent: May 22, 2012

(54) SUBSTITUTED IMIDAZOLES AS BOMBESIN RECEPTOR SUBTYPE-3 MODULATORS

(75) Inventors: Peter H. Dobbelaar, Morris Plains, NJ (US); Christopher L. Franklin, Keasbey, NJ (US); Allan Goodman, Media, PA (US); Cheng Guo, Schenectady, NY (US); Peter R. Guzzo, Niskayuna, NY (US); Mark Hadden, Albany, NY (US); Shuwen He, Edison, NJ (US); Alan J. Henderson, Albany, NY (US); Tianying Jian, Westfield, NJ (US); Linus S. Lin, Westfield, NJ (US); Jian Liu, Edison, NJ (US); Ravi P. Nargund, East Brunswick, NJ (US); Megan Ruenz, Grayslake, IL (US); Bruce J. Sargent, Delmar, NY (US); Iyassu K. Sebhat, Jersey City, NJ (US); Larry Yet, Albany, NY (US)

(73) Assignees: Merck Sharp & Dohme Corp., Rahway, NJ (US); Albany Molecular Research, Inc., Albany, NY (US)

( * ) Notice: Subject to any disclaimer, the term of this patent is extended or adjusted under 35 U.S.C. 154(b) by 409 days.

(21) Appl. No.: 12/311,672

(22) PCT Filed: Oct. 16, 2007

(86) PCT No.: PCT/US2007/022081
§ 371 (c)(1),
(2), (4) Date: Apr. 8, 2009

(87) PCT Pub. No.: WO2008/051405
PCT Pub. Date: May 2, 2008

(65) Prior Publication Data
US 2010/0204236 A1    Aug. 12, 2010

Related U.S. Application Data

(60) Provisional application No. 60/853,272, filed on Oct. 20, 2006.

(51) Int. Cl.
*A61K 31/4178* (2006.01)
*A61K 31/4164* (2006.01)
*C07D 471/04* (2006.01)
*C07D 401/10* (2006.01)
*C07D 403/10* (2006.01)
*C07D 233/64* (2006.01)

(52) U.S. Cl. ........ 514/393; 514/360; 514/385; 514/387; 514/390; 548/126; 548/300.1; 548/416; 548/578; 546/113; 546/272.7; 544/333; 544/405

(58) Field of Classification Search .............. 514/249, 514/341, 255.05, 365, 400, 256, 372, 383, 514/397, 252.05, 360, 385, 387, 390, 393; 546/113, 272.7; 544/333, 405; 548/198, 548/315.1, 346.1, 311.7, 312.7, 126, 300.1, 416, 578
See application file for complete search history.

(56) References Cited

U.S. PATENT DOCUMENTS

| | | | |
|---|---|---|---|
| 4,962,117 A | 10/1990 | Young et al. | |
| 5,721,251 A * | 2/1998 | Chen et al. | 514/318 |
| 6,673,941 B2 | 1/2004 | Heerding et al. | |
| 7,141,596 B2 | 11/2006 | Combs et al. | |
| 2002/0009116 A1 | 1/2002 | Kobayashi et al. | |
| 2004/0167188 A1 | 8/2004 | Xin et al. | |
| 2004/0192743 A1 | 9/2004 | Mjalli et al. | |
| 2004/0248956 A1 | 12/2004 | Hagmann et al. | |
| 2005/0130973 A1 | 6/2005 | Xiang et al. | |
| 2005/0187277 A1 | 8/2005 | Mjalli et al. | |
| 2005/0272778 A1 | 12/2005 | Combs et al. | |

FOREIGN PATENT DOCUMENTS

| | | |
|---|---|---|
| JP | 07-243068 | 9/1995 |
| JP | 11-217348 | 8/1999 |
| JP | 2003-321455 | 11/2003 |
| WO | 93/17681 | 9/1993 |
| WO | 97/40017 | 10/1997 |
| WO | 98/28269 | 7/1998 |
| WO | 99/32454 | 7/1999 |
| WO | 02/14291 | 2/2002 |
| WO | 02/098840 | 12/2002 |
| WO | 03/016291 | 2/2003 |
| WO | 03/104196 | 12/2003 |
| WO | 2004/007464 | 1/2004 |
| WO | 2004/046091 | 6/2004 |
| WO | 2004/048351 | 6/2004 |
| WO | 2004/058176 | 7/2004 |
| WO | 2004/071447 | 8/2004 |

(Continued)

OTHER PUBLICATIONS

Campfield, "Strategies and potential molecular targes for obesity treatment", Science (1998), 1383-1387, vol. 280. Liu, "Molecular basis of the pharmacological difference between rat and human . . . ", Biochemistry (2002), 8954-8960, vol. 41.
Breslow, "Synthesis of some polyimidazole ligands related to zinc enzymes", J. Am. Chem. Soc. (1983), 5337-5342 , vol. 105.
Porcher, "Bombesin receptor subtype-3 is expressed by the enteric nervous . . . ", Cell Tissue Res. (2005), 21-31, vol. 320.
Tan, "Wound repair and proliferation of bronchial epithelial cells . . . ", Peptides (2006), 1852-1858, vol. 27.
Ohki-Hamazaki, "Mice lacking bombesin receptor subtype-3 . . . ", Nature (1997), 165-169, vol. 390.
Lebacq-Verheyden, "Bombesin and gastrin-releasing peptide: . . . ", Handbook of Exper. Pharmacol. (1990), 71-124, vol. 95.
Srinivasan, "The preparation of alpha-hydroxy ketones by oxidation . . . ", Synthesis (1979), 520-521.

(Continued)

Primary Examiner — Sreeni Padmanabhan
Assistant Examiner — Sahar Javanmard
(74) Attorney, Agent, or Firm — Baerbel R. Brown; John C. Todaro

(57) ABSTRACT

Certain novel substituted imidazoles are ligands of the human bombesin receptor and, in particular, are selective ligands of the human bombesin receptor subtype-3 (BRS-3). They are therefore useful for the treatment, control, or prevention of diseases and disorders responsive to the modulation of BRS-3, such as obesity, and diabetes.

15 Claims, No Drawings

FOREIGN PATENT DOCUMENTS

| | | |
|---|---|---|
| WO | 2004/071509 | 8/2004 |
| WO | 2004/110350 | 12/2004 |
| WO | 2005/035551 | 4/2005 |
| WO | 2005/056532 | 6/2005 |
| WO | 2005/058848 | 6/2005 |
| WO | 2005/080390 | 9/2005 |
| WO | 2005/107762 | 11/2005 |
| WO | 2008/051404 | 5/2008 |
| WO | 2008/051406 | 5/2008 |

OTHER PUBLICATIONS

Claffey, "Synthesis of the C1-C28 portion of spongistatin 1 . . . ", J. Org. Chem. (1999), 8267-8274, vol. 64.

Haruta, "An effective and selective conjugate propargylation reaction . . . ", J. Org. Chem. (1990), 4853-4859, vol. 55.

Zhu, "Practical syntheses of beta-amino alcohols . . . ", J. Org. Chem. (1998), 8100-8101, vol. 63.

Wissner, "2-Hetero substituted silylated ketene acetals: . . . ", J. Org. Chem. (1979), 4617-4622, vol. 44.

Leanna, "N-(Boc)-L-(2-bromoallyl)-glycine: . . . ", Tetra. Letters (1993), 4485-4488, vol. 34.

Tsunoda, "Trimethylsilyi trifluoromethanesulfonate as a catalyst . . . ", Tetra. Letters (1980), 71-74, vol. 21.

McCormick, "alpha-Hdroxylation of ketones: . . . ", Tetra. Letters (1981), 607-610, vol. 22.

Sakaguchi, "Oxidation of dials and ethers . . . ", Bulletin of the Chem. Soc. of Japan (1997), 2561-2566, vol. 70.

\* cited by examiner

SUBSTITUTED IMIDAZOLES AS BOMBESIN RECEPTOR SUBTYPE-3 MODULATORS

CROSS-REFERENCE TO RELATED APPLICATIONS

This application is a U.S. National Phase application under 35 U.S.C. §371 of PCT Application No. PCT/US2007/022081, filed 16 Oct. 2007, which claims priority from and the benefit of U.S. Provisional Application No. 60/853272, filed Oct. 20, 2006.

BACKGROUND OF THE INVENTION

Obesity is a major health concern in Western societies. It is estimated that about 97 million adults in the United States are overweight or obese. Epidemiological studies have shown that increasing degrees of overweight and obesity are important predictors of decreased life expectancy. Obesity causes or exacerbates many health problems, both independently and in association with other diseases. The medical problems associated with obesity, which can be serious and life-threatening, include hypertension; type 2 diabetes mellitus; elevated plasma insulin concentrations; insulin resistance; hyperinsulinemia; glucose intolerance; dyslipidemias; hyperlipidemia; endometrial, breast, prostate and colon cancer; osteoarthritis; respiratory complications, such as obstructive sleep apnea; cholescystitis; cholelithiasis; gout; gallstones; gall bladder disease; respiratory problems; psychological disorders (such as depression, eating disorders, distorted body image and low self esteem); arterioscelerosis; heart disease; abnormal heart rhythms; angina pectoris; and heart arrythmias (Kopelman, P. G., Nature 404, 635-643 (2000)). Obesity is further associated with premature death and with a significant increase in mortality and morbidity from stroke, myocardial infarction, congestive heart failure, coronary heart disease, and sudden death. Recent studies have found that obesity and its associated health risks also affect children and adolescents.

Obesity is now recognized as a chronic disease that requires treatment to reduce its associated health risks. Important outcomes for the treatment of obesity include weight loss, and weight management to improve cardiovascular and metabolic health and to reduce obesity-related morbidity and mortality. It has been shown that 5-10% loss of body weight can substantially improve metabolic values, such as blood glucose, blood pressure, and lipid concentrations. Hence, it is believed that a 5-10% intentional reduction in body weight may reduce morbidity and mortality.

Rodent genetics and pharmacology have implicated BRS-3 in the development of obesity and diabetes (Ohki et al. Nature 390: 165-69 (1997)). Bombesin receptor subtype 3 is a G protein coupled receptor expressed primarily in the central nervous system, particularly the hypothalamus, a major region in the central nervous system for the regulation of food intake, metabolic rate, and body weight (Liu et al. Biochem 41: 8154-8160 (2002)). Bombesin, bombesin-like peptides, and related receptors participate in a diverse array of physiological processes. Although the natural ligand for the BRS-3 receptor has not yet been identified, bombesin-like peptides are widely distributed in the central nervous system and the gastrointestinal tract, where they bind to bombesin receptor subtype 3 (BRS-3), neuromedin B, and gastrin-releasing peptide (GRP-R) receptors, and modulate smooth muscle contraction, exocrine and endocrine processes, metabolism and behavior. BRS-3 has been implicated in the regulation of neuroendocrine function and energy metabolism (Ohki et al. Nature 390: 165-69 (1997)). One study showed that mice lacking the bombesin subtype-3 (BRS-3) receptor develop metabolic defects and obesity (Ohki et al. Nature 390: 165-69 (1997)). Specifically, mice lacking functional BRS-3 are hyperphagic and have a reduced metabolic rate, reduced core temperature which leads to the development of obesity, insulin resistance, diabetes and hypertension as they age. Additionally, bombesin-like peptides may contribute to the pathogenesis of some human carcinomas (For review' see Lebacq-Verheyden et ale in Handbook of Experime'tal Pharmacology, Sporn, M. N. and Roberts, A. B., eds., Vol. 95, pp. 71-124, Springer-Nierlag, Berlin). There is also evidence of a role for BRS-3 in cell growth and wound repair (Tan et al. Peptides 27:1852-58 (2006)) and its distribution in the rat gastrointestinal tract suggests a role in regulation of gut motility (Porcher et al., Cell Tissue Res 320:21-31 (2005)).

BRS-3 agonists to treat obesity/diabetes are disclosed in WO 2005/080390, WO 2005/056532, and WO 2003/104196. Imidazole compounds useful for the treatment of obesity and/or diabetes have been disclosed in WO 04/058176, WO 04/071447, WO 04/048351, WO 04/046091, WO 05/035551, US 2005/0187277 and US 2005/0272778. Other imidazoles are disclosed in U.S. Pat. No. 4,962,117, US 2002/0091116, US 2004/0167188, WO 93/17681, WO 97/40017, WO 98/28269, WO 99/32454, WO 04/007464, WO 04/110350, and JP 7-243068.

Weight loss drugs that are currently used in monotherapy for the treatment of obesity have limited efficacy and significant side effects. Because of the unresolved deficiencies of the various pharmacological agents used in the treatment of obesity and diabetes, there is a continuing need for a weight loss treatment with enhanced efficacy and fewer undesirable side effects. The instant invention addresses this problem by providing bombesin receptor agonists, and in particular selective agonists of the bombesin receptor subtype-3 (BRS-3), useful in the treatment and prevention of obesity, diabetes, obesity-related disorders, and diabetes related disorders.

SUMMARY OF THE INVENTION

The present invention relates to novel substituted imidazoles of formula I:

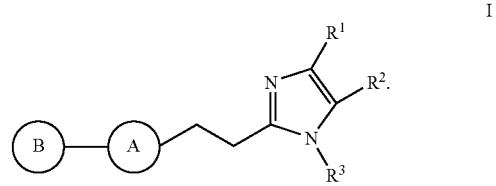

The compounds of formula I are effective as bombesin receptor ligands and are particularly effective as selective ligands of the bombesin receptor subtype-3. They are therefore useful for the treatment and/or prevention of disorders responsive to the modulation of the bombesin receptor subtype-3, such as obesity, diabetes, obesity-related disorders and diabetes-related disorders.

The present invention also relates to pharmaceutical compositions comprising the compounds of the present invention and a pharmaceutically acceptable carrier.

The present invention also relates to methods for the treatment or prevention of disorders, diseases, or conditions responsive to the modulation of the bombesin receptor subtype-3 in a mammal in need thereof by administering the compounds and pharmaceutical compositions of the present invention.

The present invention further relates to the use of the compounds of the present invention in the preparation of a medicament useful for the treatment or prevention of of disorders, diseases, or conditions responsive to the modulation of the bombesin receptor subtype-3 in a mammal in need thereof by administering the compounds and pharmaceutical compositions of the present invention.

DETAILED DESCRIPTION OF THE INVENTION

The present invention relates to substituted imidazoles useful as bombesin receptor modulators, in particular, as selective bombesin receptor subtype-3 agonists. Compounds of the present invention are described by formula I:

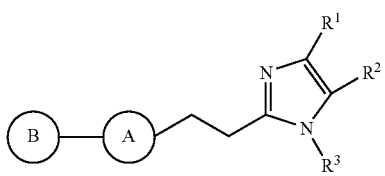

I or a pharmaceutically acceptable salt thereof; wherein
A is a ring selected from the group consisting of:
  (1) aryl, and
  (2) heteroaryl,
wherein aryl and heteroaryl are unsubstituted or substituted with 0 to 4 substituents selected from $R^4$;
B is a mono- or bicyclic ring selected from the group consisting of:
  (1) —$C_{3-8}$cycloalkyl,
  (2) —$C_{3-8}$cycloalkenyl,
  (3) —$C_{2-8}$heterocycloalkyl,
  (4) —$C_{2-8}$heterocycloalkenyl,
  (5) -aryl, and
  (6) -heteroaryl,
wherein cycloalkyl, cycloalkenyl, heterocycloalkyl, heterocycloalkenyl, aryl, and heteroaryl are unsubstituted or substituted with 0 to 4 substituents selected from $R^5$;
$R^1$ and $R^2$ are each independently selected from the group consisting of:
  (1) hydrogen,
  (2) —$(CH_2)_n$halogen,
  (3) —$(CH_2)_n OR^8$,
  (4) —$(CH_2)_n CN$,
  (5) —$(CH_2)_n CF_3$,
  (6) —$(CH_2)_n CHF_2$,
  (7) —$(CH_2)_n CH_2F$,
  (8) —$(CH_2)_n CCl_3$,
  (9) —$C_{1-8}$alkyl,
  (10) —$(CH_2)_n C_{2-8}$alkene,
  (11) —$(CH_2)_n C_{2-8}$alkyne,
  (12) —$(CH_2)_n C_{3-10}$cycloalkyl,
  (13) —$(CH_2)_n C_{3-10}$cycloalkenyl,
  (14) —$(CH_2)_n C_{2-12}$heterocycloalkyl,
  (15) —$SC_{1-8}$alkyl,
  (16) —$SC_{3-8}$cycloalkyl,
  (17) —$(CH_2)_n$aryl,
  (18) —$(CH_2)_n$heteroaryl,
  (19) —$(CH_2)_n CO_2 R^7$, and
  (20) —$(CH_2)_n COC_{1-8}$alkyl, provided that $R^1$ and $R^2$ are not both hydrogen, wherein alkyl, alkene, alkyne, cycloalkyl, cycloalkenyl, heterocycloalkyl, aryl, heteroaryl, and $(CH_2)_n$ are unsubstituted or substituted with 1 to 5 substituents selected from $R^6$, and wherein two $R^6$ substituents together with the atom to which they are attached may form a 3-6 membered cycloalkyl or cycloalkenyl ring containing 0 to 3 heteroatoms independently selected from oxygen, sulfur, and $NR^7$, wherein the 3-6 membered cycloalkyl or cycloalkenyl ring is unsubstituted or substituted with 1 to 4 substituents selected from $R^6$;
$R^3$ is selected from the group consisting of:
  (1) hydrogen,
  (2) —$C_{1-6}$alkyl, and
  (3) —$COC_{1-6}$alkyl;
$R^4$ is selected from the group consisting of:
  (1) —$C_{1-6}$alkyl,
  (2) —$(CH_2)_n$halogen,
  (3) —$(CH_2)_n OR^8$,
  (4) —$(CH_2)_n CN$,
  (5) —$(CH_2)_n CF_3$,
  (6) —$(CH_2)_n CO_2 R^7$,
  (7) —$(CH_2)_n N(R^8)_2$,
  (8) —$(CH_2)_n NO_2$,
  (9) —$(CH_2)_n NR^7 COC_{1-6}$alkyl,
  (10) —$(CH_2)_n NR^7 CO_2 C_{1-6}$alkyl,
  (11) —$(CH_2)_n NR^7 SO_2 C_{1-6}$alkyl, and
  (12) —$(CH_2)_n SO_{0-2} C_{1-6}$alkyl,
wherein alkyl is substituted with 1 to 3 halogens;
$R^5$ is selected from the group consisting of:
  (1) —$(CH_2)_n$halogen,
  (2) —$C_{1-6}$alkyl,
  (3) —$C_{2-6}$alkenyl,
  (4) —$(CH_2)_n C_{3-8}$cycloalkyl,
  (5) —$(CH_2)_n$heterocycloalkyl,
  (6) oxo,
  (7) —$(CH_2)_n OR^8$,
  (8) —$(CH_2)_n CN$,
  (9) —$(CH_2)_n COR^7$,
  (10) —$(CH_2)_n CO_2 R^8$,
  (11) —$(CH_2)_n CONR^7 N(R^7)_2$,
  (12) —$(CH_2)_n O(CH_2)_n CO_2 R^7$,
  (13) —$(CH_2)_n NO_2$,
  (14) —$(CH_2)_n CON(R^7)_2$,
  (15) —$(CH_2)_n N(R^8)_2$,
  (16) —$(CH_2)_n NR^7 (CH_2)_n CO_2 R^7$,
  (17) —$(CH_2)_n NR^7 COC_{1-6}$alkyl,
  (18) —$(CH_2)_n SO_2 N(R^7)_2$,
  (19) —$(CH_2)_n NR^7 SO_2 C_{1-6}$alkyl,
  (20) —$(CH_2)_n SO_{0-2} R^8$,
  (21) —$(CH_2)_n OP(O)_2 OH$,
  (22) —$CH=N-OH$,
  (23) —$(CH_2)_n$aryl,
  (24) —$(CH_2)_n$heteroaryl, and
  (25) —$(CH_2)_n O(CH_2)_n$heteroaryl,
wherein alkyl, alkenyl, cycloalkyl, heterocycloalkyl, aryl, heteroaryl, and —$(CH_2)_n$ are unsubstituted or substituted with 1 to 3 halogens;
$R^6$ is independently selected from the group consisting of:
  (1) halogen,
  (2) —OH,
  (3) oxo,
  (4) —CN,
  (5) —$CCl_3$,
  (6) —$CF_3$,
  (7) —$CHF_2$,
  (8) —$CH_2F$,
  (9) —$SO_2 C_{1-6}$alkyl,

(10) —COC$_{1-8}$alkyl,
(11) —CO$_2$C$_{1-8}$alkyl,
(12) —CO$_2$H,
(13) —C$_{1-8}$alkyl, and
(14) —C$_{1-8}$alkoxy,
wherein alkyl and alkoxy are unsubstituted or substituted with 1 to 4 substituents selected from —C$_{1-6}$alkyl and halogen, and wherein the —C$_{1-6}$alkyl substituent is unsubstituted or substituted with 1 to 3 halogens;
R$^7$ is selected from the group consisting of:
 (1) hydrogen, and
 (2) —C$_{1-6}$alkyl,
wherein alkyl is unsubstituted or substituted with 1 to 3 substituents selected from halogen and —OH;
R$^8$ is selected from the group consisting of:
 (1) hydrogen,
 (2) —C$_{1-6}$alkyl,
 (3) —C$_{3-8}$cycloalkyl,
 (4) —C$_{2-7}$heterocycloalkyl,
 (5) —(CH$_2$)$_m$phenyl, and
 (6) —(CH$_2$)$_m$heteroaryl,
wherein alkyl, cycloalkyl, and heterocycloalkyl are unsubstituted or substituted with 1 to 3 halogens or —OH, and wherein phenyl and heteroaryl are unsubstituted or substituted with 1 to 3 halogens;
each n is independently 0, 1, 2, 3, 4, or 5; and
each m is independently 1, 2, 3 or 4.

In a further embodiment of the compounds of the present invention, there are provided compounds of formula II:

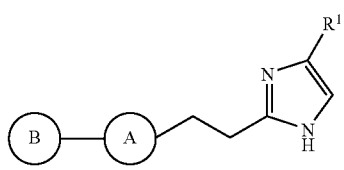

II or a pharmaceutically acceptable salt thereof.

In a further embodiment of the compounds of the present invention, there are provided compounds of formula III:

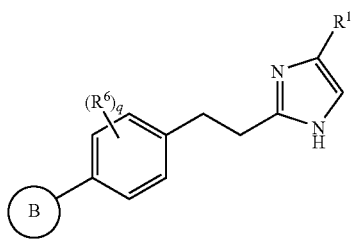

III or a pharmaceutically acceptable salt thereof.

In a further embodiment of the compounds of the present invention, there are provided compounds of formula IV:

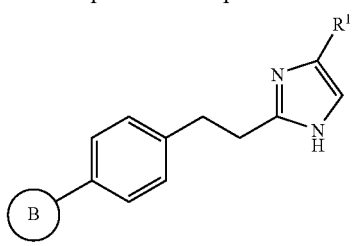

IV or a pharmaceutically acceptable salt thereof.

In one embodiment of the present invention, A is a ring selected from the group consisting of: aryl, and heteroaryl, wherein aryl and heteroaryl are unsubstituted or substituted with 0 to 4 substituents selected from R$^4$. In a class of this embodiment, A is a ring selected from the group consisting of phenyl, thiene, thiazole, oxadiazole, oxazole, pyridine, triazole, oxadiazole, and thiadiazole, wherein the ring is unsubstituted or substituted with 0 to 4 substituents selected from R$^4$. In a subclass of this class, A is a ring selected from the group consisting of: phenyl, thiene, 1,3-thiazole, 1,2,3-oxadiazole, 1,3-oxazole, pyridine, 1,2,4-triazole, 1,3,4-oxadiazole, and 1,3,4-thiadiazole, wherein the ring is unsubstituted or substituted with 0 to 4 substituents selected from R$^4$. In another class of this embodiment, A is a ring selected from the group consisting of phenyl, thiene, pyridine, pyrimidine, triazole, oxadiazole, imidazole, thiazole, thiadiazole, and oxazole, wherein A is unsubstituted or substituted with 0 to 4 substituents selected from R$^4$.

In another embodiment of the present invention, A is heteroaryl, wherein heteroaryl is unsubstituted or substituted with 0 to 4 substituents selected from R$^4$. In a class of this embodiment, A is a ring selected from the group consisting of: thiene, 1,3-thiazole, 1,2,3-oxadiazole, 1,3-oxazole, pyridine, 1,2,4-triazole, 1,3,4-oxadiazole, and 1,3,4-thiadiazole, wherein the ring is unsubstituted or substituted with 0 to 4 substituents selected from R$^4$. In another class of this embodiment, A is selected from the group consisting of: thiene, pyridine, pyrimidine, triazole, oxadiazole, imidazole, thiazole, thiadiazole, and oxazole, wherein A is unsubstituted or substituted with 0 to 4 substituents selected from R$^4$.

In another embodiment of the present invention, A is aryl, wherein aryl is unsubstituted or substituted with 0 to 4 substituents selected from R$^4$. In a class of this embodiment, A is phenyl, wherein phenyl is unsubstituted or substituted with 0 to 4 substituents selected from R$^4$.

In another embodiment of the present invention, ring A and ring B are connected via a carbon-carbon bond. In another embodiment of the present invention, ring A and ring B are connected via a carbon-nitrogen bond. In another embodiment of the present invention, ring A and ring B are connected via a nitrogen-carbon bond. In another embodiment of the present invention ring A and ring B are connected via a nitrogen-nitrogen bond.

In another embodiment of the present invention, ring A and the ethylene linker carbon are connected via a carbon-carbon bond. In another embodiment of the present invention, ring A and the ethylene linker carbon are connected via a nitrogen-carbon bond.

In another embodiment of the invention, Ring A is selected from the group consisting of:

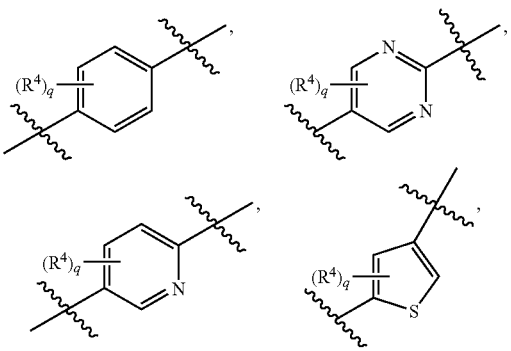

-continued

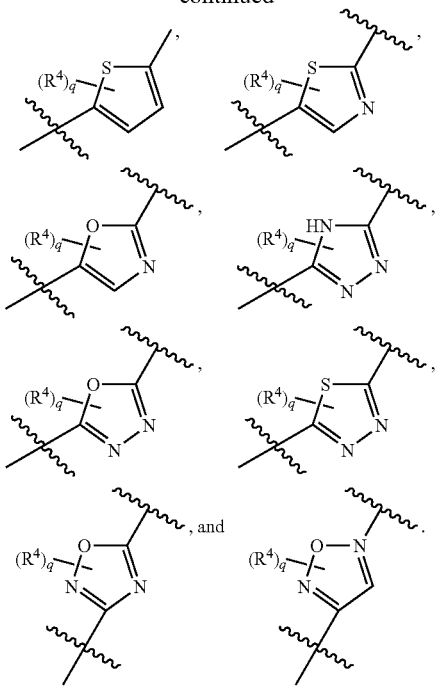

In a class of this embodiment, q is 0.
In another class of this embodiment, A is

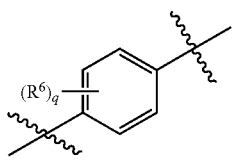

In a subclass of this class, q is 0.

In another embodiment of the present invention, B is a mono- or bicyclic ring selected from the group consisting of: —$C_{3-8}$cycloalkyl, —$C_{3-8}$cycloalkenyl, —$C_{2-8}$heterocycloalkyl, —$C_{2-8}$heterocycloalkenyl, -aryl, and -heteroaryl, wherein cycloalkyl, cycloalkenyl, heterocycloalkyl, heterocycloalkenyl, aryl, and heteroaryl are unsubstituted or substituted with 0 to 4 substituents selected from $R^5$.

In another embodiment of the present invention, B is a mono- or bicyclic ring selected from the group consisting of: —$C_{3-8}$cycloalkyl, —$C_{2-8}$heterocycloalkyl, —$C_{2-8}$heterocycloalkenyl, -aryl, and -heteroaryl, wherein cycloalkyl, heterocycloalkyl, heterocycloalkenyl, aryl, and heteroaryl are unsubstituted or substituted with 0 to 4 substituents selected from $R^5$.

In a class of this embodiment, B is selected from the group consisting of: cyclohexyl; cyclopentyl; piperazine; azepane; hexahydropyridazine; morpholine; piperidine; pyrrolidine; 1,2-dihydropyridine; 1,2,3,4-tetrahydropyrazine; phenyl; thiophene; pyridine; quinoline; isoquinoline; benzotriazole; benzimidazole; benzopyrazole; benzodioxole; thiazole; isothiazole; thiadiazole; pyrazine; pyrazole; pyrimidine; triazole; imidazo[1,2-a]pyrazine; isoxazole; imidazole; tetrazole; pyridazine; triazolopyridine; benzopyrrole; 1-H-pyrrolo[2,3-b]pyridine; 1,2,3,4-tetrahydroquinoline; 1,2,3,4-tetrahydro-1,8-naphthyridine; and 3a,4,5,6,7,7a-hexahydro-1H-pyrazolo[3,4-b]pyridine; wherein B is unsubstituted or substituted with 0 to 4 substituents selected from $R^5$.

In another class of this embodiment, B is a mono or bicyclic ring selected from the group consisting of cyclohexyl, piperidine, tetrahydro-pyrazolopyridine, oxodihydropyridine, tetrahydropyrazine, phenyl, pyrazole, imidazole, pyrazine, pyridazine, pyridine, pyrimidine, thiazole, isothiazole, thiadiazole, triazole, thiene, indazole, isoquinoline, triazolopyridine, pyrrolopyridine, imidazopyrazine, and pyrazolopyridine, wherein the ring is unsubstituted or substituted with 0 to 4 substituents selected from $R^5$.

In a subclass of this class, B is a mono or bicyclic ring selected from the group consisting of: cyclohexyl; piperidine; 4,5,6,7-tetrahydro-1H-pyrazolo[3,4-b]pyridine; oxodihydropyridine; 1,2,3,4-tetrahydropyrazine; phenyl pyrazole, imidazole, pyrazine, pyridazine, pyridine, pyrimidine, thiazole, isothiazole, thiadiazole, triazole, thiene, indazole, isoquinoline, 1H-1,2,3-triazolo[4,5-b]pyridine, 1H-pyrrolo[2,3,-b]pyridine, imidazo[1,2-a]pyrazine, and 1H-pyrazolo[3,4-b]pyridine, wherein the ring is unsubstituted or substituted with 0 to 4 substituents selected from $R^5$.

In another subclass of this class, B is a mono or bicyclic ring selected from the group consisting of: cyclohexane; piperidine; 4,5,6,7-tetrahydro-1H-pyrazolo[3,4-b]pyridine; phenyl, pyrazole, and indazole, wherein the ring is unsubstituted or substituted with 0 to 4 substituents selected from $R^5$.

In another embodiment of the present invention, B is selected from the group consisting of: —$C_{3-8}$cycloalkyl, -aryl, and -heteroaryl, wherein cycloalkyl, aryl, and heteroaryl are unsubstituted or substituted with 0 to 4 substituents selected from $R^5$. In a class of this embodiment, B is selected from the group consisting of cyclohexyl, phenyl, pyridine, and pyrazole, wherein B is unsubstituted or substituted with 0 to 4 substituents selected from $R^5$. In another class of this embodiment, B is selected from the group consisting of: cyclohexyl, phenyl, and pyridine, wherein B is unsubstituted or substituted with 0 to 4 substituents selected from $R^5$. In another class of this embodiment, B is pyrazole, wherein pyrazole is unsubstituted or substituted with 0 to 4 substituents selected from $R^5$.

In another embodiment of the present invention, B is is selected from the group consisting of: —$C_{3-8}$cycloalkyl, and -aryl, wherein cycloalkyl, and aryl are unsubstituted or substituted with 0 to 4 substituents selected from $R^5$. In a class of this embodiment, B is selected from the group consisting of: cyclohexyl and phenyl, wherein cyclohexyl and phenyl are unsubstituted or substituted with 0 to 4 substituents selected from $R^5$.

In another embodiment of this invention, B is —$C_{3-8}$cycloalkyl, wherein cycloalkyl is unsubstituted or substituted with 0 to 4 substituents selected from $R^5$. In a class of this embodiment, B is cyclohexane, wherein cyclohexane is unsubstituted or substituted with 0 to 4 substituents selected from $R^5$.

In another embodiment of this invention, B is aryl, wherein aryl is unsubstituted or substituted with 0 to 4 substituents selected from $R^5$. In a class of this embodiment, B is phenyl, wherein phenyl is unsubstituted or substituted with 0 to 4 substituents selected from $R^5$. In another class of this embodiment, B is phenyl, wherein phenyl is unsubstituted or substituted with 0 to 4 substituents selected from $R^5$, provided that $R^5$ is not alkyl.

In another embodiment of this invention, B is heteroaryl, wherein heteroaryl is unsubstituted or substituted with 0 to 4 substituents selected from $R^5$. In a class of this embodiment, B is pyridine or pyrazole, wherein B is unsubstituted or substituted with 0 to 4 substituents selected from $R^5$. In another class of this embodiment, B is pyridine, wherein pyridine is unsubstituted or substituted with 0 to 4 substituents selected from R⁵. In another class of this embodiment, B is pyrazole, wherein pyrazole is unsubstituted or substituted with 0 to 4 substituents selected from R⁵.

In another embodiment of the present invention, B is selected from the group consisting of: —C₃₋₈cycloalkyl, —C₃₋₈cycloalkenyl, —C₂₋₈heterocycloalkyl, —C₂₋₈heterocycloalkenyl, -aryl, and -heteroaryl, wherein cycloalkyl, cycloalkenyl, heterocycloalkyl, heterocycloalkenyl, aryl, and heteroaryl are unsubstituted or substituted with 0 to 4 substituents selected from R⁵, provided that when B is phenyl, R⁵ is not alkyl. In another embodiment of the present invention, B is a monocyclic or a bicyclic ring selected from the group consisting of: —C₃₋₈cycloalkyl, —C₂₋₈heterocycloalkyl, —C₂₋₈heterocycloalkenyl, -aryl, and -heteroaryl, wherein cycloalkyl, heterocycloalkyl, heterocycloalkenyl, aryl, and heteroaryl are unsubstituted or substituted with 0 to 4 substituents selected from R⁵, provided that when B is phenyl, R⁵ is not alkyl. In a class of this embodiment, B is selected from the group consisting of: cyclohexyl; cyclopentyl; piperazine; azepane; hexahydropyridazine; morpholine; piperidine; pyrrolidine; 1,2-dihydropyridine; 1,2,3,4-tetrahydropyrazine; phenyl; thiophene; pyridine; quinoline; isoquinoline; benzotriazole; benzimidazole; benzopyrazole; benzodioxole; thiazole; isothiazole; thiadiazole; pyrazine; pyrazole; pyrimidine; triazole; imidazo[1,2-a]pyrazine; isoxazole; imidazole; tetrazole; pyridazine; triazolopyridine; benzopyrrole; 1-H-pyrrolo[2,3-b]pyridine; 1,2,3,4-tetrahydroquinoline; 1,2,3,4-tetrahydro-1,8-naphthyridine; and 3a,4,5,6,7,7a-hexahydro-1H-pyrazolo[3,4-b]pyridine; wherein B is unsubstituted or substituted with 0 to 4 substituents selected from R⁵, provided that when B is phenyl, R⁵ is not alkyl.

In another class of this embodiment, B is a mono or bicyclic ring selected from the group consisting of: cyclohexyl, piperidine, tetrahydro-pyrazolopyridine, oxodihydropyridine, tetrahydropyrazine, phenyl, pyrazole, imidazole, pyrazine, pyridazine, pyridine, pyrimidine, thiazole, isothiazole, thiadiazole, triazole, thiene, indazole, isoquinoline, triazolopyridine, pyrrolopyridine, imidazopyrazine, and pyrazolopyridine, wherein the ring is unsubstituted or substituted with 0 to 4 substituents selected from R⁵, provided that when B is phenyl, R⁵ is not alkyl.

In a subclass of this class, B is a mono or bicyclic ring selected from the group consisting of: cyclohexyl; piperidine; 4,5,6,7-tetrahydro-1H-pyrazolo[3,4-b]pyridine; oxodihydropyridine; 1,2,3,4-tetrahydropyrazine; phenyl, pyrazole, imidazole, pyrazine, pyridazine, pyridine, pyrimidine, thiazole, isothiazole, thiadiazole, triazole, thiene, indazole, isoquinoline, 1H-1,2,3-triazolo[4,5-b]pyridine, 1H-pyrrolo[2,3,-b]pyridine, imidazo[1,2-a]pyrazine, and 1H-pyrazolo[3,4-b]pyridine, wherein the ring is unsubstituted or substituted with 0 to 4 substituents selected from R⁵, provided that when B is phenyl, R⁵ is not alkyl.

In another subclass of this class, B is a mono or bicyclic ring selected from the group consisting of cyclohexane; piperidine; 4,5,6,7-tetrahydro-1H-pyrazolo[3,4-b]pyridine; phenyl, pyrazole, and indazole, wherein the ring is unsubstituted or substituted with 0 to 4 substituents selected from R⁵, provided that when B is phenyl, R⁵ is not alkyl.

In another embodiment of the present invention, B is selected from the group consisting of: —C₃₋₈cycloalkyl, -aryl, and -heteroaryl, wherein cycloalkyl, aryl, and heteroaryl are unsubstituted or substituted with 0 to 4 substituents selected from R⁵, provided that when B is phenyl, R⁵ is not alkyl.

In a class of this embodiment, B is selected from the group consisting of: cyclohexyl, phenyl, pyridine, and pyrazole, wherein B is unsubstituted or substituted with 0 to 4 substituents selected from R⁵, provided that when B is phenyl, R⁵ is not alkyl.

In another class of this embodiment, B is selected from the group consisting of: cyclohexyl, phenyl, and pyridine, wherein B is unsubstituted or substituted with 0 to 4 substituents selected from R⁵, provided that when B is phenyl, R⁵ is not alkyl.

In another embodiment of the present invention, B is is selected from the group consisting of: —C₃₋₈cycloalkyl, and -aryl, wherein cycloalkyl, and aryl are unsubstituted or substituted with 0 to 4 substituents selected from R⁵, provided that when B is phenyl, R⁵ is not alkyl. In a class of this embodiment, B is selected from the group consisting of cyclohexyl and phenyl, wherein cyclohexyl and phenyl are unsubstituted or substituted with 0 to 4 substituents selected from R⁵, provided that when B is phenyl, R⁵ is not alkyl. In another embodiment of the present invention, B is selected from the group consisting of: —C₃₋₈cycloalkyl, —C₃₋₈cycloalkenyl, —C₂₋₈heterocycloalkyl, —C₂₋₈heterocycloalkenyl, -aryl, and -heteroaryl, wherein cycloalkyl, cycloalkenyl, heterocycloalkyl, heterocycloalkenyl, aryl, and heteroaryl are unsubstituted or substituted with 0 to 4 substituents selected from R⁵, provided that B is not a six membered ring.

In another embodiment of the present invention, B is a monocyclic or a bicyclic ring selected from the group consisting of —C₃₋₈cycloalkyl, —C₂₋₈heterocycloalkyl, —C₂₋₈heterocycloalkenyl, -aryl, and -heteroaryl, wherein cycloalkyl, heterocycloalkyl, heterocycloalkenyl, aryl, and heteroaryl are unsubstituted or substituted with 0 to 4 substituents selected from R⁵ provided that B is not a six membered ring.

In another embodiment of the present invention, B is selected from the group consisting of: —C₃₋₈cycloalkyl, -aryl, and -heteroaryl, wherein cycloalkyl, aryl, and heteroaryl are unsubstituted or substituted with 0 to 4 substituents selected from R⁵ provided that B is not a six membered ring.

In another embodiment of the present invention, B is is selected from the group consisting of: —C₃₋₈cycloalkyl, and -aryl, wherein cycloalkyl, and aryl are unsubstituted or substituted with 0 to 4 substituents selected from R⁵, provided that B is not a six membered ring.

In another embodiment of the invention, Ring B is selected from the group consisting of:

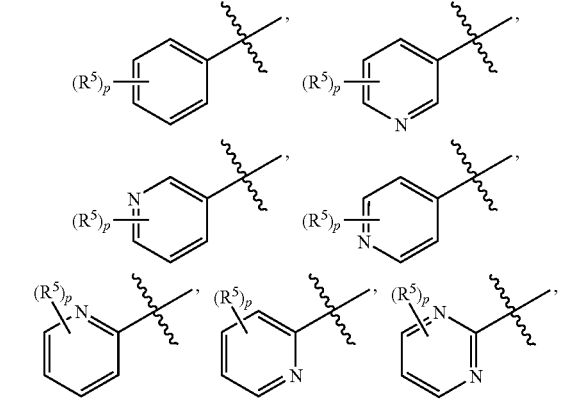

-continued
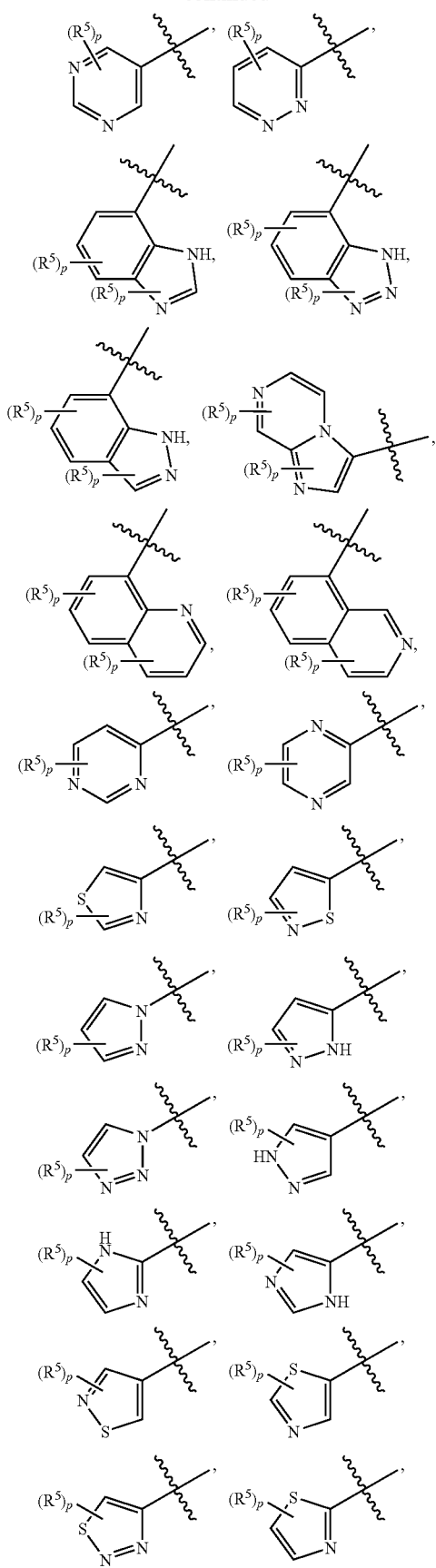
-continued
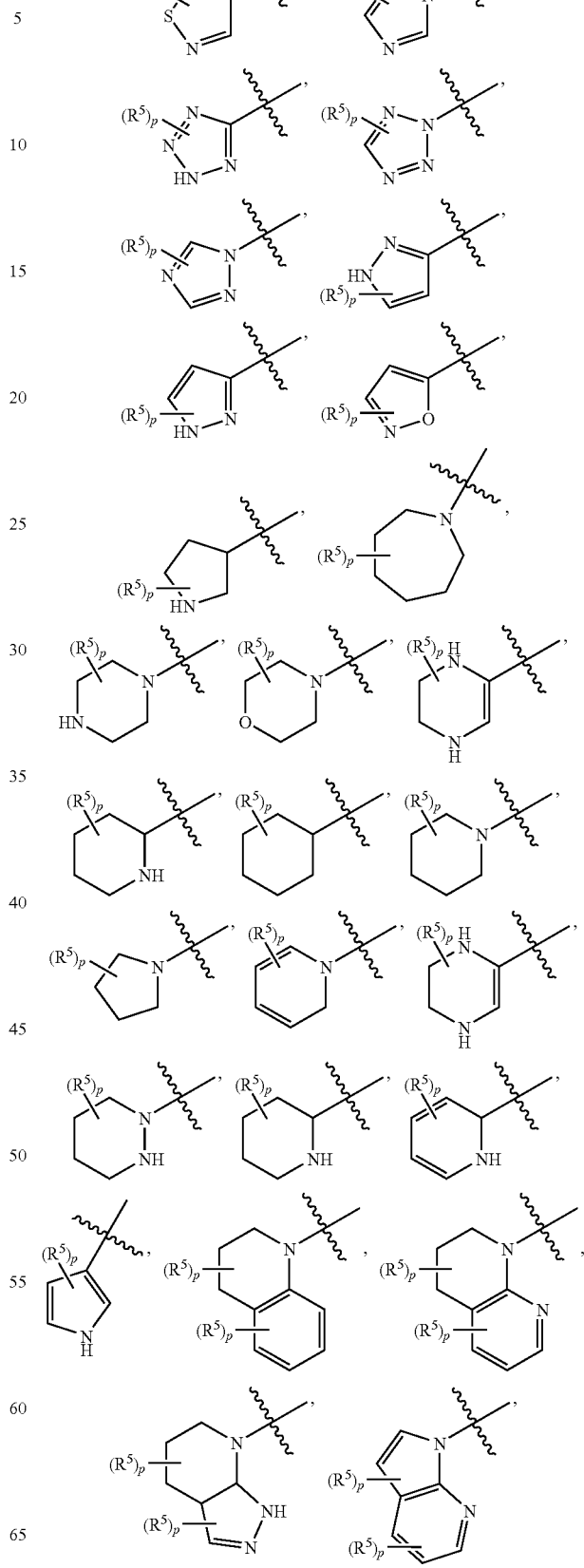

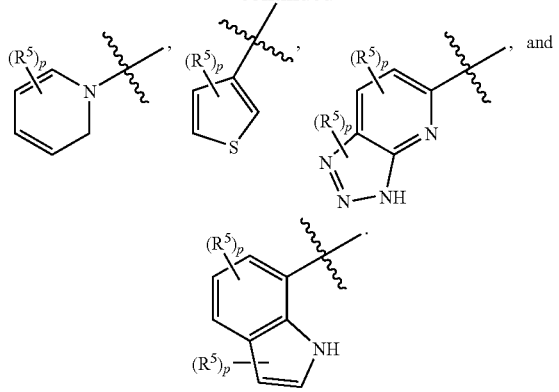
In a subclass of this class, p is 0. In another subclass of this class p is 0 to 3.
In another embodiment of the invention, Ring B is selected from the group consisting of:
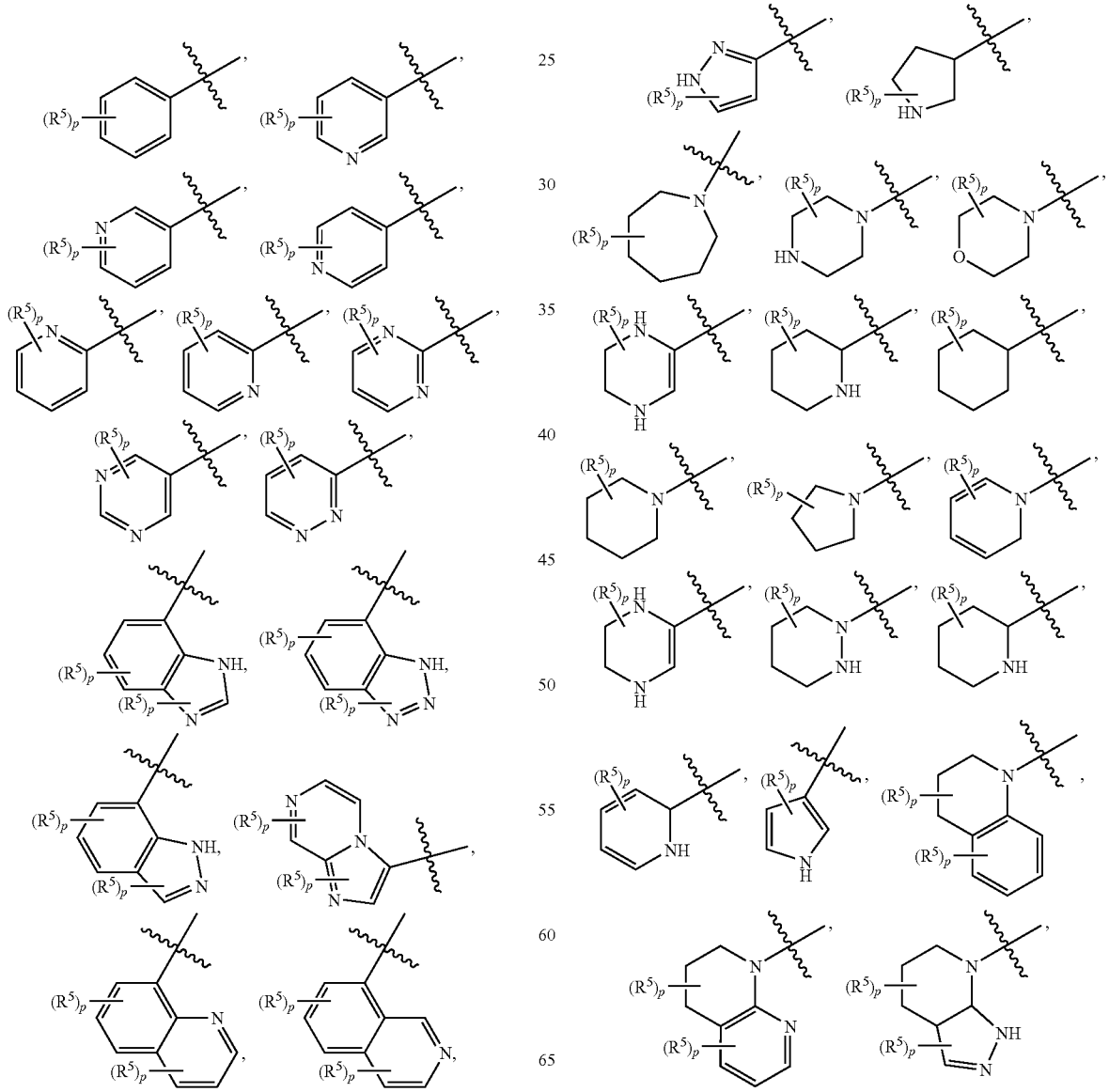
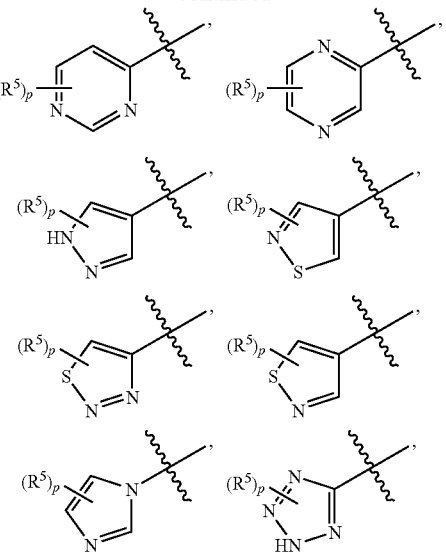

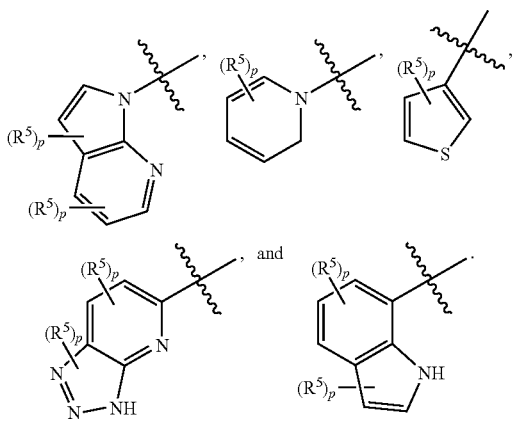
In a subclass of this class, p is 0. In another subclass of this class p is 0 to 3.
In another embodiment of the invention, Ring B is selected from the group consisting of:
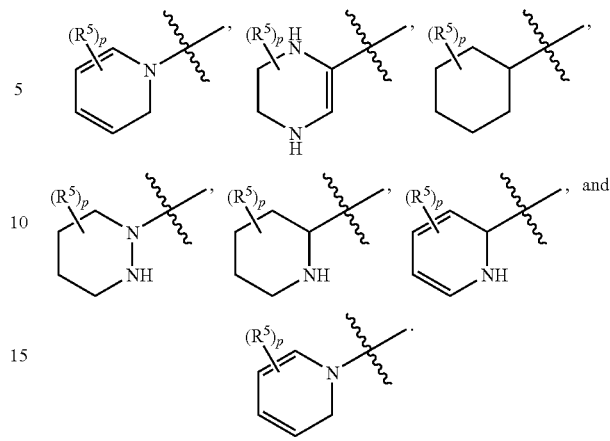
In a subclass of this class, p is 0. In another subclass of this class p is 0 to 3.
In another embodiment of the invention, Ring B is selected from the group consisting of:
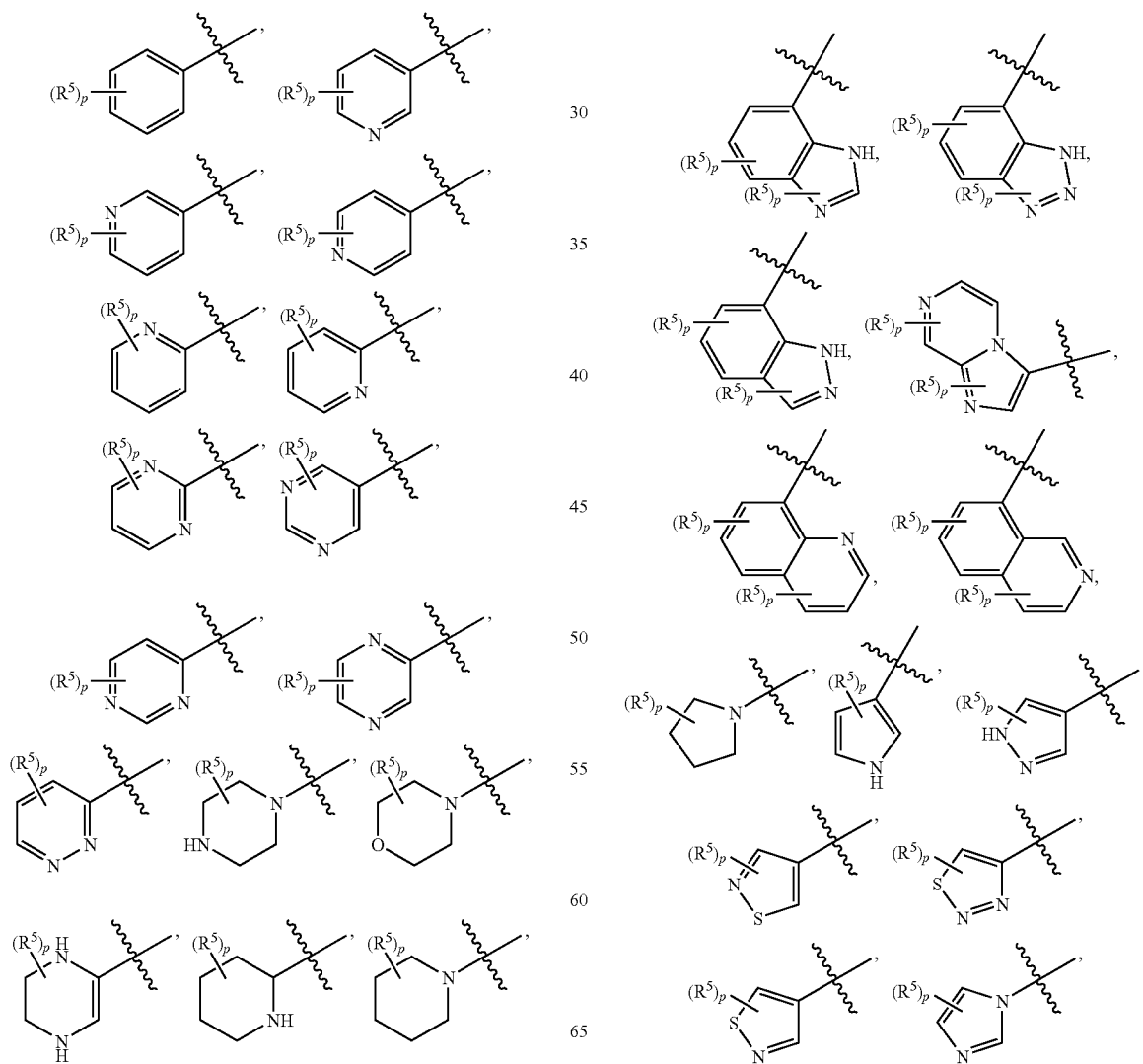

-continued

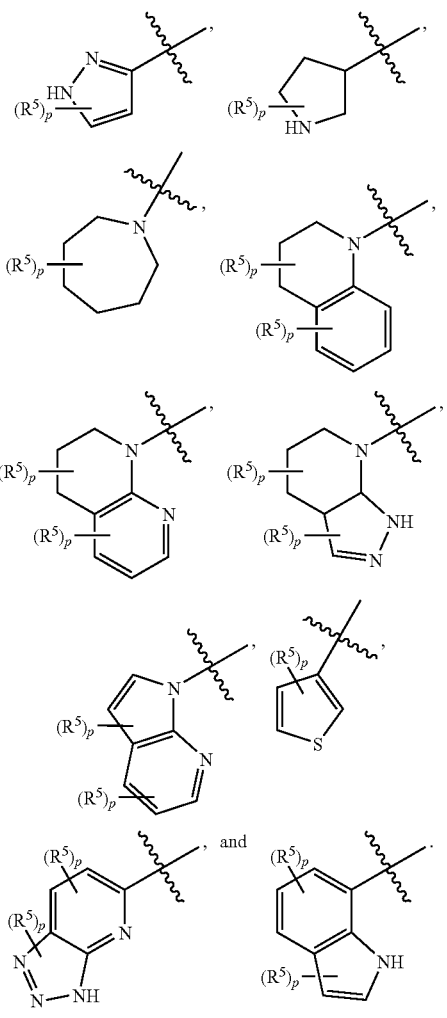

In a subclass of this class, p is 0. In another subclass of this class p is 0 to 3.

In another embodiment of the invention, Ring B is selected from the group consisting of:

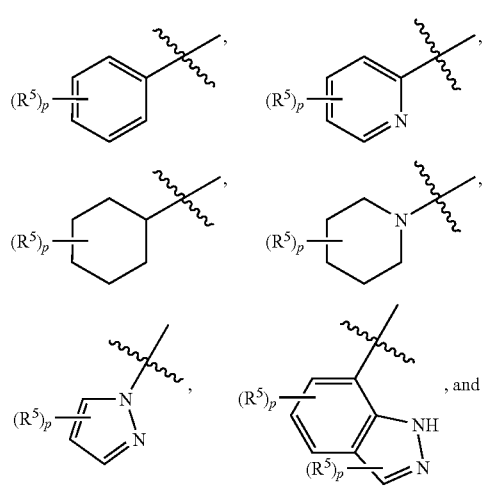

-continued

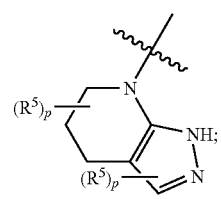

or a pharmaceutically acceptable salt thereof. In a subclass of this class, p is 0, 1, 2 or 3.

In another embodiment of the invention, Ring B is selected from the group consisting of:

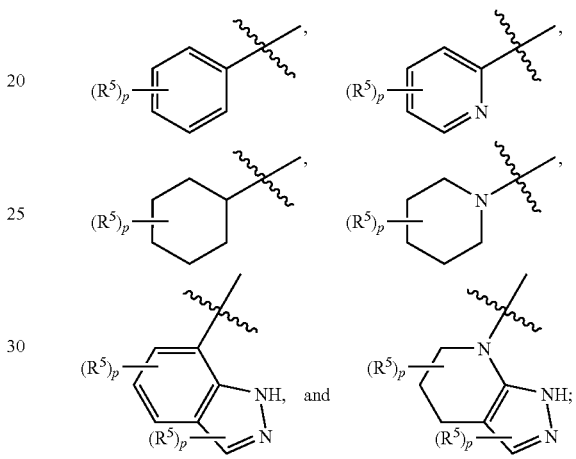

or a pharmaceutically acceptable salt thereof. In a subclass of this class, p is 0, 1, 2 or 3.

In another embodiment of the invention, Ring B is selected from the group consisting of:

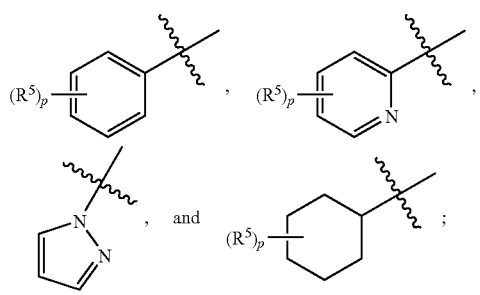

or a pharmaceutically acceptable salt thereof. In a subclass of this class, p is 0, 1, 2 or 3.

In another embodiment of the invention, Ring B is selected from the group consisting of:

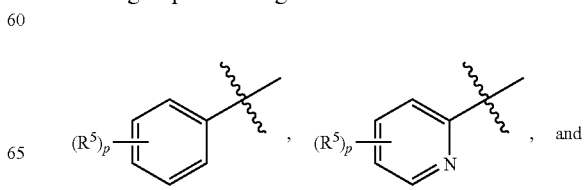

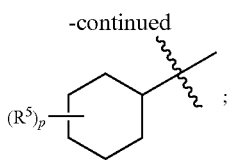

or a pharmaceutically acceptable salt thereof. In a subclass of this class, p is 0, 1, 2 or 3.

In another embodiment of the present invention, $R^1$ and $R^2$ are each independently selected from the group consisting of: hydrogen, —$(CH_2)_n$halogen, —$(CH_2)_nOR^8$, —$(CH_2)_nCN$, —$(CH_2)_nCF_3$, —$(CH_2)_nCHF_2$, —$(CH_2)_nCH_2F$, —$(CH_2)_nCCl_3$, —$C_{1-8}$alkyl, —$(CH_2)_nC_{2-8}$alkene, —$(CH_2)_nC_{2-8}$alkyne, —$(CH_2)_nC_{3-10}$cycloalkyl, —$(CH_2)_nC_{3-10}$cycloalkenyl, —$(CH_2)_nC_{2-12}$heterocycloalkyl, $(CH_2)_nSC_{1-8}$alkyl, —$(CH_2)_nSC_{3-8}$cycloalkyl, —$(CH_2)_n$aryl, —$(CH_2)_n$heteroaryl, —$(CH_2)_nCO_2R^7$, and —$(CH_2)_nCOC_{1-8}$alkyl, provided that $R^1$ and $R^2$ are not both hydrogen, wherein alkyl, alkene, alkyne, cycloalkyl, cycloalkenyl, heterocycloalkyl, aryl, heteroaryl, and $(CH_2)_n$ are unsubstituted or substituted with 1 to 5 substituents selected from $R^6$, and wherein two $R^6$ substituents together with the atom to which they are attached may form a 3-6 membered cycloalkyl or cycloalkenyl ring containing 0 to 3 heteroatoms independently selected from oxygen, sulfur, and $NR^7$, wherein the 3-6 membered cycloalkyl or cycloalkenyl ring is unsubstituted or substituted with 1 to 4 substituents selected from $R^6$. In a class of this embodiment, $R^6$ is not -phenyl. In another class of this embodiment, $R^2$ is selected from the group consisting of: hydrogen, —$(CH_2)_n$halogen, and —$C_{1-8}$alkyl. In a subclass of this class, $R^2$ is selected from the group consisting of: hydrogen, I, and —$CH_3$. In a subclass of this class, $R^6$ is not -phenyl.

In another embodiment of the present invention, $R^1$ and $R^2$ are each independently selected from the group consisting of: hydrogen, —$(CH_2)_n$halogen, —$(CH_2)_nOR^8$, —$(CH_2)_nCN$, —$(CH_2)_nCF_3$, —$(CH_2)_nCHF_2$, —$(CH_2)_nCH_2F$, —$(CH_2)_nCCl_3$, —$(CH_{1-8}$alkyl, —$(CH_2)_nC_{2-8}$alkene, —$(CH_2)_nC_{2-8}$alkyne, —$(CH_2)_nC_{3-10}$cycloalkyl, —$(CH_2)C_{3-10}$cycloalkenyl, —$(CH_2)_nC_{2-12}$heterocycloalkyl, —$(CH_2)_nSC_{1-8}$alkyl, —$(CH_2)_nSC_{3-8}$cycloalkyl, —$(CH_2)_n$aryl, —$(CH_2)_n$heteroaryl, —$(CH_2)_nCO_2R^7$, and —$(CH_2)_nCOC_{1-8}$alkyl, provided that $R^1$ and $R^2$ are not both hydrogen, wherein alkyl, alkene, alkyne, cycloalkyl, cycloalkenyl, heterocycloalkyl, aryl, heteroaryl, and $(CH_2)_n$ are unsubstituted or substituted with 1 to 5 substituents selected from $R^6$. In a class of this embodiment, $R^6$ is not -phenyl. In another class of this embodiment, $R^2$ is selected from the group consisting of hydrogen, —$(CH_2)_n$halogen, and —$C_{1-8}$alkyl. In a subclass of this class, $R^2$ is selected from the group consisting of: hydrogen, I, and —$CH_3$. In a subclass of this class, $R^6$ is not -phenyl.

In another embodiment of the present invention, $R^1$ and $R^2$ are each independently selected from the group consisting of hydrogen, —$(CH_2)_n$halogen, —$(CH_2)_nOR^8$, —$(CH_2)_nCF_3$, —$(CH_2)_nCCl_3$, —$C_{1-8}$alkyl, —$C_{1-8}$alkoxy, —$(CH_2)_nC_{2-8}$alkene, —$(CH_2)_nC_{3-10}$cycloalkyl, —$(CH_2)_nC_{3-10}$cycloalkenyl, —$(CH_2)_nC_{2-8}$heterocycloalkyl, —$(CH_2)_n$aryl, —$(CH_2)_n$heteroaryl, —$(CH_2)_nCO_2R^7$, and —$(CH_2)_nCOC_{1-8}$alkyl, provided that $R^1$ and $R^2$ are not both hydrogen, wherein alkyl, alkene, alkoxy, cycloalkyl, cycloalkenyl, heterocycloalkyl, aryl, heteroaryl, and $(CH_2)_n$ are unsubstituted or substituted with 1 to 5 substituents selected from $R^6$. In a class of this embodiment, $R^6$ is not -phenyl. In another class of this embodiment, $R^2$ is selected from the group consisting of: hydrogen, —$(CH_2)_n$halogen, and —$C_{1-8}$alkyl. In a subclass of this class, $R^2$ is selected from the group consisting of: hydrogen, I, and —$CH_3$. In another subclass of this class, $R^6$ is not -phenyl.

In another embodiment of the present invention, $R^1$ and $R^2$ are each independently selected from the group consisting of: hydrogen, I, —$(CH_2)_4OH$, —$(CH_2)_3OH$, —$CH_2C(CH_3)_2C(CH_3)_2OH$, —$CH_2C(CH_3)_2CH_2OH$, —$(CH_2)_2CF_3$, —$(CH_2)_2CCl_3$, —$(CH_2)_{0-4}CH_3$, —$(CH_2)_{0-1}C(CH_3)_3$, —$CH_2C(CH_3)_2CH_2CH_3$, —$(CH_2)_2OCH_3$, —$(CH_2)_{1-2}$cyclopentene, —$(CH_2)_{1-2}$cyclohexene, adamantane, —$(CH_2)_{0-2}$cyclopropane, —$(CH_2)_{0-2}$cyclobutane, —$(CH_2)_{0-2}$cyclopentane, —$(CH_2)_{0-2}$cyclohexane, —$(CH_2)_{0-2}$cycloheptane, —$(CH_2)_{0-2}$cyclooctane, —$CH_2$-tetrahydropyran, —$CH_2$-tetrahydrofuran, —$(CH_2)_{1-2}$-phenyl, —$CH_2$-naphthalene, benzocyclobutene, —$(CH_2)_{1-3}$thienyl, —$CH_2$-benzodioxole, —$(CH_2)_{2-3}CO_2CH_3$, and —$(CH_2)_{2-3}COCH_2CH_3$, provided that $R^1$ and $R^2$ are not both hydrogen, wherein alkyl, alkene, alkyne, alkoxy, cycloalkyl, heterocycloalkyl, aryl, heteroaryl, and $(CH_2)_n$ are unsubstituted or substituted with 1 to 5 substituents selected from $R^6$. In a class of this embodiment, $R^6$ is not -phenyl. In another class of this embodiment, $R^2$ is selected from the group consisting of: hydrogen, —$(CH_2)_n$halogen, and —$C_{1-8}$alkyl. In a subclass of this class, $R^2$ is selected from the group consisting of: hydrogen, I, and —$CH_3$. In another subclass of this class, $R^6$ is not -phenyl.

In another embodiment of the present invention, $R^1$ and $R^2$ are each independently selected from the group consisting of: hydrogen, —$(CH_2)_n$halogen, —$(CH_2)_nOR^8$, —$(CH_2)_nCN$, —$(CH_2)_nCF_3$, —$(CH_2)_nCCl_3$, —$(CH_2)_nCHF_2$, —$(CH_2)_nCH_2F$, —$C_{1-8}$alkyl, —$(CH_2)_nC_{2-8}$alkenyl, —$(CH_2)_nC_{2-8}$alkynyl, —$(CH_2)_nC_{3-12}$cycloalkyl, —$(CH_2)_nC_{3-12}$cycloalkenyl, —$(CH_2)_nC_{2-12}$heterocycloalkyl, —$(CH_2)_n$aryl, —$(CH_2)_n$heteroaryl, —$(CH_2)_nC(O)C_{1-8}$alkyl, and —$(CH_2)_nCO_2R^7{}_{1-6}$alkyl, provided that $R^1$ and $R^2$ are not both hydrogen and that $R^1$ and $R^2$ are not -phenyl, wherein alkyl, alkenyl, alkynyl, cycloalkyl, cycloalkenyl, heterocycloalkyl, aryl, heteroaryl, and $(CH_2)_n$ are unsubstituted or substituted with 1 to 5 substituents selected from $R^6$, and wherein two $R^6$ substituents together with the atom to which they are attached may form a 3-6 membered cycloalkyl or cycloalkenyl ring containing 0 to 3 heteroatoms independently selected from oxygen, sulfur, and $NR^7$, wherein the 3-6 membered cycloalkyl or cycloalkenyl ring is unsubstituted or substituted with 1 to 4 substituents selected from $R^6$. In a class of this embodiment, $R^6$ is not -phenyl.

In another embodiment of the present invention, $R^1$ and $R^2$ are each independently selected from the group consisting of: hydrogen, —$(CH_2)_n$halogen, —$(CH_2)_nOR^8$, —$(CH_2)_nCN$, —$(CH_2)_nCF_3$, —$(CH_2)_nCCl_3$, —$C_{1-8}$alkyl, —$(CH_2)_nC_{2-8}$alkenyl, —$(CH_2)_nC_{3-12}$cycloalkyl, —$(C_2)_nC_{3-12}$cycloalkenyl, —$(CH_2)_nC_{2-12}$heterocycloalkyl, —$(CH_2)_n$aryl, —$(CH_2)_n$heteroaryl, —$(CH_2)_nC(O)C_{1-6}$alkyl, and —$(CH_2)_nCO_2C_{1-6}$alkyl, provided that $R^1$ and $R^2$ are not both hydrogen, wherein alkyl, alkenyl, cycloalkyl, cycloalkenyl, heterocycloalkyl, aryl, heteroaryl, and $(CH_2)_n$ are unsubstituted or substituted with 1 to 5 substituents selected from $R^6$, and wherein two $R^6$ substituents together with the atom to which they are attached may form a 3-6 membered cycloalkyl or cycloalkenyl ring containing 0 to 3 heteroatoms independently selected from oxygen, sulfur, and $NR^7$, wherein the 3-6 membered cycloalkyl or cycloalkenyl ring is unsubstituted or substituted with 1 to 5 substituents selected from $R^6$. In a class of this embodiment, $R^6$ is not -phenyl. In another class of this embodiment, $R^1$ and $R^2$ are each independently selected from the group consisting of: —(CH$_2$)$_4$F, CH$_2$F, Br, Cl, I, —(CH$_2$)$_{0-4}$OH, —(CH$_2$)$_2$C(CH$_3$)$_2$OH, —(CH$_2$)$_2$CN, —CH$_2$C(CH$_2$CH$_3$)$_2$CN, —(CH$_2$)$_2$CF$_3$, —(CH$_2$)$_{2-3}$CCl$_3$, —(CH$_2$)$_{0-4}$CH$_3$, —CH(CH$_3$)CH$_2$CH$_3$, —CH$_2$CH(CH$_3$)CH$_2$CH$_3$, —CH$_2$C(CH$_3$)$_2$CH$_2$CH$_3$, —CH$_2$C(CH$_3$)(CH$_2$CH$_3$)CH$_2$CH$_3$, —(CH$_2$)$_{1-2}$CH(CH$_3$)$_2$, —(CH$_2$)$_{1-2}$CH(CH$_2$CH$_3$)$_2$, —(CH$_2$)$_{1-2}$C(CH$_3$)$_2$CH$_2$CH$_3$, —CH$_2$C(CH$_2$F)$_2$CH$_2$CH$_3$, —CH=C(CH$_3$)$_2$, —CH=CH$_2$, —CH$_2$C(CH$_3$)$_2$CH=CH$_2$, —CH$_2$C(CH$_3$)$_2$CH=CHCH$_3$, —CH$_2$C(CH$_2$CH$_3$)$_2$CH=CH$_2$, —(CH$_2$)$_3$OCH$_2$Phenyl, —(CH$_2$)$_{0-2}$cyclopropyl, —(CH$_2$)$_{0-2}$cyclobutyl, —(CH$_2$)$_{0-2}$cyclopentyl, —(CH$_2$)$_{0-2}$cyclohexyl, —(CH$_2$)$_{0-2}$cycloheptyl, —(CH$_2$)$_{0-2}$cyclooctyl, —(CH$_2$)$_{0-2}$adamantane, —(CH$_2$)$_{0-1}$cyclopentene, —(CH$_2$)$_{0-1}$cyclohexene, —CH$_2$tetrahydrofuran, —CH$_2$tetrahydropyran, —(CH$_2$)$_{1-2}$phenyl, —CH$_2$naphthalene, benzocyclobutene, —CH$_2$benzodioxole, —(CH$_2$)$_{0-1}$pyridine, —(CH$_2$)$_3$thiophene, —C(CH$_3$)$_2$CO$_2$CH$_3$, —CH$_2$C(CH$_3$)$^2$C(O)CH$_2$CH$_3$, —C(O)C(CH$_3$)$_3$, —CH$_2$C(CH$_3$)$_2$CH$_2$CO$_2$CH$_3$, and —CH$_2$cyclopentyl, provided that R$^1$ and R$^2$ are not both hydrogen, wherein alkyl, alkenyl, alkynyl, cycloalkyl, heterocycloalkyl, aryl, heteroaryl, and (CH$_2$)$_n$ are unsubstituted or substituted with 1 to 5 substituents selected from R$^6$, and wherein two R$^6$ substituents together with the atom to which they are attached may form a 3-6 membered cycloalkyl or cycloalkenyl ring containing 0 to 3 heteroatoms independently selected from oxygen, sulfur, and NR$^7$, wherein the 3-6 membered cycloalkyl or cycloalkenyl ring is unsubstituted or substituted with 1 to 5 substituents selected from R$^6$. In a subclass of this class, R$^6$ is not -phenyl.

In another embodiment of the present invention, R$^1$ is selected from the group consisting of hydrogen, —(CH$_2$)$_n$halogen, —(CH$_2$)$_n$OR$^8$, —(CH$_2$)$_n$CN, —(CH$_2$)$_n$CF$_3$, —(CH$_2$)$_n$CHF$_2$, —(CH$_2$)$_n$CH$_2$F, —(CH$_2$)$_n$CCl$_3$, —C$_{1-8}$alkyl, —(CH$_2$)$_n$C$_{2-8}$alkene, —(CH$_2$)$_n$C$_{3-10}$cycloalkyl, —(CH$_2$)$_n$C$_{3-10}$cycloalkenyl, —(CH$_2$)$_n$C$_{2-12}$heterocycloalkyl, —(CH$_2$)$_n$C$_2$)$_n$C$_{2-12}$heterocycloalkenyl, —(CH$_2$)$_n$SC$_{1-8}$alkyl, —(CH$_2$)$_n$SC$_{3-8}$cycloalkyl, —(CH$_2$)$_n$aryl, —(CH$_2$)$_n$heteroaryl, —(CH$_2$)$_n$CO$_2$R$^7$, —(CH$_2$)$_n$COC$_{1-8}$alkyl, provided that R$^1$ and R$^2$ are not both hydrogen, wherein alkyl, alkene, alkyne, cycloalkyl, cycloalkenyl, heterocycloalkyl, heterocycloalkenyl, aryl, heteroaryl, and (CH$_2$)$_n$ are unsubstituted or substituted with 1 to 5 substituents selected from R$^6$, and wherein two R$^6$ substituents together with the atom to which they are attached may form a 3-6 membered cycloalkyl or cycloalkenyl ring containing 0 to 3 heteroatoms independently selected from oxygen, sulfur, and NR$^7$, and wherein the 3-6 membered cycloalkyl or cycloalkenyl ring is unsubstituted or substituted with 1 to 4 substituents selected from R$^6$. In a class of this embodiment, R$^6$ is not -phenyl. In another class of this embodiment, R$^2$ is selected from the group consisting of: hydrogen, —(CH$_2$)$_n$ halogen, and —C$_{1-8}$alkyl. In a subclass of this class, R$^2$ is selected from the group consisting of hydrogen, I, and —CH$_3$. In a subclass of this class, R$^6$ is not -phenyl.

In another embodiment of the present invention, R$^1$ is selected from the group consisting of —(CH$_2$)$_n$halogen, —(CH$_2$)$_n$OR$^8$, —(CH$_2$)$_n$CN, —(CH$_2$)$_n$CF$_3$, —(CH$_2$)$_n$CCl$_3$, —C$_{1-8}$alkyl, —C$_{1-8}$alkoxy, —(CH$_2$)$_n$C$_{2-8}$alkene, —(CH$_2$)$_n$C$_{3-10}$cycloalkyl, —(CH$_2$)$_n$C$_{3-10}$cycloalkenyl, —(CH$_2$)$_n$heterocycloalkyl, —(CH$_2$)$_n$aryl, —(CH$_2$)$_n$heteroaryl, —(CH$_2$)$_n$CO$_2$R$^7$, and —(CH$_2$)$_n$COC$_{1-8}$alkyl, provided that R$^1$ and R$^2$ are not both hydrogen, wherein alkyl, alkene, alkoxy, cycloalkyl, cycloalkenyl, heterocycloalkyl, aryl, heteroaryl, and (CH$_2$)$_n$ are unsubstituted or substituted with 1 to 5 substituents selected from R$^6$.

In another embodiment of the present invention, R$^1$ is selected from the group consisting of: —(CH$_2$)$_n$halogen, —(CH$_2$)$_n$OR$^8$, —(CH$_2$)$_n$CN, —(CH$_2$)$_n$CF$_3$, —(CH$_2$)$_n$CCl$_3$, —C$_{1-8}$alkyl, —C$_{1-8}$alkoxy, —(CH$_2$)$_n$C$_{2-8}$alkene, —(CH$_2$)$_n$C$_{3-10}$cycloalkyl, —(CH$_2$)$_n$C$_{3-10}$cycloalkenyl, —(CH$_2$)$_n$heterocycloalkyl, —(CH$_2$)$_n$aryl, —(CH$_2$)$_n$heteroaryl, —(CH$_2$)$_n$CO$_2$R$^7$, and —(CH$_2$)$_n$COC$_{1-8}$alkyl, provided that R$^1$ and R$^2$ are not both hydrogen, wherein alkyl, alkene, alkoxy, cycloalkyl, cycloalkenyl, heterocycloalkyl, aryl, heteroaryl, and (CH$_2$)$_n$ are unsubstituted or substituted with 1 to 5 substituents selected from R$^6$; and R$^2$ is selected from the group consisting of: hydrogen, —(CH$_2$)$_n$halogen, and —C$_{1-8}$alkyl, wherein alkyl and (CH$_2$)$_n$ are unsubstituted or substituted with 1 to 5 substituents selected from R$^6$. In a subclass of this class, R$^6$ is not -phenyl.

In another embodiment of the present invention, R$^1$ is independently selected from the group consisting of —(CH$_2$)$_4$F, CH$_2$F, —(CH$_2$)$_{0-4}$OH, —(CH$_2$)$_2$C(CH$_3$)$_2$OH, —(CH$_2$)$_2$CN, —(CH$_2$)$_2$CF$_3$, —(CH$_2$)$_{2-3}$CCl$_3$, —(CH$_2$)$_{0-4}$CH$_3$, —CH(CH$_3$)CH$_2$CH$_3$, —CH$_2$CH(CH$_3$)CH$_2$CH$_3$, —CH$_2$C(CH$_3$)$_2$CH$_2$CH$_3$, —CH$_2$C(CH$_3$)(CH$_2$CH$_3$)CH$_2$CH$_3$, —(CH$_2$)$_{1-2}$CH(CH$_3$)$_2$, —(CH$_2$)$_{1-2}$CH(CH$_2$CH$_3$)$_2$, —(CH$_2$)$_{1-2}$C(CH$_3$)$_3$, —CH(CH$_3$)$_3$, —CH=C(CH$_3$)$_2$, —CH=CH$_2$, —CH$_2$C(CH$_3$)$_2$CH$_2$CH=CH$_2$, —CH$_2$C(CH$_3$)$_2$CH$_2$CH=CHCH$_3$, —(CH$_2$)$_3$OCH$_2$phenyl, —(CH$_2$)$_{0-2}$cyclopropyl, —(CH$_2$)$_{0-2}$cyclobutyl, —(CH$_2$)$_{0-2}$cyclopentyl, —(CH$_2$)$_{0-2}$cyclohexyl, —(CH$_2$)$_{0-2}$cycloheptyl, —(CH$_2$)$_{0-2}$cyclooctyl, —(CH$_2$)$_{0-2}$adamantane, —(CH$_2$)$_{0-1}$cyclopentene, —(CH$_2$)$_{0-1}$cyclohexene, —CH$_2$tetrahydrofuran, —CH$_2$tetrahydropyran, —(CH$_2$)$_{1-2}$phenyl, —CH$_2$naphthalene, benzocyclobutene, —CH$_2$benzodioxole, —(CH$_2$)$_{0-1}$pyridine, —(CH$_2$)$_3$thiophene, —CH$_2$C(CH$_3$)$_2$C(O)CH$_2$CH$_3$, —C(O)C(CH$_3$)$_3$, —C(CH$_3$)$_2$CO$_2$CH$_3$, and —CH$_2$C(CH$_3$)$_2$CH$_2$CO$_2$CH$_3$, provided that R$^1$ and R$^2$ are not both hydrogen, wherein R$^1$ is unsubstituted or substituted with 1 to 5 substituents selected from R$^6$, and wherein two R$^6$ substituents together with the atom to which they are attached may form a 3-6 membered cycloalkyl or cycloalkenyl ring containing 0 to 3 heteroatoms independently selected from oxygen, sulfur, and NR$^7$, wherein the 3-6 membered cycloalkyl or cycloalkenyl ring is unsubstituted or substituted with 1 to 5 substituents selected from R$^6$. In a subclass of this class, R$^6$ is not -phenyl.

In another embodiment of the present invention, R$^1$ is selected from the group consisting of: —(CH$_2$)$_4$OH, —(CH$_2$)$_3$OH, —CH$_2$C(CH$_3$)$_2$C(CH$_3$)$_2$OH, —CH$_2$C(CH$_3$)$_2$CH$_2$OH, —(CH$_2$)$_2$CF$_3$, —(CH$_2$)$_2$CCl$_3$, —(CH$_2$)$_{0-4}$CH$_3$, —(CH$_2$)$_{0-1}$C(CH$_3$)$_3$, —CH$_2$C(CH$_3$)$_2$CH$_2$CH$_3$, —(CH$_2$)$_2$OCH$_3$, —(CH$_2$)$_{1-2}$cyclopentene, —(CH$_2$)$_{1-2}$cyclohexene, adamantane, —(CH$_2$)$_{0-2}$cyclopropane, —(CH$_2$)$_{0-2}$cyclobutane, —(CH$_2$)$_{0-2}$cyclopentane, —(CH$_2$)$_{0-2}$cyclohexane, —(CH$_2$)$_{0-2}$cycloheptane, —(CH$_2$)$_{0-2}$cyclooctane, —CH$_2$-tetrahydropyran, —CH$_2$-tetrahydrofuran, —(CH$_2$)$_{1-2}$-phenyl, —CH$_2$-naphthalene, benzocyclobutene, —(CH$_2$)$_{1-3}$thienyl, —CH$_2$-benzodioxole, —(CH$_2$)$_{2-3}$CO$_2$CH$_3$, and —and (CH$_2$)$_{2-3}$COCH$_2$CH$_3$, wherein alkyl, alkene, alkyne, alkoxy, cycloalkyl, heterocycloalkyl, aryl, heteroaryl, and (CH$_2$)$_n$ are unsubstituted or substituted with 1 to 5 substituents selected from R$^6$; and R$^2$ is selected from the group consisting of: hydrogen, I, and —CH$_3$, wherein —CH$_3$ is unsubstituted or substituted with 1 to 5 substituents selected from R$^6$. In a subclass of this class, R$^6$ is not -phenyl.

In another embodiment, R$^1$ is selected from the group consisting of: —C$_{1-8}$alkyl, —(CH$_2$)$_n$C$_{3-12}$cycloalkyl, wherein alkyl, cycloalkyl, and (CH$_2$)$_n$ are unsubstituted or substituted with 1 to 5 substituents selected from R$^6$, and wherein two R$^6$ substituents together with the atom to which they are attached may form a 3-6 membered cycloalkyl or cycloalkenyl ring containing 0 to 3 heteroatoms independently selected from oxygen, sulfur, and $NR^7$, wherein the 3-6 membered cycloalkyl or cycloalkenyl ring is unsubstituted or substituted with 1 to 4 substituents selected from $R^6$. In another embodiment, $R^1$ is selected from the group consisting of —$C_{1-8}$alkyl, —$(CH_2)_nC_{3-12}$cycloalkyl, wherein alkyl, cycloalkyl, and $(CH_2)_n$ are unsubstituted or substituted with 1 to 4 substituents selected from $R^6$. In a class of this embodiment, $R^2$ is hydrogen. In a class of this embodiment, $R^1$ is selected from the group consisting of: —$CH_2C(CH_3)_3$, —$CH_2C(CH_3)_2CH_2CH_3$, —$CH_2C(CH_2F)_2CH_2CH_3$, —$CH_2C(CH_3)_2$cyclopropane, —$CH_2$cyclopentane, —$CH_2$cyclohexane. In a subclass of this class, $R^2$ is hydrogen.

In another embodiment of the present invention, $R^1$ is selected from the group consisting of: —$C_{1-8}$alkyl, and —$(CH_2)_nC_{3-12}$cycloalkyl, wherein alkyl, cycloalkyl, and $(CH_2)_n$ are unsubstituted or substituted with 1 to 5 substituents selected from $R^6$. In a class of this embodiment, $R^1$ is selected from the group consisting of: —$CH_2C(CH_3)_2CH_2CH_3$, and —$CH_2$cyclohexyl, wherein $R^1$ is unsubstituted or substituted with 1 to 5 substituents selected from $R^6$. In a subclass of this class, $R^1$ is selected from the group consisting of: —$CH_2C(CH_3)_2CH_2CH_3$, and —$CH_2$cyclohexyl. In another subclass of this class, $R^1$ is —$CH_2C(CH_3)_2CH_2CH_3$. In another subclass of this class, $R^1$ is —$CH_2$cyclohexyl. In another class of this embodiment, $R^2$ is hydrogen.

In another embodiment of the present invention, $R^2$ is selected from the group consisting of hydrogen, —$(CH_2)_n$halogen, —$(CH_2)_nOR^8$, —$(CH_2)_nCN$, —$(CH_2)_nCF_3$, —$(CH_2)_nCHF_2$, —$(CH_2)_nCH_2F$, —$(CH_2)_nCCl_3$, —$C_{1-8}$alkyl, —$(CH_2)_nC_{2-8}$alkene, —$(CH_2)_nC_{2-8}$alkyne, —$(CH_2)_nC_{3-10}$cycloalkyl, —$(CH_2)_nC_{3-10}$cycloalkenyl, —$(CH_2)_nC_{2-12}$heterocycloalkyl, —$(CH_2)_nSC_{1-8}$alkyl, —$(CH_2)_nSC_{3-8}$cycloalkyl, —$(CH_2)_n$aryl, —$(CH_2)_n$heteroaryl, —$(CH_2)_nCO_2R^7$, —$(CH_2)_nCOCl_{1-8}$alkyl, provided that $R^1$ and $R^2$ are not both hydrogen, wherein alkyl, alkene, alkyne, cycloalkyl, cycloalkenyl, heterocycloalkyl, aryl, heteroaryl, and $(CH_2)_n$ are unsubstituted or substituted with 1 to 5 substituents selected from $R^6$, and wherein two $R^6$ substituents together with the atom to which they are attached may form a 3-6 membered cycloalkyl or cycloalkenyl ring containing 0 to 3 heteroatoms independently selected from oxygen, sulfur, and $NR^7$, wherein the 3-6 membered cycloalkyl or cycloalkenyl ring is unsubstituted or substituted with 1 to 4 substituents selected from $R^6$. In a class of this embodiment, $R^6$ is not -phenyl. In another class of this embodiment, $R^2$ is selected from the group consisting of: hydrogen, —$(CH_2)_n$halogen, and —$C_{1-8}$alkyl. In a subclass of this class, $R^2$ is selected from the group consisting of: hydrogen, I, and —$CH_3$. In a subclass of this class, $R^6$ is not -phenyl.

In another embodiment, $R^2$ is independently selected from the group consisting of hydrogen, halogen, —$(CH_2)_nOH$, —$(CH_2)_nCN$, —$(CH_2)_nCF_3$, —$(CH_2)_nCHF_2$, —$(CH_2)_nCH_2F$, —$C_{1-8}$alkyl, —$(CH_2)_nC_{2-8}$alkenyl, —$(CH_2)_nC_{2-8}$alkynyl, —$(CH_2)_nC_{3-8}$cycloalkyl, —$(CH_2)_n$heterocycloalkyl, —$(CH_2)_n$phenyl, and —$(CH_2)_n$heteroaryl, provided that $R^1$ and $R^2$ are not both hydrogen, wherein alkyl, alkene, alkyne, cycloalkyl, heterocycloalkyl, phenyl, heteroaryl, and $(CH_2)_n$ are unsubstituted or substituted with 1 to 4 substituents selected from $R^6$.

In another embodiment of the present invention, $R^2$ is independently selected from the group consisting of: hydrogen, halogen, —$C_{1-8}$alkyl, and —$(CH_2)_nC_{3-8}$cycloalkyl, provided that $R^1$ and $R^2$ are not both hydrogen, wherein alkyl, cycloalkyl, and $(CH_2)_n$ are unsubstituted or substituted with 1 to 4 substituents selected from $R^6$. In a class of this embodiment, $R^2$ is independently selected from the group consisting of: hydrogen, Br, Cl, I, —$CH_3$, —$CH_2C(CH_3)_3$, and —$CH_2$cyclopentyl, provided that $R^1$ and $R^2$ are not both hydrogen, wherein alkyl, cycloalkyl, and $(CH_2)_n$ are unsubstituted or substituted with 1 to 4 substituents selected from $R^6$.

In another embodiment, $R^2$ is hydrogen.

In another embodiment of the present invention, $R^3$ is selected from the group consisting of: hydrogen, —$C_{1-6}$alkyl and —$COC_{1-6}$alkyl. In a class of this embodiment, $R^3$ is hydrogen. In another class of this embodiment, $R^3$ is —$C_{1-6}$alkyl. In a subclass of this class, $R^3$ is —$CH_3$ or —$CH_2CH_3$. In yet another class of this embodiment, $R^3$ is —$COC_{1-6}$alkyl.

In another embodiment of the present invention, $R^4$ is selected from the group consisting of: —$C_{1-6}$alkyl, —$(CH_2)_n$halogen, —$(CH_2)_nOR^8$, —$(CH_2)_nCN$, —$(CH_2)_nCF_3$, —$(CH_2)_nCO_2R^7$, —$(CH_2)_nN(R^8)_2$, —$(CH_2)_nNO_2$, —$(CH_2)_nNR^7COC_{1-6}$alkyl, —$(CH_2)_nNR^7CO_2C_{1-6}$alkyl, —$(CH_2)_nNR^7SO_2C_{1-6}$alkyl, and —$(CH_2)_nSO_{0-2}C_{1-6}$alkyl; wherein alkyl is substituted with 1 to 3 halogens. In a class of this embodiment, $R^4$ is selected from the group consisting of —$C_{1-6}$alkyl, —halogen, —$(CH_2)_nOR^8$, —CN, —$CF_3$, —$CO_2R^7$, —$N(R^8)_2$, —$NO_2$, —$NR^7COC_{1-6}$alkyl, —$NR^7CO_2C_{1-6}$alkyl, —$NR^7SO_2C_{1-6}$alkyl, and —$SO_{0-2}C_{1-6}$alkyl; wherein alkyl is substituted with 1 to 3 halogens.

In another embodiment of the present invention, $R^4$ is selected from the group consisting of: —$C_{1-6}$alkyl, —$(CH_2)_n$halogen, —$(CH_2)_nOR^8$, —$(CH_2)_nCN$, —$(CH_2)_nCO_2R^7$, —$(CH_2)_nN(R^8)_2$, —$(CH_2)_nNR^7COC_{1-6}$alkyl, —$(CH_2)_nNR^7CO_2C_{1-6}$alkyl, —$(CH_2)_nNR^7SO_2C_{1-7}$alkyl, and —$(CH_2)_nSO_{0-2}C_{1-6}$alkyl. In a class of this embodiment, $R^4$ is selected from the group consisting of: —$C_{1-6}$alkyl, -halogen, —$(CH_2)_nOR^8$, —CN, —$CO_2R^7$, —$N(R^8)_2$, —$NR^7CO_2C_{1-6}$alkyl, —$NR^7CO_2C_{1-6}$alkyl, —$NR^7SO_2C_{1-6}$alkyl, and —$SO_{0-2}C_{1-6}$alkyl.

In another embodiment of the present invention, $R^4$ is selected from the group consisting of: —$C_{1-6}$alkyl, halogen, —$OR^8$, —CN, —$CO_2H$, —$CO_2C_{1-6}$alkyl, —$N(R^8)_2$, —NHCOC$_{1-6}$alkyl, —NHCO$_2$C$_{1-6}$alkyl, —NHSO$_2$C$_{1-6}$alkyl, and —SO$_{0-2}$C$_{1-6}$alkyl. In another embodiment of the present invention, $R^4$ is selected from the group consisting of: —$C_{1-6}$alkyl, halogen, —$OR^8$, —CN, —$CO_2H$, and —$CO_2C_{1-6}$alkyl. In a class of this embodiment of the present invention, $R^4$ is selected from the group consisting of: —$CH_3$, F, —OH, —CN, and —$CO_2H$. In another embodiment of the present invention, $R^4$ is selected from the group consisting of: —$C_{1-6}$alkyl, halogen, —$OR^8$, and —CN. In a class of this embodiment, $R^4$ is selected from the group consisting of: —$CH_3$, F, —OH, and —CN. In another embodiment of the present invention, $R^4$ is selected from the group consisting of: —$C_{1-6}$alkyl, halogen, —$OR^8$, —CN, —$N(R^8)_2$, —NHCOC$_{1-6}$alkyl, —NHCO$_2$C$_{1-6}$alkyl, —NHSO$_2$C$_{1-6}$alkyl, and —SO$_{0-2}$C$_{1-6}$alkyl. In another embodiment of the present invention, $R^4$ is selected from the group consisting of —$C_{1-6}$alkyl, halogen, —$OR^8$, and —CN. In a class of this embodiment of the present invention, $R^4$ is selected from the group consisting of: —$CH_3$, F, —OH, and —CN. In another embodiment of the present invention, $R^4$ is selected from the group consisting of: —$C_{1-6}$alkyl, halogen, —$OR^8$, and —CN. In a class of this embodiment, $R^4$ is selected from the group consisting of: —$CH_3$, F, —OH, and —CN.

In another embodiment of the invention, $R^4$ is selected from the group consisting of: —$C_{1-6}$alkyl, —$C_{1-6}$alkoxy, halogen, —CN, —$CF_3$, —$CO_2H$, —$CO_2C_{1-6}$alkyl, —OH, —$N(R^8)_2$, —$NO_2$, —NHCOC$_{1-6}$alkyl, —NHCO$_2$C$_{1-6}$alkyl, and —SO$_{0-2}$C$_{1-6}$alkyl. In a class of this embodiment, $R^4$ is selected from the group consisting of: —CH$_3$, —OCH$_3$, Cl, F, —CN, —CF$_3$, —CO$_2$H, —CO$_2$CH$_3$, —OH, —NH$_2$, and —NO$_2$. In another embodiment of the invention, R$^4$ is selected from the group consisting of: —C$_{1-6}$alkyl, —C$_{1-6}$alkoxy, halogen, —OC$_{1-6}$alkyl, —CN, —CF$_3$, —OH, —N(R$^8$)$_2$, —NO$_2$, —NHCOC$_{1-6}$alkyl, —NHCO$_2$C$_{1-6}$alkyl, and —SO$_{0-2}$C$_{1-6}$alkyl. In a class of this embodiment, R$^4$ is selected from the group consisting of: —CH$_3$, —OCH$_3$, Cl, F, —CN, —CF$_3$, —OH, —NH$_2$, and —NO$_2$. In another embodiment of the invention, R$^4$ is selected from the group consisting of —C$_{1-6}$alkoxy, —OC$_{1-6}$alkyl, —CN, —OH, —N(R$^8$)$_2$, —NO$_2$, —NHCOC$_{1-6}$alkyl, —NHCO$_2$C$_{1-6}$alkyl, and —SO$_{0-2}$C$_{1-6}$alkyl. In a class of this embodiment, R$^4$ is selected from the group consisting of: —OCH$_3$, —CN, —OH, —NH$_2$, and —NO$_2$.

In another embodiment of the invention, R$^5$ is selected from the group consisting of: —(CH$_2$)$_n$halogen, —C$_{1-6}$alkyl, —C$_{2-6}$alkenyl, —(CH$_2$)$_n$C$_{3-8}$cycloalkyl, —(CH$_2$)$_n$heterocycloalkyl, oxo, —(CH$_2$)$_n$OR$^8$, —(CH$_2$)$_n$CN, —(CH$_2$)$_n$COR$^7$, —(CH$_2$)$_n$CO$_2$R$^8$, —(CH$_2$)$_n$CONR$^7$N(R$^7$)$_2$, —(CH$_2$)$_n$O(CH$_2$)$_n$CO$_2$R$^7$, —(CH$_2$)$_n$NO$_2$, —(CH$_2$)$_n$CON(R$^7$)$_2$, —(CH$_2$)$_n$N(R$^8$)$_2$, —(CH$_2$)$_n$NR$^7$(CH$_2$)$_n$CO$_2$R$^7$, —(CH$_2$)$_n$NR$^7$COC$_{1-6}$alkyl, —(CH$_2$)$_n$SO$_2$N(R$^7$)$_2$, —(CH$_2$)$_n$NR$^7$SO$_2$C$_{1-6}$alkyl, —(CH$_2$)$_n$SO$_{0-2}$R$^8$, —(CH$_2$)$_n$OP(O)$_2$OH, —CH=N—OH, —(CH$_2$)$_n$aryl, —(CH$_2$)$_n$heteroaryl, and —(CH$_2$)$_n$O(CH$_2$)$_n$heteroaryl, wherein alkyl, alkenyl, cycloalkyl, heterocycloalkyl, aryl, heteroaryl, and —(CH$_2$)$_n$ are unsubstituted or substituted with 1 to 3 halogens. In another embodiment of the invention, R$^5$ is selected from the group consisting of: —(CH$_2$)$_n$halogen, —C$_{1-6}$alkyl, —C$_{2-6}$alkenyl, —(CH$_2$)$_n$C$_{3-8}$cycloalkyl, —(CH$_2$)$_n$heterocycloalkyl, —(CH$_2$)$_n$OR$^8$, —(CH$_2$)$_n$CN, —(CH$_2$)$_n$COR$^7$, —(CH$_2$)$_n$CO$_2$R$^8$, —(CH$_2$)$_n$CONR$^7$N(R$^7$)$_2$, —(CH$_2$)$_n$O(CH$_2$)$_n$CO$_2$R$^7$, —(CH$_2$)$_n$NO$_2$, —(CH$_2$)$_n$CON(R$^7$)$_2$, —(CH$_2$)$_n$N(R$^8$)$_2$, —(CH$_2$)$_n$NR$^7$(CH$_2$)$_n$CO$_2$O, —(CH$_2$)$_n$NR$^7$COC$_{1-6}$alkyl, —(CH$_2$)$_n$SO$_2$N(R$^7$)$_2$, —(CH$_2$)$_n$NR$^7$SO$_2$C$_{1-6}$alkyl, —(CH$_2$)$_n$SO$_{0-2}$R$^8$, —(CH$_2$)$_n$OP(O)$_2$OH, —CH=N—OH, —(CH$_2$)$_n$aryl, —(CH$_2$)$_n$heteroaryl, and —(CH$_2$)$_n$O(CH$_2$)$_n$heteroaryl, wherein alkyl, alkenyl, cycloalkyl, heterocycloalkyl, aryl, heteroaryl, and —(CH$_2$)$_n$ are unsubstituted or substituted with 1 to 3 halogens.

In another embodiment of the present invention, R$^5$ is selected from the group consisting of: —(CH$_2$)$_n$halogen, —C$_{2-6}$alkenyl, —(CH$_2$)$_n$C$_{3-8}$cycloalkyl, —(CH$_2$)$_n$heterocycloalkyl, oxo, —(CH$_2$)$_n$OR$^8$, —(CH$_2$)$_n$CN, —(CH$_2$)$_n$COR$^7$, —(CH$_2$)$_n$CO$_2$R$^8$, —(CH$_2$)$_n$O(CH$_2$)$_n$CO$_2$R$^7$, —(CH$_2$)$_n$NO$_2$, —(CH$_2$)$_n$CON(R$^7$)$_2$, —(CH$_2$)$_n$N(R$^8$)$_2$, —(CH$_2$)$_n$NR$^7$(CH$_2$)$_n$CO$_2$R$^7$, —(CH$_2$)$_n$NR$^7$COC$_{1-6}$alkyl, —(CH$_2$)$_n$SO$_2$N(R$^7$)$_2$, —(CH$_2$)$_n$NR$^7$SO$_2$C$_{1-6}$alkyl, —(CH$_2$)$_n$SO$_{0-2}$R$^8$, —(CH$_2$)$_n$OP(O)$_2$OH, —CH=N—OH, —(CH$_2$)$_n$aryl, —(CH$_2$)$_n$heteroaryl, and —(CH$_2$)$_n$O(CH$_2$)$_n$heteroaryl, wherein alkyl, alkenyl, cycloalkyl, heterocycloalkyl, aryl, heteroaryl, and —(CH$_2$)$_n$ are unsubstituted or substituted with 1 to 3 halogens. In another embodiment of the present invention, R$^5$ is selected from the group consisting of: —(CH$_2$)$_n$halogen, —C$_{2-6}$alkenyl, —(CH$_2$)$_n$C$_{3-8}$cycloalkyl, —(CH$_2$)$_n$heterocycloalkyl, —(CH$_2$)$_n$OR$^8$, —(CH$_2$)$_n$CN, —(CH$_2$)$_n$COR$^7$, —(CH$_2$)$_n$CO$_2$R$^8$, —(CH$_2$)$_n$O(CH$_2$)$_n$CO$_2$R$^7$, —(CH$_2$)$_n$NO$_2$, —(CH$_2$)$_n$CON(R$^7$)$_2$, —(CH$_2$)$_n$N(R$^8$)$_2$, —NR$^7$(CH$_2$)$_n$CO$_2$R$^7$, —NR7COC$_{1-6}$alkyl, —(CH$_2$)$_n$SO$_2$N(R$^7$)$_2$, —NR$^7$SO$_2$C$_{1-6}$alkyl, —(CH$_2$)$_n$SO$_{0-2}$R$^8$, —CH=N—OH, —(CH$_2$)$_n$aryl, —(CH$_2$)$_n$heteroaryl, and —(CH$_2$)$_n$O(CH$_2$)$_n$heteroaryl, wherein alkyl, alkenyl, cycloalkyl, heterocycloalkyl, aryl, heteroaryl, and —(CH$_2$)$_n$ are unsubstituted or substituted with 1 to 3 halogens. In another embodiment of the invention, R$^5$ is selected from the group consisting of —(CH$_2$)$_n$halogen, —C$_{2-6}$alkenyl, —C$_{3-8}$cycloalkyl, —(CH$_2$)$_n$heterocycloalkyl, —(CH$_2$)$_n$OR$^8$, —(CH$_2$)$_n$CN, —(CH$_2$)$_n$COR$^7$, —(CH$_2$)$_n$CO$_2$R$^8$, —(CH$_2$)$_n$O(CH$_2$)$_n$CO$_2$R$^7$, —(CH$_2$)$_n$NO$_2$, —(CH$_2$)$_n$CON(R$^7$)$_2$, —(CH$_2$)$_n$N(R$^8$)$_2$, —NR$^7$(CH$_2$)$_n$CO$_2$R$^7$, —NR$^7$COC$_{1-6}$alkyl, —(C$_2$)$_n$SO$_2$N(R$^7$)$_2$, —NR$^7$SO$_2$C$_{1-6}$alkyl, —(CH$_2$)$_n$SO$_{0-2}$R$^8$, —CH=N—OH, —(CH$_2$)$_n$aryl, —(CH$_2$)$_n$heteroaryl, and —(CH$_2$)$_n$O(CH$_2$)$_n$heteroaryl, wherein alkyl, alkenyl, cycloalkyl, heterocycloalkyl, aryl, heteroaryl, and —(CH$_2$)$_n$ are unsubstituted or substituted with 1 to 3 halogens. In another embodiment of the present invention, R$^5$ is selected from the group consisting of —(CH$_2$)$_n$halogen, —C$_{2-6}$alkenyl, —C$_{3-8}$cycloalkyl, oxo, —(CH$_2$)$_n$OR$^8$, —CN, —COR$^7$, —(CH$_2$)$_n$CO$_2$R$^8$, —(CH$_2$)$_n$O(CH$_2$)$_n$CO$_2$R$^7$, —NO$_2$, —CON(R$^7$)$_2$, —CO$_2$N(R$^7$)$_2$, —(CH$_2$)$_n$N(R$^8$)$_2$, —NH(CH$_2$)$_n$CO$_2$R$^7$, —NHCOC$_{1-6}$alkyl, —SOC$_{1-6}$alkyl, —SO$_2$R$^7$, —SO$_2$N(R$^7$)$_2$, —CH=N—OH, —(CH$_2$)$_n$heteroaryl, —(CH$_2$)$_n$O(CH$_2$)$_n$heteroaryl, wherein alkyl, alkenyl, heteroaryl, and —(CH$_2$)$_n$ are unsubstituted or substituted with 1 to 3 halogens. In another embodiment of the present invention, R$^5$ is selected from the group consisting of —(CH$_2$)$_n$halogen, —C$_{1-6}$alkyl, —C$_{2-6}$alkenyl, —C$_{3-8}$cycloalkyl, —(CH$_2$)$_n$OR$^8$, —CN, —COR$^7$, —(CH$_2$)$_n$CO$_2$R$^8$, —(CH$_2$)$_n$O(CH$_2$)$_n$CO$_2$R$^7$, —NO$_2$, —CON(R$^7$)$_2$, —CO$_2$N(R$^7$)$_2$, —(CH$_2$)$_n$N(R$^8$)$_2$, —NH(CH$_2$)$_n$CO$_2$R$^7$, —NHCOC$_{1-6}$alkyl, —SOC$_{1-6}$alkyl, —SO$_2$R$^7$, —SO$_2$N(R$^7$)$_2$, —CH=N—OH, —(CH$_2$)$_n$heteroaryl, —(CH$_2$)$_n$O(CH$_2$)$_n$ heteroaryl, wherein alkyl, alkenyl, heteroaryl, and —(CH$_2$), are unsubstituted or substituted with 1 to 3 halogens.

In another embodiment of the present invention, R$^5$ is selected from the group consisting of: —(CH$_2$)$_n$halogen, —C$_{2-6}$alkenyl, oxo, —(CH$_2$)$_n$OR$^8$, —CN, —COR$^7$, —(CH$_2$)$_n$CO$_2$R$^8$, —(CH$_2$)$_n$O(CH$_2$)$_n$CO$_2$R$^7$, —NO$_2$, —(CH$_2$)$_n$N(R$^8$)$_2$, —NH(CH$_2$)$_n$CO$_2$R$^7$, —NHCOC$_{1-6}$alkyl, —SO$_2$N(R$^7$)$_2$, —CH=N—OH, —(CH$_2$)$_n$heteroaryl, —(CH$_2$)$_n$O(CH$_2$)$_n$heteroaryl, wherein alkyl, alkenyl, heteroaryl, and —(CH$_2$)$_n$ are unsubstituted or substituted with 1 to 3 halogens. In a class of this embodiment, R$^5$ is selected from the group consisting of: F, Cl, Br, —CH$_3$, —CH$_2$CH$_3$, —CHF$_2$, —CH$_2$F, —CF$_3$, —CH=CH$_2$, oxo, —OCH$_3$, —CH$_2$OH, —CH$_2$OCH$_3$, —OH, —CN, —C(O)H, —(CH$_2$)$_{0-1}$CO$_2$H, —CH$_2$OCH$_2$CO$_2$H, —CH$_2$OCH$_2$CO$_2$CH$_3$, —OCH$_2$CO$_2$H, —NO$_2$, —NH$_2$, NHCH$_3$, —(CH$_2$)$_n$N(CH$_3$)$_2$, —NHCH$_2$CO$_2$H, —NHCOCH$_3$, —SO$_2$NH$_2$, —CH=N—OH, tetrazole, —OCH$_2$tetrazole, and —OCH$_2$triazole, wherein alkyl, alkenyl, heteroaryl, and —(CH$_2$)$_n$ are unsubstituted or substituted with 1 to 3 halogens.

In another embodiment of the present invention, R$^5$ is selected from the group consisting of: —(CH$_2$)$_n$halogen, —C$_{1-6}$alkyl, —C$_{2-6}$alkenyl, —C$_{3-8}$cycloalkyl, —(CH$_2$)$_n$OR$^8$, —CN, —COR$^7$, —(CH$_2$)$_n$CO$_2$R$^8$, —(CH$_2$)$_n$O(CH$_2$)$_n$CO$_2$R$^7$, —NO$_2$, —CON(R$^7$)$_2$, —CO$_2$N(R$^7$)$_2$, —(CH$_2$)$_n$N(R$^8$)$_2$, —NH(CH$_2$)$_n$CO$_2$R$^7$, —NHCOC$_{1-6}$alkyl, —SOC$_{1-6}$alkyl, —SO$_2$R$^7$, —SO$_2$N(R$^7$)$_2$, —CH=N—OH, —(CH$_2$)$_n$ heteroaryl, —$(CH_2)_nO(CH_2)_n$heteroaryl, wherein alkyl, alkenyl, heteroaryl, and —$(CH_2)_n$ are unsubstituted or substituted with 1 to 3 halogens. In another embodiment of the present invention, $R^5$ is selected from the group consisting of —$(CH_2)_n$halogen, —$C_{1-6}$alkyl, —$C_{2-6}$alkenyl, —$(CH_2)_n$ $OR^8$, —CN, —$COR^7$, —$(CH_2)_nCO_2R^8$, —$(CH_2)_nO(CH_2)_n$ $CO_2R_7$, —$NO_2$, —$(CH_2)_nN(R^8)_2$, —$NH(CH_2)_nCO_2R^7$, —$NHCOC_{1-6}$alkyl, —$SO_2N(R^7)_2$, —CH=N—OH, —$(CH_2)_n$heteroaryl, —$(CH_2)_nO(CH_2)_n$heteroaryl, wherein alkyl, alkenyl, heteroaryl, and —$(CH_2)_n$ are unsubstituted or substituted with 1 to 3 halogens. In a class of this embodiment, $R^5$ is selected from the group consisting of: F, Cl, Br, —$CH_3$, —$CH_2CH_3$, —$CHF_2$, —$CH_2F$, —$CF_3$, —CH=$CH_2$, —$OCH_3$, —$CH_2OH$, —$CH_2OCH_3$, —OH, —CN, —C(O)H, —$(CH_2)_{0-1}CO_2H$, —$CH_2OCH_2CO_2H$, —$CH_2OCH_2CO_2CH_3$, —$OCH_2CO_2H$, —$NO_2$, —$NH_2$, $NHCH_3$, —$(CH_2)_nN(CH_3)_2$, —$NHCH_2CO_2H$, —$NH$-$COCH_3$, —$SO_2NH_2$, —CH=N—OH, tetrazole, —$OCH_2$tetrazole, and —$OCH_2$triazole, wherein alkyl, alkenyl, heteroaryl, and —$(CH_2)_n$ are unsubstituted or substituted with 1 to 3 halogens.

In another embodiment of the present invention, $R^5$ is selected from the group consisting of: halogen, —$C_{1-6}$alkyl, —$(CH_2)_nO(CH_2)_n$heteroaryl, and —$(CH_2)_nCO_2R^8$. In a class of this embodiment, $R^5$ is selected from the group consisting of: halogen, —$C_{1-6}$alkyl, —$O(CH_2)_n$heteroaryl, and —$(CH_2)_nCO_2H$. In another class of this embodiment, $R^5$ is selected from the group consisting of: F, methyl, —$OCH_2$tetrazole and —$CO_2H$.

In another embodiment of the present invention, $R^5$ is selected from the group consisting of halogen and —$(CH_2)_n$ $CO_2R^8$. In a class of this embodiment, $R^5$ is selected from the group consisting of: halogen and —$(CH_2)_nCO_2H$. In another class of this embodiment, $R^5$ is selected from the group consisting of: F and —$CO_2H$.

In another embodiment of the present invention, $R^6$ is independently selected from the group consisting of: halogen, —OH, oxo, —CN, —$CCl_3$, —$CF_3$, —$CHF_2$, —$CH_2F$, —$SO_2C_{1-6}$alkyl, —$COC_{1-8}$alkl, —$CO_2C_{1-8}$alkyl, —$CO_2H$, —$C_{1-8}$alkyl, and —$C_{1-8}$alkoxy, wherein alkyl, alkoxy, and —$(CH_2)$n are unsubstituted or substituted with 1 to 4 substituents selected from —$C_{1-6}$alkyl and halogen, and wherein the —$C_{1-6}$alkyl substituent is unsubstituted or substituted with 1 to 3 halogens.

In another embodiment of the present invention, $R^6$ is independently selected from the group consisting of: halogen, —OH, oxo, —CN, —$CCl_3$, —$CF_3$, —$SO_2C_{1-6}$alkyl, —$CHF_2$, —$CH_2F$, —$C_{1-6}$alkyl, and —$OC_{1-6}$alkyl, wherein alkyl and —$(CH_2)$n are unsubstituted or substituted with 1 to 4 substituents selected from —$C_{1-6}$alkyl and halogen, and wherein the —$C_{1-6}$alkyl substituent is unsubstituted or substituted with 1 to 3 halogens.

In another embodiment of the invention, $R^6$ is selected from the group consisting of: oxo, —OH, halogen, —CN, —$CF_3$, —$CHF_2$, —$CH_2F$, —$C_{1-8}$alkyl, —$C_{1-8}$alkoxy, —$COC_{1-8}$alkyl, —$CO_2C_{1-8}$alkyl, and —$CO_2H$, wherein alkyl, alkoxy, and —$(CH_2)$n are unsubstituted or substituted with 1 to 4 substituents selected from —$C_{1-6}$alkyl and halogen. In another embodiment of the invention, $R^6$ is selected from the group consisting of: —OH, and —$C_{1-8}$alkoxy, wherein each alkoxy carbon is unsubstituted or substituted with 1 to 3 halogen substituents. In a class of this embodiment, $R^6$ is selected from the group consisting of: —OH, —$OCH_3$, and —$CH_2OCH_3$, wherein $R^6$ is unsubstituted or substituted with 1 to 3 halogen substituents.

In another embodiment of the present invention, $R^6$ is independently selected from the group consisting of: halogen, —OH, —CN, —$CCl_3$, —$CF_3$, —$CH_2F$, —$C_{1-6}$alkyl, and —$OC_{1-6}$alkyl, wherein alkyl, and —$(CH_2)$n are unsubstituted or substituted with 1 to 4 substituents selected from —$C_{1-6}$alkyl and halogen, and wherein the —$C_{1-6}$alkyl substituent is unsubstituted or substituted with 1 to 3 halogens.

In another embodiment of the present invention, $R^6$ is independently selected from the group consisting of: Cl, F, —OH, —CN, —$CCl_3$, —$CF_3$, —$CH_2F$, —$(CH_2)_{0-3}CH_3$, and —$OCH_3$, wherein alkyl, and —$(CH_2)$n are unsubstituted or substituted with 1 to 4 substituents selected from —$C_{1-6}$alkyl and halogen, and wherein the —$C_{1-6}$alkyl substituent is unsubstituted or substituted with 1-3 halogens.

In another embodiment of the present invention, $R^6$ is independently selected from the group consisting of: —$C_{1-6}$alkyl, wherein alkyl is unsubstituted or substituted with 1 to 4 substituents selected from —$C_{1-6}$alkyl and halogen, and wherein the —$C_{1-6}$alkyl substituent is unsubstituted or substituted with 1 to 3 halogens.

In another embodiment of the present invention, $R^7$ is selected from the group consisting of: hydrogen, and —$C_{1-6}$alkyl, wherein alkyl is unsubstituted or substituted with 1 to 3 substituents selected from halogen and —OH. In one class of this embodiment, $R^7$ is hydrogen. In another class of this embodiment, $R^7$ is —$C_{1-6}$alkyl, wherein alkyl is unsubstituted or substituted with 1 to 3 substituents selected from halogen and —OH.

In another embodiment of the present invention, $R^8$ is selected from the group consisting of: hydrogen, —$C_{1-6}$alkyl, —$C_{3-8}$cycloalkyl, —$C_{2-7}$heterocycloalkyl, —$(CH_2)_m$phenyl, and —$(CH_2)_n$heteroaryl, wherein alkyl, cycloalkyl, and heterocycloalkyl is unsubstituted or substituted with 1 to 3 halogens or —OH, and wherein phenyl and heteroaryl are unsubstituted or substituted with 1 to 3 halogens.

In another embodiment of the invention, $R^8$ is selected from the group consisting of hydrogen, —$C_{1-6}$ alkyl, —$C_{3-8}$ cycloalkyl, —$C_{2-7}$heterocycloalkyl, —$(CH_2)_m$phenyl, and $(CH_2)_n$heteroaryl, wherein each alkyl, cycloalkyl and heterocycloalkyl carbon is unsubstituted or substituted with 1 to 3 halogens or —OH, and each phenyl and heteroaryl carbon is unsubstituted or substituted with 1 to 3 halogens.

In another embodiment of the present invention, $R^8$ is selected from the group consisting of: hydrogen, —$C_{1-6}$alkyl, —$C_{3-8}$cycloalkyl, —$(CH_2)_m$phenyl, and —$(CH_2)_m$heteroaryl, wherein each alkyl carbon is unsubstituted or substituted with 1 to 3 halogens or —OH and each phenyl carbon is unsubstituted or substituted with 1 to 3 halogens.

In another embodiment of the invention, $R^8$ is selected from the group consisting of: hydrogen, —$C_{1-6}$ alkyl, —$C_{3-8}$ cycloalkyl, —$(CH_2)_n$heteroaryl, wherein each alkyl, cycloalkyl and heterocycloalkyl carbon is unsubstituted or substituted with 1 to 3 halogens or —OH, and each phenyl and heteroaryl carbon is unsubstituted or substituted with 1 to 3 halogens. In a class of this embodiment, $R^8$ is selected from the group consisting of hydrogen, —$CH_3$, cyclohexyl, thiazole, triazole, pyrazole, and tetrazole, wherein $R^8$ is unsubstituted or substituted with 1 to 3 halogens or —OH.

In another class of the embodiments, n is 0, 1, 2, 3, 4 or 5. In a subclass of this class, n is 0, 1, 2, 3 or 4. In another subclass of this class, n is 0. In another subclass of this class, n is 1. In another subclass of this class, n is 2. In another subclass of this class, n is 3. In another class of the embodiments, m is 1, 2, 3 or 4. In a subclass of this class, m is 1, 2 or 3. In another subclass of this class, m is 1. In another subclass of this class, m is 2. In another subclass of this class, m is 3. In another class of the embodiments, p is 0, 1, 2, 3 or 4. In a subclass of this class, p is 0, 1, 2 or 3. In a subclass of this class, p is 0. In another subclass of this class, p is 1. In another subclass of this class, p is 2. In another subclass of this class, p is 3. In another class of the embodiments, q is 0, 1, 2, 3 or 4. In a subclass of this class, q is 0, 1, 2 or 3. In a subclass of this class, q is 0. In another subclass of this class, q is 1. In another subclass of this class, q is 2. In another subclass of this class, q is 3.

Illustrative but nonlimiting examples of compounds of the present invention that are useful as bombesin receptor subtype-3 agonists are the following:

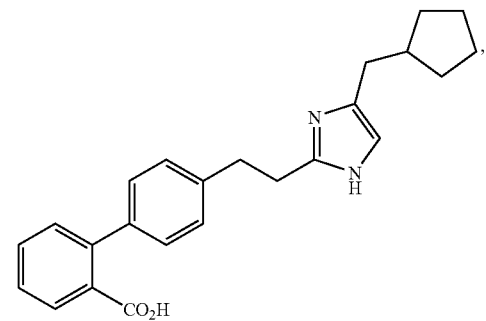

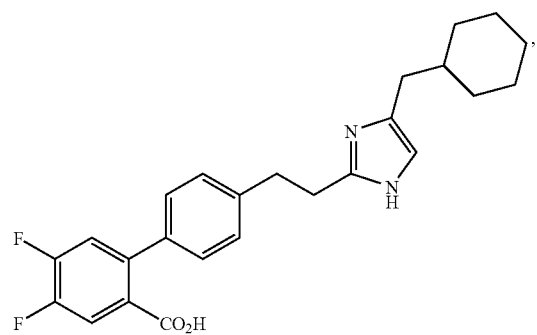

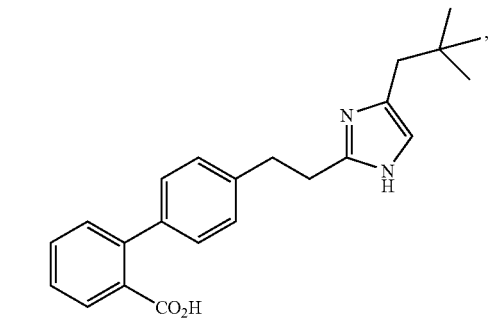

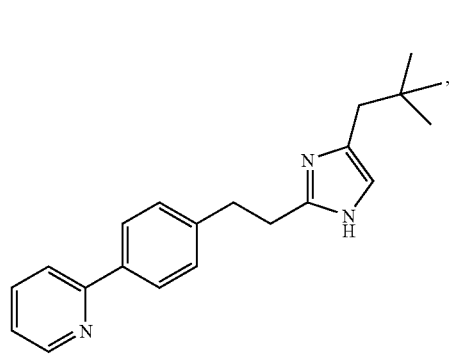

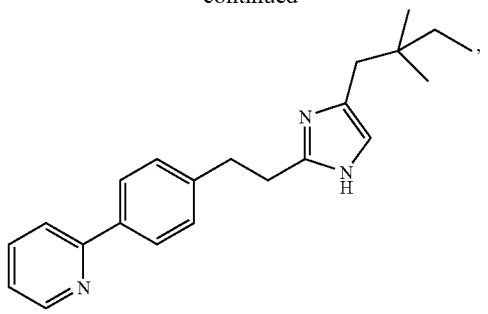

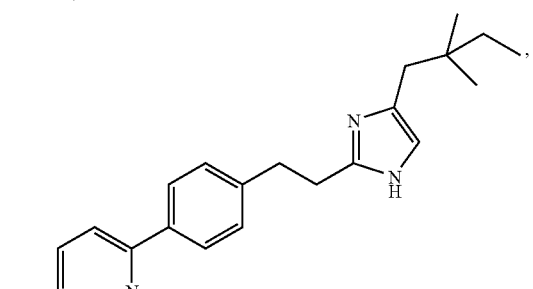

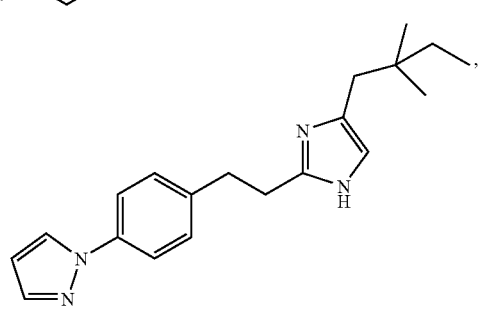

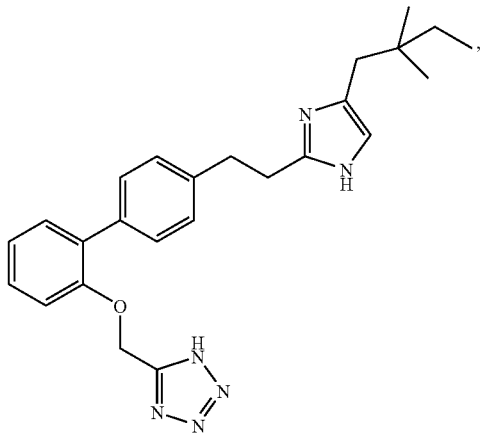

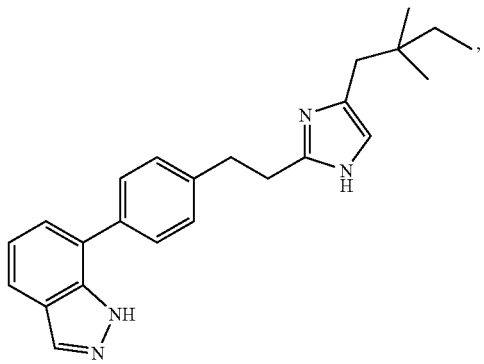

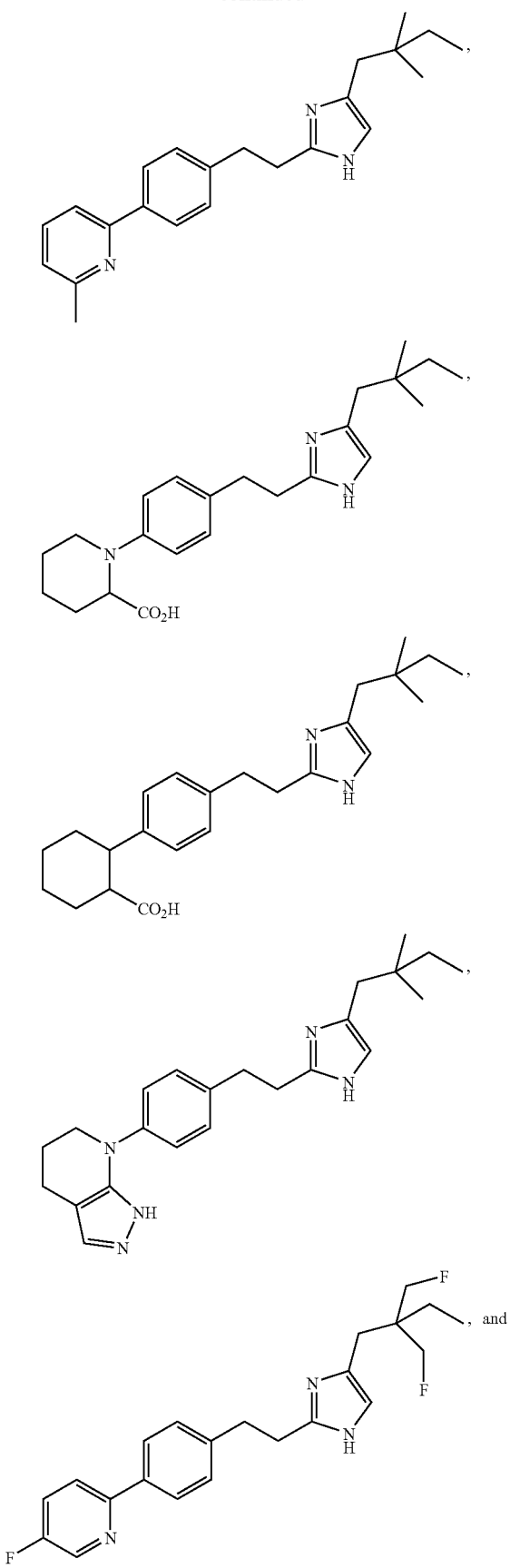

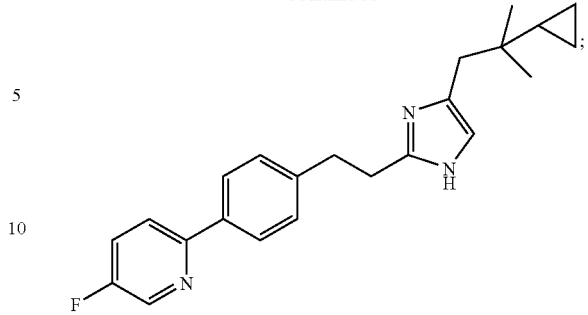

or a pharmaceutically acceptable salt thereof.

The compounds of formula I, II, III and IV are effective as bombesin receptor ligands and are particularly effective as selective ligands of the bombesin receptor subtype-3. They are therefore useful for the treatment and/or prevention of disorders responsive to the modulation of the bombesin receptor subtype-3, such as obesity, diabetes, and obesity-related disorders. More particularly, the compounds of formula I, II, III and IV are selective bombesin receptor subtype-3 (BRS-3) agonists useful for the treatment of disorders responsive to the activation of the bombesin receptor subtype-3, such as obesity, diabetes, as well as the treatment of gallstones.

One aspect of the present invention provides a method for the treatment or prevention of disorders, diseases or conditions responsive to the modulation of the bombesin receptor subtype-3 in a subject in need thereof which comprises administering to the subject a therapeutically or prophylactically effective amount of a compound of formula I, II, III or IV, or a pharmaceutically acceptable salt thereof.

Another aspect of the present invention provides a method for the treatment or prevention of obesity, diabetes, or an obesity related disorder in a subject in need thereof which comprises administering to said subject a therapeutically or prophylactically effective amount of a bombesin receptor subtype-3 agonist of the present invention. Another aspect of the present invention provides a method for the treatment or prevention of obesity in a subject in need thereof which comprises administering to the subject a therapeutically or prophylactically effective amount of a compound of formula I, II, III or IV, or a pharmaceutically acceptable salt thereof. Another aspect of the present invention provides a method for reducing food intake in a subject in need thereof which comprises administering to the subject a therapeutically or prophylactically effective amount of a compound of formula I, II, III or IV, or a pharmaceutically acceptable salt thereof. Another aspect of the present invention provides a method for increasing satiety in a subject in need thereof which comprises administering to the subject a therapeutically or prophylactically effective amount of a compound of formula I, II, III or IV, or a pharmaceutically acceptable salt thereof. Another aspect of the present invention provides a method for reducing appetite in a subject in need thereof which comprises administering to the subject a therapeutically or prophylactically effective amount of a compound of formula I, II, III or IV, or a pharmaceutically acceptable salt thereof. Another aspect of the present invention provides a method for reducing gastric emptying in a subject in need thereof which comprises administering to the subject a therapeutically or prophylactically effective amount of a compound of formula I, II, III or IV, or a pharmaceutically acceptable salt thereof. Another aspect of the present invention provides a method for the treatment or prevention of bulimia nervosa in a subject in need thereof which comprises administering to the subject a therapeutically or prophylactically effective amount of a compound of formula I, II, III or IV, or a pharmaceutically acceptable salt thereof.

Another aspect of the present invention provides a method for the treatment or prevention of diabetes mellitus in a subject in need thereof comprising administering to the subject a therapeutically or prophylactically effective amount of a compound of formula I, II, III or IV, or a pharmaceutically acceptable salt thereof. Another aspect of the present invention provides a method for the treatment or prevention of dyslipidemia in a subject in need thereof which comprises administering to the subject a therapeutically or prophylactically effective amount of a compound of formula I, II, III or IV, or a pharmaceutically acceptable salt thereof.

Another aspect of the present invention provides a method for the treatment or prevention of an obesity-related disorder selected from the group consisting of overeating, binge eating, hypertension, elevated plasma insulin concentrations, insulin resistance, hyperlipidemia, endometrial cancer, breast cancer, prostate cancer, colon cancer, kidney cancer, osteoarthritis, obstructive sleep apnea, heart disease, abnormal heart rhythms and arrythmias, myocardial infarction, congestive heart failure, coronary heart disease, sudden death, stroke, polycystic ovary disease, craniopharyngioma, metabolic syndrome, insulin resistance syndrome, sexual and reproductive dysfunction, infertility, hypogonadism, hirsutism, obesity-related gastro-esophageal reflux, Pickwickian syndrome, inflammation, systemic inflammation of the vasculature, arteriosclerosis, hypercholesterolemia, hyperuricaemia, lower back pain, gallbladder disease, gout, constipation, irritable bowel syndrome, inflammatory bowel syndrome, cardiac hypertrophy, left ventricular hypertrophy, in a subject in need thereof which comprises administering to the subject a therapeutically or prophylactically effective amount of a compound of formula I, II, III or IV, or a pharmaceutically acceptable salt thereof.

Another aspect of the present invention provides a method for the treatment or prevention of diabetes, in a subject in need thereof which comprises administering to the subject a therapeutically or prophylactically effective amount of a compound of formula I, II, III or IV, or a pharmaceutically acceptable salt thereof.

Another aspect of the present invention provides a method for the treatment or prevention of a diabetes related disorder in a subject in need thereof which comprises administering to the subject a therapeutically or prophylactically effective amount of a compound of formula I, II, III or IV, or a pharmaceutically acceptable salt thereof.

Another aspect of the present invention provides a method for the treatment or prevention of an diabetes related disorder selected from the group consisting of hyperglycemia, low glucose tolerance, insulin resistance, obesity, lipid disorders, dyslipidemia, hyperlipidemia, hypertriglyceridemia, hypercholesterolemia, low HDL levels, high LDL levels, atherosclerosis and its sequelae, vascular restenosis, irritable bowel syndrome, inflammatory bowel disease, including Crohn's disease and ulcerative colitis, other inflammatory conditions, pancreatitis, abdominal obesity, neurodegenerative disease, retinopathy, nephropathy, neuropathy, Syndrome X, and ovarian hyperandrogenism (polycystic ovarian syndrome), in a subject in need thereof which comprises administering to the subject a therapeutically or prophylactically effective amount of a compound of formula I, II, III or IV, or a pharmaceutically acceptable salt thereof.

The present invention also relates to methods for treating or preventing obesity by administering a bombesin receptor subtype-3 agonist of the present invention in combination with a therapeutically or prophylactically effective amount of another agent known to be useful to treat or prevent the condition. The present invention also relates to methods for treating or preventing diabetes by administering the bombesin receptor subtype-3 agonist of the present invention in combination with a therapeutically or prophylactically effective amount of another agent known to be useful to treat or prevent the condition. The present invention also relates to methods for treating or preventing obesity related disorders by administering the bombesin receptor subtype-3 agonist of the present invention in combination with a therapeutically or prophylactically effective amount of another agent known to be useful to treat or prevent the condition.

Yet another aspect of the present invention relates to the use of a therapeutically effective amount of a compound of formula (I), or a pharmaceutically acceptable salt or ester thereof, and a therapeutically effective amount of at least one agent selected from the group consisting of: simvastatin, mevastatin, ezetimibe, atorvastatin, sitagliptin, metformin, sibutramine, orlistat, Qnexa, topiramate, phentermine, losartan, losartan with hydrochlorothiazide, or a CB1 antagonist/inverse agonist selected from: rimonabant, N-[3-(4-chlorophenyl)-2(S)-phenyl-1(S)-methylpropyl]-2-(4-trifluoromethyl-2-pyrimidyloxy)-2-methylpropanamide, N-[1S,2S)-3-(4-chlorophenyl)-2-(3-cyanophenyl)-1-methylpropyl]-2-methyl-2-{[5-(trifluoromethyl)pyridin-2-yl]oxy)propanamide, N-[3-(4-chlorophenyl)-2-(5-chloro-3-pyridyl)-1-methylpropyl]-2-(5-trifluoromethyl-2-pyridyloxy)-2-methylpropanamide, 3-{1-[bis(4-chlorophenyl)methyl]azetidin-3-ylidene)-3-(3,5-difluorophenyl)-2,2-dimethylpropanenitrile, 1-{1-[1-(4-chlorophenyl)pentyl]-azetidin-3-yl}-1-(3,5-difluorophenyl)-2-methylpropan-2-ol, 3-((S)-(4-chlorophenyl){3-[(1S)-1-(3,5-difluorophenyl)-2-hydroxy-2-methylpropyl]azetidin-1-yl)methyl)benzonitrile, 3-((S)-4-chlorophenyl){3-[(1S)-1-(3,5-difluorophenyl)-2-fluoro-2-methylpropyl]azetidin-1-yl}methyl)-benzonitrile, 3-((4-chlorophenyl){3-[1-(3,5-difluorophenyl)-2,2-dimethylpropyl]azetidin-1-yl}methyl)benzonitrile, 3-((1S)-1-{1-[(S)-(3-cyanophenyl)(4-cyanophenyl)methyl]azetidin-3-yl}-2-fluoro-2-methylpropyl)-5-fluorobenzonitrile, 3-[(S)-(4-chlorophenyl)(3-{(1S)-2-fluoro-1-[3-fluoro-5-(4H-1,2,4-triazol-4-yl)phenyl]-2-methylpropyl}azetidin-1-yl)methyl]benzonitrile, and 5-((4-chlorophenyl){3-[1-(3,5-difluorophenyl)-2-fluoro-2-methylpropyl]azetidin-1-yl}methyl)thiophene-3-carbonitrile, or a pharmaceutically acceptable salt or ester or prodrug thereof, for the manufacture of a medicament useful for the treatment, control, or prevention of obesity, diabetes, a diabetes related disorder, or an obesity-related disorder in a subject in need of such treatment.

Another aspect of the present invention provides a pharmaceutical composition comprising a compound of formula I, II, III or IV and a pharmaceutically acceptable carrier.

Yet another aspect of the present invention relates to the use of a compound of formula I, II, III and IV for the manufacture of a medicament useful for the treatment or prevention, or suppression of a disease mediated by the bombesin receptor subtype-3 in a subject in need thereof.

Yet another aspect of the present invention relates to the use of a bombesin receptor subtype-3 agonist of the present invention for the manufacture of a medicament useful for the treatment or prevention, or suppression of a disease mediated by the bombesin receptor subtype-3, wherein the disease is selected from the group consisting of obesity, diabetes and an obesity-related disorder in a subject in need thereof.

Yet another aspect of the present invention relates to the use of a bombesin receptor subtype-3 agonist of the present invention for the manufacture of a medicament useful for the treatment or prevention of gallstones in a subject in need thereof. Yet another aspect of the present invention relates to the use of a bombesin receptor subtype-3 agonist of the present invention for the manufacture of a medicament useful for the treatment or prevention of dyslipidemia in a subject in need thereof. Yet another aspect of the present invention relates to the use of a bombesin receptor subtype-3 agonist of the present invention for the manufacture of a medicament useful for the treatment or prevention of bulimia nervosa in a subject in need thereof. Yet another aspect of the present invention relates to the use of a bombesin receptor subtype-3 agonist of the present invention for the manufacture of a medicament useful for the treatment or prevention of constipation in a subject in need thereof. Yet another aspect of the present invention relates to the use of a bombesin receptor subtype-3 agonist of the present invention for the manufacture of a medicament useful for the treatment or prevention of irritable bowel syndrome in a subject in need thereof.

Yet another aspect of the present invention relates to the use of a therapeutically effective amount of a bombesin receptor subtype-3 agonist of formula I, II, III or IV, or a pharmaceutically acceptable salt thereof, and a therapeutically effective amount of an agent selected from the group consisting of an insulin sensitizer, an insulin mimetic, a sulfonylurea, an α-glucosidase inhibitor, a dipeptidyl peptidase 4 (DPP-4) inhibitor, a glucagon like peptide 1 (GLP-1) agonist, a HMG-CoA reductase inhibitor, a serotonergic agent, a β3-adrenoreceptor agonist, a neuropeptide Y1 antagonist, a neuropeptide Y2 agonist, a neuropeptide Y5 antagonist, a pancreatic lipase inhibitor, a cannabinoid $CB_1$ receptor antagonist or inverse agonist, a melanin-concentrating hormone receptor antagonist, a melanocortin 4 receptor agonist, a bombesin receptor subtype 3 agonist, a ghrelin receptor antagonist, PYY, $PYY_{3-36}$, and a NK-1 antagonist, or a pharmaceutically acceptable salt thereof, for the manufacture of a medicament useful for the treatment, control, or prevention of obesity, diabetes or an obesity-related disorder in a subject in need of such treatment. Yet another aspect of the present invention relates to the use of a therapeutically effective amount of a bombesin receptor subtype-3 agonist of formula I, II, III or IV, and pharmaceutically acceptable salts and esters thereof, and a therapeutically effective amount of an agent selected from the group consisting of an insulin sensitizer, an insulin mimetic, a sulfonylurea, an α-glucosidase inhibitor, a dipeptydyl peptidase 4 inhibitor, a glucagon-like peptide 1 agonist, a HMG-CoA reductase inhibitor, a serotonergic agent, a β3-adrenoreceptor agonist, a neuropeptide Y1 antagonist, a neuropeptide Y2 agonist, a neuropeptide Y5 antagonist, a pancreatic lipase inhibitor, a cannabinoid $CB_1$ receptor antagonist or inverse agonist, a melanin-concentrating hormone receptor antagonist, a melanocortin 4 receptor agonist, a bombesin receptor subtype 3 agonist, a ghrelin receptor antagonist, PYY, $PYY_{3-36}$, and a NK-1 antagonist, or a pharmaceutically acceptable salt thereof, for the manufacture of a medicament for treatment or prevention of obesity, diabetes or an obesity-related disorder which comprises an effective amount of a bombesin receptor subtype-3 agonist of formula I, II, III or IV and an effective amount of the agent, together or separately. Yet another aspect of the present invention relates to a product containing a therapeutically effective amount of a bombesin receptor subtype-3 agonist of formula I, II, III or IV, or a pharmaceutically acceptable salt thereof; and and a therapeutically effective amount of an agent selected from the group consisting of an insulin sensitizer, an insulin mimetic, a sulfonylurea, an α-glucosidase inhibitor, a HMG-CoA reductase inhibitor, a serotonergic agent, a β3-adrenoreceptor agonist, a neuropeptide Y1 antagonist, a neuropeptide Y2 agonist, a neuropeptide Y5 antagonist, a pancreatic lipase inhibitor, a cannabinoid $CB_1$ receptor antagonist or inverse agonist, a melanocortin 4 receptor agonist, a melanin-concentrating hormone receptor antagonist, a bombesin receptor subtype 3 agonist, a ghrelin receptor antagonist, PYY, $PYY_{3-36}$, and a NK-1 antagonist, or a pharmaceutically acceptable salt thereof, as a combined preparation for simultaneous, separate or sequential use in obesity, diabetes, or an obesity-related disorder.

The compounds of formula I, II, III or IV can be provided in kit. Such a kit typically contains an active compound in dosage forms for administration. A dosage form contains a sufficient amount of active compound such that a beneficial effect can be obtained when administered to a patient during regular intervals, such as 1, 2, 3, 4, 5 or 6 times a day, during the course of 1 or more days. Preferably, a kit contains instructions indicating the use of the dosage form for weight reduction (e.g., to treat obesity) and the amount of dosage form to be taken over a specified time period.

Throughout the instant application, the following terms have the indicated meanings:

The term "alkyl", as well as other groups having the prefix "alk", such as alkoxy, alkanoyl, means carbon chains of the designated length which may be in a straight or branched configuration, or combinations thereof. Examples of alkyl groups include methyl, ethyl, n-propyl, isopropyl, n-butyl, 1-methylpropyl, 2-methylpropyl, tert-butyl, n-pentyl, 1-methylbutyl, 2-methylbutyl, 3-methylbutyl, 1,2-dimethylpropyl, 1,1-dimethylpropyl, 2,2-dimethylpropyl, n-hexyl, 1-methylpentyl, 2-methylpentyl, 3-methylpentyl, 4-methylpentyl, 1-ethylbutyl, 2-ethylbutyl, 3-ethylbutyl, 1,1-dimethyl butyl, 1,2-dimethylbutyl, 1,3-dimethylbutyl, 2,2-dimethylbutyl, 2,3-dimethylbutyl, 3,3-dimethyl butyl, n-heptyl, 1-methylhexyl, 2-methylhexyl, 3-methylhexyl, 4-methylhexyl, 5-methylhexyl, 1-ethylpentyl, 2-ethylpentyl, 3-ethylpentyl, 4-ethylpentyl, 1-propylbutyl, 2-propylbutyl, 3-propylbutyl, 1,1-dimethylpentyl, 1,2-dimethylpentyl, 1,3-dimethylpentyl, 1,4-dimethylpentyl, 2,2-dimethylpentyl, 2,3-dimethylpentyl. 2,4-dimethylpentyl, 3,3-dimethylpentyl, 3,4-dimethylpentyl, 4,4-dimethylpentyl, 1-methyl-1-ethylbutyl, 1-methyl-2-ethylbutyl, 2-methyl-2-ethylbutyl, 1-ethyl-2-methylbutyl, 1-ethyl-3-methylbutyl, 1,1-diethylpropyl, n-octyl, n-nonyl, and the like.

The term "alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

The term "alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

The term "alkoxy" means alkyl chains of the designated length which contain at least one ether linkage, in which any carbon of the alkyl chain may be substituted with an oxygen, and which may be linear or branched or combinations thereof. Examples of alkoxy include methoxy, ethoxy, 1-propoxy, 2-propoxy, 1-butoxy, 2-butoxy, methylmethoxy, methylethoxy, methyl-1-propoxy, methyl-2-propoxy, ethyl-2-methoxy, ethyl-1-methoxy and the like.

The term "halogen" includes fluorine, chlorine, bromine and iodine.

The term "aryl" includes monocyclic aromatic rings containing only carbon atoms, and bicyclic aromatic ring systems, wherein at least one ring is an aromatic ring containing only carbon atoms. Examples of aryl include phenyl, naphthyl, benzodioxole and benzocyclobutene.

The term "heteroaryl" includes monocyclic aromatic rings that contain from 1 to 4 heteroatoms selected from nitrogen, oxygen and sulfur, and bicyclic heteroaromatic ring systems containing at least one aromatic ring that contains from 1 to 4 heteroatoms selected from nitrogen, oxygen and sulfur. Examples thereof include, but are not limited to, pyridinyl, furyl, thienyl, pyrrolyl, oxazolyl, thiophenyl, thiazolyl, isothiazolyl, triazolyl, triazinyl, tetrazolyl, thiadiazolyl, imidazolyl, isoxazolyl, isothiazolyl, oxadiazolyl, pyrazolyl, pyrimidinyl, pyrazinyl, pyridazinyl, quinolyl, isoquinolyl, benzimidazolyl, benzofuryl, benzothienyl, indolyl, benzthiazolyl, benzoxazolyl, and the like. In one embodiment of the present invention, heteroaryl is selected from the group consisting of pyridinyl, furyl, thienyl, pyrrolyl, oxazolyl, thiazolyl, triazolyl, triazinyl, tetrazolyl, thiadiazolyl, imidazolyl, pyrazolyl, isoxazolyl, isothiazolyl, oxathiazolyl, pyrimidinyl, pyrazinyl, pyridazinyl, quinolyl, isoquinolyl, benzimidazolyl, benzofuryl, benzothienyl, indolyl, benzthiazolyl, and benzoxazolyl. Bicyclic heteroaromatic rings include, but are not limited to, benzothiadiazole, indole, indazole, benzothiophene, benzofuran, benzimidazole, benzisoxazole, benzothiazole, quinoline, quinazoline, benzotriazole, benzoxazole, isoquinoline, purine, furopyridine, thienopyridine, benzisodiazole, triazolopyrimidine, and 5,6,7,8-tetrahydroquinoline, 1,2,3,4-tetrahydroquinoline; 1,2,3,4-tetrahydro-1,8-naphthyridine; 1-H-pyrrolo[2,3-b]pyridine; imidazo[1,2-a]pyrazine; benzopyrazole; benzodioxole; triazolopyridine; and benzopyrrole.

The term "cycloalkyl" includes mono- or bicyclic non-aromatic rings containing only carbon atoms. Examples of cycloalkyl include, but are not limited to, cyclopropyl, cyclobutyl, cyclopentyl, cyclohexyl, cycloheptyl.

The term "cycloalkenyl" includes mono- or bicyclic non-aromatic rings containing only carbon atoms and containing at least one double bond. Examples of cycloalkenyl include, but are not limited to, cyclopropenyl, cyclobutenyl, cyclopentenyl, cyclohexenyl, and cycloheptenyl.

The term "heterocycloalkyl" includes non-aromatic heterocycles containing one to four heteroatoms selected from nitrogen, oxygen and sulfur. Examples of heterocycloalkyls include, but are not limited to, azetidine, piperidine, morpholine, thiamorpholine, pyrrolidine, imidazolidine, tetrahydrofuran, piperazine, 1-thia-4-aza-cyclohexane, azepane; thiazolidine; and hexahydropyridazine.

The term "heterocycloalkenyl" includes non-aromatic heterocycles containing one to four heteroatoms selected from nitrogen, oxygen and sulfur, and containing at least one double bond. Examples of heterocycloalkenyl include, but are not limited to, 3a,4,5,6,7,7a-hexahydro-1H-pyrazolo[3,4-b]pyridine; 1,2-dihydropyridine; and 1,2,3,4-tetrahydropyrazine.

The term "oxo" means a double bond to oxygen. The term "thio" means a double bond to sulfur.

Certain of the above defined terms may occur more than once in the above formula and upon such occurrence each term shall be defined independently of the other; thus for example, $NR^8R^8$ may represent $NH_2$, $NHCH_3$, $N(CH_3)CH_2CH_3$, and the like.

The term "subject" means a mammal. One embodiment of the term "mammal" is a "human," said human being either male or female. The instant compounds are also useful for treating or preventing obesity and obesity related disorders in cats and dogs. As such, the term "mammal" includes companion animals such as cats and dogs. The term "mammal in need thereof" refers to a mammal who is in need of treatment or prophylaxis as determined by a researcher, veterinarian, medical doctor or other clinician.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

By a bombesin receptor subtype 3 (BRS-3) "agonist" is meant an endogenous or drug substance or compound that can interact with a bombesin subtype 3 receptor and initiate a pharmacological or biochemical response characteristic of bombesin subtype 3 receptor activation. The "agonistic" properties of the compounds of the present invention were measured in the functional assay described below.

By "binding affinity" is meant the ability of a compound/drug to bind to its biological target, in the present instance, the ability of a compound of formula I, II, III and IV, to bind to the bombesin subtype 3 receptor. Binding affinities for the compounds of the present invention were measured in the binding assay described below and are expressed as $IC_{50}$'s.

"Efficacy" describes the relative intensity of response which different agonists produce even when they occupy the same number of receptors and with the same affinity. Efficacy is the property that describes the magnitude of response. Properties of compounds can be categorized into two groups, those which cause them to associate with the receptors (binding affinity) and those that produce a stimulus (efficacy). The term "efficacy" is used to characterize the level of maximal responses induced by agonists. Not all agonists of a receptor are capable of inducing identical levels of maximal responses. Maximal response depends on the efficiency of receptor coupling, that is, from the cascade of events, which, from the binding of the drug to the receptor, leads to the desired biological effect.

The functional activities expressed as $EC_{50}$'s and the "agonist efficacy" for the compounds of the present invention were measured in the functional assay described below. Compounds of formula I, II, III or IV, may contain one or more asymmetric or chiral centers and can exist in different stereoisomeric forms, such as racemates and racemic mixtures, single enantiomers, enantiomeric mixtures, individual diastereomers and diastereomeric mixtures. All stereoisomeric forms of the intermediates and compounds of the present invention as well as mixtures thereof, including racemic and diastereomeric mixtures, which possess properties useful in the treatment of the conditions discussed herein or are intermediates useful in the preparation of compounds having such properties, form a part of the present invention.

The compounds of formulas I, II, III and IV encompass any enantiomers. Compounds of structural formula I may be separated into their individual enantiomers and diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration.

Alternatively, any stereoisomer of a compound of the general formula I, II, III and IV may be obtained by stereospecific synthesis using optically pure starting materials or reagents of known absolute configuration.

It will be understood that the compounds of the present invention include hydrates, solvates, polymorphs, crystalline, hydrated crystalline and amorphous forms of the compounds of the present invention, and pharmaceutically acceptable salts thereof.

Generally, one of the enantiomers will be more active biologically than the other enantiomer. Racemic mixtures can subsequently be separated into each enantiomer using standard conditions, such as resolution or chiral chromatography. Diastereomeric mixtures may be separated into their individual diastereoisomers on the basis of their physical chemical differences by methods well known to those skilled in the art, such as by chiral chromatography using an optically active stationary phase and/or fractional crystallization from a suitable solvent. Absolute stereochemistry may be determined by X-ray crystallography of crystalline products or crystalline intermediates which are derivatized, if necessary, with a reagent containing an asymmetric center of known absolute configuration. Enantiomers may be separated by use of a chiral HPLC column and by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Alternatively, any stereoisomer of a compound of the general formula I, II, III and IV may be obtained by stereospecific synthesis using optically pure starting materials or reagents of known absolute configuration.

The present invention is meant to comprehend all such isomeric forms of the compounds of formula I, II, III and IV, including the E and Z geometric isomers of double bonds and mixtures thereof. A number of the compounds of the present invention and intermediates therefor exhibit tautomerism and therefore may exist in different tautomeric forms under certain conditions. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. A specific example of a proton tautomer is an imidazole moiety where the hydrogen may migrate between the ring nitrogens. Valence tautomers include interconversions by reorganization of some of the bonding electrons. All such tautomeric forms (e.g., all keto-enol and imine-enamine forms) are within the scope of the invention. The depiction of any particular tautomeric form in any of the structural formulas herein is not intended to be limiting with respect to that form, but is meant to be representative of the entire tautomeric set.

The present invention also encompasses isotopically labeled compounds which are identical to the compounds of Formula (I) or intermediates thereof but for the fact that one or more atoms are replaced by an atom having an atomic mass or mass number different from the atomic mass or mass number usually found in nature. Examples of isotopes that can be incorporated into the intermediates or compounds of the invention include isotopes of hydrogen, carbon, nitrogen, oxygen, phosphorus, sulfur, fluorine, iodine, and chlorine, such as 2H, 3H, 11C, 13C, 14C, 13N, 15N, 15O, 17O, 18O, 31P, 32P, 35S, 18F, 123I, 125I and 36Cl, respectively. Compounds of the present invention, prodrugs thereof and pharmaceutically acceptable salts, hydrates and solvates of said compounds and of said prodrugs which contain the aforementioned isotopes and/or other isotopes of other atoms are within the scope of the present invention. Certain isotopically labeled compounds of the present invention (e.g., those labeled with 3H and 14C) are useful in compound and/or substrate tissue distribution assays. Tritiated (i.e., 3H) and carbon-14 (i.e., 14C) isotopes are particularly preferred for their ease of preparation and detectability. Further, substitution with heavier isotopes such as deuterium (i.e., 2H) may afford certain therapeutic advantages resulting from greater metabolic stability (e.g., increased in vivo half-life or reduced dosage requirements) and hence may be preferred in some circumstances. Positron emitting isotopes such as 15O, 13N, 11C, and 18F are useful for positron emission tomography (PET) studies to examine substrate receptor occupancy. Isotopically labeled compounds of the present invention can generally be prepared by following procedures analogous to those disclosed in the Schemes and/or in the Examples herein by substituting an isotopically labeled reagent for a non-isotopically labeled reagent.

The compounds of the present invention and intermediates may exist in unsolvated as well as solvated forms with solvents such as water, ethanol, isopropanol and the like, and both solvated and unsolvated forms are included within the scope of the invention. Solvates for use in the methods aspect of the invention should be with pharmaceutically acceptable solvents. It will be understood that the compounds of the present invention include hydrates, solvates, polymorphs, crystalline, hydrated crystalline and amorphous forms of the compounds of the present invention, and pharmaceutically acceptable salts thereof.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, TEA, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Particularly preferred are citric, fumaric, hydrobromic, hydrochloric, maleic, phosphoric, sulfuric, and tartaric acids.

It will be understood that, as used herein, references to the compounds of formula I, II; III and IV are meant to also include the pharmaceutically acceptable salts, such as the hydrochloride salt.

Compounds of formula I, II, III and IV are bombesin receptor ligands and as such are useful in the treatment, control or prevention of diseases, disorders or conditions responsive to the modulation of one or more of the bombesin receptors. In particular, the compounds of formula I, II, III and IV act as bombesin receptor subtype-3 agonists useful in the treatment, control or prevention of diseases, disorders or conditions responsive to the activation of the bombesin receptor subtype-3. Such diseases, disorders or conditions include, but are not limited to, obesity (by reducing food intake, reducing appetite, increasing metabolic rate, increasing satiety, reducing carbohydrate craving, reducing gastric emptying), diabetes mellitus (by enhancing glucose tolerance, decreasing insulin resistance), bulimia nervosa and related eating disorders, dyslipidemia, hypertension, hyperlipidemia, osteoarthritis, cancer, gall stones, cholelithiasis, cholecystitis, gall bladder disease, sleep apnea, depression, anxiety, compulsion, neuroses, irritable bowel syndrome, inflammatory bowel syndrome, constipation, pain, neuroprotective and cognitive and memory enhancement including the treatment of Alzheimer's disease. Such diseases, conditions and disorders also include non-obese overweight conditions and normal weight conditions where weight control or management is desired in order to prevent an obese or overweight condition from developing, or to maintain a healthy weight.

The compounds and compositions of the present invention are useful for the treatment or prevention of disorders associated with excessive food intake, such as obesity and obesity-related disorders. The obesity herein may be due to any cause, whether genetic or environmental.

The obesity-related disorders herein are associated with, caused by, or result from obesity. Examples of obesity-related disorders include overeating, binge eating, bulimia nervosa, hypertension, type 2 diabetes, elevated plasma insulin concentrations, hyperinsulinemia, insulin resistance, glucose intolerance, dyslipidemia, hyperlipidemia, endometrial cancer, breast cancer, prostate cancer, kidney cancer, colon cancer, osteoarthritis, obstructive sleep apnea, cholelithiasis, cholecystitis, gallstones, gout, gallbladder disease, abnormal heart rhythms and arrythmias, myocardial infarction, congestive heart failure, coronary heart disease, angina pectoris, sudden death, stroke, metabolic syndrome, psychological disorders (depression, eating disorders, distorted body-weight, and low self esteem), and other pathological conditions showing reduced metabolic activity or a decrease in resting energy expenditure as a percentage of total fat-free mass, e.g, children with acute lymphoblastic leukemia. Further examples of obesity-related disorders are sexual and reproductive dysfunction, such as polycystic ovary disease, infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer. Additionally, the present compounds are useful in the treatment of any condition in which it is desirable to lose weight or to reduce food intake. Additionally, the present compounds are useful in the treatment of any condition in which it is desirable to enhance cognition and memory, such as Alzheimer's Disease. The compositions of the present invention are also useful for reducing the risk of secondary outcomes of obesity, such as reducing the risk of left ventricular hypertrophy. Therefore, the present invention provides methods of treatment or prevention of such diseases, conditions and/or disorders modulated by BRS-3 receptor agonists in an animal which comprises administering to the animal in need of such treatment a compound of formula I, II, III and IV, in particular a therapeutically or prophylactically effective amount thereof.

Some agonists encompassed by formula I, II, III and IV show highly selective affinity for the bombesin receptor subtype-3 (BRS-3) relative to the neuromedin 1 (BB1) receptor and the gastrin release peptide (BB2) receptor, which makes them especially useful in the prevention and treatment of obesity, diabetes, and obesity related disorders.

The term "metabolic syndrome", also known as syndrome X, is defined in the Third Report of the National Cholesterol Education Program Expert Panel on Detection, Evaluation and Treatment of High Blood Cholesterol in Adults (ATP-III). E. S. Ford et al., JAMA, vol. 287 (3), Jan. 16, 2002, pp 356-359. Briefly, a person is defined as having metabolic syndrome if the person has three or more of the following symptoms: abdominal obesity, hypertriglyceridemia, low HDL cholesterol, high blood pressure, and high fasting plasma glucose. The criteria for these are defined in ATP-III.

The term "diabetes," as used herein, includes both insulin-dependent diabetes mellitus (i.e., IDDM, also known as type I diabetes) and non-insulin-dependent diabetes mellitus (i.e., NIDDM, also known as Type II diabetes). Type I diabetes, or insulin-dependent diabetes, is the result of an absolute deficiency of insulin, the hormone which regulates glucose utilization. Type II diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type II diabetics are also obese. The compositions of the present invention are useful for treating both Type I and Type II diabetes. The compositions are especially effective for treating Type II diabetes. The compounds or combinations of the present invention are also useful for treating and/or preventing gestational diabetes mellitus.

Diabetes is characterized by a fasting plasma glucose level of greater than or equal to 126 mg/dl. A diabetic subject has a fasting plasma glucose level of greater than or equal to 126 mg/dl. Prediabetes is characterized by an impaired fasting plasma glucose (FPG) level of greater than or equal to 110 mg/dl and less than 126 mg/dl; or impaired glucose tolerance; or insulin resistance. A prediabetic subject is a subject with impaired fasting glucose (a fasting plasma glucose (FPG) level of greater than or equal to 110 mg/dl and less than 126 mg/dl); or impaired glucose tolerance (a 2 hour plasma glucose level of $\geqq$140 mg/dl and <200 mg/di); or insulin resistance, resulting in an increased risk of developing diabetes.

"Diabetes related disorders" are diseases, disorders and conditions that are related to Type 2 diabetes, and therefore may be treated, controlled or in some cases prevented, by treatment with the compounds of this invention: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), and other disorders where insulin resistance is a component. In Syndrome X, also known as Metabolic Syndrome, obesity is thought to promote insulin resistance, diabetes, dyslipidemia, hypertension, and increased cardiovascular risk. Therefore, BRS-3 agonists may also be useful to treat hypertension associated with this condition.

Treatment of diabetes mellitus refers to the administration of a compound or combination of the present invention to treat diabetes. One outcome of treatment may be decreasing the glucose level in a subject with elevated glucose levels. Another outcome of treatment may be improving glycemic control. Another outcome of treatment may be decreasing insulin levels in a subject with elevated insulin levels. Another outcome of the treatment of diabetes is to reduce an increased plasma glucose concentration. Another outcome of the treatment of diabetes is to reduce an increased insulin concentration. Still another outcome of the treatment of diabetes is to reduce an increased blood triglyceride concentration. Still another outcome of the treatment of diabetes is to increase insulin sensitivity. Still another outcome of the treatment of diabetes may be enhancing glucose tolerance in a subject with glucose intolerance. Still another outcome of the treatment of diabetes is to reduce insulin resistance. Another outcome of the treatment of diabetes is to lower plasma insulin levels. Still another outcome of treatment of diabetes is an improvement in glycemic control, particulary in type 2 diabetes.

Prevention of diabetes mellitus, in particular diabetes associated with obesity, refers to the administration of a compound or combination of the present invention to prevent or treat the onset of diabetes in a subject in need thereof. A subject in need of preventing diabetes in a prediabetic subject.

"Obesity" is a condition in which there is an excess of body fat. The operational definition of obesity is based on the Body Mass Index (BMI), which is calculated as body weight per height in meters squared ($kg/m^2$). "Obesity" refers to a condition whereby an otherwise healthy subject has a Body Mass Index (BMI) greater than or equal to 30 $kg/m^2$, or a condition whereby a subject with at least one co-morbidity has a BMI greater than or equal to 27 $kg/m^2$. An "obese subject" is an otherwise healthy subject with a Body Mass Index (BMI) greater than or equal to 30 $kg/m^2$ or a subject with at least one co-morbidity with a BMI greater than or equal to 27 $kg/m^2$. A "subject at risk of obesity" is an otherwise healthy subject with a BMI of 25 $kg/m^2$ to less than 30 $kg/m^2$ or a subject with at least one co-morbidity with a BMI of 25 $kg/m^2$ to less than 27 $kg/m^2$.

The increased risks associated with obesity occur at a lower Body Mass Index (BMI) in Asians. In Asian countries, including Japan, "obesity" refers to a condition whereby a subject with at least one obesity-induced or obesity-related co-morbidity, that requires weight reduction or that would be improved by weight reduction, has a BMI greater than or equal to 25 $kg/m^2$. In Asian countries, including Japan, an "obese subject" refers to a subject with at least one obesity-induced or obesity-related co-morbidity that requires weight reduction or that would be improved by weight reduction, with a BMI greater than or equal to 25 $kg/m^2$. In Asia-Pacific, a "subject at risk of obesity" is a subject with a BMI of greater than 23 $kg/m^2$ to less than 25 $kg/m^2$.

As used herein, the term "obesity" is meant to encompass all of the above definitions of obesity.

Obesity-induced or obesity-related co-morbidities include, but are not limited to, diabetes, non-insulin dependent diabetes mellitus-type II (2), impaired glucose tolerance, impaired fasting glucose, insulin resistance syndrome, dyslipidemia, hypertension, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, diabetes mellitus, and other obesity-related conditions.

Treatment of obesity and obesity-related disorders refers to the administration of the compounds or combinations of the present invention to reduce or maintain the body weight of an obese subject. One outcome of treatment may be reducing the body weight of an obese subject relative to that subject's body weight immediately before the administration of the compounds or combinations of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and in weight reduction in subjects in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

Prevention of obesity and obesity-related disorders refers to the administration of the compounds or combinations of the present invention to reduce or maintain the body weight of a subject at risk of obesity. One outcome of prevention may be reducing the body weight of a subject at risk of obesity relative to that subject's body weight immediately before the administration of the compounds or combinations of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovary disease, cardiovascular diseases, osteoarthritis, hypertension, dyslipidemia, insulin resistance, hypercholesterolemia, hypertriglyceridemia, and cholelithiasis.

The terms "administration of and or "administering" a compound should be understood to mean providing a compound of the invention or a prodrug of a compound of the invention to a subject in need of treatment. The administration of the compounds of the present invention in order to practice the present methods of therapy is carried out by administering a therapeutically effective amount of the compound to a subject in need of such treatment or prophylaxis. The need for a prophylactic administration according to the methods of the present invention is determined via the use of well known risk factors.

The term "therapeutically effective amount" as used herein means the amount of the active compound that will elicit the biological or medical response in a tissue, system, subject, mammal, or human that is being sought by the researcher, veterinarian, medical doctor or other clinician, which includes alleviation of the symptoms of the disorder being treated. The novel methods of treatment of this invention are for disorders known to those skilled in the art. The term "prophylactically effective amount" as used herein means the amount of the active compound that will elicit the biological or medical response in a tissue, system, subject, mammal, or human that is being sought by the researcher, veterinarian, medical doctor or other clinician, to prevent the onset of the disorder in subjects as risk for obesity or the disorder. The therapeutically or prophylactically effective amount, or dosage, of an individual compound is determined, in the final analysis, by the physician in charge of the case, but depends on factors such as the exact disease to be treated, the severity of the disease and other diseases or conditions from which the patient suffers, the chosen route of administration, other drugs and treatments which the patient may concomitantly require, and other factors in the physician's judgement.

Administration and Dose Ranges

Any suitable route of administration may be employed for providing a subject or mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I, II, III and IV are administered orally or topically.

The effective dosage of active ingredient employed may vary depending on the particular compound employed, the mode of administration, the condition being treated and the severity of the condition being treated. Such dosage may be ascertained readily by a person skilled in the art.

When treating obesity, in conjunction with diabetes and/or hyperglycemia, or alone, generally satisfactory results are obtained when the compounds of formula I, II, III and IV are administered at a daily dosage of from about 0.001 milligram to about 50 milligrams per kilogram of animal body weight, preferably given in a single dose or in divided doses two to six times a day, or in sustained release form. In the case of a 70 kg adult human, the total daily dose will generally be from about 0.07 milligrams to about 3500 milligrams. This dosage regimen may be adjusted to provide the optimal therapeutic response.

When treating diabetes mellitus and/or hyperglycemia, as well as other diseases or disorders for which compounds of formula I, II, III and IV are useful, generally satisfactory results are obtained when the compounds of the present invention are administered at a daily dosage of from about 0.001 milligram to about 50 milligram per kilogram of animal body weight, preferably given in a single dose or in divided doses two to six times a day, or in sustained release form. In the case of a 70 kg adult human, the total daily dose will generally be from about 0.07 milligrams to about 3500 milligrams. This dosage regimen may be adjusted to provide the optimal therapeutic response.

When treating dyslipidemia, bulimia nervosa, and gallstones satisfactory results are obtained when the compounds of formula I, II, III and IV are administered at a daily dosage of from about 0.001 milligram to about 50 milligrams per kilogram of animal body weight, preferably given in a single dose or in divided doses two to six times a day, or in sustained release form. In the case of a 70 kg adult human, the total daily dose will generally be from about 0.07 milligrams to about 3500 milligrams. This dosage regimen may be adjusted to provide the optimal therapeutic response.

In the case where an oral composition is employed, a suitable dosage range is, e.g. from about 0.01 mg to about 1500 mg of a compound of Formula I, II, III and IV per day, preferably from about 0.1 mg to about 600 mg per day, more preferably from about 0.1 mg to about 100 mg per day. For oral administration, the compositions are preferably provided in the form of tablets containing from 0.01 to 1,000 mg, preferably 0.01, 0.05, 0.1, 0.5, 1, 2.5, 5, 10, 15, 20, 25, 30, 40, 50, 100, 250, 500, 600, 750, 1000, 1250 or 1500 milligrams of the active ingredient for the symptomatic adjustment of the dosage to the patient to be treated.

For use where a composition for intranasal administration is employed, intranasal formulations for intranasal administration comprising 0.001-10% by weight solutions or suspensions of the compounds of formula I, II, III and IV in an acceptable intranasal formulation may be used.

For use where a composition for intravenous administration is employed, a suitable dosage range is from about 0.001 mg to about 50 mg, preferably from 0.01 mg to about 50 mg, more preferably 0.1 mg to 10 mg, of a compound of formula I, II, III and IV per kg of body weight per day. This dosage regimen may be adjusted to provide the optimal therapeutic response. It may be necessary to use dosages outside these limits in some cases.

For the treatment of diseases of the eye, ophthalmic preparations for ocular administration comprising 0.001-1% by weight solutions or suspensions of the compounds of formula I, II, III and IV in an acceptable ophthalmic formulation may be used.

The magnitude of prophylactic or therapeutic dosage of the compounds of the present invention will, of course, vary depending on the particular compound employed, the mode of administration, the condition being treated and the severity of the condition being treated. It will also vary according to the age, weight and response of the individual patient. Such dosage may be ascertained readily by a person skilled in the art.

Compounds of formula I, II, III and IV may be used in combination with other drugs that are used in the treatment/prevention/suppression or amelioration of the diseases or conditions for which compounds of formula I, II, III and IV are useful. Such other drugs may be administered, by a route and in an amount commonly used therefor, contemporaneously or sequentially with a compound of formula I, II, III and IV. When a compound of formula I, II, III and IV is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of formula I, II, III or IV.

Examples of other active ingredients that may be combined with a compound of formula I, II, III and IV for the treatment or prevention of obesity and/or diabetes, either administered separately or in the same pharmaceutical compositions, include, but are not limited to:

(a) Anti-diabetic agents, for example, (1) glitazones (e.g., ciglitazone, darglitazone, englitazone, isaglitazone (MCC-555), pioglitazone, rosiglitazone, troglitazone, tularik, BRL49653, CLX-0921, 5-BTZD), and PPAR-γ agonists such as GW-0207, LG-100641 and LY-300512; (2) biguanides such as buformin, metformin and phenformin; (3) protein tyrosine phosphatase-1B (PTP-1B) inhibitors; (4) sulfonylureas such as acetohexamide, chlorpropamide, diabinese, glibenclamide, glipizide, glyburide, glimepiride, gliclazide, glipentide, gliquidone, glisolamide, tolazamide and tolbutamide; (5) meglitinides such as repaglinide, nateglinide, and the like; (6) α-glucosidase inhibitors such as acarbose, adiposine, camiglibose, emiglitate, miglitol, voglibose, pradimicin-Q, salbostatin, CKD-711, MDL-25,637, MDL-73,945, and MOR14; (7) α-amylase inhibitors such as tendamistat, trestatin, and Al-3688; (8) insulin secretagogues such as linogliride, A-4166 and the like; (9) fatty acid oxidation inhibitors such as clomoxir, and etomoxir; (10) α-2 antagonists such as midaglizole, isaglidole, deriglidole, idazoxan, earoxan, and fluparoxan; (11) insulin and insulin mimetics such as biota, LP-100, novarapid, insulin detemir, insulin lispro, insulin glargine, insulin zinc suspension (lente and ultralente), Lys-Pro insulin, GLP-1 (73-7) (insulintropin), and GLP-1 (7-36)-NH$_2$; (12) non-thiazolidinediones such as JT-501, farglitazar (GW-2570/GI-262579), and muraglitazar; PPAR α/δ agonists, such as muraglitazar, and the compounds disclosed in U.S. Pat. No. 6,414,002; (13) PPAR-α/γ dual agonists such as MK-0767/ICRP-297, CLX-0940, GW-1536, GW-1929, GW-2433, L-796449, LR-90, and SB219994; (14) other insulin sensitizers; (15) VPAC2 receptor agonists; (16) glucokinase activators; (17) DPP-4 inhibitors, such as sitagliptin (Januvia™), isoleucine thiazolidide (P32/98); NVP-DPP-728; vildagliptin (LAF 237); P93/01; denagliptin (GSK 823093), SYR322, RO 0730699, TA-6666, and saxagliptin (BMS 477118); and (18) glucagon receptor anatonists;

(b) lipid lowering agents, for example, (1) bile acid sequestrants such as cholestyramine, colesevelam, colestipol, dialkylaminoalkyl derivatives of a cross-linked dextran, Colestid®, LoCholest®, and Questran®, and the like; (2) HMG-CoA reductase inhibitors such as atorvastatin, itavastatin, fluvastatin, lovastatin, pitavastatin, pravastatin, rivastatin, rosuvastatin, and simvastatin, ZD-4522, and the like; (3) HMG-CoA synthase inhibitors; (4) cholesterol absorption inhibitors such as stanol esters, β-sitosterol, sterol glycosides such as tiqueside, and azetidinones like ezetimibe; (5) acyl coenzyme A-cholesterol acyl-transferase (ACAT) inhibitors such as avasimibe, eflucimibe, KY505, and SMP797, and the like; (6) CETP inhibitors such as JTT705, torcetrapib, CP532632, BAY63-2149, SC591, and SC795, and the like; (7) squalene synthase inhibitors; (8) antioxidants such as probucol; (9) PPAR-α agoists such as beclofibrate, benzafibrate, ciprofibrate, clofibrate, etofibrate, fenofibrate, gemcabene, gemfibrozil, and other fibric acid derivatives, e.g., GW7647, BM170744, LY518674, Atromid®, Lopid®, and Tricor®, and compounds described in WO 97/36579, and the like; (10) FXR receptor modulators such as GW4064, SR103912, and the like; (11) LXR receptor ligands such as GW3965, T9013137, and XTC0179628, and the like; (12) lipoprotein synthesis inhibitors such as niacin; (13) renin/angiotensin system inhibitors; (14) PPAR-δ partial agonists; (15) bile acid reabsorption inhibitors such as BARI1453, SC435, PHA384640, S8921, AZD7706, and the like; (16) PPAR-δ agonists such as GW501516, GW590735, and compounds described in WO97/28149, and the like; (17) triglyceride synthesis inhibitors, (18) microsomal triglyceride transport (MTTP) inhibitors such as inplitapide, LAB687, and CP346086; (19) transcription modulators, (20) squalene epoxidase inhibitors; (21) low-density lipoprotein (LDL) receptor inducers; (22) platelet aggregation inhibitors; (23) 5-LO or FLAP inhibitors; and (24) niacin receptor agonists; and (c) anti-hypertensive agents, for example, (1) diuretics such as thiazides including chlorthalidone, chlorothiazide, dichlorphenamide, hydroflumethiazide, indapamide and hydrochlorothiazide; loop diuretics such as bumetanide, ethacrynic acid, furosemide, and torsemide; potassium sparing agents such as amiloride, triamterene; aldosterone antagonists such as spironolactone, and epirenone, and the like; (2) β-adrenergic blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, propanolol, sotalol, tertatolol, tilisolol, and timolol, and the like; (3) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodipine, nisoldipine, nitrendipine, manidipine, pranidipine, and verapamil, and the like; (4) angiotensin converting enzyme (ACE) inhibitors such as benazepril, captopril, cilazapril, delapril, enalapril, fosinopril, imidapril, lisinopril, moexipril, quinapril, quinaprilat, ramipril, perindopril, perindropril, quanipril, spirapril, tenocapril, trandolapril, and zofenopril, and the like; (5) neutral endopeptidase inhibitors such as omapatrilat, cadoxatril, ecadotril, fosidotril, sampatrilat, AVE7688, ER4030, and the like; (6) endothelin antagonists such as bosentan, tezosentan, A308165, and YM62899, and the like; (7) vasodilators such as hydralazine, clonidine, minoxidil, and nicotinyl alcohol; (8) angiotensin II receptor antagonists such as candesartan, eprosartan, irbesartan, losartan, losartan and hydrochlorothiazide, pratosartan, tasosartan, telmisartan, valsartan, EXP-3137, FI6828K, and RNH6270, and the like; (9) α/β-adrenergic blockers such as nipradilol, arotinolol, and amosulalol; (10) α1 blockers such as terazosin, urapidil, prazosin, bunazosin, trimazosin, doxazosin, naftopidil, indoramin, WHIP 164, and XEN010; (11) α2 agonists such as lofexidine, tiamenidine, moxonidine, rilmenidine, and guanobenz; (12) aldosterone inhibitors; and (d) anti-obesity agents, such as (1) growth hormone secretagogues, growth hormone secretagogue receptor agonists/antagonists, such as NN703, hexarelin, MK-0677, SM-130686, CP-424,391, L-692,429, and L-163,255, and such as those disclosed in U.S. Pat. Nos. 5,536,716, and 6,358,951, U.S. Patent Application Nos. 2002/049196 and 2002/022637, and PCT Application Nos. WO 01/56592 and WO 02/32888; (2) protein tyrosine phosphatase-1B (PTP-1B) inhibitors; (3) cannabinoid receptor ligands, such as cannabinoid $CB_1$ receptor antagonists or inverse agonists, such as rimonabant (Sanofi Synthelabo), AMT-251, and SR-14778 and SR 141716A (Sanofi Synthelabo), SLV-319 (Solvay), BAY 65-2520 (Bayer), and those disclosed in U.S. Pat. Nos. 5,532,237, 4,973,587, 5,013,837, 5,081,122, 5,112,820, 5,292,736, 5,624,941, 6,028,084, PCT Application Nos. WO 96/33159, WO 98/33765, WO98/43636, WO98/43635, WO 01/09120, WO98/31227, WO98/41519, WO98/37061, WO00/10967, WO00/10968, WO97/29079, WO99/02499, WO 01/58869, WO 01/64632, WO 01/64633, WO 01/64634, WO02/076949, WO 03/007887, WO 04/048317, and WO 05/000809; and EPO Application No. EP-658546, EP-656354, EP-576357; (4) anti-obesity serotonergic agents, such as fenfluramine, dexfenfluramine, phentermine, and sibutramine; (5) β3-adrenoreceptor agonists, such as AD9677/TAK677 (Dainippon/Takeda), CL-316,243, SB 418790, BRL-37344, L-796568, BMS-196085, BRL-35135A, CGP12177A, BTA-243, Trecadrine, Zeneca D7114, SR 59119A, and such as those disclosed in U.S. Pat. No. 5,705,515, and U.S. Pat. No. 5,451,677 and PCT Patent Publications WO94/18161, WO95/29159, WO97/46556, WO98/04526 and WO98/32753, WO 01/74782, and WO 02/32897; (6) pancreatic lipase inhibitors, such as orlistat (Xenical®), Triton WR1339, RHC80267, lipstatin, tetrahydrolipstatin, teasaponin, diethylumbelliferyl phosphate, and those disclosed in PCT Application No. WO 01/77094; (7) neuropeptide Y1 antagonists, such as B1BP3226, J-115814, BIBO 3304, LY-357897, CP-671906, GI-264879A, and those disclosed in U.S. Pat. No. 6,001,836, and PCT Patent Publication Nos. WO 96/14307, WO 01/23387, WO 99/51600, WO 01/85690, WO 01/85098, WO 01/85173, and WO 01/89528; (8) neuropeptide Y5 antagonists, such as GW-569180A, GW-594884A, GW-587081X, GW-548118X, FR226928, FR 240662, FR252384, 1229U91, GI-264879A, CGP71683A, LY-377897, PD-160170, SR-120562A, SR-120819A and JCF-104, and those disclosed in U.S. Pat. Nos. 6,057,335; 6,043,246; 6,140,354; 6,166,038; 6,180,653; 6,191,160; 6,313,298; 6,335,345; 6,337,332; 6,326,375; 6,329,395; 6,340,683; 6,388,077; 6,462,053; 6,649,624; and 6,723,847, hereby incorporated by reference in their entirety; European Patent Nos. EP-01010691, and EP-01044970; and PCT International Patent Publication Nos. WO 97/19682, WO 97/20820, WO 97/20821, WO 97/20822, WO 97/20823, WO 98/24768; WO 98/25907; WO 98/25908; WO 98/27063, WO 98/47505; WO 98/40356; WO 99/15516; WO 99/27965; WO 00/64880, WO 00/68197, WO 00/69849, WO 01/09120, WO 01/14376; WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/22592, WO 0248152, and WO 02/49648; WO 02/094825; WO 03/014083; WO 03/10191; WO 03/092889; WO 04/002986; and WO 04/031175; (9) melanin-concentrating hormone (MCH) receptor antagonists, such as those disclosed in WO 01/21577 and WO 01/21169; (10) melanin-concentrating hormone 1 receptor (MCH1R) antagonists, such as T-226296 (Takeda), and those disclosed in PCT Patent Application Nos. WO 01/82925, WO 01/87834, WO 02/051809, WO 02/06245, WO 02/076929, WO 02/076947, WO 02/04433, WO 02/51809, WO 02/083134, WO 02/094799, WO 03/004027, and Japanese Patent Application Nos. JP 13226269, and JP 2004-139909; (11) melanin-concentrating hormone 2 receptor (MCH2R) agonist/antagonists; (12) orexin-1 receptor antagonists, such as SB-334867-A, and those disclosed in PCT Patent Application Nos. WO 01/96302, WO 01/68609, WO 02/51232, and WO 02/51838; (13) serotonin reuptake inhibitors such as fluoxetine, paroxetine, and sertraline, and those disclosed in U.S. Pat. No. 6,365,633, and PCT Patent Application Nos. WO 01/27060 and WO 01/162341; (14) melanocortin agonists, such as Melanotan II (Chiron), ME-10142, and ME-10145 (Melacure), CHIR86036 (Chiron); PT-141, and PT-14 (Palatin); (15) other MC4R (melanocortin 4 receptor) agonists, such as those disclosed in: U.S. Pat. Nos. 6,410,548; 6,294,534; 6,350,760; 6,458,790; 6,472,398; 6,376,509; and 6,818,658; US Patent Publication No. US2002/0137664; US2003/0236262; US2004/009751; US2004/0092501; and PCT Application Nos. WO 99/64002; WO 00/74679; WO 01/70708; WO 01/70337; WO 01/74844; WO 01/91752; WO 01/991752; WO 02/15909; WO 02/059095; WO 02/059107; WO 02/059108; WO 02/059117; WO 02/067869; WO 02/068387; WO 02/068388; WO 02/067869; WO 02/11715; WO 02/12166; WO 02/12178; WO 03/007949; WO 03/009847; WO 04/024720; WO 04/078716; WO 04/078717; WO 04/087159; WO 04/089307; and WO 05/009950; (16) 5HT-2 agonists; (17) 5HT2C (serotonin receptor 2C) agonists, such as BVT933, DPCA37215, WAY161503, R-1065, and those disclosed in U.S. Pat. No. 3,914,250, and PCT Application Nos. WO 02/36596, WO 02/48124, WO 02/10169, WO 01/66548, WO 02/44152, WO 02/51844, WO 02/40456, and WO 02/40457; (18) galanin antagonists; (19) CCK agonists; (20) CCK-1 agonists (cholecystokinin-A) agonists, such as AR-R 15849, GI 181771, JMV-180, A-71378, A-71623 and SR146131, and those described in U.S. Pat. No. 5,739,106; (21) GLP-1 agonists; (22) corticotropin-releasing hormone agonists; (23) histamine receptor-3 (H3) modulators; (24) histamine receptor-3 (H3) antagonists/inverse agonists, such as hioperamide, 3-(1H-imidazol-4-yl)propyl N-(4-pentenyl)carbamate, clobenpropit, iodophenpropit, imoproxifan, GT2394 (Gliatech), and those described and disclosed in PCT Application No. WO 02/15905, and O-[3-(1H-imidazol-4-yl)propano]-carbamates (Kiec-Kononowicz, K. et al., Pharmazie, 55:349-55 (2000)), piperidine-containing histamine H3-receptor antagonists (Lazewska, D. et al., Pharmazie, 56:927-32 (2001), benzophenone derivatives and related compounds (Sasse, A. et al., Arch. Pharm. (Weinheim) 334:45-52 (2001)), substituted N-phenylcarbamates (Reidemeister, S. et al., Pharmazie, 55:83-6 (2000)), and proxifan derivatives (Sasse, A. et al., J. Med. Chem., 43:3335-43 (2000)); (25) β-hydroxy steroid dehydrogenase-1 inhibitors (β-HSD-1); 26) PDE (phosphodiesterase) inhibitors, such as theophylline, pentoxifylline, zaprinast, sildenafil, amrinone, milrinone, cilostamide, rolipram, and cilomilast; (27) phosphodiesterase-3B (PDE3B) inhibitors; (28) NE (norepinephrine) transport inhibitors, such as GW 320659, despiramine, talsupram, and nomifensine; (29) ghrelin receptor antagonists, such as those disclosed in PCT Application Nos. WO 01/87335, and WO 02/08250; (30) leptin, including recombinant human leptin (PEG-OB, Hoffman La Roche) and recombinant methionyl human leptin (Amgen); (31) leptin derivatives, such as those disclosed in U.S. Pat. Nos. 5,552,524, 5,552,523, 5,552,522, 5,521,283, and PCT International Publication Nos. WO 96/23513, WO 96/23514, WO 96/23515, WO 96/23516, WO 96/23517, WO 96/23518, WO 96/23519, and WO 96/23520; (32) other BRS3 (bombesin receptor subtype 3) agonists such as [D-Phe6,beta-Ala11, Phe13,Nle14]Bn(6-14) and [D-Phe6,Phe13]Bn(6-13)propylamide, and those compounds disclosed in Pept. Sci. 2002 August; 8(8): 461-75); (33) CNTF (Ciliary neurotrophic factors), such as GI-181771 (Glaxo-SmithKline), SR146131 (Sanofi Synthelabo), butabindide, PD170,292, and PD 149164 (Pfizer); (34) CNTF derivatives, such as axokine (Regeneron), and those disclosed in PCT Application Nos. WO 94/09134, WO 98/22128, and WO 99/43813; (35) monoamine reuptake inhibitors, such as sibutramine, and those disclosed in U.S. Pat. Nos. 4,746,680, 4,806,570, and 5,436,272, U.S. Patent Publication No. 2002/0006964 and PCT Application Nos. WO 01/27068, and WO 01/62341; (36) UCP-1 (uncoupling protein-1), 2, or 3 activators, such as phytanic acid, 4-[(E)-2-(5,6,7,8-tetrahydro-5,5,8,8-tetramethyl-2-napthalenyl)-1-propenyl]benzoic acid (TTNPB), retinoic acid, and those disclosed in PCT Patent Application No. WO 99/00123; (37) thyroid hormone β agonists, such as KB-2611 (KaroBioBMS), and those disclosed in PCT Application No. WO 02/15845, and Japanese Patent Application No. JP 2000256190; (38) FAS (fatty acid synthase) inhibitors, such as Cerulenin and C75; (39) DGAT1 (diacylglycerol acyltransferase 1) inhibitors; (40) DGAT2 (diacylglycerol acyltransferase 2) inhibitors; (41) ACC2 (acetyl-CoA carboxylase-2) inhibitors; (42) glucocorticoid antagonists; (43) acyl-estrogens, such as oleoyl-estrone, disclosed in del Mar-Grasa, M. et al., Obesity Research, 9:202-9 (2001); (44) dipeptidyl peptidase IV (DP-IV) inhibitors, such as isoleucine thiazolidide, valine pyrrolidide, NVP-DPP728, LAF237, P93/01, TSL 225, TMC-2A/2B/2C, FE 999011, P9310/K364, VIP 0177, SDZ 274-444 and sitagliptin; and the compounds disclosed in U.S. Pat. No. 6,699,871, which is incorporated herein by reference; and International Patent Application Nos. WO 03/004498; WO 03/004496; EP 1 258 476; WO 02/083128; WO 02/062764; WO 03/000250; WO 03/002530; WO 03/002531; WO 03/002553; WO 03/002593; WO 03/000180; and WO 03/000181; (46) dicarboxylate transporter inhibitors; (47) glucose transporter inhibitors; (48) phosphate transporter inhibitors; (49) Metformin (Glucophage®); and (50) Topiramate (Topimax®); and (50) peptide YY, PYY 3-36, peptide YY analogs, derivatives, and fragments such as BIM-43073D, BIM-43004C (Olitvak, D. A. et al., Dig. Dis. Sci. 44(3):643-48 (1999)), and those disclosed in U.S. Pat. No. 5,026,685, U.S. Pat. No. 5,604,203, U.S. Pat. No. 5,574,010, U.S. Pat. No. 5, 696,093, U.S. Pat. No. 5,936,092, U.S. Pat. No. 6,046, 162, U.S. Pat. No. 6,046, 167, U.S. Pat. No. 6,093,692, U.S. Pat. No. 6,225,445, U.S. Pat. No. 5,604,203, U.S. Pat. No. 4,002,531, U.S. Pat. No. 4,179,337, U.S. Pat. No. 5,122,614, U.S. Pat. No. 5,349,052, U.S. Pat. No. 5,552,520, U.S. Pat. No. 6,127,355, WO 95/06058, WO 98/32466, WO 03/026591, WO 03/057235, WO 03/027637, and WO 2004/066966, which are incorporated herein by reference; (51) Neuropeptide Y2 (NPY2) receptor agonists such NPY3-36, N acetyl [Leu(28,31)] NPY 24-36, TASP-V, and cyclo-(28/32)-Ac-[Lys28-Glu32]-(25-36)-pNPY; (52) Neuropeptide Y4 (NPY4) agonists such as pancreatic peptide (PP) as described in Batterham et al., J. Clin. Endocrinol. Metab. 88:3989-3992 (2003), and other Y4 agonists such as 1229U91; (54) cyclo-oxygenase-2 inhibitors such as etoricoxib, celecoxib, valdecoxib, parecoxib, lumiracoxib, BMS347070, tiracoxib or JTE522, ABT963, CS502 and GW406381, and pharmaceutically acceptable salts thereof; (55) Neuropeptide Y1 (NPY1) antagonists such as B1BP3226, J-115814, BIBO 3304, LY-357897, CP-671906, GI-264879A and those disclosed in U.S. Pat. No. 6,001,836; and PCT Application Nos. WO 96/14307, WO 01/23387, WO 99/51600, WO 01/85690, WO 01/85098, WO 01/85173, and WO 01/89528; (56) Opioid antagonists such as nalmefene (Revex®), 3-methoxynaltrexone, naloxone, naltrexone, and those disclosed in: PCT Application No. WO 00/21509; (57) 11β HSD-1 (11-beta hydroxy steroid dehydrogenase type 1) inhibitors such as BVT 3498, BVT 2733, and those disclosed in WO 01/90091, WO 01/90090, WO 01/90092, and U.S. Pat. No. 6,730,690 and US Publication No. US 2004-0133011, which are incorporated by reference herein in their entirety; and (58) aminorex; (59) amphechloral; (60) amphetamine; (61) benzphetamine; (62) chlorphentermine; (63) clobenzorex; (64) cloforex; (65) clominorex; (66) clortermine; (67) cyclexedrine; (68) dextroamphetamine; (69) diphemethoxidine, (70) N-ethylamphetamine; (71) fenbutrazate; (72) fenisorex; (73) fenproporex; (74) fludorex; (75) fluminorex; (76) furfurylmethylamphetamine; (77) levamfetamine; (78) levophacetoperane; (79) mefenorex; (80) metamfepramone; (81) methamphetamine; (82) norpseudoephedrine; (83) pentorex; (84) phendimetrazine; (85) phenmetrazine; (86) picilorex; (87) phytopharm 57; (88) zonisamide, (89) neuromedin U and analogs or derivatives thereof, (90) oxyntomodulin and analogs or derivatives thereof, (91) Neurokinin-1 receptor antagonists (NK-1 antagonists) such as the compounds disclosed in: U.S. Pat. Nos. 5,162,339, 5,232,929, 5,242,930, 5,373,003, 5,387,595, 5,459,270, 5,494,926, 5,496,833, and 5,637,699; and (92) Qnexa; and (e) smoking cessation agents, such as a nicotine agonist or a partial nicotine agonist such as varenicline, or a monoamine oxidase inhibitor (MAOI), or another active ingredient demonstrating efficacy in aiding cessation of tobacco consumption; for example, an antidepressant such as bupropion, doxepine, ornortriptyline; or an anxiolytic such as buspirone or clonidine.

Specific compounds of use in combination with a compound of the present invention include: simvastatin, mevastatin, ezetimibe, atorvastatin, sitagliptin, metformin, sibutramine, orlistat, Qnexa, topiramate, naltrexone, bupriopion, phentermine, and losartan, losartan with hydrochlorothiazide. Specific CB1 antagonists/inverse agonists of use in combination with a compound of the present invention include: those described in WO03/077847, including: N-[3-(4-chlorophenyl)-2(S)-phenyl-1(S)-methylpropyl]-2-(4-trifluoromethyl-2-pyrimidyloxy)-2-methylpropanamide, N-[3-(4-chlorophenyl)-2-(3-cyanophenyl)-1-methylpropyl]-2-(5-trifluoromethyl-2-pyridyloxy)-2-methylpropanamide, N-[3-(4-chlorophenyl)-2-(5-chloro-3-pyridyl)-1-methylpropyl]-2-(5-trifluoromethyl-2-pyridyloxy)-2-methylpropanamide, and pharmaceutically acceptable salts thereof; as well as those in WO05/000809, which includes the following: 3-{1-[bis(4-chlorophenyl)methyl]azetidin-3-ylidene}-3-(3,5-difluorophenyl)-2,2-dimethylpropanenitrile, 1-{1-[1-(4-chlorophenyl)pentyl]azetidin-3-yl}-1-(3,5-difluorophenyl)-2-methylpropan-2-ol. 3-((S)-(4-chlorophenyl){3-[(1S)-1-(3,5-difluorophenyl)-2-hydroxy-2-methylpropyl]azetidin-1-yl}methyl)benzonitrile, 3-((S)-(4-chlorophenyl){3-[(1S)-1-(3,5-difluorophenyl)-2-fluoro-2-methylpropyl]azetidin-1-yl)methyl)benzonitrile, 3-((4-chlorophenyl){3-[1-(3,5-difluorophenyl)-2,2-dimethylpropyl]azetidin-1-yl)methyl)benzonitrile, 3-((1S)-1-{1-[(S)-(3-cyanophenyl)(4-cyanophenyl)methyl]azetidin-3-yl}-2-methylpropyl)-5-fluorobenzonitrile, 3-[(S)-(4-chlorophenyl)(3-{(1S)-2-fluoro-1-[3-fluoro-5-(4H-1,2,4-triazol-4-yl)phenyl]-2-methylpropyl}azetidin-1-yl)methyl]benzonitrile, and 5-((4-chlorophenyl){3-[(1S)-1-(3,5-difluorophenyl)-2-fluoro-2-methylpropyl]azetidin-1-yl}methyl)thiophene-3-carbonitrile, and pharmaceutically acceptable salts thereof; as well as: 3-[(S)-(4-chlorophenyl)(3-{(1S)-2-fluoro-1-[3-fluoro-5-(5-oxo-4,5-dihydro-1,3,4-oxadiazol-2-yl)phenyl]-2-methylpropyl)azetidin-1-yl)methyl]benzonitrile, 3-[(S)-(4-chlorophenyl)(3-{(1S)-2-fluoro-1-[3-fluoro-5-(1,3,4-oxadiazol-2-yl)phenyl]-2-methylpropyl}azetidin-1-yl) methyl]benzonitrile, 3-[(S)-(3-{(1S)-1-[3-(5-amino-1,3,4-oxadiazol-2-yl)-5-fluorophenyl]-2-fluoro-2-methylpropyl}azetidin-1-yl)(4-chlorophenyl)methyl] benzonitrile, 3-[(S)-(4-cyanophenyl)(3-{(1S)-2-fluoro-1-[3-fluoro-5-(5-oxo-4,5-dihydro-1,3,4-oxadiazol-2-yl)phenyl]-2-methylpropyl}azetidin-1-yl)methyl]benzonitrile, 3-[(S)-(3-{(1S)-1-[3-(5-amino-1,3,4-oxadiazol-2-yl)-5-fluorophenyl]-2-fluoro-2-methylpropyl}azetidin-1-yl)(4-cyanophenyl)methyl]benzonitrile, 3-[(S)-(4-cyanophenyl)(3-{(1S)-2-fluoro-1-[3-fluoro-5-(1,3,4-oxadiazol-2-yl)phenyl]-2-methylpropyl)azetidin-1-yl)methyl]benzonitrile, 3-[(S)-(4-chlorophenyl)(3-{(1S)-2-fluoro-1-[3-fluoro-5-(1,2,4-oxadiazol-3-yl)phenyl]-2-methylpropyl}azetidin-1-yl) methyl]benzonitrile, 3-[(1S)-1-(1-{(S)-(4-cyanophenyl)[3-(1,2,4-oxadiazol-3-yl)phenyl]-methyl}azetidin-3-yl)-2-fluoro-2-methylpropyl]-5-fluorobenzonitrile, 5-(3-{1-[1-(diphenylmethyl)azetidin-3-yl]-2-fluoro-2-methylpropyl)-5-fluorophenyl)-1H-tetrazole, 5-(3-{1-[1-(diphenylmethyl)azetidin-3-yl]-2-fluoro-2-methylpropyl}-5-fluorophenyl)-1-methyl-1H-tetrazole, 5-(3-{1-[1-(diphenylmethyl)azetidin-3-yl]-2-fluoro-2-methylpropyl}-5-fluorophenyl)-2-methyl-2H-tetrazole, 3-[(4-chlorophenyl)(3-{2-fluoro-1-[3-fluoro-5-(2-methyl-2H-tetrazol-5-yl)phenyl]-2-methylpropyl}azetidin-1-yl)methyl]benzonitrile, 3-[(4-chlorophenyl)(3-{2-fluoro-1-[3-fluoro-5-(1-methyl-1H-tetrazol-5-yl)phenyl]-2-methylpropyl}azetidin-1-yl)methyl] benzonitrile, 3-[(4-cyanophenyl)(3-{2-fluoro-1-[3-fluoro-5-(1-methyl-1H-tetrazol-5-yl)phenyl]-2-methylpropyl}azetidin-1-yl)methyl]benzonitrile, 3-[(4-cyanophenyl)(3-{2-fluoro-1-[3-fluoro-5-(2-methyl-2H-tetrazol-5-yl)phenyl]-2-methylpropyl}azetidin-1-yl)methyl]benzonitrile, 5-{3-[(S)-{3-[(1S)-1-(3-bromo-5- fluorophenyl)-2-fluoro-2-methylpropyl]azetidin-1-yl}(4-chlorophenyl)methyl]phenyl}-1,3,4-oxadiazol-2(3H)-one, 3-[(1S)-1-(1-{(S)-(4-chlorophenyl)[3-(5-oxo-4,5-dihydro-1,3,4-oxadiazol-2-yl)phenyl]methyl}azetidin-3-yl)-2-fluoro-2-methylpropyl]-5-fluorobenzonitrile, 3-[(1S)-1-(1-{(S)-(4-cyanophenyl)[3-(5-oxo-4,5-dihydro-1,3,4-oxadiazol-2-yl)phenyl]methyl}azetidin-3-yl)-2-fluoro-2-methylpropyl]-5-fluorobenzonitrile, 3-[(1S)-1-(1-{(S)-(4-cyanophenyl)[3-(1,3,4-oxadiazol-2-yl)phenyl]methyl}azetidin-3-yl)-2-fluoro-2-methylpropyl]-5-fluorobenzonitrile, 3-[(1S)-1-(1-{(S)-(4-chlorophenyl)[3-(1,3,4-oxadiazol-2-yl)phenyl]methyl]azetidin-3-yl)-2-fluoro-2-methylpropyl]-5-fluorobenzonitrile, 3-((1S)-1-{1-[(S)-[3-(5-amino-1,3,4-oxadiazol-2-yl)phenyl](4-chlorophenyl)methyl]azetidin-3-yl}-2-fluoro-2-methylpropyl)-5-fluorobenzonitrile, 3-((1S)-1-{1-[(S)-[3-(5-amino-1,3,4-oxadiazol-2-yl)phenyl](4-cyanophenyl)methyl]azetidin-3-yl}-2-fluoro-2-methylpropyl)-5-fluorobenzonitrile, 3-[(1S)-1-(1-{(S)-(4-cyanophenyl)[3-(1,2,4-oxadiazol-3-yl)phenyl]methyl}azetidin-3-yl)-2-fluoro-2-methylpropyl]-5-fluorobenzonitrile, 3-[(1S)-1-(1-{(S)-(4-chlorophenyl)[3-(1,2,4-oxadiazol-3-yl)phenyl]methyl}azetidin-3-yl)-2-fluoro-2-methylpropyl]-5-fluorobenzonitrile, 5-[3((S)-(4-chlorophenyl){3-[(1S)-1-(3,5-difluorophenyl)-2-fluoro-2-methylpropyl]azetidin-1-yl}methyl)phenyl]-1,3,4-oxadiazol-2(3H)-one, 5-[3-((S)-(4-chlorophenyl){3-[(1S)-1-(3,5-difluorophenyl)-2-fluoro-2-methylpropyl]azetidin-1-yl}methyl)phenyl]-1,3,4-oxadiazol-2(3H)-one, 4-{(S)-{3-[(1S)-1-(3,5-difluorophenyl-2-fluoro-2-methylpropyl]azetidin-1-yl}[3-(5-oxo-4,5-dihydro-1,3,4-oxadiazol-2-yl)phenyl]methyl}-benzonitrile, and pharmaceutically acceptable salts thereof.

Specific NPY5 antagonists of use in combination with a compound of the present invention include: 3-oxo-N-(5-phenyl-2-pyrazinyl)-spiro[isobenzofuran-1(3H),4'-piperidine]-1'-carboxamide, 3-oxo-N-(7-trifluoromethylpyrido[3,2-b]pyridin-2-yl)spiro-[isobenzofuran-1(3H),4'-piperidine]-1'-carboxamide, N-[5-(3-fluorophenyl)-2-pyrimidinyl]-3-oxospiro-[isobenzofuran-1(3H),4'-piperidine]-1'-carboxamide, trans-3'-oxo-N-(5-phenyl-2-pyrimidinyl)spiro[cyclohexane-1,1'(3'H)-isobenzofuran]-4-carboxamide, trans-3'-oxo-N-[1-(3-quinolyl)-4-imidazolyl]spiro[cyclohexane-1,1'(3'H)-isobenzofuran]-4-carboxamide, trans-3-oxo-N-(5-phenyl-2-pyrazinyl)spiro[4-azaiso-benzofuran-1(3H),1'-cyclohexane]-4'-carboxamide, trans-N-[5-(3-fluorophenyl)-2-pyrimidinyl]-3-oxospiro[5-azaisobenzofuran-1(3H),1'-cyclohexane]-4'-carboxamide, trans-N-[5-(2-fluorophenyl)-2-pyrimidinyl]-3-oxospiro[5-azaisobenzofuran-1(3H),1'-cyclohexane]-4'-carboxamide, trans-N-[1-(3,5-difluorophenyl)-4-imidazolyl]-3-oxospiro[7-azaisobenzofuran-1(3H),1'-cyclohexane]-4'-carboxamide, trans-3-oxo-N-(1-phenyl-4-pyrazolyl)spiro[4-azaisobenzofuran-1(3H),1'-cyclohexane]-4'-carboxamide trans-N-[1-(2-fluorophenyl)-3-pyrazolyl]-3-oxospiro[6-azaisobenzofuran-1(3H),1'-cyclohexane]-4'-carboxamide, trans-3-oxo-N-(1-phenyl-3-pyrazolyl)spiro[6-azaisobenzofuran-1(3H),1'-cyclohexane]-4'-carboxamide, trans-3-oxo-N-(2-phenyl-1,2,3-triazol-4-yl)spiro[6-azaisobenzofuran-1(3H),1'-cyclohexane]-4'-carboxamide, and pharmaceutically acceptable salts and esters thereof.

Specific ACC-1/2 inhibitors of use in combination with a compound of the present invention include: 1'-[(4,8-dimethoxyquinolin-2-yl)carbonyl]-6-(1H-tetrazol-5-yl)spiro[chroman-2,4'-piperidin]-4-one; (5-{1'-[(4,8-dimethoxyquinolin-2-yl)carbonyl]-4-oxospiro[chroman-2,4'-piperidin]-6-yl}-2H-tetrazol-2-yl)methyl pivalate; 5-{1'-[(8-cyclopropyl-4-methoxyquinolin-2-yl)carbonyl]-4-oxospiro [chroman-2,4'-piperidin]-6-yl}nicotinic acid; 1'-(8-methoxy-4-morpholin-4-yl-2-naphthoyl)-6-(1H-tetrazol-5-yl)spiro[chroman-2,4'-piperidin]-4-one; and 1'-[(4-ethoxy-8-ethylquinolin-2-yl)carbonyl]-6-(1H-tetrazol-5-yl)spiro [chroman-2,4'-piperidin]-4-one; and pharmaceutically acceptable salts and esters thereof.

Specific MCH1R antagonist compounds of use in combination with a compound of the persent invention include: 1-{4-[(1-ethylazetidin-3-yl)oxy]phenyl}-4-[(4-fluorobenzyl)oxy]pyridin-2(1H)-one, 4-[(4-fluorobenzyl)oxy]-1-{4-[(1-isopropylazetidin-3-yl)oxy]phenyl}pyridin-2(1H)-one, 1-[4-(azetidin-3-yloxy)phenyl]-4-[(5-chloropyridin-2-yl)methoxy]pyridin-2(1H)-one, 4-[(5-chloropyridin-2-yl)methoxy]-1-{4-[(1-ethylazetidin-3-yl)oxy]phenyl}pyridin-2(1H)-one, 4-[(5-chloropyridin-2-yl)methoxy]-1-{4-[(1-propylazetidin-3-yl)oxy]phenyl}pyridin-2(1H)-one, and 4-[(5-chloropyridin-2-yl)methoxy]-1-(4-{[(2S)-1-ethylazetidin-2-yl]methoxy}phenyl)pyridin-2(1H)-one, or a pharmaceutically acceptable salt thereof.

Specific DP-IV inhibitors of use in combination with a compound of the present invention are selected from 7-[(3R)-3-amino-4-(2,4,5-trifluorophenyl)butanoyl]-3-(trifluoromethyl)-5,6,7,8-tetrahydro-1,2,4-triazolo[4,3-a]pyrazine. In particular, the compound of formula I is favorably combined with 7-[(3R)-3-amino-4-(2,4,5-trifluorophenyl)butanoyl]-3-(trifluoromethyl)-5,6,7,8-tetrahydro-1,2,4-triazolo[4,3-a] pyrazine, and pharmaceutically acceptable salts thereof.

Specific H3 (histamine H3) antagonists/inverse agonists of use in combination with a compound of the present invention include: those described in WO05/077905, including: 3-{4-[(1-cyclobutyl-4-piperidinyl)oxy]phenyl}-2-ethylpyrido[2,3-d]-pyrimidin-4(3H)-one, 3-{4-[(1-cyclobutyl-4-piperidinyl)oxy]phenyl}-2-methylpyrido[4,3-d]pyrimidin-4(3H)-one, 2-ethyl-3-(4-{3-[(3S)-3-methylpiperidin-1-yl] propoxy}phenyl)pyrido[2,3-d]pyrimidin-4(3H)-one 2-methyl-3-(4-{3-[(3S)-3-methylpiperidin-1-yl] propoxy}phenyl)pyrido[4,3-d]pyrimidin-4(3H)-one, 3-{4-[(1-cyclobutyl-4-piperidinyl)oxy]phenyl}-2,5-dimethyl-4(3H)-quinazolinone, 3-{4-[(1-cyclobutyl-4-piperidinyl)oxy] phenyl}-2-methyl-5-trifluoromethyl-4(3H)-quinazolinone, 3-{4-[(1-cyclobutyl-4-piperidinyl)oxy]phenyl}-5-methoxy-2-methyl-4(3H)-quinazolinone, 3-{4-[(1-cyclobutylpiperidin-4-yl)oxy]phenyl}-5-fluoro-2-methyl-4(3H)-quinazolinone, 3-{4-[(1-cyclobutylpiperidin-4-yl)oxy]phenyl}-7-fluoro-2-methyl-4(3H)-quinazolinone, 3-{4-[(1-cyclobutylpiperidin-4-yl)oxy]phenyl}-6-methoxy-2-methyl-4(3H)-quinazolinone, 3-{4-[(1-cyclobutylpiperidin-4-yl)oxy]phenyl}-6-fluoro-2-methyl-4(3H)-quinazolinone, 3-{4-[(1-cyclobutylpiperidin-4-yl)oxy]phenyl}-8-fluoro-2-methyl-4(3H)-quinazolinone, 3-{4-[(1-cyclopentyl-4-piperidinyl)oxy]phenyl}-2-methylpyrido[4,3-d]pyrimidin-4(3H)-one, 3-{4-[(1-cyclobutylpiperidin-4-yl)oxy]phenyl}-6-fluoro-2-methylpyrido[3,4-d]pyrimidin-4(3H)-one, 3-{4-[(1-cyclobutyl-4-piperidinyl)oxy]phenyl}-2-ethylpyrido[4,3-d]pyrimidin-4(3H)-one, 6-methoxy-2-methyl-3-{4-[3-(1-piperidinyl)propoxy]phenyl}pyrido[3,4-d]pyrimidin-4(3H)-one, 6-methoxy-2-methyl-3-{4-[3-(1-pyrrolidinyl)propoxy] phenyl}pyrido[3,4-d]pyrimidin-4(3H)-one, 2,5-dimethyl-3-{4-[3-(1-pyrrolidinyl)propoxy]phenyl}-4(3H)-quinazolinone, 2-methyl-3-{4-[3-(1-pyrrolidinyl)propoxy] phenyl}-5-trifluoromethyl-4(3H)-quinazolinone, 5-fluoro-2-methyl-3-{4-[3-(1-piperidinyl)propoxy]phenyl}-4(3H)-quinazolinone, 6-methoxy-2-methyl-3-{4-[3-(1-piperidinyl) propoxy]phenyl}-4(3H)-quinazolinone, 5-methoxy-2-methyl-3-(4-{3-[(3S)-3-methylpiperidin-1-yl] propoxy}phenyl)-4(3H)-quinazolinone, 7-methoxy-2-methyl-3-(4-{3-[(3S)-3-methylpiperidin-1-yl]

propoxy}phenyl)-4(3H)-quinazolinone, 2-methyl-3-(4-{3-[(3S)-3-methylpiperidin-1-yl]propoxy}phenyl)pyrido[2,3-d]pyrimidin-4(3H)-one, 5-fluoro-2-methyl-3-(4-{3-[(2R)-2-methylpyrrolidin-1-yl]propoxy}phenyl)-4(3H)-quinazolinone, 2-methyl-3-(4-{3-[(2R)-2-methylpyrrolidin-1-yl]propoxy}phenyl)pyrido[4,3-d]pyrimidin-4(3H)-one, 6-methoxy-2-methyl-3-(4-{3-[(2R)-2-methylpyrrolidin-1-yl]propoxy}phenyl)-4(3H)-quinazolinone, 6-methoxy-2-methyl-3-(4-{3-[(2S)-2-methylpyrrolidin-1-yl]propoxy}phenyl)-4(3H)-quinazolinone, and pharmaceutically acceptable salts thereof.

Specific CCK1R agonists of use in combination with a compound of the present invention include: 3-(4-{[1-(3-ethoxyphenyl)-2-(4-methylphenyl)-1H-imidazol-4-yl]carbonyl}-1-piperazinyl)-1-naphthoic acid; 3-(4-{[1-(3-ethoxyphenyl)-2-(2-fluoro-4-methylphenyl-1H-imidazol-4-yl]carbonyl}-1-piperazinyl)-1-naphthoic acid; 3-(4-{[1-(3-ethoxyphenyl)-2-(4-fluorophenyl)-1H-imidazol-4-yl]carbonyl}-1-piperazinyl)-1-naphthoic acid; 3-(4-{[1-(3-ethoxyphenyl)-2-(2,4-difluorophenyl)-1H-imidazol-4-yl]carbonyl}-1-piperazinyl)-1-naphthoic acid; and 3-(4-{[1-(2,3-dihydro-1,4-benzodioxin-6-yl)-2-(4-fluorophenyl)-1H-imidazol-4-yl]carbonyl}-1-piperazinyl)-1-naphthoic acid; and pharmaceutically acceptable salts thereof.

Specific MC4R agonists of use in combination with a compound of the present invention include: 1) (5S)-1'-{[(3R,4R)-1-tert-butyl-3-(2,3,4-trifluorophenyl)piperidin-4-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 2) (5R)-1'-{[(3R,4R)-1-tert-butyl-3-(2,3,4-trifluorophenyl)-piperidin-4-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 3) 2-(1'-{[(3S,4R)-1-tert-butyl-4-(2,4-difluorophenyl)pyrrolidin-3-yl]carbonyl}-3-chloro-2-methyl-5H-spiro[furo[3,4-b]pyridine-7,4'-piperidin]-5-yl)-2-methylpropanenitrile; 4) 1'-{[(3S,4R)-1-tert-butyl-4-(2,4-difluorophenyl)pyrrolidin-3-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 5) N-[(3R,4R)-3-({3-chloro-2-methyl-5-[1-methyl-1-(1-methyl-1H-1,2,4-triazol-5-yl)ethyl]-1'H,5H-spiro[furo-[3,4-b]pyridine-7,4'-piperidin]-1'-yl}carbonyl)-4-(2,4-difluorophenyl)-cyclopentyl]-N-methyltetrahydro-2H-pyran-4-amine; 6) 2-[3-chloro-1'-({(1R,2R)-2-(2,4-difluorophenyl)-4-[methyl(tetrahydro-2H-pyran-4-yl)amino]-cyclopentyl)-carbonyl)-2-methyl-5H-spiro[furo[3,4-b]pyridine-7,4'-piperidin]-5-yl]-2-methyl-propane-nitrile; and pharmaceutically acceptable salts thereof. Still further, neurokinin-1 (NK-1) receptor antagonists may be favorably employed with the BRS-3 receptor agonists of the present invention. NK-1 receptor antagonists of use in the present invention are fully described in the art. Specific neurokinin-1 receptor antagonists of use in the present invention include: (±)-(2R3R,2S3S)—N-{[2-cyclopropoxy-5-(trifluoromethoxy)-phenyl]methyl}-2-phenylpiperidin-3-amine; 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine; aperpitant; CJ17493; GW597599; GW679769; R673; RO67319; R1124; R1204; SSR146977;SSR240600; T-2328; and T2763; or a pharmaceutically acceptable salts thereof. Examples of other anti-obesity agents that can be employed in combination with a compound of formula I, II, III or IV are disclosed in "Patent focus on new anti-obesity agents," *Exp. Opin. Ther. Patents,* 10: 819-831 (2000); "Novel anti-obesity drugs," *Exp. Opin. Invest. Drugs,* 9: 1317-1326 (2000); and "Recent advances in feeding suppressing agents: potential therapeutic strategy for the treatment of obesity, *Exp. Opin. Ther. Patents,* 11: 1677-1692 (2001). The role of neuropeptide Y in obesity is discussed in *Exp. Opin. Invest. Drugs,* 9: 1327-1346 (2000). Cannabinoid receptor ligands are discussed in *Exp. Opin. Invest. Drugs,* 9: 1553-1571 (2000).

The instant invention also includes administration of a single pharmaceutical dosage formulation which contains both the BRS-3 ligand or agonist in combination with a second active ingredient, as well as administration of each active agent in its own separate pharmaceutical dosage formulation. Where separate dosage formulations are used, the individual components of the composition can be administered at essentially the same time, i.e., concurrently, or at separately staggered times, i.e. sequentially prior to or subsequent to the administration of the other component of the composition. The instant invention is therefore to be understood to include all such regimes of simultaneous or alternating treatment, and the terms "administration" and "administering" are to be interpreted accordingly. Administration in these various ways are suitable for the present compositions as long as the beneficial pharmaceutical effect of the combination of the BRS-3 ligand or agonist and the second active ingredient is realized by the patient at substantially the same time. Such beneficial effect is preferably achieved when the target blood level concentrations of each active ingredient are maintained at substantially the same time. It is preferred that the combination of the BRS-3 ligand or agonist and the second active ingredient be co-administered concurrently on a once-a-day dosing schedule; however, varying dosing schedules, such as the BRS-3 ligand or agonist once a day and the second active ingredient once, twice or more times per day or the BRS-3 ligand or agonist three times a day and the second active ingredient once, twice or more times per day, is also encompassed herein. A single oral dosage formulation comprised of both a BRS-3 ligand or agonist and a second active ingredient is preferred. A single dosage formulation will provide convenience for the patient, which is an important consideration especially for patients with diabetes or obese patients who may be in need of multiple medications.

The compounds in the combinations of the present invention may be administered separately, therefore the invention also relates to combining separate pharmaceutical compositions into a kit form. The kit, according to this invention, comprises two separate pharmaceutical compositions: a first unit dosage form comprising a prophylactically or therapeutically effective amount of the bombesin receptor subtype-3 agonist, or a pharmaceutically acceptable salt or ester thereof, and a pharmaceutically acceptable carrier or diluent in a first unit dosage form, and a second unit dosage form comprising a prophylactically or therapeutically effective amount of the second active ingredient or drug, or a pharmaceutically acceptable salt or ester thereof, and a pharmaceutically acceptable carrier or diluent in a second unit dosage form. In one embodiment, the kit further comprises a container. Such kits are especially suited for the delivery of solid oral forms such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days or time in the treatment schedule in which the dosages can be administered.

Another aspect of the present invention provides pharmaceutical compositions which comprise a compound of formula I, II, III or IV, as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of formula I, II, III and IV can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the typical oral dosage unit form, in which case solid pharmaceutical carriers are typically employed. If desired, tablets may be coated by standard aqueous or non-aqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil. Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I, II, III or IV may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

The compounds of formula I, II, III and IV of the present invention can be prepared according to the procedures of the following Schemes and Examples, using appropriate materials and are further exemplified by the following specific examples. Moreover, by utilizing the procedures described herein, one of ordinary skill in the art can readily prepare additional compounds of the present invention claimed herein. The compounds illustrated in the examples are not, however, to be construed as forming the only genus that is considered as the invention. The Examples further illustrate details for the preparation of the compounds of the present invention. Those skilled in the art will readily understand that known variations of the conditions and processes of the following preparative procedures can be used to prepare these compounds. The instant compounds are generally isolated in the form of their pharmaceutically acceptable salts, such as those described previously hereinabove. The free amine bases corresponding to the isolated salts can be generated by neutralization with a suitable base, such as aqueous sodium hydrogencarbonate, sodium carbonate, sodium hydroxide, and potassium hydroxide, and extraction of the liberated amine free base into an organic solvent followed by evaporation. The amine free base isolated in this manner can be further converted into another pharmaceutically acceptable salt by dissolution in an organic solvent followed by addition of the appropriate acid and subsequent evaporation, precipitation, or crystallization. All temperatures are degrees Celsius unless otherwise noted. Mass spectra (MS) were measured by electron-spray ion-mass spectroscopy.

The phrase "standard peptide coupling reaction conditions" means coupling a carboxylic acid with an amine using an acid activating agent such as EDC, DCC, and BOP in an inert solvent such as dichloromethane in the presence of a catalyst such as HOBT. The use of protecting groups for the amine and carboxylic acid functionalities to facilitate the desired reaction and minimize undesired reactions is well documented. Conditions required to remove protecting groups are found in standard textbooks such as Greene, T, and Wuts, P. G. M., *Protective Groups in Organic Synthesis,* John Wiley & Sons, Inc., New York, N.Y., 1991. CBZ and BOC are commonly used protecting groups in organic synthesis, and their removal conditions are known to those skilled in the art. For example, CBZ may be removed by catalytic hydrogenation in the presence of a noble metal or its oxide such as palladium on activated carbon in a protic solvent such as methanol or ethanol. In cases where catalytic hydrogenation is contraindicated due to the presence of other potentially reactive functionalities, removal of CBZ groups can also be achieved by treatment with a solution of hydrogen bromide in acetic acid or by treatment with a mixture of TFA and dimethylsulfide. Removal of BOC protecting groups is carried out with a strong acid, such as trifluoroacetic acid, hydrochloric acid, or hydrogen chloride gas, in a solvent such as methylene chloride, methanol, or ethyl acetate.

Reaction Scheme 1 illustrates the methods employed in the synthesis of the compounds of the present invention of formula I, II, III and IV. All substituents are as defined above unless indicated otherwise.

Scheme 1

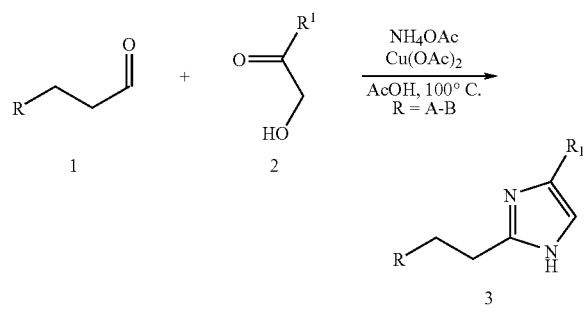

In Scheme 1, an appropriately substituted aldehyde 1 is heated up with hydroxyketone 2, ammonium acetate and copper acetate to afford the imidazole 3. Compounds of the present invention may be prepared by procedures illustrated in the accompanying scheme, intermediates and examples. In order to illustrate the invention, the following examples are included. These examples do not limit the invention. They are only meant to suggest a method of reducing the invention to practice. Those skilled in the art may find other methods of practicing the invention which are readily apparent to them. However, those methods are also deemed to be within the scope of this invention.

The LC/MS analyses were preformed using a MICROMASS ZMD mass spectrometer coupled to an AGILENT 1100Series HPLC utilizing a YMC ODS-A 4.6×50 mm column eluting at 2.5 mL/min with a solvent gradient of 10 to 95% B over 4.5 min, followed by 0.5 min at 95% B: solvent A=0.06% TFA in water; solvent B=0.05% TFA in acetonitrile. $^1$H-NMR spectra were obtained on a 500 MHz VARIAN Spectrometer in CDCl$_3$ or CD$_3$OD as indicated and chemical shifts are reported as δ using the solvent peak as reference and coupling constants are reported in hertz (Hz).

Abbreviations used in the following Schemes, Intermediates, and Examples are: Ac is acetate; aq. is aqueous; API-ES is atmospheric pressure ionization-electrospray (mass spectrum term); BOC (Boc) is t-butyloxycarbonyl, Bn is benzyl, n-Bu is butyl, calc. or calc'd is Calculated, celite is Celite™ diatomaceous earth, CBZ (Cbz) is benzyloxycarbonyl; cat. is catalytic; DCC is dicyclohexylcarbodiimide, DMA is diisopropyl-ethylamine, DEAD is diethyl azodicarboxylate; DIBAL-H is di-isobutyl aluminum hydride; DMAP is dimethylamino pyridine; DME is ethylene glycol dimethyl ether; DMF is dimethylformamide; DMSO is dimethylsulfoxide; dppf is 1,1'-bis(diphenylphosphino)ferrocene; EDC is 1-ethyl-3-(3-dimethylaminopropyl)-carbodiimide hydrochloride; ES-MS and ESI-MS are electron spray ion-mass spectroscopy, Et is ethyl, EPA is ethylene polyacrylamide (a plastic); eq is equivalent; Et$_2$O is diethyl ether; EtOAc is ethyl acetate; g is gram(s); h or hr is hours; Hex is hexane; HOAT is 1-hydroxy-7-azabenzotriazole; HOBt is 1-hydroxybenzotriazole; HPLC is high pressure liquid chromatography; HPLC/MS is high pressure liquid chromatography/mass spectrum; in vacuo is rotoevaporation; IPAC is isopropyl acetate; KHMDS is potassium hexamethyldisilazide; L is liter; LAH is lithium aluminum hydride; LC is Liquid chromatography; LCMS or LC-MASS is liquid chromatography mass spectrum; LDA is lithium diisopropylamide, M is molar; Me is methyl; MeOH is methanol, MF is molecular formula, MW is molecular weight; min is minutes; mg is milligram(s); mL is milliliter, MeOH is methanol; min is minute(s); mmol is millimole; MS or ms is mass spectrum; MTBE is tert-butyl methyl ether, NaHMDS is sodium hexamethyl disilazide, N is normal; NaHMDS is sodium hexamethyldisilazide; NMM is N-Methylmorpholine, NMO is N-Methylmorpholine-N-oxide; NaOtBu is sodium tert-butoxide, NMR is nuclear magnetic resonance; OTf is trifluoromethanesulfonyl, PCC is pyridinium chlorochromate; PE is petroleum ether; Pd(OAc)$_2$ is palladium acetate; Pd$_2$(dba)$_3$ is tris(dibenzylideneacetone) dipalladium (0); psi is pound per square inch; PyBOP is (benzotriazol-1-yloxy)tripyrrolidino-phosphonium hexafluorophosphate; R$_t$ is retention time; rt or RT is room temperature; SEMCl is trimethylsilylethoxy methyl chloride; TBAF is tetrabutyl ammonium fluoride; TEA or Et$_3$N is triethylamine; TFA is trifluoroacetic acid; TEMPO is 2,2,6,6-tetramethyl-1-piperidinyloxy free radical; Tf$_2$O is triflic anhydride; THF is tetrahydrofuran; TLC is thin layer chromatography; TMS is trimethyl silyl; TosMIC or TOSMIC is tosylmethylisonitrile; and wt % is weight percent.

Intermediate 1

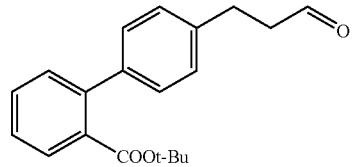

tert-Butyl 4'-(3-oxopropyl)biphenyl-2-carboxylate

Step A: To a suspension of lithium aluminum hydride (2.39 g, 62.9 mmol) in diethyl ether (100 mL) at 0° C. was added 3-(4-bromophenyl)propionic acid (9.59 g, 41.9 mmol) in THF (100 mL). After stirring at rt for 2 h, the reaction mixture was cooled to 0° C. and H$_2$O (2.5 mL), NaOH (15% aq., 2.5 mL), H$_2$O (5 mL), Et$_2$O (200 mL), hexane (50 ml), and anhydrous Na$_2$SO$_4$ were added sequentially. The suspension was stirred at it for 1 h and was filtered, and the filtrate was concentrated to afford 3-(4-bromophenyl)-propanol.

Step B: A mixture of 3-(4-bromophenyl)propanol (8.15 g, 37.9 mmol), potassium acetate (11.2 g, 113.7 mmol), bis (pinacolato)diboron (10.6 g, 41.7 mmol), dimethyl sulfoxide (150 mL) and 1,1'-bis(diphenyl-phosphino) ferrocene-palladium dichloride dichloromethane complex (1:1) (1.55 g, 1.89 mmol) was heated at 80° C. under nitrogen overnight. Upon cooling, the reaction mixture was poured into water (~300 mL), and the product was extracted with Et$_2$O-hexanes (1:1) (3×300 mL). The combined organic extracts were washed with water (~300 mL), brine, dried (Na$_2$SO$_4$) and concentrated to afford 3-[4-(4,4,5,5-tetramethyl-1,3,2-dioxaborolan-2-yl)phenyl]propanol, which was used without further purification.

Step C: A mixture of 3-[4-(4,4,5,5-tetramethyl-1,3,2-dioxaborolan-2-yl)phenyl]propanol (37.9 mmol), tert-butyl 2-iodobenzoate (11.5 g, 37.9 mmol), sodium carbonate (10 g, 94.8 mmol), 1,1'-bis(diphenylphosphino)ferrocene-palladium dichloride dichloromethane complex (1:1), DMF (170 mL) and water (22 mL) was heated at 80° C. under nitrogen overnight. The reaction mixture was cooled to RT, poured into water, and the product was extracted with EtOAc-Hexanes (1:1). The combined organic extracts were washed with water and brine, dried (Na$_2$SO$_4$) and concentrated, and the residue was purified on silica gel (Hexane/EtOAc, from 2/1 to 1/1) to afford tert-butyl 4'-(3-hydroxypropyl)biphenyl-2-carboxylate.

Step D: To a solution of tert-butyl 4'-(3-hydroxypropyl) biphenyl-2-carboxylate (7.00 g, 22.4 mmol) in CH$_2$Cl$_2$ (200 mL) at 0° C. was added trichloroisocyanuric acid (5.47 g, 23.5 mmol) and 2,2,6,6-tetramethyl-1-piperidinyloxy free radical (35 mg, 0.224 mmol). After stirring at it for 20 min, the reaction mixture was diluted with Et$_2$O (200 mL) and filtered through a silica gel pad, rinsing with Et$_2$O (400 mL). The filtrate was concentrated, and the residue was purified by silica gel column chromatography (5-75% EtOAc in Hexanes) to afford the title compound.

Intermediate 2

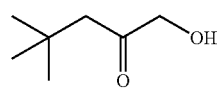

4,4-Dimethyl-1-hydroxypentan-2-one

To a mixture of 4,4-dimethyl-1-pentene (10 g), acetone (600 mL), water (140 mL) and acetic acid (13.5 mL) at rt was added a solution of potassium permanganate (22.3 g) in water (85 mL), followed by additional acetone (270 mL). After stirring for 40 min, sodium nitrite (11.7 g) was added, followed by dilute sulfuric acid (12%, 221 mL). The product was extracted with ether:hexanes (1:1), and the extracts were washed with saturated sodium bicarbonate and brine, dried (sodium sulfate) and concentrated. The resulting residue was purified on silica gel column (5-100% ether in hexanes) to give the title compound.

Intermediate 3

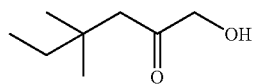

4,4-Dimethyl-1-hydroxyhexan-2-one

The title compound was prepared following the same procedure described for intermediate 2 and replacing 4,4-dimethyl-1-pentene with 4,4-dimethyl-1-hexene.

Intermediate 4

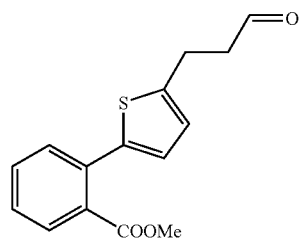

Methyl 2-[5-(3-oxopropyl)-2-thienyl]benzoate

The title compound was prepared following a procedure analogous to the one described for Intermediate 1 by substituting 3-(4-bromophenyl)propionic acid with 3-(5-bromo-2-thienyl)propionic acid.

Intermediate 5

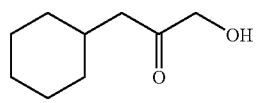

3-Cyclohexyl-1-hydroxypropan-2-one

The title compound was prepared following the same procedure described for intermediate 2 and replacing 4,4-dimethyl-1-pentene with allylcyclohexane.

Intermediate 6

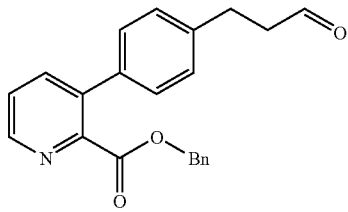

Benzyl 3-[4-(3-oxopropyl)phenyl]pyridine-2-carboxylate

Step A: Benzyl 3-[4-(3-hydroxypropyl)phenyl]pyridine-2-carboxylate was prepared following the procedure described for intermediate 1 (Step A to C) replacing tert-butyl 2-iodobenzoate with benzyl 3-bromopicolinic ester. The product was purified by flash column chromatography on silica gel eluting with 10 to 40% ethyl acetate in hexanes.

Step B: To 3-[4-(3-hydroxypropyl)phenyl]pyridine-2-carboxylate (245 mg, 0.704 mmol) in dichloromethane (3 ml) and pyridine (357 uL, 3.52 mmol) was added a solution of Dess-Martin periodinane (358 mg, 0.845 mmol) in dichloromethane (3 mL). After stirring at rt for 30 min, the reaction was quenched by addition of a mixture of 15% Na$_2$S$_2$O$_3$ (2 mL) and saturated NaHCO$_3$ (3 mL). The organic layer was separated and the aqueous layer was extracted by ethyl acetate (3×). The combined extracts were washed with water and brine, dried over MgSO$_4$, filtered and concentrated, and the residue was purified by flash column chromatography on silica gel eluting 10-50% ethyl acetate in hexanes) to afford the title compound. LC-MS: m/e 346 (M+H)$^+$. $^1$HNMR (CDCl$_3$, 500 MHz): δ 9.86 (1H, t, J=1.5 Hz), 8.68 (1H, dd, J=4.5, 1.7 Hz), 7.76 (1H, dd, J=8.0, 1.7 Hz), 7.48 (1H, dd, J=8.0, 4.5 Hz), 7.30 (3H, m), 7.26 (2H, d, J=8.0 Hz), 7.19 (2H, d, J=8.0 Hz), 7.14 (2H, dd, J=7.5, 2.0 Hz), 5.22 (2H, s), 3.00 (2H, t, J=7.5 Hz), 2.82 (2H, t, 7.5 Hz).

Intermediate 7

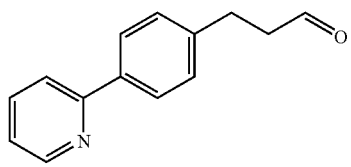

3-(4-Pyridin-2-ylphenyl)propanal

A mixture of 4-(2-pyridyl)benzaldehyde (6.0 g, 32.8 mmol), (1,3-dioxolan-2-ylmethyl)triphenylphosphonium bromide (18.3 g, 42.6 mmol), tris[2-(2-methoxyethoxy)ethyl]amine (13.76 g, 42.6 mmol), dichloromethane (200 mL) and saturated potassium carbonate (200 mL) was heated to reflux overnight. The reaction was cooled to rt and the product was extracted with ethyl acetate-hexanes (2×). The extracts were washed with water and brine, and concentrated to afford 2-{4-[2-(1,3-dioxolan-2-yl)vinyl]-phenyl)pyridine, which was dissolved in methanol (120 mL) and was stirred with Pd on carbon (10%, 1.75 g) under 1 atmosphere of hydrogen overnight. The reaction mixture was filtered through Celite, and the filtrate was concentrated to afford crude 2-{4-[2-(1,3-dioxolan-2-yl)ethyl]phenyl}pyridine, which was dissolved in acetone (80 mL) and treated with 4 M HCl (aq., 80 mL). After stirring at rt for 20 h, the product was extracted with ethyl acetate-hexanes (2×). The extracts were washed with water and brine, and concentrated, and the residue was purified on silica gel eluted with a 5-100% ethyl acetate in hexanes to afford the title compound.

Intermediate 8

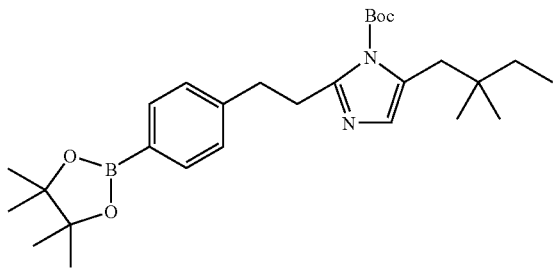

tert-Butyl 5-(2,2-dimethylbutyl)-2-{2-[4-(4,4,5,5-tetramethyl-1,3,2-dioxaborolan-2-yl)phenyl]ethyl}-1H-imidazole-1-carboxylate Step A: A mixture of 4-bromoiodobenzene (19.43 g, 68.7 mmol), ally alcohol (9.33 mL, 137.4 mmol), Pd(OAc)$_2$ (308 mg, 1.37 mmol), tetrabutylammonium chloride (21.0 g, 75.6 mmol), sodium bicarbonate (17.32 g, 206.2 mmol) and DMF (150 mL) was degassed and filled with nitrogen (repeated three times). Then the reaction mixture was stirred at 40° C. for 15 h. After cooling to rt, the reaction mixture was partitioned between water (250 mL) and ether (300 mL). The organic layer was separated and the aqueous layer was extracted with ether (3×). The extracts were washed with water (2×), brine, dried over MgSO$_4$, filtered and concentrated, and the residue was purified by flash column chromatography on silica gel (5-15% ethyl acetate in hexanes) to afford 3-(4-bromophenyl)propan-1-al.

Step B: A mixture of 3-(4-bromophenyl)propan-1-al (7.8 g, 36 mmol) 1-hydroxy-4,4-dimethylhexan-2-one (intermediate 3, 10 g, 718 mmol), Cu(OAc)$_2$ (14 g, 75 mmol), ammonium acetate (14 g, 178 mmol) and acetic acid (100 mL) was heated at 100° C. for 40 min. The volatiles were removed, and the residue was partitioned between water (200 mL) and ethyl acetate (250 mL). The organic layer was separated, and the aqueous layer was extracted with ethyl acetate (3×). The extracts were washed by water (2×), brine, dried over MgSO$_4$, filtered and concentrated, and the residue was purified by flash column chromatography on silica gel eluting with 50% ethyl acetate in hexanes to 10% MeOH/0.5% ammonium hydroxide in dichloromethane to afford 2-{2-(4-bromophenyl)ethyl}-5-(2,2-dimethylbutyl)1H-imidazole. LC-MS: m/e 335 (M+H)$^+$.

Step C: To a solution of 2-{2-(4-bromophenyl)ethyl}-5-(2,2-dimethylbutyl)1H-imidazole (4.36 g, 13.0 mmol), triethylamine (5.0 mL, 39.0 mmol) and 4-dimethylaminopyridine (50 mg, 0.4 mmol) in dichloromethane (30 mL) was added Boc anhydride. After stirring at rt for 15 h, the reaction mixture was diluted with ethyl acetate (100 mL) and washed with water (2×), brine, dried over MgSO$_4$, filtered and concentrated. The resulting residue was purified by flash column chromatography on silica gel eluting with 5-15% ethyl acetate in hexanes to afford t-butyl 2-[2-(4-bromophenyl)ethyl]-5-(2,2-dimethylbutyl)-1H-imidazole-1-carboxylate. LC-MS: m/e 435 (M+H)$^+$.

Step D: A mixture of t-butyl 2-[2-(4-bromophenyl)ethyl]-5-(2,2-dimethylbutyl)-1H-imidazole-1-carboxylate (4.54 g, 10.43 mmol), bis(pinacolate)diboron (3.44 g, 13.57 mmol), 1,1'-bis(diphenylphosphino)ferrocene-palladium dichloride dichoromethane complex (1:1) (255 mg, 0.313 mmol), potassium acetate (3.07 g, 31.29 mmol) and DMSO (40 mL) was degassed and refilled with nitrogen (repeated 3×), and the mixture was stirred at 80° C. for 4 hours. After cooling to rt, the reaction mixture was diluted with water (50 mL), and the product was extracted with ether (3×100 mL). The extracts were washed with water (2×50 mL), brine, dried over MgSO$_4$, filtered and concentrated, and the residue was purified by flash column chromatography on silica gel eluting with 5-40% ethyl acetate in hexanes to afford the title compound. LC-MS: m/e 483 (M+H)$^+$. $^1$HNMR (CDCl$_3$, 500 MHz): δ 7.73 (2H, d, J=8 Hz), 7.26 (7.5 Hz), 6.99 (1H, s), 3.31 (2H, t, 8.0 Hz), 3.07 (2H, t, J =8.0 Hz), 2.39 (2H, s), 1.60 (9H, s), 1.35 (12H, s), 1.27 (2H, q, J=7.5 Hz), 0.89 (3H, t, J=7.5 Hz), 0.88 (6H, s).

Intermediate 9

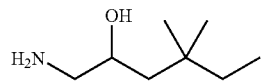

1-Amino-4,4-dimethylhexan-2-ol

Step A: To a stirred solution of 4,4-dimethylhex-1-ene (49.5 g, 442 mmol) in methylene chloride (1 L) at 0° C. was added m-CPBA (120 g, 535 mmol), and the reaction was stirred at rt for 16 h. The reaction mixture was filtered through Celite and the filtrate was washed with saturated sodium hydrogen sulfite (1×1 L), saturated sodium carbonate (2×1 L), dried over sodium sulfate and concentrated to give 2-(2, 2-dimethylbutyl)oxirane, which was dissolved in methanol (400 mL). To this solution was added sodium azide (22.8 g, 351 mmol), ammonium chloride (18.8 g, 351 mmol) and water (100 mL). After heating at 80° C. overnight, the volatiles were removed and the residue was partitioned between water (300 mL) and ethyl acetate (300 mL). The organic layer was separated, dried over sodium sulfate and concentrated, and the residue was purified by passing through a silica gel pad (13 cm×10 cm) eluted with 1:9 ethyl acetate/hexanes to provide 1-azido-4,4-dimethylhexan-2-ol. $^1$H NMR (500 MHz, CDCl$_3$) δ 3.88 (m, 1H), 3.29 (dd, J=12.2 Hz, J=3.7 Hz, 1H), 3.23 (dd, J=12.2 Hz, J=7.7 Hz, 1H), 1.90 (d, J=4.5 Hz, 1H), 1.40 (dd, J=14.7 Hz, J=8.2 Hz, 1H), 1.28 (m, 3H), 0.93 (m, 3H), 0.90 (s, 3H), 0.83 (t, J=7.5 Hz, 3H).

Step B: A mixture of 1-azido-4,4-dimethylhexan-2-ol (54.8 g, 320 mmol), 5% Pd/C (4 g) and ethanol (500 mL) were stirred under hydrogen (40 psi) for 2 days. The reaction mixture was filtered through Celite and the filtrate was concentrated to provide the title compound. $^1$H NMR (500 MHz, CDCl$_3$) δ 3.61 (m, 1H), 2.77 (dd, J=12.5 Hz, J=3.4 Hz, 1H), 2.49 (dd, J=12.5 Hz, J=8.9 Hz, 1H), 2.00 (brs, 2H), 1.30 (m, 3H), 1.24 (dd, J=14.5 Hz, J=2.6 Hz, 1H), 0.92 (s, 3H), 0.90 (s, 3H), 0.83 (t, J=7.5 Hz, 3H).

Intermediate 10

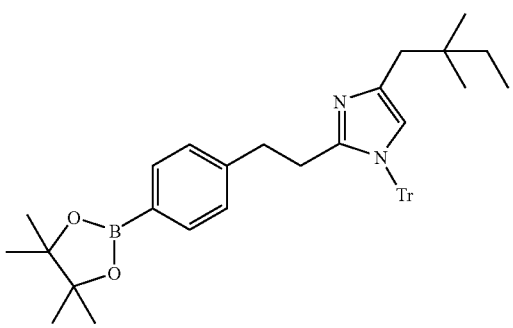

4-(2,2-Dimethylbutyl)-1-trityl-2-{2-[4-(4,4,5,5-tetramethyl-[1,3,2]dioxaborolan-2-yl)phenyl]ethyl}-1H-imidazole Step A: To a vigorously stirred mixture of intermediate 9 (33.2 g, 229 mmol), methylene chloride (500 mL) and saturated sodium bicarbonate (500 mL) was added 3-(4-bromophenyl)propionyl chloride (51.5 g, 208 mmol) in methylene chloride (400 mL) over 20 min. Another batch of saturated sodium bicarbonate (500 mL) was added and the stirring continued for 2 h. The organic layer was separated, dried over sodium sulfate and concentrated to provide 3-(4-bromophenyl)-N-(2-hydroxy-4,4-dimethylhexyl)propionamide, which was used without further purification.

Step B: To a stirred solution of 3-(4-bromophenyl)-N-(2-hydroxy-4,4-dimethylhexyl)propionamide (71.9 g, 202 mmol) in methylene chloride (1 L) was added Dess-Martin periodinane (100 g, 226 mmol). After 1.5 h, saturated sodium bicarbonate (500 mL) and saturated sodium thiosulfate (500 mL) were added and the mixture was stirred for another 10 minutes. The organic layer was separated and treated with another batch of saturated sodium bicarbonate (500 mL) and saturated sodium thiosulfate (500 mL). The organic layer was separated, dried over sodium sulfate, and concentrated to provide 3-(4-bromophenyl)-N-(4,4-dimethyl-2-oxohexyl)propionamide, which was used without further purification.

Step C: A mixture of 3-(4-bromophenyl)-N-(4,4-dimethyl-2-oxohexyl)propionamide (71.5 g, 202 mmol), ammonium acetate (770 g, 10 mol) and acetic acid (700 mL) was heated at 160° C. for 20 h. Upon cooling, the reaction mixture was poured onto ice (600 mL), and the pH was adjusted to ~10 with concentrated ammonium hydroxide. The product was extracted with ethyl acetate, and the extracts were dried over sodium sulfate and concentrated to provide 2-[2-(4-bromophenyl)ethyl]-4-(2,2-dimethylbutyl)-1H-imidazole, which was used without purification.

Step D: To a solution of 2-[2-(4-bromophenyl)ethyl]-4-(2,2-dimethylbutyl)-1H-imidazole (33.4 g, 100 mmol) in methylene chloride (500 mL) was added trityl chloride (41.8 g, 150 mmol) and triethylamine (42 mL, 300 mmol). The reaction was stirred for 2 h, then washed with water, dried over sodium sulfate and concentrated to give a residue. The residue was purified by silica gel column chromatography eluting with ethyl acetate/hexanes (2:8). The chromatography was repeated eluting with methylene chloride/2-propanol 99.8:0.02) and then methylene chloride/methanol (95:5) to provide 2-[2-(4-bromophenyl)ethyl]-4-(2,2-dimethylbutyl)-1-trityl-1H-imidazole.

Step E: A mixture of 2-[2-(4-bromophenyl)ethyl]-4-(2,2-dimethylbutyl)-1-trityl-1H-imidazole (3.81 g, 6.60 mmol), dry DMSO (50 mL), bis-pinacolatodiboron (1.84 g, 7.26 mmol) and potassium acetate (1.94 g, 19.8 mmol) was flushed with a nitrogen stream while warming up to 80° C. Then Pd(dppf)Cl$_2$ (0.27 g, 0.33 mmol) was added and the reaction was stirred at 80° C. under nitrogen for 10 h. Upon cooling, the mixture was poured into water (200 mL), and the precipitate was collected by filtration and purified by passing through a silica gel plug (4.5 cm×4.5 cm) eluting with ethyl acetate:hexanes (1:1) to provide the title compound. $^1$H NMR (300 MHz, CDCl$_3$) δ 7.57 (d, J=8.0 Hz, 2H), 7.29 (m, 9H), 7.11 (m, 6H), 6.78 (d, J=8.0 Hz, 2H), 6.32 (s, 1H), 2.41 (m, 4H), 2.24 (m, 2H), 1.25 (m, 14H), 0.83 (m, 9H).

Intermediate 11

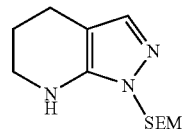

1-(2-Trimethylsilanylethoxymethyl)-4,5,6,7-tetrahydro-1H-pyrazolo[3,4-b]pyridine To a solution of 1H-pyrazolo[3,4-b]pyridine (380 mg, 3.2 mmol) in DMF (5 mL) was added NaH (60% dispersion in mineral oil, 153 mg, 3.8 mmol). After stirring for 20 min, the mixture was heated with a heat gun and then allowed to cool to rt. SEM-Cl (647 μL, 3.8 mmol) was added dropwise and stirring continued for 2 h. The resulting mixture was partitioned between water and ethyl acetate. The organic layer was separated and concentrated, and the residue was purified by flash column chromatography (silica gel, eluting with 0-50% ethyl acetate in hexanes) to provide 1-(2-trimethylsilanylethoxymethyl)-1H-pyrazolo[3,4-b]pyridine, which was dissolved in ethanol (30 mL) and flushed with a nitrogen stream. Palladium on charcoal (5% wet on carbon, ~50 mg) was added and the mixture was placed under hydrogen (50 psi) for 2 days. The reaction mixture was filtered, and the filtrate was concentrated to provide the title compound: $^1$H NMR (500 MHz, CDCl$_3$) δ 7.13 (s, 1H), 5.24 (s, 2H), 3.68 (br, 1H), 3.54 (t, J=8.2 Hz, 2H), 3.28 (m, 2H), 2.51 (t, J=6.1, 2H), 1.81 (m, 2H), 0.89 (t, J=8.2 Hz, 2H), −0.01 (s, 9H).

Intermediate 12

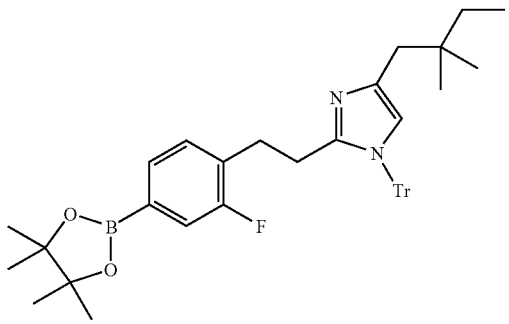

4-(2,2-Dimethylbutyl)-2-{2-[2-fluoro-4-(4,4,5,5-tetramethyl-[1,3,2]dioxaborolan-2-yl)phenyl]ethyl}-1-trityl-1H-imidazole The title compound was prepared following the procedure described for intermediate 10 by substituting 3-(4-bromophenyl)propionyl chloride with 3-(4-bromo-2-fluorophenyl)propionyl chloride. ¹H NMR (300 MHz, CDCl₃) δ 7.27-7.31 (m, 11H), 7.07-7.12 (m, 6H), 6.81 (t, J=7.2 Hz, 1H), 6.32 (s, 1H), 2.59 (t, J=7.9 Hz, 2H), 2.39 (s, 2H), 2.20 (t, J=7.9 Hz, 2H), 1.22-1.35 (m, 14H), 0.82-0.87 (m, 9H); LC-MS: m/e 643 (M+H).

Intermediate 13

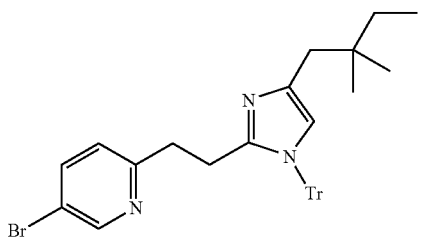

5-Bromo-2-{2-[4-(2,2-dimethylpropyl)-1-trityl-1H-imidazol-2-yl]ethyl}pyridine

Step A: A mixture of 3-(5-bromopyridin-2-yl)propan-1-ol (2.07 g, 9.60 mmol, *J. Org. Chem.* 1988, 53, 386), sodium bromide (195 mg, 1.90 mmol), TEMPO (30 mg, 0.20 mmol), and trichloroisocyanuric acid (4.46 g, 19.2 mmol), acetone (90 mL) and 15% sodium bicarbonate (30 mL) was stirred at 0° C. for 15 minutes and rt for 4 h. The reaction was quenched with isopropanol (6 mL), and the resulting mixture was filtered through Celite. The filtrate was concentrated, and the resulting residue was partitioned between water (100 mL) and ethyl acetate (125 mL) with the pH of the aqueous layer adjusted to 7 with 1N HCl. The organic layer was separated and the aqueous layer extracted with ethyl acetate (3×125 mL). The extracts were concentrated and the residue was purified by flash column chromatography on silica gel eluting with 0-20% CH₃OH in CH₂Cl₂ to give 3-(5-bromopyridin-2-yl)propionic acid. Step B: A solution of 3-(5-bromopyridin-2-yl)propionic acid (1.28 g, 5.56 mmol), intermediate 9 (887 mg, 6.12 mmol), EDC (1.61 g, 8.35 mmol), HOBt (1.13 g, 8.35 mmol) and diisopropylethylamine (4.1 mL, 23.4 mmol) in DMF (30 mL) was stirred at rt for 4 hours. The reaction mixture was diluted with water (50 mL) and extracted with ethyl acetate (3×75 mL). The extracts were washed with 5% lithium chloride (2×75 mL), dried over sodium sulfate and concentrated. The resulting residue was purified by flash column chromatography (silica gel, eluting with 0% to 5% methanol in methylene chloride) to give 3-(5-bromopyridin-2-yl)-N-(2-hydroxy-4,4-dimethylhexyl)propionamide.

Step C: 3-(5-Bromopyridin-2-yl)-N-(2-hydroxy-4,4-dimethylhexyl)propionamide was converted to the title compound following the procedure analogous to that described for intermediate 10, Step B-D. The final product was purified by flash column chromatography (silica gel, eluting with 0-3% methanol in methylene chloride). ¹H NMR (500 MHz, CDCl₃) δ 8.42 (s, 1H) 7.52 (d, J=8.3 Hz, 1H), 7.31-7.23 (m, 9H), 7.10-7.05 (m, 6H), 6.83 (d, J=8.3 Hz, 1H), 6.35 (s, 1H), 2.69 (t, J=7.5 Hz, 2H), 2.35 (s, 2H), 2.28 (t, J=7.6 Hz, 2H), 1.26-1.21 (m, 2H), 0.85-0.81 (m, 9H); LC-MS: m/e 578 (M+H).

Intermediate 14

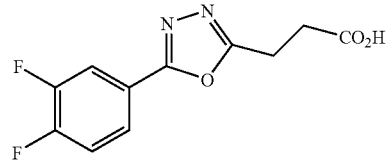

3-[5-(3,4-Difluorophenyl)-[1,3,4]oxadiazol-2-yl] propionic acid

Step A: To a vigorously stirred suspension of N-(3,4-difluorobenzoyl)hydrazide (880 mg, 5.6 mmol) in ethyl acetate (20 mL) and saturated sodium bicarbonate (20 mL) was added ethyl succinyl chloride (0.8 mL, 5.6 mmol). After 2 h, the organic phase was separated and concentrated, and the residue was purified by flash column chromatography on silica gel eluting with 0-100 ethyl acetate in hexanes to provide 4-[N'-(3,4-difluorobenzoyl)hydrazino]-4-oxo-butyric acid ethyl ester.

Step B: To a solution of 4-[N'-(3,4-difluorobenzoyl)hydrazino]-4-oxo-butyric acid ethyl ester (590 mg, 1.96 mmol) and pyridine (474 µL, 5.88 mmol) in methylene chloride (25 mL) at −78° C. was added dropwise triflic anhydride (397 µL, 2.35 mmol) and the reaction was allowed to warm up to rt overnight. The reaction mixture was diluted with methylene chloride (100 mL), washed with 0.1 M HCl and brine, dried over sodium sulfate and concentrated to provide 3-[5-(3,4-difluorophenyl)-[1,3,4]oxadiazol-2-yl]propionic acid ethyl ester. ¹H NMR (300 MHz, CDCl₃) δ 7.89-7.77 (m, 2H), 7.31 (m, 1H), 4.19 (q, J=7.1 Hz, 2H), 3.24 (t, J=7.2 Hz, 2H), 2.92 (t, J=7.4 Hz, 2H), 1.27 (t, J=7.1 Hz, 3H).

Step C: 3-[5-(3,4-Difluorophenypl)-[1,3,4]oxadiazol-2-yl]propionic acid ethyl ester (520 mg, 1.8 mmol) was hydrolyzed with lithium hydroxide monohydrate to provide the title compound. LC-MS: m/e 255 (M+H).

Intermediate 15

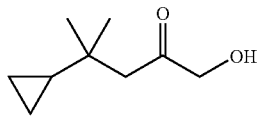

4-Cyclopropyl-1-hydroxy-4-methylpentan-2-one

Step A: To a suspension of copper(I) iodide (7.61 g, 40.0 mmol) in THF (50 mL) at −50° C. was added cyclopropylmagnesium bromide (160 mL, 80.0 mmol, 0.5 M in THF) under nitrogen. After stirring for 15 minutes, the suspension was allowed to warm up and stirred at rt for 20 min before cooling back to −50° C. A solution of diethyl isopropylidenemalonate (4.0 g, 20.0 mmol) in THF (50 mL) was added, and the reaction was allowed to warm to rt over 3 h. The reaction mixture was then quenched with saturated sodium bicarbonate (200 mL), and filtered through Celite. The filtrate was extracted with ethyl acetate (3×250 mL). The combined extracts were dried over sodium sulfate and concentrated, and the resulting residue was purified by silica gel chromatography eluting with diethyl ether/hexanes (1:10) to afford 2-(1-cyclopropyl-1-methylethyl)malonic acid diethyl ester.

Step B: A mixture of 2-(1-cyclopropyl-1-methylethyl)malonic acid diethyl ester (5.10 g, 21.2 mmol), lithium chloride (1.79 g, 42.2 mmol), water (0.5 mL) and DMSO (40 mL) was heated at 170° C. for 24 h, and then poured into ice-water. The product was extracted with ethyl acetate (3×200 mL), and the extracts were washed with brine (200 mL), dried over sodium sulfate and concentrated to give 3-cyclopropyl-3-methylbutyric acid ethyl ester, which was used without further purification.

Step C: A mixture of 3-cyclopropyl-3-methylbutyric acid ethyl ester (3.0 g, 17.6 mmol) and lithium hydroxide monohydrate (3.5 g, 105 mmol) in THF/$H_2O$/MeOH (24 mL, 2:1:1 v/v) was stirred at rt overnight. The reaction mixture was diluted with water (100 mL), and washed with ethyl acetate (2×50 mL). The aqueous layer was acidified with 2M HCl and extracted with ethyl acetate (3×100 mL). The combined organic extracts were washed with brine (200 mL), dried over sodium sulfate and concentrated to give 3-cyclopropyl-3-methylbutyric acid.

Step D: To a solution of 3-cyclopropyl-3-methylbutyric acid (1.50 g, 10.6 mmol) and DMF (2 drops) in methylene chloride (50 mL) under nitrogen at it was added oxalyl chloride (2.0 g, 15.8 mmol). After stirring for 2 h, the reaction was concentrated to give the acid chloride, which was mixed with tris(trimethylsilyloxy)ethylene (6.42 g, 21.9 mmol) and heated at 95° C. for 4 h under nitrogen. After cooling to rt, dioxane (5 mL) and 1N HCl (2 mL) were added. The resulting mixture was heated at 95° C. for 30 minutes, and then quenched by pouring into saturated sodium bicarbonate/ice-water (50 mL). The product was extracted with ethyl acetate (3×50 mL), and the extracts were dried over sodium sulfate and concentrated. Purification of the residue by silica gel chromatography eluting with diethyl ether/hexanes (2:3) provided the title compound. $^1$H NMR (300 MHz, $CDCl_3$) δ 4.11 (s, 2H), 3.06 (bs, 1H), 2.35 (s, 2H), 0.88 (s, 6H), 0.72-0.82 (m, 1H), 0.29-0.35 (m, 2H), 0.19-0.27 (m, 2H).

Intermediate 16

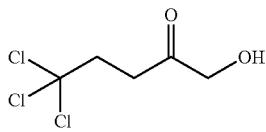

5,5,5-Trichloro-1-hydroxypentan-2-one

The title compound was prepared from 4,4,4-trichlorobutanoic acid following the procedure described for Step D of Intermediate 15. The crude product was purified by flash column chromatography (silica gel, eluting with 0-50% diethyl ether/hexanes) to give the title compound. NMR (500 MHz, $CDCl_3$) δ 4.35 (s, 2H), 3.12-3.09 (m, 2H), 2.97-2.95 (m, 1H), 2.93-2.90 (m, 2H).

Intermediate 17

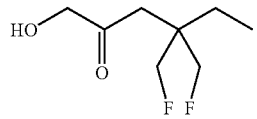

4,4-Bis(fluoromethyl)-1-hydroxyhexan-2-one

Step A: To a stirred solution of diethyl ethylmalonate (43.0 mL, 0.228 mol) in THF (500 mL) at 0° C. was added sodium hydride (60%; 9.2 g, 0.228 mol) in portions. The mixture was warmed to rt and stirred at rt for 75 min, and was added allyl bromide (23.9 mL, 0.275 mol). The reaction was stirred at rt for 4 h, and then cooled to 0° C. and quenched with water (400 mL) and 6 N hydrochloric acid (80 mL). The product was extracted with diethyl ether (4×200 mL), and the extracts were washed with brine (2×200 mL), dried over sulfate and concentrated. The residue was distilled to give 2-allyl-2-ethylmalonic acid diethyl ester (b.p. 89-91° C./ca. 2 mm Hg).

Step B: To a stirred suspension of lithium aluminum hydride (7.8 g, 0.20 mol) in THF (350 mL) was added 2-allyl-2-ethylmalonic acid diethyl ester (23.5 g, 0.10 mol) in THF (150 mL) over 2 h. After stirring at rt for 2 days, the reaction was carefully quenched with dilute sulfuric acid (7%, 250 mL). The product was extracted with diethyl ether (3×100 mL) and ethyl acetate (3×100 mL), and the combined extracts were washed with brine (300 mL), dried over sodium sulfate and concentrated to give 2-allyl-2-ethylpropane-1,3-diol.

Step C: To a stirred solution ofp-toluenesulfonyl choride (58.4 g, 0.32 mmol) in pyridine (90 mL) at 0° C. was added 2-allyl-2-ethylpropane-1,3-diol (14.7 g, 0.10 mol) in pyridine (40 mL). After stirring at 0° C. for 2 h and at rt overnight, the reaction mixture was poured onto ice (300 g) and the product was extracted with diethyl ether (4×200 mL). The extracts were washed successively with 1 N hydrochloric acid (150 mL), 1 N sodium bicarbonate (150 mL), and water (2×150 mL), dried over sulfate and concentrated to give a residue. The resulting residue was purified flash column chromatography on silica gel eluting with 0-50% ethyl acetate in hexanes to give toluene-4-sulfonic acid 2-ethyl-2-(toluene-4-sulfonyloxy)methylpent-4-enyl ester.

Step D: A mixture of toluene-4-sulfonic acid 2-ethyl-2-(toluene-4-sulfonyloxy)methylpent-4-enyl ester (44.2 g, 97 mmol) and 1 M tetrabutylammonium fluoride in THF (390 mL, 0.39 mol) was stirred at rt for 2 days and at reflux for 7 hours. Additional tetrabutylammonium fluoride in THF (110 mL, 0.12 mol) was added, and reflux continued for 6 days. The reaction mixture was diluted with hexanes (1 L) and passed through a silica gel plug. The filtrate was distilled under vacuum to provide 4,4-bis(fluoro-methyphex-1-ene.

Step E: To a stirred solution of 4,4-bis(fluoromethyl)hex-1-ene (9.1 g, 62 mmol) in acetone (360 mL)/water (120 mL) at rt was added osmium tetroxide (155 mg, 0.62 mmol) and potassium periodate (29.7 g; 129 mmol) (the latter in portions). After stirring for 15 h, the reaction mixture was diluted with diethyl ether (180 mL). The organic layer was separated, and the aqueous layer was extracted with diethyl ether (3×180 mL). The extracts were washed with saturated sodium thiosulfate (250 mL) and brine (250 mL), dried over sodium sulfate and concentrated to give a residue. The resulting residue was distilled under vacuum to provide 3,3-bis(fluoromethyl)pentanal.

Step F: A mixture of 3,3-bis(fluoromethyl)pentanal (6.8 g, 45 mmol) and Oxone® (27.9 g, 45 mmol) in N,N-dimethylformamide (120 mL) was stirred at rt for 4 h. The reaction was quenched with 2N hydrochloric acid (200 mL) and extracted with ethyl acetate (4×100 mL). The extracts were washed with 2 N hydrochloric acid (150 mL) and 5% aqueous lithium chloride (150 mL), dried over sodium sulfate and concentrated to give 3,3-bis(fluoromethyl)pentanoic acid.

Step G: 3,3-Bis(fluoromethyl)pentanoic acid was converted to the title compound following the procedure described for Intermediate 15, Step D. $^1$H NMR (500 MHz, CDCl$_3$) δ 4.43 (dqd, J=47.0, 9.2, 1.4 Hz, 4H), 4.24 (s, 2H), 2.44 (s, 2H), 1.56 (q, J=7.6 Hz, 2H), 0.91 (t, J=7.6 Hz, 3H).

Intermediate 18

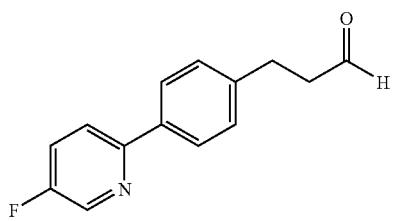

3-[4-(5-Fluoropyridin-2-yl)phenyl]propionaldehyde

The title compound was prepared following the procedure described for intermediate 1 substituting tert-butyl 2-iodobenzoate with 2-bromo-5-fluropyridine. $^1$H NMR (500 MHz, CDCl$_3$) δ 9.83 (s, 1H), 8.52 (d, J=2.9 Hz, 1H), 7.86 (d, J=8.2 Hz, 2H), 7.67-7.70 (m, 1H), 7.42-7.46 (m, 1H), 7.29 (d, J=8.2 Hz, 2H), 3.0 (t, J=7.6 Hz, 2H), 2.82 (t, J=7.3 Hz, 2H).

Intermediate 19

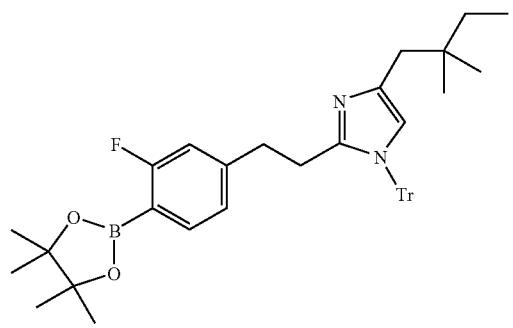

4-(2,2-Dimethylbutyl)-2-{2-[3-fluoro-4-(4,4,5,5-tetramethyl-[1,3,2]dioxaborolan-2-yl)phenyl]ethyl)-1-trityl-1H-imidazole Step A: 2-[2-(4-Bromo-3-fluorophenyl)ethyl]-5-(2,2-dimethylbutyl)-1H-imidazole was prepared following the procedure described for intermediate 8, Step A-B by substituting 4-bromoiodobenzene with 1-bromo-2-fluoro-4-iodobenene. The product was purified by flash column chromatography on silica gel column eluting with methylene chloride/methanol/ammonium hydroxide (200:10:1).

Step B: 2-[2-(4-Bromo-3-fluorophenyl)ethyl]-5-(2,2-dimethylbutyl)-1H-imidazole was converted to the title compound following the procedure described for intermediate 10, Step D-E. $^1$H NMR (300 MHz, CDCl$_3$) δ 7.29-7.32 (m, 9H), 7.05-7.13 (m, 6H), 6.75 (ddd, J=13.6 Hz, 6.0 Hz, 1.8 Hz, 1H), 6.61 (d, J=7.6 Hz, 1H), 6.44 (t, J=0.5 Hz, 1H), 6.33 (s, 1H), 2.46 (s, 2H), 2.39 (t, J=7.0 Hz, 2H), 2.21 (t, J=7.1 Hz, 2H), 1.22-1.35 (m, 14H), 0.82-0.88 (m, 9H); LC-MS: m/e 643 (M+H).

Intermediate 20

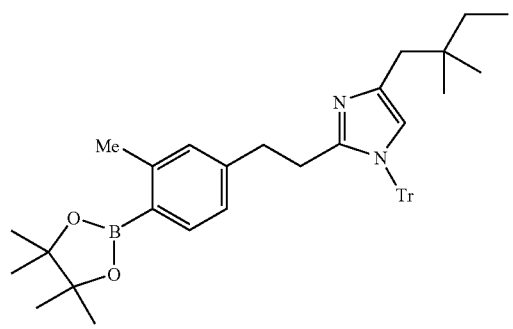

4-(2,2-Dimethylbul)-2-{2-[3-methyl-4-(4,4,5,5-tetramethyl-[1,3,2]dioxaborolan-2-yl)phenyl]ethyl}-1-trityl-1H-imidazole The title compound was prepared following the procedure described for intermediate 19 by substituting 1-bromo-2-fluoro-4-iodobenene with 1-bromo-2-methyl-4-iodobenene. $^1$H NMR (300 MHz, CDCl$_3$) δ 7.60-7.20 (m, 10H), 7.18-7.10 (m, 6H), 6.50-6.60 (m, 1H), 6.40-6.43 (m, 1H), 6.26-6.31 (m, 1H), 2.62 (s, 2H), 2.50-2.42 (m, 4H), 2.25 (s, 3H), 1.28-1.19 (m, 14H), 0.90-0.80 (m, 9H).

Intermediate 21

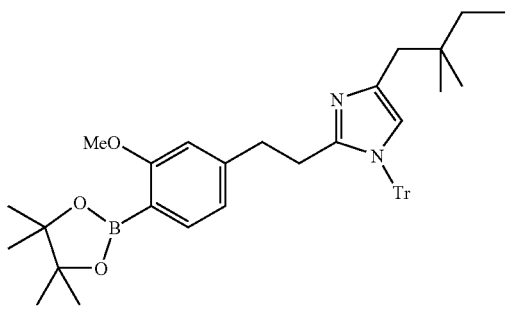

4-(2,2-Dimethylbutyl)-2-{2-[3-methoxy-4-(4,4,5,5-tetramethyl-[1,3,2]dioxaborolan-2-yl)phenyl]ethyl}-1-trityl-1H-imidazole The title compound was prepared following the procedure described for intermediate 19 by substituting 1-bromo-2-fluoro-4-iodobenene with 1-bromo-2-methoxy-4-iodobenene. LC-MS: m/e 655 (M+H).

Intermediate 22

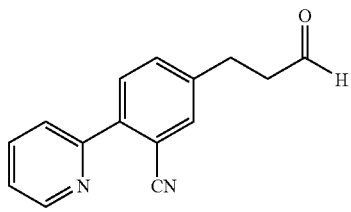

5-(3-Oxopropyl)-2-pyridin-2-ylbenzonitrile

Step A: A mixture of Pd(PPh$_3$)$_4$ (116 mg, 0.1 mmol), 3-cyano-4-bromonitrobenzene (558 mg, 2.0 mmol) and pyridine-2-zinc bromide (0.5 M solution in THF, 8 mL, 4 mmol) in THF (5 mL) was stirred at rt under nitrogen for 3 h. An additional batch of Pd(PPh$_3$)$_4$ and pyridine-2-zinc bromide were added, and the reaction was heated at 80° C. fo 6 h. The reaction was quenched by pouring into a saturated aqueous ammonium chloride, and the product was extracted with methylene chloride. The organic extracts were washed with brine, dried over sodium sulfate and concentrated to give a residue, which was purified by flash column chromatography on silica gel eluting with 0-33% ethyl acetate in hexanes to provide 5-nitro-2-pyridin-2-ylbenzonitrile.

Step B: A mixture of 5-nitro-2-pyridin-2-ylbenzonitrile (370 mg, 1.69 mmol), iron powder (473 mg, 8.45 mmol), ammonium chloride (99 mg, 1.86 mmol), ethanol (20 mL) and water (10 mL) was heated at reflux for 1 h. Upon cooling, the reaction mixture was filtered through Celite, rinsed with ethyl acetate, and the filtrate was concentrated. The resulting residue was purified by flash column chromatography on silica gel eluting with 0-50% ethyl acetate hexanes to provide 5-amino-2-pyridin-2-ylbenzonitrile.

Step C: Dinitrogen tetroxide (2.2 equiv.) was added to a suspension of 5-amino-2-pyridin-2-ylbenzonitrile (0.85 mmol) in acetonitrile (8.5 mL) at −30° C. After 5 min, sodium iodide (1.28 mmol, 1.5 equiv.), and the mixture was stirred for 10 minutes. Water (10 mL) was added and the reaction was allowed to warm to room temperature over 30 min. The product was extracted with methylene chloride and the extracts were washed with saturated sodium thiosulfate solution and brine, dried over sodium sulfate and concentrated. The resulting residue was passed through a silica gel plug, rinsing with 2% methanol in methylene chloride to provide 5-iodo-2-pyridin-2-ylbenzonitrile, which was used without further purification.

Step D: 5-Iodo-2-pyridin-2-ylbenzonitrile was converted to the title compound following the procedure described for intermediate 8, Step A. The crude product was purified by flash column chromatography on silica gel eluting with 0-50% ethyl acetate in hexanes to give the title compound. $^1$H NMR (300 MHz, CDCl$_3$) δ 9.84 (s, 1H), 8.77-8.75 (d, J=4.8 Hz, 1H), 7.90-7.75 (m, 3H), 7.64 (s, 1H), 7.55-7.53 (d, J=8.1 Hz, 1H), 7.37-7.33 (m, 1H), 3.06-3.02 (t, J=7.4 Hz, 2H), 2.89-2.84 (t, J=7.2 Hz, 2H).

Intermediate 23

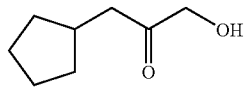

3-Cyclopentyl-1-hydroxypropan-2-one

The title compound was prepared following the same procedure described for intermediate 2 by substituting 4,4-dimethyl-1-pentene with allylcyclopentane.

Intermediate 24

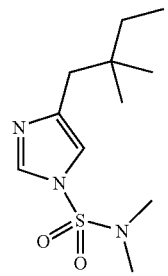

4-(2,2-Dimethylbutyl)-N,N-dimethyl-1H-imidazole-1-sulfonamide

Step A: 2-Methyl-2-butanol (480 mL, 4.4 mol) and vinylidene chloride (508 mL, 5.2 mol) were added to sulfuric acid (2 L) at 10° C. Methanol (1750 mL) was added slowly allowing exotherm to attain 40-60° C. for 15 minutes. The reaction mixture was cooled and poured into a stirred mixture of ether and ice water. The ethereal layer was washed with 1 N aqueous sodium hydroxide and brine, dried (magnesium sulfate), filtered, and concentrated in vacuo to afford methyl 3,3-dimethylpentanoate, which was without further purification.

Step B: DIBAL-H (1 M in methylene chloride) (2.41 L, 2.4 mol) was added to a −50° C. solution of methyl 3,3-dimethylpentanoate (172 g, 1.2 mol) in methylene chloride (1 L). After stirring at 0° C. for 30 minutes the reaction mixture was poured into saturated aqueous sodium potassium tartrate (3 L) and the product was extracted with methylene chloride. The combined extracts were washed with brine, dried over magnesium sulfate, filtered and concentrated in vacuo to afford 3,3-dimethylpentan-1-ol, which was used without further purification.

Step C: Celite (200 g) and pyridinium chlorochromate (500 g, 2.3 mol) were added to a solution of 3,3-dimethylpentan-1-ol (1.2 mol) in methylene chloride (1.2 L). After stirring at 30° C. for 1 h, the reaction mixture was filtered through a plug of silica gel eluting with methylene chloride. The filtrate was washed with water, saturated aqueous sodium bicarbonate, and brine, dried over magnesium sulfate, filtered and concentrated to afford 3,3-dimethylpentanal, which was used without further purification.

Step D: Toluenesulfonylmethyl isocyanide (154 g, 0.9 mol) was added to a saturated solution of ammonia in methanol (7 L). After stirring at rt for 1 h, 3,3-dimethylpentanal (0.6 mol) was added over 20 min. After stirring at reflux for 3 h, the reaction mixture was poured into cold 1 N hydrochloric acid and washed with hexane. The aqueous layer was basified with 10 N aqueous sodium hydroxide and extracted with ether. The combined extracts were washed with brine, dried (magnesium sulfate), filtered and concentrated in vacuo. Chromatography over silica gel eluting with 5-10% methanol/methylene chloride afforded 4-(2,2-dimethylbutyl)-1H-imidazole.

Step E: N-Methylmorpholine (54 mL, 0.48 mol) was added to a solution of 4-(2,2-dimethylbutyl)-1H-imidazole (36 g, 0.24 mol) in dimethoxyethane (360 mL). After warming to 40° C., N,N-dimethylsulfamoyl chloride (38 mL, 0.36 mol) was added over 15 min. After stirring at 40° C. for 2 h, N-methylmorpholine (11 mL) and N,N-dimethylsulfamoyl chloride (8 mL) were added. After stirring for additional 2 h, the reaction mixture was cooled and filtered rinsing with ether. The filtrate was extracted with ether and the combined extracts were washed with brine, dried (magnesium sulfate), filtered, concentrated in vacuo. Chromatography over silica gel afforded the title compound.

Intermediate 25

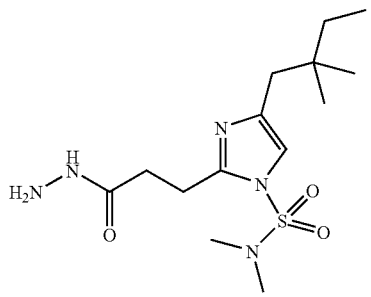

4-(2,2-Dimethylbutyl)-2-(3-hydrazino-3-oxopropyl)-N,N-dimethyl-1H-imidazole-1-sulfonamide Step A: n-Butyllithium (1.6 M in hexanes) (12 mL, 19.2 mmol) was added to a solution of intermediate 24 (4.53 g, 17.5 mmoL) in THF (40 mL) at −78° C. over 30 min. After stirring at −78° C. for 1 hr, DMF (2.7 mL, 34.9 m mol) was added. After stirring at −78° C. for 2 hr, the reaction mixture was allowed to warm to rt overnight and the volatiles were removed in vacuo. The residue was dissolved in ether (100 mL) and washed with water (50 mL), dried over sodium sulfate and concentrated in vacuo to give a residue. Chromatography of the residue over silica gel eluting with 0-60% ethyl acetate/hexane afforded 4-(2,2-dimethylbutyl)-2-formyl-N,N-dimethyl-1H -imidazole-1-sulfonamide.

Step B: Trimethyl phosphonoacetate (1 mL, 7.0 mmol) was added to a suspension of lithium chloride (354 mg, 8.4 mmol) in THF (6 mL). After stirring at rt for 5 minutes, triethylamine (1.1 mL, 8 mmol) was added, and stirring was continued for 10 min before the dropwise addition of 4-(2,2-dimethylbutyl)-2-formyl-N,N-dimethyl-1H -imidazole-1-sulfonamide (2 g, 7.0 mmol) in THF (1 mL). After stirring at rt overnight, the reaction mixture was diluted with ethyl acetate and washed with water and brine, dried over sodium sulfate and concentrated in vacuo to afford methyl 3-[1-(dimethylamino)sulfonyl]-4-(2,2-dimethylbutyl)-1H-imidazol-2-yl]acrylate, was used without further purification.

Step C: A suspension of Pd (10 wt % on carbon) in a solution of methyl 3-[1-[(dimethylamino)sulfonyl]-4-(2,2-dimethylbutyl)-1H-imidazol-2-yl]acrylate (2.39 g, 7 mmol) in methanol (75 mL) was stirred under an atmosphere of hydrogen overnight. The reaction mixture was filtered through Celite and concentrated in vacuo. Chromatography of the residue over silica gel eluting with 0-60% ethyl acetate/hexane afforded methyl 3-[1-[(dimethylarnino)sulfonyl]-4-(2,2-dimethylbutyl)-1H-imidazol-2-yl]propanoate.

Step D: Hydrazine (0.45 mL, 14.5 mmol) was added to a solution of methyl 3-[1-[(dimethyl-amino)sulfonyl]-4-(2,2-dimethylbutyl)-1H-imidazol-2-yl]propanoate (1 g, 2.9 mmol) in dry methanol (2 mL). After stirring at rt for 3 hr, volatiles were removed in vacuo, and chromatography of the resulting residue over silica eluting with 0-40% ethyl acetate/hexane afforded the title compound.

Intermediate 26

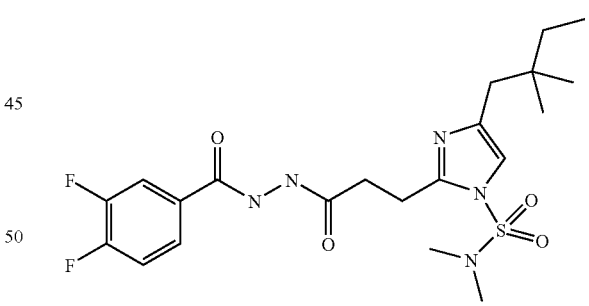

2-{3-[2-(3,4-Difluorobenzoyl)hydrazino]-3-oxopropyl}-4-(2,2-dimethylbutyl)-N,N-dimethyl-1H-imidazole-1-sulfonamide 3,4-Difluorobenzoyl chloride (0.11 mL, 0.86 mmol) was added to a solution of intermediate 25 (269 mg, 0.78 mmol) and sodium bicarbonate (72 mg, 0.86 mmol) in THF/water (1:1) (12 mL) at rt. After stirring at rt for 3 hr, the reaction mixture was concentrated and partitioned between ethyl acetate and brine. The aqueous phase was extracted with ethyl acetate, and the combined extracts were dried (sodium sulfate) and concentrated in vacuo. Chromatography of the residue over silica gel eluting with 80-100% ethyl acetate/hexane afforded the title compound.

Intermediate 27

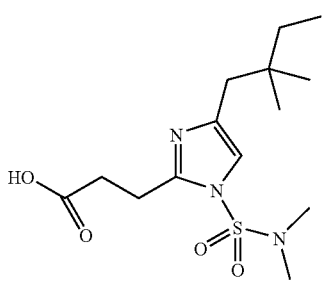

3-[1-[(dimethylamino)sulfonyl]-4-(2,2-dimethylbutyl)-1H-imidazol-2-yl]propanoic acid A solution of lithium hydroxide monohydrate (182 mg, 4.3 mmol) in water (1.5 mL) was added to a solution of methyl 3-[1-[(dimethylamino)sulfonyl]-4-(2,2-dimethylbutyl)-1H-imidazol-2-yl]propanoate (for synthesis see intermediate 25) (500 mg, 1.4 mmol) in methanol (1.6 mL) and THF (1.6 mL). After stirring at rt overnight, the reaction mixture was concentrated and 2M hydrochloric acid was added. The resulting reaction mixture was concentrated to dryness to afford the title compound, which was used without further purification.

Intermediate 28

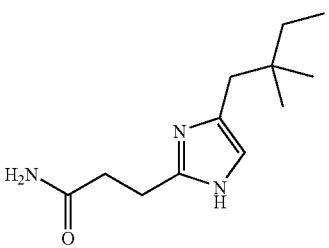

3-[4-(2,2-Dimethylbutyl)-1H-imidazol-2-yl]propanamide

Step A: Oxalyl chloride (0.42 mL, 4.8 mmol) followed by DMF (0.02 mL) were added to a suspension of intermediate 27 (1.4 mL, 4.3 mmol) in methylene chloride (15 mL) at 0° C. After stirring at rt overnight, the volatiles were removed in vacuo, followed by azeotroping with toluene to afford 3-[4-(2,2-dimethylbutyl)-1H-imidazol-2-yl]propanoyl chloride, which was used without further purification.

Step B: 3-[4-(2,2-dimethylbutyl)-1H-imidazol-2-yl]propanoyl chloride in methylene chloride (0.3 M) (7.8 mL, 2.3 mmol) was added to a rapidly stirred solution of concentrated aqueous ammonium hydroxide (2.5 mL) at 0° C. After stirring at rt for 1 h, the volatiles were removed to afford the title compound, which was used without further purification.

EXAMPLE 1

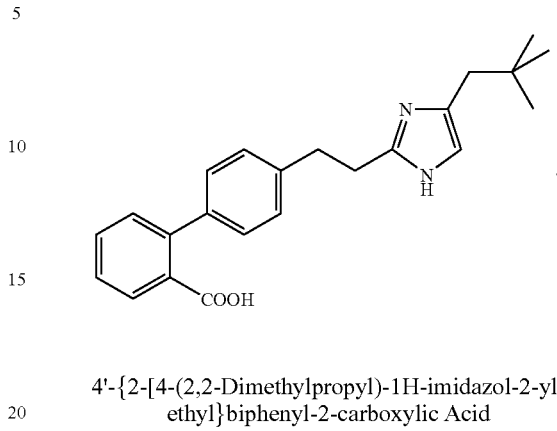

4'-{2-[4-(2,2-Dimethylpropyl)-1H-imidazol-2-yl]ethyl}biphenyl-2-carboxylic Acid

A mixture of intermediate 1 (923 mg, 7.1 mmol), intermediate 2 (2.0 g, 6.45 mmol), copper (II) acetate (2.58 g, 14.2 mmol), ammonium acetate (24.8 g, 323 mmol) and acetic acid (50 mL) was heated at 100° C. for 40 min. After cooling to rt, the reaction mixture was poured into ammonium hydroxide and ice, and the product was extracted with EtOAc-Hexanes (2×). The extracts were washed with brine, dried ($Na_2SO_4$) and concentrated, and the residue was purified by silica gel column chromatography (5% acetone in hexanes to 100% acetone) to give 4'-{2-[4-(2,2-dimethylpropyl)-1H-imidazol-2-yl]ethyl}biphenyl-2-carboxylic acid tert-butyl ester, which was treated with TFA (3 mL) at rt overnight. After concentration, the resulting residue was purified with reverse phase HPLC to afford the title compound. LCMS: m/e 363.2 $(M+H)^+$. $^1H$ NMR (500 MHz, $CD_3OD$): δ 7.79 (1H, d, J=7.6 Hz), 7.51 (1H, t, J=7.6 Hz), 7.39 (1H, t, J=7.5 Hz), 7.29 (1H, d, J=7.5 Hz), 7.24 (2H, d, J=8.0 Hz), 7.11 (2H, d, J=8.0 Hz), 7.04 (1H, s), 3.23 (2H, t, J=7.4 Hz), 3.08 (2H, t, J=7.3 Hz), 1.30 (9H, s).

EXAMPLE 2

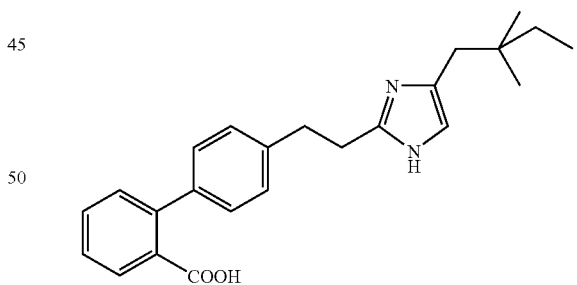

4'-{2-[4-(2,2'-Dimethylbutyl)-1H-imidazol-2-yl]ethyl}biphenyl-2-carboxylic Acid

The title compound was prepared from intermediate 1 and intermediate 3 following the same procedure described for Example 1. LCMS: m/e 377.2 $(M+H)^+$. $^1H$ NMR (500 MHz, $CD_3OD$): δ 7.79 (1H, d, J=7.8 Hz), 7.54 (1H, t, J=7.6 Hz), 7.43 (1H, t, J=7.7 Hz), 7.31 (1H, d, J=7.6 Hz), 7.25 (2H, m), 7.13 (3H, m), 3.27 (2H, t, J=7.3 Hz), 3.12 (2H, t, J=7.2 Hz), 2.51 (2H, s), 1.24 (2H, q, J=7.6 Hz), 0.88 (3H, t, J=7.4 Hz), 0.85 (6H, s).

The compounds in Table 1 were prepared from intermediate 1 and appropriate hydroxyketones following procedures described for Example 1. The hydroxyketones were prepared following procedures similar to those described for intermediate 2 or those described in the literature (eg. *Synthesis*, 1979, 520; *Bull. Chem. Soc. Jpn.*, 1997, 70, 2561; *J. Org. Chem.* 1979, 44, 4617; *J. Org. Chem.* 1998, 63, 8100; *J. Org. Chem.* 1990, 55, 4853; *J. Org. Chem.* 1999, 64, 8267; *Tetrahedron Lett.* 1981, 607; *Tetrahedron Lett.* 1980, 71; *Tetrahedron Lett.* 1993, 4485.)

TABLE 1

| Example | R₁ | R₂ | LCMS: found m/e (M + H) |
|---|---|---|---|
| 3. | 3-chlorobenzyl | H | 417.1 |
| 4. | 2-methylbenzyl | H | 397.4 |
| 5. | 4-chlorobenzyl | H | 417.3 |
| 6. | 2-chlorobenzyl | H | 417.1 |
| 7. | 4-methylbenzyl | H | 397.4 |
| 8. | 3-methylbenzyl | H | 397.4 |
| 9. | 3-cyanobenzyl | H | 408.3 |
| 10. | 2-cyanobenzyl | H | 408.3 |
| 11. | 4-methoxybenzyl | H | 413.4 |
| 12. | pentafluorobenzyl | H | 473.3 |
| 13. | isobutyl | H | 349.5 |
| 14. | 3,4-methylenedioxybenzyl | H | 427.3 |
| 15. | 2,3-dimethylbenzyl | H | 411.2 |
| 16. | 2-isopropylbenzyl | H | 425.2 |
| 17. | cyclopentylmethyl | H | 361.3 |

TABLE 1-continued

[Structure: biphenyl with ethyl-imidazole (R1, R2) and COOH]

| Example | R₁ | R₂ | LCMS: found m/e (M + H) |
|---|---|---|---|
| 18. | cyclooctyl-CH(Me)- | H | 403.4 |
| 19. | 3,3-diethylpentyl-type | H | 391.4 |
| 20. | 5-methylhexyl-type | H | 377.3 |
| 21. | CH₂C(Me)₂C(O)OMe | H | 407.7 |
| 22. | n-Bu | Me | 363.16 |
| 23. | —CH₂Ph | H | 383.11 |
| 24. | —CH₂CH₂Ph | H | 397.10 |
| 25. | 4-methylpentyl-type | H | 363.18 |
| 26. | cyclopentylmethyl-type | H | 375.17 |
| 27. | cyclohexylmethyl-type | H | 389.21 |
| 28. | 3-methylpentyl-type | H | 363.13 |
| 29. | 1-methoxycyclohexylmethyl-type | H | 419.20 |

TABLE 1-continued

[Structure: biphenyl with ethyl-imidazole (R1, R2) and COOH]

| Example | R₁ | R₂ | LCMS: found m/e (M + H) |
|---|---|---|---|
| 30. | tetrahydropyran-2-ylmethyl-type | H | 391.3 |
| 31. | cyclohexyl-type | H | 375.18 |
| 32. | CH₂CH₂C(Me)₂OCH₂Ph | H | 469.52 |
| 33. | CH₂CH₂C(Me)₂OH | H | 379.70 |
| 34. | 3-methoxybenzyl-type | H | 413.2 |
| 35. | 2-methoxybenzyl-type | H | 413.4 |
| 36. | 4-fluorobenzyl-type | H | 401.3 |
| 37. | 2-trifluoromethylbenzyl-type | H | 451.3 |

TABLE 1-continued
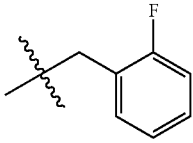
| Example | R₁ | R₂ | LCMS: found m/e (M + H) |
|---|---|---|---|
| 38. | 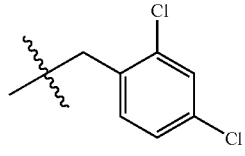 | H | 401.3 |
| 39. | 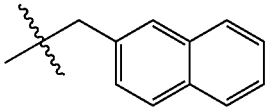 | H | 451.3 |
| 40. | 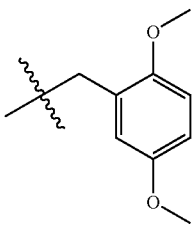 | H | 433.3 |
| 41. | 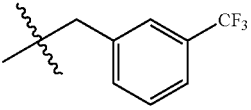 | H | 443.3 |
| 42. | 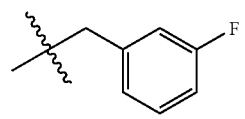 | H | 451.3 |
| 43. | 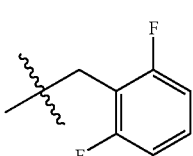 | H | 401.3 |
| 44. | 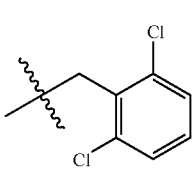 | H | 419.3 |
| 45. | 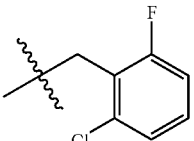 | H | 451.2 |
TABLE 1-continued
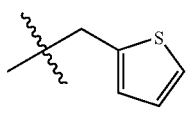
| Example | R₁ | R₂ | LCMS: found m/e (M + H) |
|---|---|---|---|
| 46. | 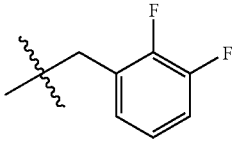 | H | 435.2 |
| 47. | 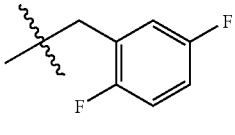 | H | 389.2 |
| 48. | 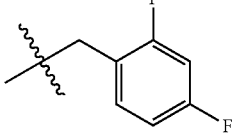 | H | 419.2 |
| 49. | 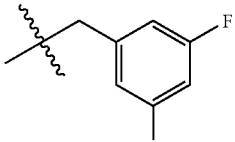 | H | 419.2 |
| 50. | 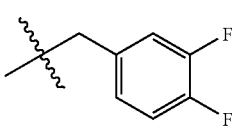 | H | 419.2 |
| 51. | | H | 419.3 |
| 52. | | H | 419.3 |
| 53. | 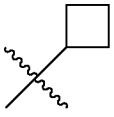 | H | 347.3 |

TABLE 1-continued

Structure: 2-[4-(2-(4-R1-5-R2-1H-imidazol-2-yl)ethyl)phenyl]benzoic acid

| Example | R1 | R2 | LCMS: found m/e (M + H) |
|---|---|---|---|
| 54. | -C(CH3)2-CH2-CH2-cyclopropyl | H | 361.3 |
| 55. | -C(CH3)2-CH2-CH2-cyclohexyl | H | 403.4 |
| 56. | -C(CH3)2-CH2-CH2-CH2-(thiophen-2-yl) | H | 417.6 |
| 57. | -C(CH3)2-CH2-CH2-CCl3 | H | 439.2 |
| 58. | -C(CH3)2-CH2-C(=O)-CH2-CH3 | H | 419.5 |
| 59. | -C(CH3)2-CH2-C(=CH-CH3)(CH2-CH3) (Z or E) | H | 417.5 |
| 60. | -C(CH3)2-CH2-CH2-CF3 | H | 389.4 |
| 61. | -C(CH3)2-CH2-cyclobutyl | H | 361.7 |
| 62. | -C(CH3)2-CH2-(1-methylcyclopent-2-en-1-yl) | H | 387.8 |
| 63. | -C(CH3)2-CH2-(1-methylcyclopentyl) | H | 389.8 |
| 64. | -C(CH3)2-CH2-(1-methylcyclohex-2-en-1-yl) | H | 401.8 |
| 65. | -C(CH3)2-CH2-(1-methylcyclohexyl) | H | 403.5 |
| 66. | -C(CH3)2-CH2-C(CH2CH3)2-CH=CH2 | H | 403.5 |
| 67. | -C(CH3)2-CH2-CH(CH2CH3)2 | H | 377.5 |
| 68. | -C(CH3)2-CH2-C(CH2CH3)3 | H | 405.5 |
| 69. | -C(CH3)2-CH2-(tetrahydro-2H-pyran-4-yl) | H | 391.21 |
| 70. | -CH(CH3)-cyclopropyl | H | 347.2 |
| 71. | -C(CH3)2-CH2-cycloheptyl | H | 403.3 |
| 72. | -C(CH3)2-CH(CH3)-phenyl | H | 397.3 |

TABLE 1-continued (Structure: biphenyl-2-carboxylic acid with ethyl linker to imidazole bearing R₁ and R₂)

| Example | R₁ | R₂ | LCMS: found m/e (M + H) |
|---|---|---|---|
| 73. | (bicyclo[4.2.0] benzocyclobutenyl) | H | 395.3 |
| 74. | (3,3-dimethylbut-3-enyl) | H | 375.42 |
| 75. | (CH₂C(CH₃)₂CH₂COOMe) | H | 421.43 |
| 76. | (CH₂C(CH₃)₂CH₂CH₂OH) | H | 393.41 |
| 77. | (CH₂C(CH₃)₂-cyclopropyl) | H | 389.17 |
| 78. | (CH₂C(CH₃)₂CH₂C(CH₃)=CH₂) | H | 403.43 |
| 79. | (CH₂CH₂C(CH₃)₃ type) | H | 377.67 |
| 80. | (CH₂C(CH₃)₂CH₂Ph) | H | 425.69 |
| 81. | (adamantyl) | H | 427.4 |
| 82. | (neopentyl/t-butyl methyl) | H | 349.3 |

TABLE 1-continued

| Example | R₁ | R₂ | LCMS: found m/e (M + H) |
|---|---|---|---|
| 83. | (sec-butyl methyl) | H | 349.3 |
| 84. | (CH₂C(CH₃)₂OMe) | H | 379.3 |
| 85. | (tetrahydrofuran-2-ylmethyl) | H | 377.15 |

EXAMPLE 86

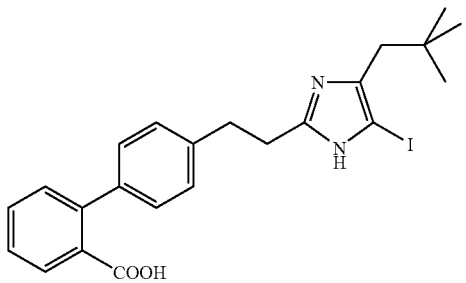

4'-{2-[4-(2,2-Dimethylbutyl)-5-iodo-1H-imidazol-2-yl]ethyl}biphenyl-2-carboxylic Acid The title compound was prepared by iodination (as described in A. Wahhab, J. R. Smith, R. C. Ganter, D. M. Moore, J. Hondrelis, et al. *Arzneim. Forsch.* 1993, 43, 1157) of 4'-{2-[4-(2,2-dimethylpropyl)-1H-imidazol-2-yl]ethyl}biphenyl-2-carboxylic acid, tert-butyl ester (intermediate of Example 1), followed by treatment with TFA as described in Example 1. LCMS: found m/e 489.2 (M+H)⁺.

EXAMPLE 87

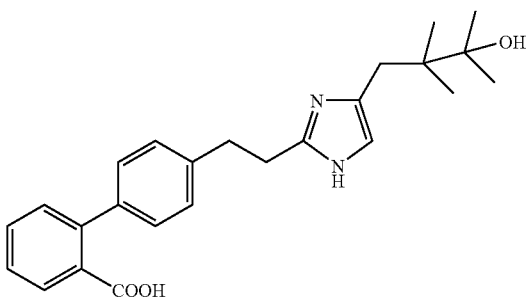

4'-{2-[4-(2,2-Dimethyl-3-hydroxy-3-methyllbutyl)-1H-imidazol-2-yl]ethyl}biphenyl-2-carboxylic Acid The title compound was prepared by methyl Grignard addition to 4'-{2-[4-(3-methyl-3-methoxy-carbonylpropyl)-1H-imidazol-2-yl]ethyl}biphenyl-2-carboxylic acid, tert-butyl ester (intermediate of Example 21), followed by treatment with TFA as described in Example 1. LCMS: m/e 407.7 (M+H)+.

EXAMPLE 88

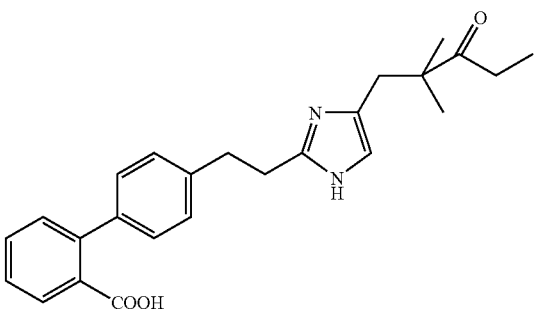

4'-{2-[4-(2,2-Dimethy-3-oxopentyl)-1H-imidazol-2-yl]ethyl}biphenyl-2-carboxylic Acid The title compound was prepared by ethyl Grignard addition to 4'-{2-[4-(3-methyl-3-methoxycarbonylpropyl)-1H-imidazol-2-yl]ethyl}biphenyl-2-carboxylic acid, tert-butyl ester (intermediate of Example 21), followed by treatment with TFA as described in Example 1. LCMS: found m/e 407.7 (M+H)+.

EXAMPLE 89

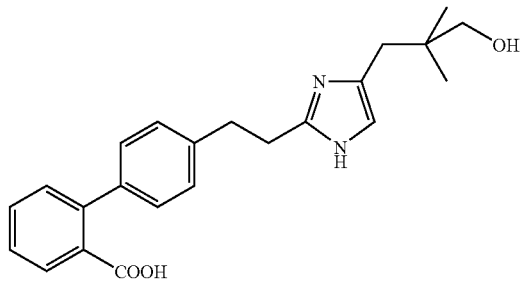

4'-{2-[4-(2,2-Dimethy-3-hyrodroxypropyl)-1H-imidazol-2-yl]ethyl}biphenyl-2-carboxylic Acid The title compound was prepared by lithium hydroxide hydrolysis of 4'-{2-[4-(3-methyl-3-methoxy-carbnylpropyl)-1H-imidazol-2-yl]ethyl}biphenyl-2-carboxylic acid, tert-butyl ester (intermediate of Example 21), followed by borane reduction and treatment with TFA as described in Example 1. LCMS: found m/e 379.5 (M+H)+.

EXAMPLE 90

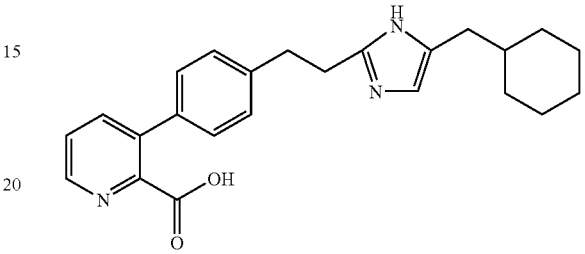

4'-{2-[4-(2,2-Dimethy-3-hyrodroxypropyl)-1H-imidazol-2-yl]ethyl}biphenyl-2-carboxylic Acid Step A: A mixture of 3-[4-(3-oxopropyl)phenyl]pyridine-2-carboxylate (intermediate 6, 156 mg, 0.45 mmol),1-hydroxy-3-hexylacetone (intermediate 5, 104 mg, 0.68 mmol), Cu(OAc)$_2$ (180 mg, 0.99 mmol), ammonium acetate (193 mg, 2.71 mmol) and acetic acid (5 mL) was heated at 100° C. under nitrogen for 40 minutes. The reaction mixture was concentrated, and the resulting residue was partitioned between water (20 mL) and ethyl acetate (25 mL). The organic layer was separated, and the aqueous layer was extracted with ethyl acetate (3×). The combined extracts were washed with water (2×), brine, dried over MgSO$_4$, filtered and concentrated. The resulting residue was purified by preparative TLC (eluting with 10% methanol in dichloromethane) to afford benzyl 3-(4-{2-[5-(cyclohexylmethyl)-1H-imidazole-2-yl]ethyl}phenyl)pyridine-2-carboxylate. LCMS: m/e 480 (M+H)+.

Step B: A mixture of benzyl 3-(4-{2-[5-(cyclohexylmethyl)-1H-imidazole-2-yl]ethyl}phenyl)pyridine-2-carboxylate (70 mg, 0.146 mmol), palladium on carbon (7 mg) and ethanol (3 mL) was stirred under a hydrogen atmosphere for 2 hours. The mixture was filtered, and the filtrate was concentrated to afford 3-(4-{2-[5-(cyclohexylmethyl)-1H-imidazole-2-yl]ethyl}phenyl)pyridine-2-carboxylic acid. LCMS: m/e 390 (M+H)+. $^1$HNMR (CD$_3$OD, 500 MHz): δ 7.79 (1H, d, J=7.5 Hz), 7.42 (1H, d, J=7.5 Hz), 7.08 (1H, 7.5 Hz), 7.01 (1H, s), 3.11 (2H, t, J=6.0 Hz), 2.97 (2H, t, J=6.5 Hz), 2.45 (2H, d, J=7.5 Hz), 1.65 (4H, m), 1.51 (1H, m), 1.16 (4H, m), 0.90 (2H, m).

The compounds in Table 2 were prepared following procedures similar to the procedure described for Example 90.

TABLE 2

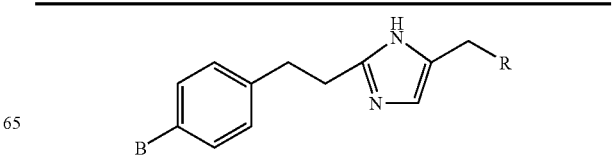

| Example | B | R | LCMS m/e (M + H) |
|---|---|---|---|
| 91. | pyridine-4-carboxylic acid with methyl | cyclohexyl | 390 |
| 92. | pyridine-2-carboxylic acid with methyl | cyclopentyl | 376 |
| 93. | 4-fluoro-2-methylbenzoic acid | cyclohexyl | 407 |
| 94. | 4,5-difluoro-2-methylbenzoic acid | cyclohexyl | 425 |
| 95. | 4,5-difluoro-2-methylbenzoic acid | cyclopentyl | 411 |
| 96. | 2-methylphenylacetic acid | cyclohexyl | 403 |

EXAMPLE 97

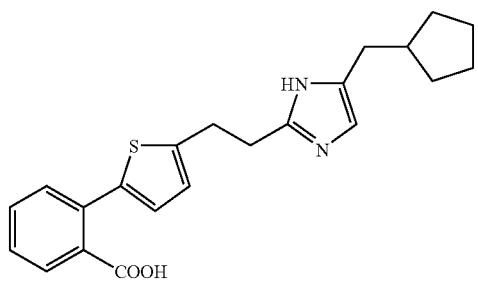

2-(5-{2-[5-(Cyclopentylmethyl)-1H-imidazol-2-yl]ethyl}-2-thienyl)benzoic Acid

The title compound was prepared from Intermediate 4 and intermediate 23 following the procedure described for Example 1, followed by alkaline hydrolysis of the methyl ester. LCMS: m/e 381.1 (M+H)$^+$.

EXAMPLE 98

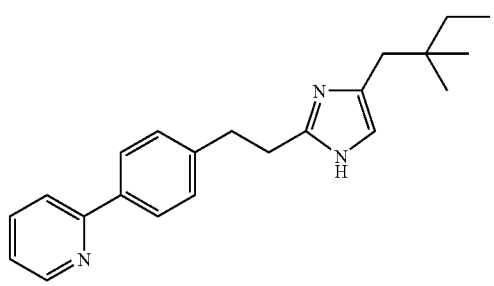

2-(4-{2-[4-(2,2-Dimethylbutyl)-1H-imidazol-2-yl]ethyl)phenyl)pyridine

The title compound was prepared from intermediate 7 and intermediate 3 following the cylization procedure described in Example 1. LCMS: m/e 334.3 (M+H)$^+$. $^1$H NMR (500 MHz, CDCl$_3$): δ 8.68 (1H, d, J=4.6 Hz), 7.90 (2H, d, J=8.3 Hz), 7.75 (1H, td, J=7.7 Hz, J=6.85 Hz), 7.70 (1H, m), 7.23 (3H, m), 6.62 (1H, s), 3.07 (2H, t, J=6.75 Hz), 3.02 (2H, t, J=6.85 Hz), 2.40 (2H, s), 1.23 (2H, q, J=7.5 Hz), 0.83 (9H, m).

The compounds in Table 3 were prepared following the procedure described for Example 98 by substituting intermediate 7 with an appropriate aldehyde.

TABLE 3

| Example | B | LCMS m/e (M + H) |
|---|---|---|
| 99. | 1,2,4-triazol-1-yl-methyl | 338.7 |
| 100. | imidazol-1-yl-methyl | 337.8 |

TABLE 3-continued
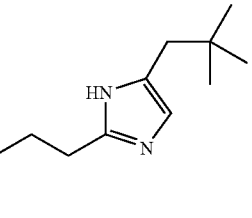
| Example | B | LCMS m/e (M + H) |
|---|---|---|
| 101. | 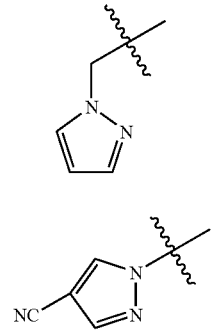 | 337.8 |
| 102. | 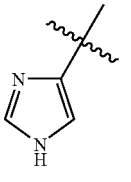 | 348.8 |
| 103. | 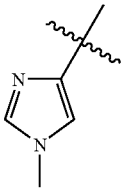 | 323.7 |
| 104. | 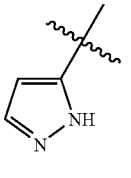 | 337.5 |
| 105. | 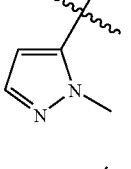 | 323.66 |
| 106. | 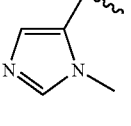 | 337.71 |
| 107. | 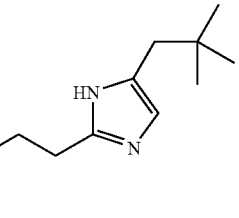 | 337.50 |
TABLE 3-continued
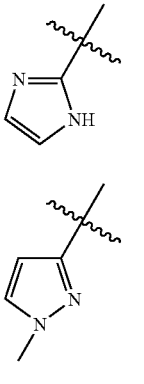
| Example | B | LCMS m/e (M + H) |
|---|---|---|
| 108. | 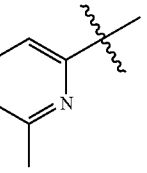 | 323.48 |
| 109. | 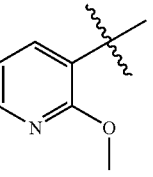 | 337.67 |
| 110. | 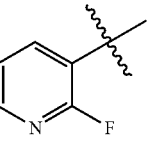 | 348.3 |
| 111. | 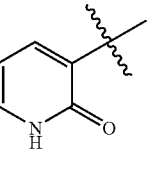 | 364.52 |
| 112. | 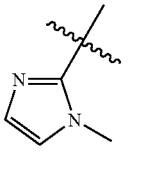 | 352.61 |
| 113. | 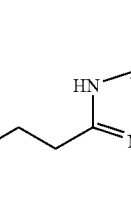 | 350.50 |
| 114. | 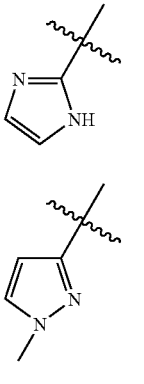 | 337.5 |

TABLE 3-continued

| Example | B | LCMS m/e (M + H) |
|---|---|---|
| 115. | (pyrazole) | 323.66 |
| 116. | (N-methylpyrazole) | 337.66 |

EXAMPLE 117

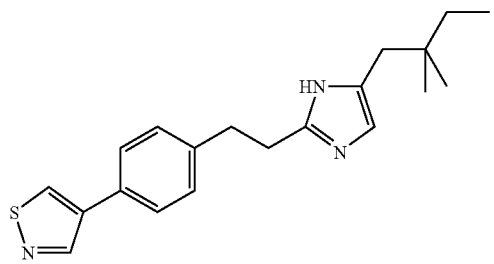

4-(4-{2-[5(2,2-Dimethylbutyl)-1H-imidazole-2-yl]ethyl}phethyl)isothiazole

Step A: A mixture of t-butyl 5-(2,2-dimethylbutyl)-2-{2-[4-(4,4,5,5-tetramethyl-1,3,2-dioxaborolan-2-yl)phenyl]ethyl}1H-imidazole-1-carboxylate (intermediate 8, 3.59 g, 7.45 mmol), 4-bromoisothiazole (2.44 g, 14.90 mmol), 1,1'-bis(diphenylphosphino)ferrocene-palladium dichloride dichoromethane complex (1:1) (608 mg, 0.745 mmol), potassium carbonate (5.15 g, 37.25 mmol) and DME (35 mL) was degassed and filled with nitrogen. After stirring at 80° C. overnight, the mixture was cooled and partitioned between water (50 mL) and ethyl acetate (50 mL). The organic layer was separated and the aqueous layer was extracted with ethyl acetate (3×). The combined organic extracts were washed by water, brine, dried over MgSO$_4$, filtered and concentrated. The residue was purified by silica gel chromatography (eluting with 5 to 20% ethyl acetate in hexanes) to afford t-butyl 5-(2,2-dimethylbutyl)-2-[2-(4-isothiazol-4-ylphenyl)ethyl]-1H-1-carboxylate. LCMS: found m/e 440 (M+H)$^+$.

Step B: A mixture of t-butyl 5-(2,2-dimethylbutyl)-2-[2-(4-isothiazol-4-ylphenyl)ethyl]-1H-1-carboxylate (2.35 g, 5.35 mmol), methanol (15 mL) and concentrated HCl (5 mL) was heated at 40° C. for 1 hour. The volatiles were removed and the residue was purified by reverse phase HPLC (20 to 80% acetonitrile in water) to afford the title compound. LCMS: m/e 340 (M+H)$^+$. $^1$HNMR (CD$_3$OD, 500 MHz): δ 9.05 (1H, s), 8.83 (1H, s), 7.62 (2H, d, J=5.0 Hz), 7.22 (2H, d, J=5.5 Hz), 7.12 (1H, s), 3.30 (2H, br), 3.14 (2H, br), 2.48 (2H, s), 1.19 (1H, q, J=6.5 Hz), 0.83 (3H, t, J=6.5 Hz), 0.78 (6H, s).

The compounds in Table 4 were prepared following the procedure described for Example 117 by substituting 4-bromoisothiazole with an appropriate bromo or dodo heterocycle.

TABLE 4

| Example | B | LCMS m/e (M + H) |
|---|---|---|
| 118. | (3-pyridyl) | 334 |
| 119. | (6-methoxypyridyl) | 364 |
| 120. | (pyridyl-CHO) | 362 |
| 121. | (pyridyl-CH$_2$OH) | 364 |
| 122. | (pyridyl-CH=NOH) | 377 |
| 123. | (fluoro-methylpyridyl) | 366 |

TABLE 4-continued

[Structure: imidazole with neopentyl substituent, linked via ethylene to 4-B-phenyl group]

| Example | B | LCMS m/e (M + H) |
|---|---|---|
| 124. | 2-methyl-3-carboxylic acid pyridine | 378 |
| 125. | 2-methyl-3-hydroxymethyl pyridine | 364 |
| 126. | 2-methyl-3-formyl pyridine | 362 |
| 127. | 2-methyl-3-(hydroxyiminomethyl) pyridine | 377 |
| 128. | 6-methyl-2-pyridone | 364 |
| 129. | 6-methyl-2-(difluoromethyl) pyridine | 384 |
| 130. | 6-methyl-2-vinyl pyridine | 360 |
| 131. | 6-methyl-2-ethyl pyridine | 362 |
| 132. | 3-methyl-2-amino pyridine | 450 |
| 133. | 3,6-dimethyl-2-amino pyridine | 364 |
| 134. | 5-methyl-2-fluoro pyridine | 352 |
| 135. | 3-methyl-2-chloro pyridine | 368 |
| 136. | 5-methyl isothiazole | 340 |
| 137. | 4-methyl thiazole | 340 |
| 138. | 4-methyl-3-methoxy isothiazole | 370 |
| 139. | 3-methyl-2-(methylamino) pyridine | 363 |
| 140. | 6-methyl-2-amino pyridine | 349 |
| 141. | 5-methyl-4-amino thiazole | 355 |

TABLE 4-continued

| Example | B | LCMS m/e (M + H) |
|---|---|---|
| 142. | thiazol-2-yl | 340 |
| 143. | 4-methyl-1,2,3-thiadiazol-5-yl | 341 |
| 144. | 3-methyl-4-methyl-isothiazol-5-yl | 354 |
| 145. | 2-amino-3,5-dimethylpyridin-6-yl | 363 |
| 146. | 6-methyl-3-nitropyridin-2-yl | 379 |
| 147. | 5-chloro-3-methyl-2-(methylamino)pyridin-6-yl | 397 |
| 148. | 2-amino-5-fluoro-3-methylpyridin-6-yl | 367 |
| 149. | 3-amino-4-methylisothiazol-5-yl | 355 |
| 150. | 4-methyl-3-carboxyisothiazol-5-yl | 384 |
| 151. | 5-chloro-3-methyl-4-methylisothiazol | 388 |

| Example | B | LCMS m/e (M + H) |
|---|---|---|
| 152. | 3-(hydroxymethyl)-4-methylisothiazol-5-yl | 370 |
| 153. | 3-(fluoromethyl)-4-methylisothiazol-5-yl | 385 |
| 154. | 3-(methoxymethyl)-4-methylisothiazol-5-yl | 402 |
| 155. | methyl ester of 156 | 442 |
| 156. | 4-methyl-3-((carboxymethoxy)methyl)isothiazol-5-yl | 428 |
| 157. | 5-methylpyridin-2-yl | 334 |
| 158. | 4-methylisothiazol-5-yl | 326 |
| 159. | 3-methylpyrazin-2-yl | 321 |
| 160. | 3-methylimidazo[1,2-a]pyrazin-2-yl | 374 |
| 161. | 3,5-dimethylisothiazol-4-yl | 354 |
| 162. | 3-hydroxy-4-methylisothiazol-5-yl | 356 |

TABLE 4-continued

| Example | B | LCMS m/e (M + H) |
|---|---|---|
| 163. | (5-methyl-6-aminopyridin-3-yl) | 449 |
| 164. | (5-amino-3,4-dimethylisothiazol-5-yl) | 369 |
| 165. | (2-methylamino-3-methyl-5-nitropyridin-6-yl) | 408 |
| 166. | (2-amino-3-methyl-5-nitropyridin-6-yl) | 394 |
| 167. | (2-amino-3-methyl-5-chloropyridin-6-yl) | 383 |
| 168. | (2-methylamino-3-methyl-5-trifluoromethylpyridin-6-yl) | 431 |
| 169. | (2-amino-3-methyl-5-trifluoromethylpyridin-6-yl) | 417 |
| 170. | (2-methylamino-3-methyl-5-aminopyridin-6-yl) | 378 |
| 171. | (2-amino-3-methyl-5-aminopyridin-6-yl) | 364 |

TABLE 4-continued

| Example | B | LCMS m/e (M + H) |
|---|---|---|
| 172. | (6-methyl-5-trifluoromethylpyridin-2-yl) | 402 |
| 173. | (2-acetamido-3,5-dimethylpyridin-6-yl) | 405 |
| 174. | (2,3-dimethylpyridin-6-yl) | 348 |
| 175. | (3-amino-5-bromo-6-methylpyrazin-2-yl) | 428 |
| 176. | (5-amino-3-methylpyrazin-2-yl) | 350 |
| 177. | (2-amino-3-methyl-6-fluoropyridin-5-yl) | 367 |
| 178. | (3-amino-2-methyl-piperazin-5-yl) | 354 |
| 179. | (6-amino-2-fluoro-3-methylpyridin-5-yl) | 367 |
| 180. | (6-amino-3-methylpyrazin-2-yl) | 349 |
| 181. | (3-amino-2-methylpyrazin-5-yl) | 350 |

TABLE 4-continued
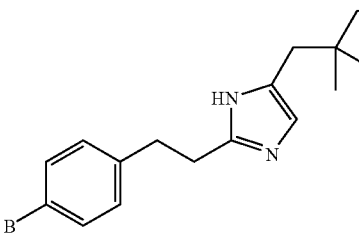
| Example | B | LCMS m/e (M + H) |
|---|---|---|
| 182. | 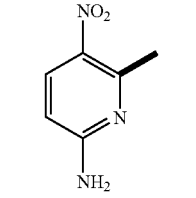 | 394 |
| 183. | 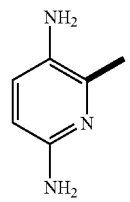 | 394 |
| 184. | 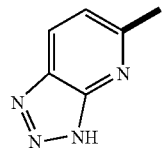 | 364 |
| 185. | 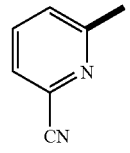 | 375 |
| 186. | 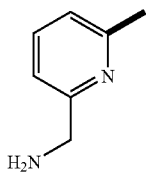 | 359 |
| 187. | 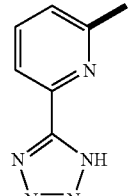 | 363 |
| 188. | 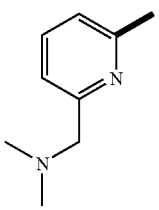 | 402 |
TABLE 4-continued
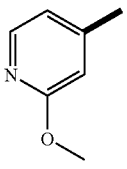
| Example | B | LCMS m/e (M + H) |
|---|---|---|
| 189. | 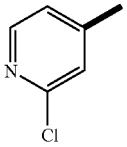 | 391 |
| 190. | 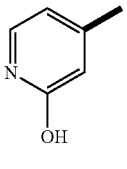 | 364 |
| 191. | 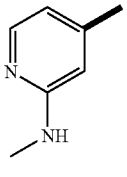 | 368 |
| 192. | 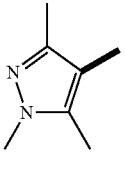 | 350 |
| 193. | 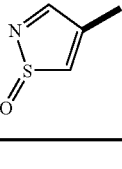 | 363 |
| 194. | | 365 |
| 195. | | 356 |

EXAMPLE 196

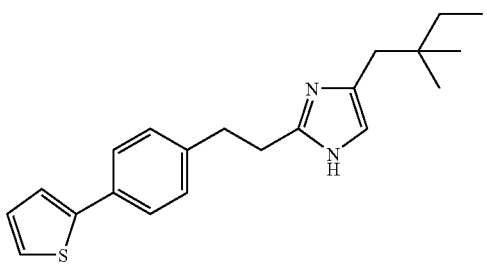

4-(2,2-Dimethylbutyl)-2-[2-(4-thiophen-2-ylphenyl)ethyl]-1H-imidazole

A mixture of intermediate 10 (2.20 mmol), 2-bromothiophene (2.42 mmol, 1.1 equiv) and sodium carbonate (6.60 mmol, 3 equiv), DMF (50 mL) and water (25 mL) was flushed with a nitrogen stream while warming up to 80° C. Pd(dppf)Cl$_2$ (0.11 mmol, 0.05 equiv) was added and the reaction was stirred at 80° C. under nitrogen for 18 h. Upon cooling, the mixture was poured into water (100 mL) with vigorous stirring. The product was extracted with ethyl acetate and the combined extracts were washed with 5% lithium chloride (5×), dried over sodium sulfate and concentrated to provide the crude coupled product, which was treated with trifluoroacetic acid (10 mL) at 60° C. After 30 minutes, the mixture was cooled and concentrated to give a residue.

The residue was purified by flash column chromatography on silica gel (eluting with methylene chloride to methylene chloride/methanol/ammonium hydroxide) to afford the title compound, which was converted to the HCl salt with 1N HCl in diethylether. $^1$H NMR (300 MHz, CD$_3$OD) δ 7.53 (d, J=8.1 Hz, 2H), 7.35-7.32 (m, 2H), 7.14 (d, J=8.8 Hz, 3H), 7.09-7.05 (m, 1H), 3.32-3.24 (m, 2H), 3.11 (t, J=7.2 Hz, 2H), 2.47 (s, 2H), 1.24-1.15 (m, 2H), 0.91-0.78 (m, 9H); LCMS: m/e 339 (M+H).

EXAMPLE 197

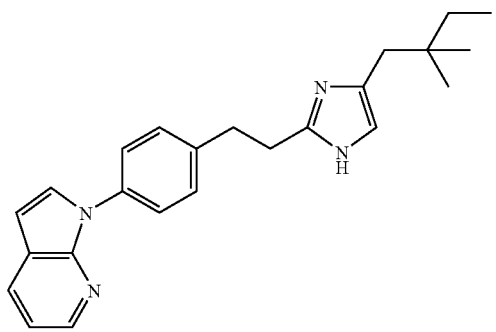

1-(4-{2-[4-(2,2-Dimethylbutyl)-1-trityl-1H-imidazol-2-yl]ethyl}phenyl)-[2,3-b]pyridine To a suspension of sodium hydride (60% suspension in mineral oil, 2 eq) in DMF (5 mL) was added 1H-pyrrolo[2,3-b]pyridine (330 mg, 2.8 mmol), and the reaction was stirred at rt under nitrogen for 45 min. Intermediate 10 (404 mg, 0.7 mmol) and copper powder (0.26 mmol) were then added, and the reaction was heated at reflux, allowing the solvent slowly evaporate over 3-5 h. After cooling, the residue was partitioned between methylene chloride and water. The organic layer was separated, washed with saturated ammonium chloride and 5% lithium chloride (5×), dried over sodium sulfate and concentrated to give a residue. The residue was purified by flash column chromatography (silica gel, eluting with 0-50% ethyl acetate/hexanes) to afford the title compound. $^1$H NMR (500 MHz, CDCl$_3$) δ 8.32 (dd, J=4.7, 1.6 Hz, 1H), 7.93 (dd, J=7.9, 1.6 Hz, 1H), 7.46 (m, 2H), 7.41 (d, J=3.6 Hz, 1H), 7.35-7.29 (m, 9H), 7.14 (m, 6H), 7.08 (dd, J=7.8, 4.7 Hz, 1H), 6.93 (d, J=8.3 Hz, 2H), 6.57 (d, J=3.5 Hz, 1H), 6.34 (s, 1H), 2.42 (m, 4H), 2.31 (m, 2H), 1.27 (m, 2H), 0.89 (m, 9H)

The compounds in Table 5 were prepared following the procedure described for Example 197 by substituting 1H-pyrrolo[2,3-b]pyridine with an appropriate heterocycle.

TABLE 5

| Example | B | LCMS m/e (M + H) |
|---|---|---|
| 198. | imidazolyl | 323 |
| 199. | indazolyl | 373 |
| 200. | 4-Me-pyrazolyl | 337 |
| 201. | 2-pyridinonyl | 350 |
| 202. | 1,2,4-triazolyl | 324 |
| 203. | 2-Me-imidazolyl | 337 |
| 204. | pyrazolyl | 324 |

EXAMPLE 205

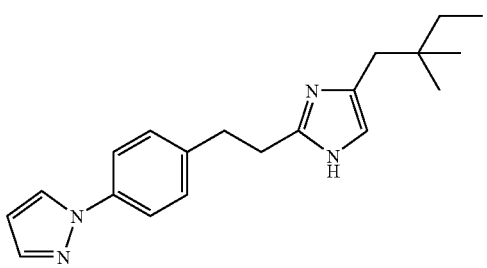

1-(4-{2-[4-(2,2-dimethylbutyl)-1H-imidazol-2-yl]ethyl}phenyl)-1H-pyrazole

The title compound was prepared following the procedure described for Example 197 by substituting 1H-pyrrolo[2,3-b]pyridine with pyrazole, except 5 equivalents each of NaH and pyrazole were used. The final product was purified by flash column chromatography on silica gel eluting with 0-10% 9:1 methanol/ammonium hydroxide mixture in methylene chloride to give the title compound, which was converted to the HCl salt using 1M HCl in diethyl ether. $^1$H NMR (500 MHz, CD$_3$OD) δ 8.23 (s, 1H), 7.77 (d, 1H), 7.67-7.65 (d, J=8.5 Hz, 2H), 7.31-7.29 (d, J=8.4 Hz, 2H), 7.13 (s, 1H), 6.55 (s, 1H), 3.32-3.30 (t, 2H, partially masked by solvent), 3.19-3.16 (t, J=7.2 Hz, 2H), 2.49 (s, 2H), 1.23-1.18 (q, J=7.5 Hz, 2H), 0.85-0.82 (t, J=7.4 Hz, 3H), 0.80 (s, 6H); LC-MS: m/e 323 (M+H).

EXAMPLE 206

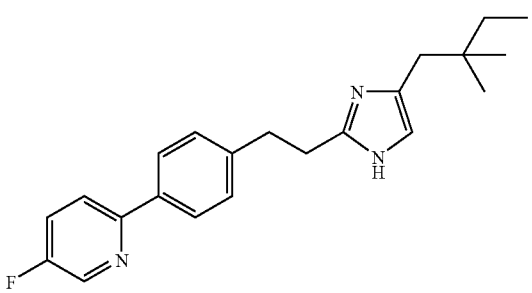

2-(4-{2-[4-(2,2-Dimethylbutyl)-1-trityl-1H-imidazol-2-yl]ethyl}phenyl)-5-fluoropyridine The title compound was prepared following the procedure described for Example 196 by substituting 2-bromothiophene with 5-fluoro-2-bromopyridine. The final product was purified by flash column chromatography (silica gel, eluting with 1-20% ethyl acetate/hexanes) to give the title compound. $^1$H NMR (300 MHz, CDCl$_3$) δ 8.48 (s, 1H), 7.69-7.67 (m, 2H), 7.62-7.61 (m, 1H), 7.32-7.30 (m, 1H), 7.25 (s, 9H), 7.13-7.11 (m, 6H), 6.90-6.88 (d, J=6 Hz, 2H), 6.33 (s, 1H), 2.43-2.41 (m, 2H), 2.29 (s, 2H), 2.31-2.25 (m, 2H), 1.27-1.24 (m, 2H), 0.86-0.83 (m, 9H); LCMS: m/e 594 (M+H).

EXAMPLE 207

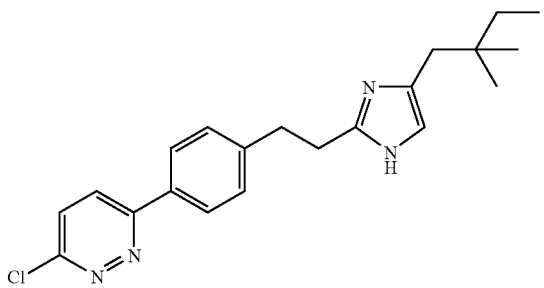

3-Chloro-6-(4-{2-[4-(2,2-dimethylbutyl)-1-trityl-1H-imidazol-2-yl]ethyl}phenyl)-pyridazine The title compound was prepared following the procedure described for Example 196 by substituting 2-bromothiophene with 3,6-dichloropyridazine. The crude product was purified by flash column chromatography (silica gel, eluting with 0-10% 10:1 methanol/ammonium hydroxide mixture in methlyene chloride) to afford the title compound. $^1$H NMR (500 MHz, CDCl$_3$) δ 7.73-7.71 (d, J=9 Hz, 1H), 7.50-7.47 (d, J=9 Hz, 1H), 7.03-7.00 (m, 2H), 6.85-6.82 (m, 2H), 6.59 (s, 1H), 3.00-2.93 (s, 4H), 2.38 (s, 2H), 1.21-1.16 (q, J=7.5 Hz, 2H), 0.85-0.80 (m, 9H); LC-MS: m/e 369 (M+H).

EXAMPLE 208

2-Chloro-4-(4-{2-[4-(2,2-dimethylbutyl)-1-trityl-1H-imidazol-2-yl]ethyl}phenyl)pyrimidine The title compound was prepared following the procedure described for Example 196 by substituting 2-bromothiophene with 2,4-dichloropyrimidine. The crude product was purified by flash column chromatography (silica gel, eluting with 0-40% ethyl acetate/hexanes) to give the title compound. $^1$H NMR (500 MHz, CDCl$_3$) δ 8.55 (d, J=5.2 Hz, 1H), 7.84 (dd, J=6.8, 1.7 Hz, 2H), 7.54 (d, J=5.3 Hz, 1H), 7.30 (m, 9H), 7.11 (m, 6H), 6.94 (d, J=8.3 Hz, 2H), 6.34 (s, 1H), 2.48 (m, 2H), 2.41 (s, 2H), 2.27 (m, 2H), 1.26 (q, J=7.3 Hz, 2H), 0.86 (m, 9H).

The compounds in Table 6 were prepared following the procedure described for Example 196 substituting 2-bromothiophene with an appropriate aromatic bromide, iodide or triflate.

TABLE 6

| Example | R | LCMS m/e (M + H) |
|---|---|---|
| 209. | 2-methyl-phenol | 349 |
| 210. | 4,5-difluoro-2-methyl-phenol | 385 |
| 211. | 2,5-dimethyl-pyridine | 348 |
| 212. | 2,4-dimethyl-pyridine | 348 |
| 213. | 3,4-dimethyl-pyridine | 348 |
| 214. | 3-fluoro-2-methyl-pyridine | 352 |
| 215. | 4-methyl-pyridine | 334 |
| 216. | 2-chloro-4-methyl-pyridine | 368 |
| 217. | 5-fluoro-3-methyl-pyridine | 352 |
| 218. | 2-methyl-phenyl-SOMe | 395 |
| 219. | 4-chloro-2-methyl-pyridine | 368 |
| 220. | 2-methyl-phenoxy-CH2CO2H | 407 |
| 221. | 7-methyl-1H-indazole | 373 |
| 222. | 8-methyl-isoquinoline | 384 |
| 223. | 2-methyl-phenyl-SO2NH2 | 412 |

EXAMPLE 224

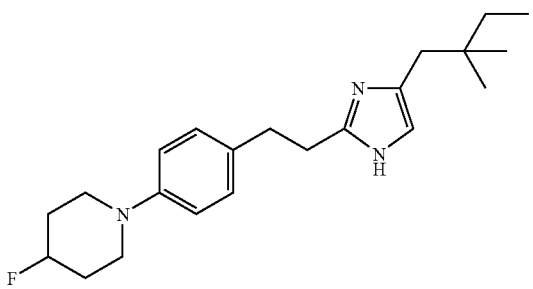

N-(4-{2-[5-(2,2-Dimethylbutyl)-1H-imidazol-2-yl]ethyl}phenyl)-4-fluoropiperidine To a stirred mixture of intermediate 10 (0.433 mmol), 4-fluropiperidine (0.65 mmol, 1.5 eq), $K_2CO_3$ (1.3 mmol, 3 eq) and DMSO (1 mL) was added L-proline (0.087 mmol, 0.2 eq) and copper iodide (0.043 mmol, 0.1 eq). The reaction was heated at 70-90° C. under nitrogen for 20 hours. After cooling, the reaction mixture was partitioned between methylene chloride and water. The organic layer was separated, dried over sodium sulfate and concentrated to give a residue. The residue was purified by flash column chromatography (silica gel, eluting with 0-90% ethyl acetate/hexanes) to give a N-(4-{2-[5-(2,2-dimethylbutyl)-1-trityl-1H-imidazol-2-yl]ethyl}phenyl)-4-fluoropiperidine, which was treated with trifluoroacetic acid. Concentration and flash column chromatography of the residue on silica gel (eluting with 0-10% methanol/conc. ammonium hydroxide mixture (10:1) in methylene chloride) provided the title compound. $^1$H NMR (500 MHz, CDCl$_3$) δ 7.03-7.00 (d, J=15 Hz, 2H), 6.85-6.82 (d, J=15 Hz, 2H), 6.59 (s, 1H) 4.89-4.70 (m, 1H), 3.30-3.27 (m, 2H), 3.15-3.09 (m, 2H), 3.00-2.93 (m, 4H), 2.38 (s, 2H), 2.02-1.94 (m, 4H), 1.21-1.16 (m, 2H), 0.85-0.80 (m, 9H); LC-MS: m/e 358 (M+H).

EXAMPLE 225

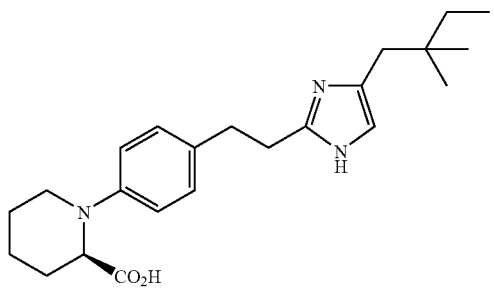

(R)-N-(4-{2-[4-(2,2-Dimethylbutyl)-1H-imidazol-2-yl]ethyl}phenyl)piperidine-2-carboxylic acid The title compound was prepared following the procedure described for Example 224 by substituting proline with 4 eq of D-pipecolinic acid. The crude product was purified by flash column chromatography (silica gel, eluting with 0-10% 9:1 methanol/ammonium hydroxide mixture in methylene chloride to give the title compound, which was converted to the HCl salt with 1 M HCl in ether. [α]$^{25}_D$+12.6° (c 0.45, Methanol); $^1$H NMR (500 MHz, CD$_3$OD) δ 7.53-7.51 (d, J=8.1 Hz, 2H), 7.35-7.33 (d, J=8.4 Hz, 2H), 7.13 (s, 1H), 4.72-4.69 (dd, J=10.7, 3.5 Hz, 1H) 3.57-3.55 (m, 2H), 3.28-3.25 (t, J=7.5 Hz, 2H), 3.15-3.12 (t, J=7.6 Hz, 2H), 2.53 (s, 2H), 2.37-2.31 (m, 1H), 2.09-1.92 (m, 4H), 1.86-1.78 (m, 1H), 1.31-1.26 (q, J=7.6 Hz, 2H), 0.92-0.89 (t, J=7.5 Hz, 3H), 0.86 (s, 6H); LC-MS: m/e 384 (M+H).

EXAMPLE 226

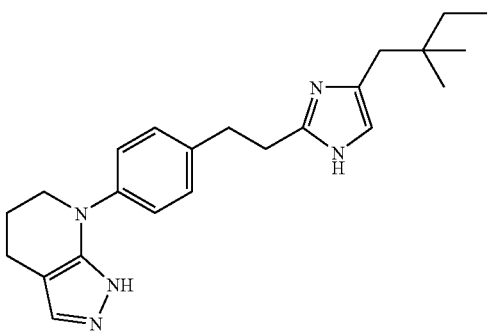

7-(4-{2-[5-(2,2-Dimethylbutyl)-1H-imidazol-2-yl]ethyl}phenyl)-4,5,6,7-tetrahydro-1H-pyrazolo[3,4-b]pyridine A mixture of intermediate 10 (132 mg, 0.23 mmol), intermediate 11 (116 mmol, 0.46 mmol), dicyclohexylbiphenylphosphine (~2 mg) and sodium tert-butoxide (45 mg, 0.46 mmol) in dry toluene (3 mL) was degassed and filled with nitrogen. Palladium acetate (~2 mg) was added, and the mixture was sealed, placed in a microwave reactor and irradiated with microwaves (maximum 150 W) to maintain a temperature of 150° C. for 20 minutes. The reaction mixture was concentrated to give a residue. The residue was purified by flash chromatography (silica gel, eluting with 0-50% ethyl acetate/hexanes) to afford 7-(4-{2-[4-(2,2-dimethylbutyl)-1-trityl-1H-imidazol-2-yl]ethyl}phenyl)-1-(2-trimethylsilanyl-ethoxymethyl)-4,5,6,7-tetrahydro-1H-pyrazolo[3,4-b]pyridine, which was dissolved in a mixture of TFA (15 mL) and water (1 mL), and heated to 60° C. for 30 minutes. The reaction mixture was concentrated and partitioned between methylene chloride and saturated NaHCO$_3$ solution. The organic phase was separated and concentrated, and the residue was purified by flash chromatography (silica gel, eluting with 0-15% 9:1 methanol/ammonium hydroxide mixture in methylene chloride) to afford the title compound, which was converted to the HCl salt using 1M HCl in diethyl ether. $^1$H NMR (500 MHz, CD$_3$OD) δ 7.74 (s, 1H), 7.33 (m, 4H), 7.16 (s, 1H), 3.69 (m, 2H), 3.28 (t, J=7.6 Hz, 2H), 3.13 (t, J=7.6 Hz, 2H), 2.72 (t, J=6.3 Hz, 2H), 2.52 (s, 2H), 2.10 (m, 2H), 1.27 (q, J=7.6 Hz, 2H), 0.89 (t, J=7.5 Hz, 3H), 0.85 (s, 6H); LC-MS: m/e 378 (M+H).

EXAMPLE 227

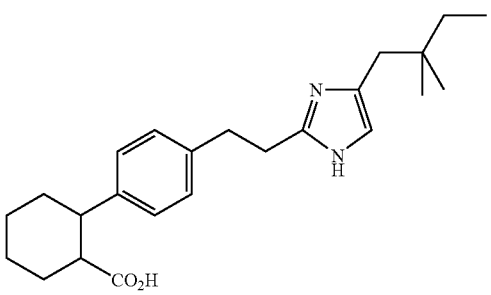

2-(4-{2-[4-(2,2-Dimethylbutyl)-1H-imidazol-2-yl]ethyl}phenyl)cyclohexanecarboxylic acid To a solution of 2-(4-{2-[4-(2,2-dimethylbutyl)-1-trityl-1H-imidazol-2-yl]ethyl}phenyl)cyclohex-1-enecarboxylic acid ethyl ester (400 mg, 0.62 mmol) (obtained by reaction of intermediate 10 and 2-trifluoromethanesulfonyloxy-cyclohex-1-enecarboxylic acid ethyl ester following the procedure described for Example 196) in methanol (5 mL) was added sodium hydroxide (246 mg, 6.15 mmol), and the mixture was heated at reflux for 3 hours. After cooling to rt, the mixture was concentrated and the residue partitioned between methylene chloride and water. The pH of the aqueous phase was adjusted to 5-6 with 2N HCl, and the organic phase was separated, dried over sodium sulfate, and concentrated to provide 2-(4-{2-[4-(2,2-dimethylbutyl)-1-trityl-1H-imidazol-2-yl]ethyl}phenyl)cyclohex-1-enecarboxylic acid, which was dissolved in methanol (4 mL) and was hydrogenated (40 psi $H_2$) with 5% palladium on carbon (340 mg) as a catalyst for 18 hours. The reaction mixture was filtered through Celite, and the filtrate was concentrated to give a residue, which was purified by flash column chromatography (silica gel; eluting with 0-10% 9:1 methanol/ammonium hydroxide mixture in methylene chloride) to provide the title compound. $^1$H NMR (500 MHz; $CD_3OD$) δ 7.19-7.17 (d, J=8.0 Hz, 2H), 6.98-6.96 (d, J=8.0 Hz, 2H), 6.75 (s, 1H), 3.01-2.84 (m, 6H), 2.44-2.37 (s+m, 3H), 2.04-2.02 (m, 1H), 1.83-1.65 (m, 4H), 1.59-1.51 (m, 1H), 1.47-1.39 (m, 1H), 1.27-1.23 (q, J=7.5 Hz, 2H), 0.89-0.86 (t, J=7.5 Hz, 3H), 0.83 (s, 6H); LC-MS: m/e 383 (M+H).

EXAMPLE 228

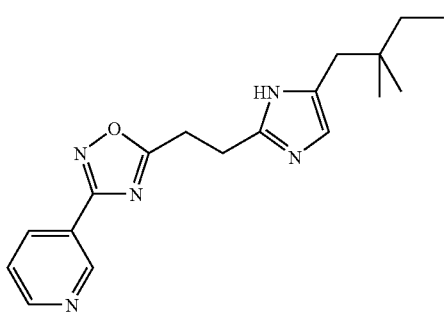

2-(5-{2-[5-(2,2-Dimethylbutyl)-1H-imidazol-2-yl]ethyl}-[1,2,4]oxadiazol-3-yl)pyridine Step A: To a solution of N-(2-hydnixy-4,4-dimethylhexyl)-3-(3-pyridin-2-yl-[1,2,4]oxadiazol-5-yl)propionamide (prepared by reaction of 3-(3-pyridin-2-yl-[1,2,4]oxadiazol-5-yl)propionic acid and intermediate 9 under standard peptide coupling conditions) in methylene chloride was added Dess-Martin periodinate (1.5 eq), and the mixture was stirred at rt for 1 hour. Saturated sodium bicarbonate and sodium thiosulfate were added to the reaction mixture, and stirring continued for 45 min. The product was extracted with methylene chloride (3×50 mL), and the extracts were dried over sodium sulfate and concentrated to give a residue, which was purified by flash column chromatography (silica gel, eluting with 0-10% 9:1 methanol/ammonium hydroxide mixture in methylene chloride) to give N-(4,4-dimethyl-2-oxohexyl)-3-(3-pyridin-2-yl-[1,2,4]oxadiazol-5-yl)propionamide.

Step B: To N-(4,4-dimethyl-2-oxohexyl)-3-(3-pyridin-2-yl-[1,2,4]oxadiazol-5-yl)propionamide (413 mg, 1.2 mmol) in acetic acid (3 mL) was added ammonium acetate (924 mg, 12 mmol), and the mixture was heated at 180° C. for 20 minutes in a microwave reactor (maximum 150 W). The reaction mixture was poured into ethyl acetate and water, and pH of the aqueous layer was adjusted to 9 with concentrated ammonium hydroxide. The organic layer was separated and concentrated to give a residue. The residue was purified by flash column chromatography (silica gel, eluting with 0-15% 9:1 methanol/ammonium hydroxide mixture in methylene chloride) to afford the title compound, which was converted to the HCl salt with 1M HCl in diethyl ether. $^1$H NMR (500 MHz, $CD_3OD$) δ 8.83-8.85 (m, 1H), 8.32-8.35 (m, 2H), 7.84-7.89 (m, 1H), 7.22 (s, 1H), 3.59-3.61 (m, 4H), 2.21 (s, 2H), 1.26 (q, J=7.7 Hz, 2H), 0.85 (m, 9H); LC-MS: m/e 326 (M+H).

EXAMPLE 229

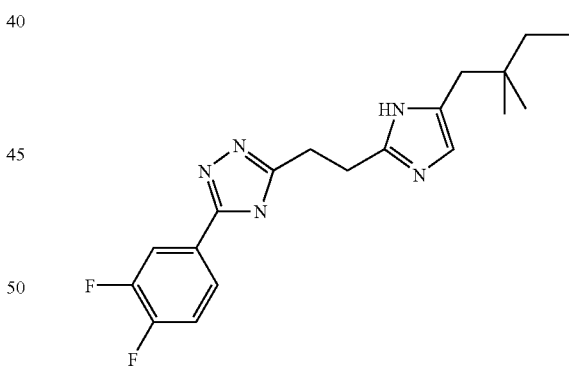

3-(3,4-Difluorophenyl)-5-{2-[5-(2,2-dimethylbutyl)-1H-imidazol-2-yl]ethyl}-1H-[1,2,4]triazole The title compound was prepared following the procedure described for Example 207 by substituting 3-(3-pyridin-2-yl-[1,2,4]oxadiazol-5-yl)propionic acid with intermediate 14. The crude product was purified by flash column chromatography (silica gel, eluting with 0-15% 9:1 methanol/ammonium hydroxide mixture in methylene chloride) to give the title compound, which was converted to the HCl salt using 1M HCl in diethyl ether. $^1$H NMR (500 MHz, $CD_3OD$) δ 7.86-7.91 (m, 1H), 7.79-7.82 (m, 1H), 7.44-7.49 (m, 1H), 7.20 (s, 1H), 3.47-3.50 (m, 2H), 3.39-3.42 (m, 2H), 2.54 (s, 2H), 1.27 (q, J=7.6, 2H), 0.85-0.89 (m, 9H); LC-MS: m/e 360 (M+H).

EXAMPLE 230

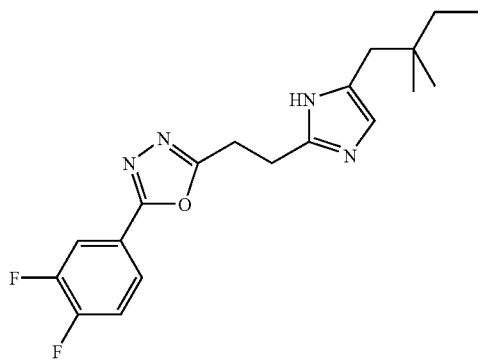

2-(3,4-Difluorophenyl)-5-{2-[5-(2,2-dimethylbutyl)-1H-imidazol-2-yl]ethyl}-1,3,4-oxadiazole Phosphorus oxychloride (316 mg, 2.1 mmol) was added to a solution of intermediate 26 (125 mg, 0.26 mmol) in dry acetonitrile (1 mL) at rt. After stirring at 80° C. for 2 h, the volatiles were removed and the residue was partitioned between ethyl acetate and saturated aqueous sodium bicarbonate. The organic phase was washed with brine, dried (sodium sulfate) and concentrated in vacuo to give a residue. The residue was treated with 2M hydrochloric acid and THF (1:1) at 80° C. for 1 h, then purified by reverse phase HPLC (KR100-5C18 100×21.2 mm column; 10-100% MeCN/H$_2$O over 12 min) to afford the title compound. LC-MS: m/e 361 (M+H).

EXAMPLE 231

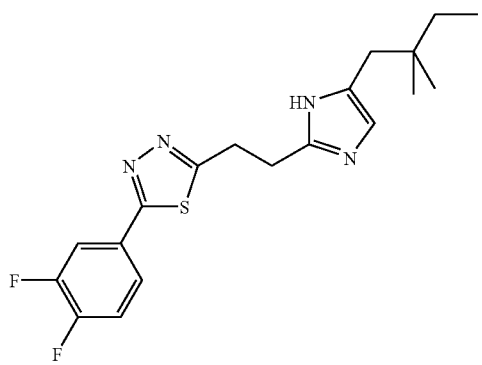

2-(3,4-Difluorophenyl)-5-{2-[5-(2,2-dimethylbutyl)-1H-imidazol-2-yl]ethyl}-1,3,4-thiadiazole Lawesson's reagent (317 mg, 0.78 mmol) was added to a solution of intermediate 26 (190 mg, 0.39 mmol) in dry toluene (4 mL) at rt. After stirring at reflux for 30 min and at rt for 60 h, the volatiles were removed to give a residue. The residue was dissolved in THF (4 mL) and 2 M HCl (4 mL) and heated at 80° C. overnight. The volatiles were removed again, and the residue was washed with ethyl acetate, basified with 1 N aqueous sodium hydroxide and extracted with ethyl acetate. The combined phases were dried over sodium sulfate and concentrated to afford the title compound. LC-MS: m/e 377 (M+H).

EXAMPLE 232

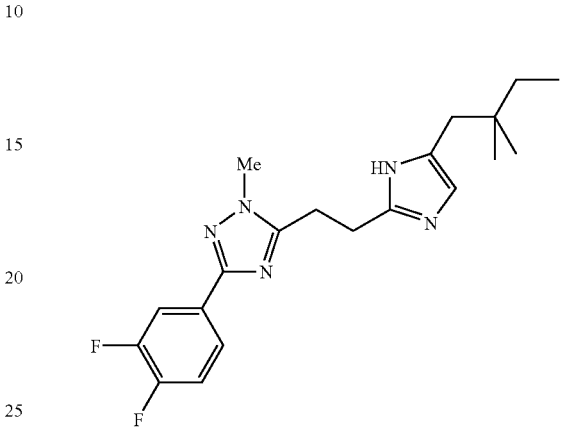

3-(3,4-Difluorophenyl)-5-{2-[5-(2,2-dimethylbutyl)-1H-imidazol-2-yl]ethyl}-1-methyl-1H-1,2,4-triazole Step A: A solution of sodium methoxide (31 mg, 0.58 mmol) in anhydrous ethanol (1 mL) was added to a solution of 3,4-difluorobenzamidine hydrochloride (84 mg, 0.43 mmol) in anhydrous ethanol (1 mL) at rt. After stirring at rt for 45 min, the slurry was filtered. Intermediate 25 (100 mg, 0.29 mmol) was added to the filtrate. After stirring at reflux for 18 hr, reaction mixture was concentrated in vacuo to afford 2-{2-[5-(3,4-difluorophenyl)-4H-1,2,4-triazol-3-yl]ethyl}-4-(2,2-dimethylbutyl)-N,N-dimethyl-1H-imidazole-1-sulfonamide, which was used without further purification.

Step B: Sodium hydride (21 mg, 0.87 mmol) was added to a solution of 2-{2-[5-(3,4-difluorophenyl)-4H-1,2,4-triazol-3-yl]ethyl}-4-(2,2-dimethylbutyl)-N,N-dimethyl-1H-imidazole-1-sulfonamide (135 mg, 0.29 mmol) in DMF (4 mL) at 0° C., and the reaction was stirred at rt for 30 min. Methyliodide (0.09 mL, 1.4 mmol) was added and stirring continued for 1 hr. The reaction mixture was partitioned between water and diethyl ether. The organic phase was washed with water and brine, dried (sodium sulfate) and concentrated to give a residue. Chromatography of the residue over silica gel (eluting with 60-100% ethyl acetate/hexane) afforded 2-{2-[3-(3,4-difluorophenyl)-1-methyl-1H-1,2,4-triazol-5-yl]ethyl}-4-(2,2-dimethylbutyl)-N,N-dimethyl-1H-imidazole-1-sulfonamide as an off-white solid.

Step C: A solution of 2-{2-[3-(3,4-difluorophenyl)-1-methyl-1H-1,2,4-triazol-5-yl]ethyl}-4-(2,2-dimethylbutyl)-N,N-dimethyl-1H-imidazole-1-sulfonamide (90 mg, 0.19 mmol) in THF (4 mL) and 2 M HCl (4 mL) was heated at 80° C. overnight. The volatiles were removed and the residue was washed with ethyl acetate, basified with 1 N aqueous sodium hydroxide and extracted with ethyl acetate. The combined phases were dried over sodium sulfate and concentrated to afford the title compound. LC-MS: m/e (374M+H).

EXAMPLE 233

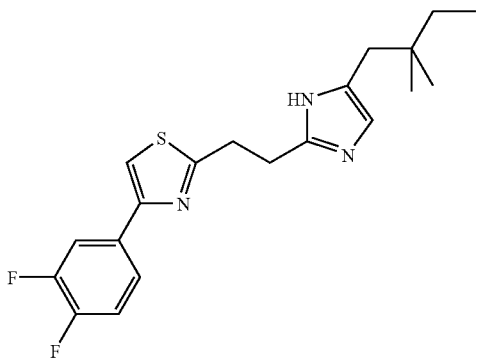

4-(3,4-Difluorophenyl)-2-{2-[5-(2,2-dimethylbutyl)-1H-imidazol-2-yl]ethyl}-1,3-thiazole Step A: Phosphorus petitasulfide (100 mg, 0.45 mmol) was added to a solution of intermediate 28 (100 mg, 0.45 mmol) in anhydrous 1,4-dioxane (1 mL). After stirring at rt overnight, the reaction mixture was filtered through Celite rinsing with ethyl acetate. The volatiles were removed to afford 3-[4-(2,2-dimethylbutyl)-1H-imidazol-2-yl]propanethioamide, which was used without further purification.

Step B: 3-[4-(2,2-Dimethylbutyl)-1H-imidazol-2-yl]propanethioamide (58 mg, 0.24 mmol) in ethanol (1 mL) was added to 2-bromo-1-(3,4-difluorophenyl)ethanone (56 mg, 0.24 mmol) in anhydrous 1,4-dioxane (4 mL). After stirring at rt overnight, the reaction mixture was concentrated to give a residue, which was purified by reverse phase HPLC (KR100-5C18 100×21.2 mm column; 10-100% MeCN/H₂O over 12 min) to afford the title compound. LC-MS: m/e 376 (M+H).

EXAMPLE 234

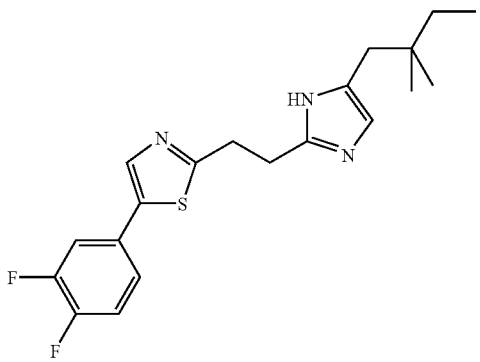

5-(3,4-Difluorophenyl)-2-{2-[5-(2,2-dimethylbutyl)-1H-imidazol-2-yl]ethyl}-1,3-thiazole Step A: Sodium azide (625 mg, 9.6 mmol) followed by ammonium chloride (514 mg, 9.6 mmol) were added to a solution of 2-(3,4-difluorophenyl)oxirane (1 g, 6.4 mmol) in methanol (10 mL) and water (2.5 mL). After stirring at 80° C. overnight, the reaction mixture was concentrated to give a residue. The residue was partitioned between water and ethyl acetate. The organic phase was washed with brine, dried (sodium sulfate) and concentrated to give a residue. Chromatography of the residue over silica gel eluting with 10-50% ethyl acetate/hexane afforded 2-azido-1-(3,4-difluorophenyl)ethanol.

Step B: A suspension of Pd (10 wt % on carbon; 232 mg, 0.22 mmol) in a solution of afforded 2-azido-1-(3,4-difluorophenyl)ethanol (435 mg, 2.2 mmol) in ethanol (20 mL) was stirred under an atmosphere of hydrogen overnight. The reaction mixture was filtered through Celite, acidified with hydrogen chloride (1 M in diethyl ether) and concentrated in vacuo to afford 2-amino-1-(3,4-difluorophenyl)ethanol, which was used without further purification.

Step C: A solution of 2-amino-1-(3,4-difluorophenyl)ethanol (63 mg, 0.36 mmol) in methylene chloride (5 mL) was added to a solution of intermediate 27 (60 mg, 0.18 mmol), EDC (69 mg, 0.36 mmol), HOBt (55 mg, 362 mmol) and NMM (0.1 mL, 0.91 mmol) in methylene chloride (5 mL) at rt. After stirring at rt overnight, the reaction mixture was poured into ethyl acetate and washed successively with 2N aqueous hydrochloric acid, saturated aqueous sodium bicarbonate and brine, dried (sodium sulfate) and concentrated to afford N-[2-(3,4-difluorophenyl)-2-hydroxyethyl]-3-[1-[(dimethylamino)sulfonyl]-4-(2,2-dimethylbutyl)-1H-imidazol-2-yl]propanamide, which was used without further purification.

Step D: Dess-Martin reagent (157 mg, 0.37 mmol) was added to a solution of N-[2-(3,4-difluorophenyl)-2-hydroxyethyl]-3-[1-[(dimethylamino)sulfonyl]-4-(2,2-dimethylbutyl)-1H-imidazol-2-yl]propanamide (90 mg, 0.19 mmol) in methylene chloride (5 mL) at rt. After stirring at rt for 2 hr, a solution of saturated aqueous sodium bicarbonate and saturated aqueous sodium thiosulfate (1:1) was added and the solution stirred until clear. The reaction mixture was extracted with ethyl acetate washed with brine, dried (sodium sulfate) and concentrated to afford N-[2-(3,4-difluorophenyl)-2-oxoethyl]-3-[1-[(dimethylamino)sulfonyl]-4-(2,2-dimethylbutyl)-1H-1H-imidazol-2-yl]propanamide, which was used without further purification.

Step E: Lawesson's reagent (50 mg, 0.12 mmol) was added to a solution of N-[2-(3,4-difluorophenyl)-2-oxoethyl]-3-[1-[(dimethylamino)sulfonyl]-4-(2,2-dimethylbutyl)-1H-imidazol-2-yl]propanamide (30 mg, 0.06 mmol) in dry toluene (4 mL) at rt. After stirring at reflux for 30 min, volatiles were removed. The resulting residue was dissolved in THF (0.5 mL), and 2M aqueous hydrochloric acid (1.5 mL) was added. After stirring at 80° C. overnight, the volatiles were removed. The aqueous phase was diluted with water and washed with 1:5 ethyl acetate/diethyl ether. The aqueous phase was basified with 1N sodium hydroxide and extracted with ethyl acetate. Combined extracts were washed with brine, dried (sodium sulfate) and concentrated to afford the title compound, which was dissolved in methylene chloride and acidified with 1M hydrogen chloride in diethyl ether. Additional diethyl ether and hexane were added, and concentration afforded the HCl salt of the title compound. LC-MS: m/e 376 (M+H).

EXAMPLE 235

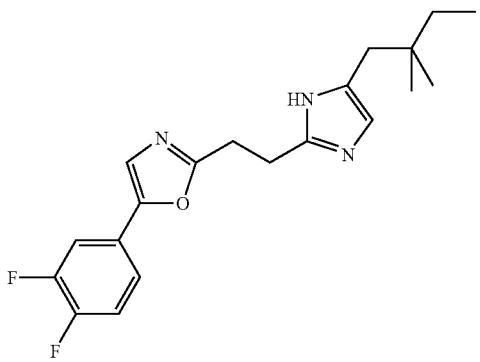

5-(3,4-Difluorophenyl)-2-{2-[5-(2,2-dimethylbutyl)-1H-imidazol-2-yl]ethyl}-1,3-oxazole Phosphorus oxychloride (190 mg, 1.2 mmol) was added to a solution of N-[2-(3,4-difluorophenyl)-2-oxoethyl]-3-[1-[(dimethylamino)sulfonyl]-4-(2,2-dimethylbutyl)-1H-imidazol-2-yl]propanamide (for synthesis see example 234) (30 mg, 0.06 mmol) in dry acetonitrile (4 mL) at rt. After stirring at 80° C. overnight, saturated sodium bicarbonate (ca. 3 mL) was added. The aqueous phase was washed with 1:5 ethyl acetate/diethyl ether, basified with 5N aqueous sodium hydroxide and extracted with ethyl acetate. Combined extracts were washed with brine, dried (sodium sulfate) and concentrated to give a residue. The residue was dissolved in methylene chloride to give the title compound, which was acidified with 1M HCl in diethyl ether. Additional diethyl ether and hexane were added, and concentration afforded the HCl salt of the title compound. LC-MS: m/e 360 (M+H).

EXAMPLE 236

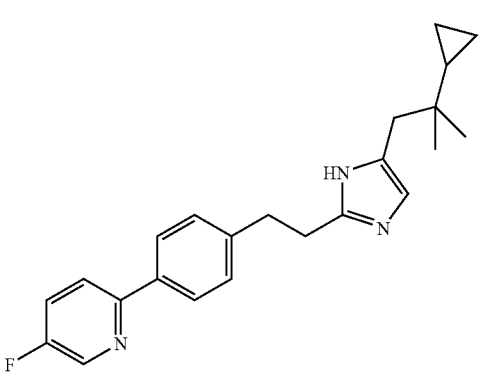

2-(4-{2-[5-(2-Cyclopropyl-2-methylpropyl)-1H-imidazol-2-yl]ethyl}phenyl)-5-fluoropyridine The title compound was prepared from intermediate 15 and intermediate 18 following the cylization procedure described in Example 1. The crude product was purified by silica gel chromatography eluting with chloroform/methanol/concentrated ammonium hydroxide (200:10:1) to afford the title compound, which was converted the HCl salt using 2M HCl in diethyl ether. $^1$H NMR (500 MHz, CD$_3$OD) δ 8.48 (s, 1H), 7.73-7.86 (m, 4H), 7.20 (d, J=8.3 Hz, 2H), 7.05 (s, 1H), 3.23 (t, J=7.2 Hz, 2H), 3.08 (t, J=7.2 Hz, 2H), 2.48 (s, 2H), 0.62 (s, 6H), 0.49-0.52 (m, 1H), 0.12-0.15 (m, 2H), 0.02-0.06 (m, 2H); LC-MS: m/e 364 (M+H).

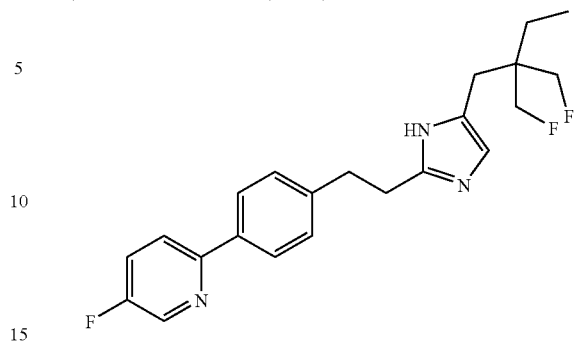

2-(4-{2-[5-(2,2-Bis(fluoromethyl)butyl)-1H-imidazol-2-yl]ethyl}phenyl)-5-fluoro-pyridine The title compound was prepared from intermediate 17 and intermediate 18 following the cyclization procedure described in Example 1. The crude product was purified by silica gel chromatography eluting with chloroform/methanol/concentrated ammonium hydroxide (200:10:1) to afford the title compound, which was converted to the HCl salt using 2M HCl in diethyl ether. $^1$H NMR (500 MHz, CD$_3$OD) δ 8.45 (d, J=2.9 Hz, 1H), 7.82 (dd, J=8.9, 4.4 Hz, 1H), 7.78 (d, J=8.3 Hz, 2H), 7.66 (td, J=8.5, 2.9 Hz, 1H), 7.18 (d, J=8.3 Hz, 2H), 7.11 (s, 1H), 4.20 (dd, J=47.6, 9.6 Hz, 2H), 4.13 (ddd, J=47.2, 9.6, 1.5 Hz, 2H), 3.19 (t, J=7.5 Hz, 2H), 3.06 (t, J=7.5 Hz, 2H), 2.62 (s, 2H), 1.20 (t, J=7.5 Hz, 2H), 0.81 (t, J=7.5 Hz, 3H); LC-MS: m/e 388 (M+H).

EXAMLPE 238

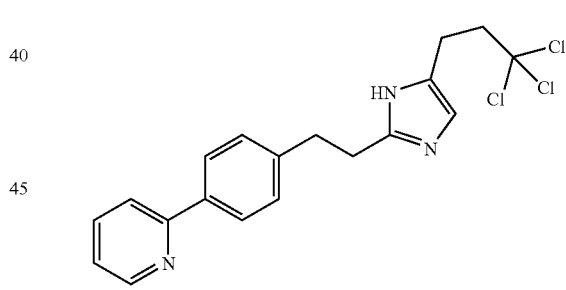

2-(4-{2-[5-(3,3,3-Trichloropropyl)-1H-imidazol-2-yl]ethyl}phenyl)pyridine

The title compound was prepared from intermediate 7 and intermediate 16 following the cylization procedure described in Example 1. The crude product was purified by silica gel chromatography eluting with 0-5% a 10:1 methanol/concentrated ammonium hydroxide mixture in chloroform to afford the title compound, which was converted to the HCl salt using 2M HCl in diethyl ether. $^1$H NMR (500 MHz, CD$_3$OD) δ 8.74-8.72 (m, 1H), 8.36-8.33 (m, 1H), 8.16 (d, J=8.2 Hz, 1H), 7.92 (d, J=8.2 Hz, 2H), 7.76-7.74 (t, J=6.3 Hz, 1H), 7.45 (d, J=8.2 Hz, 2H), 7.30 (s, 1H), 3.34-2.27 (m, 2H), 3.26-3.21 (m, 2H), 3.18-3.14 (m, 2H), 3.10-3.07 (m, 2H); LC-MS: m/e 394 (M+H).

EXAMPLE 239

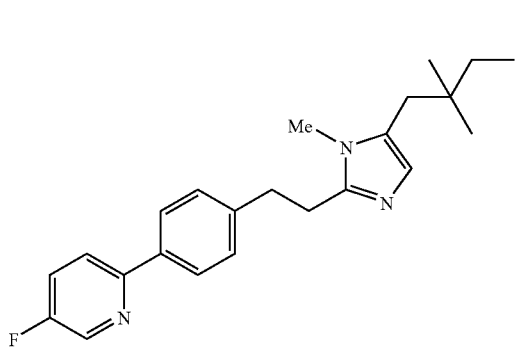

2-(4-{2-[5-(2,2-dimethylbutyl)-1-methyl-1H-imidazol-2-yl]ethyl}phenyl)-5-fluoropyridine Step A: Intermediate 9 (13.1 g, 90.2 mmol) was added to a solution of 3-(4-bromophenyl)propanoyl chloride (20.3 g, 82 mmol) in CH$_2$Cl$_2$ (175 mL) at rt. After stirring for 2 h, the solvent was removed in vacuo to give 3-(4-bromophenyl)-N-(2-hydroxy-4,4-dimethylhexyl)propanamide, which was used directly in the next step.

Step B: Dess-Martin reagent (38.8 g, 91.5 mmol) was added to a solution of 3-(4-bromophenyl)-N-(2-hydroxy-4,4-dimethylhexyl)propanamide (29.6 g, 83.2 mmol) in CH$_2$Cl$_2$ (400 mL) at rt. After stirring for 1 h, a solution of saturated aqueous NaHCO$_3$ and saturated aqueous Na$_2$S$_2$O$_3$ (1:1) was added and the solution was stirred until it became clear. The solution was extracted with ethyl acetate. The organic layer was dried (MgSO$_4$), filtered, and concentrated in vacuo to give a residue. The residue was purified by flash column chromatography on silica gel eluting with 0-50% EtOAc/hexanes to provide 3-(4-bromophenyl)-N-(4,4-dimethyl-2-oxohexyl)propanamide.

Step C: Acetic acid (1.08 mL, 18.9 mmol) and 2M methylamine in THF (1.09 mL, 2.2 mmol) were added to a solution of 3-(4-bromophenyl)-N-(4,4-dimethyl-2-oxohexyl)propanamide in xylenes (20 mL). The solution was stirred at reflux with azeotropic removal of water for 1 h. Another batch of acetic acid and methylamine were added and stirring was continued at reflux for another 4 h. After cooling to rt, the solution was washed with brine, dried (MgSO$_4$), filtered, and concentrated in vacuo to give 2-[2-(4-bromophenyl)ethyl]-5-(2,2-dimethylbutyl)-1-methyl-1H-imidazole.

Step D: Hexamethylditin (174 mg, 0.53 mmol) was added to a solution of 2-[2-(4-bromophenyl)ethyl]-5-(2,2-dimethylbutyl)-1-methyl-1H-imidazole (186 mg, 0.53 mmol), 2-bromo-5-fluoropyridine (94 mg, 0.53 mmol), and tetrakis(triphenylphosphine)palladium (0), (62 mg, 0.053 mmol) in 1,4-dioxane (25 mL). The mixture was stirred overnight at 110° C. KF on Celite (1:1) was added and the solution was stirred at rt for 1 h. The mixture was filtered, and the filtrate was washed with water, dried (MgSO$_4$), filtered, and concentrated in vacuo to give a residue. The residue was purified by flash column chromatography on silica gel eluting with 0-50% EtOAc/hexanes to provide the title compound. LC-MS: m/e 366 (M+H).

EXAMPLE 240

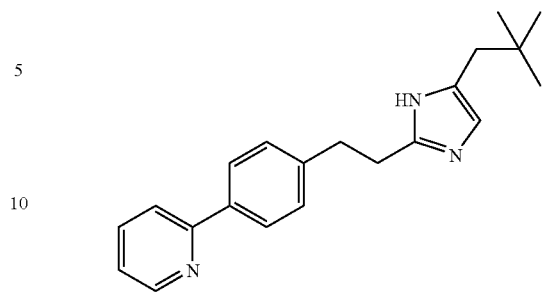

2-(4-{2-[4-(2,2-Dimethylpropyl)-1H-imidazol-2-yl]ethyl}phenyl)pyridine

The title compound was prepared from intermediate 7 and intermediate 2 following the cyclization procedure described in Example 1. The crude product was purified by preparative TLC plate silica gel chromatography with the following solvent system: CH$_2$Cl$_2$:CH$_3$OH: NH$_4$OH (200:10:1) to afford the title compound. $^1$H NMR (500 MHz, CDCl$_3$) δ 8.68 (1H, d, J=4.1 Hz), 7.90 (2H, d, J=8.0 Hz), 7.75 (1H, td, J=7.7 Hz, J=1.8 Hz), 7.70 (1H, m), 7.24 (3H, m), 6.63 (1H, s), 3.09 (2H, m), 3.02 (2H, m), 2.40 (2H, s), 0.9 (9H, s); LCMS: m/e 320.4(M+H).

EXAMPLE 241

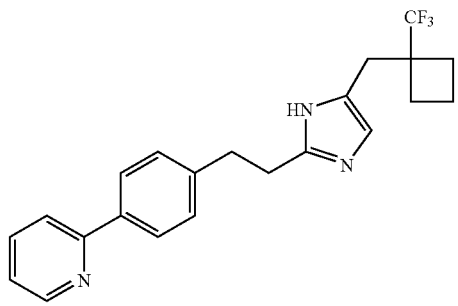

2-{4-[2-(5-{[1-(Ttrifluoromethyl)cyclobutyl]methyl}-1H-imidazol-2-yl)ethyl]phenyl}pyridine Step A: A solution of 2-methylimidazole and 4-(2-pyridyl)benzaldehyde in acetic anhydride (50 mL) was heated at reflux overnight. The volatiles were removed, and the resulting residue was chromatographed over silica gel eluting with 1-20% methanol/methylene chloride to afford 2-{4-[(2-(1H-imidazol-2-yl)vinyl]phenyl}pyridine.

Step B: A suspension of Pd (10 wt % on carbon) (2.7 g, 2.6 mmol) in a solution of 2-{4-[(2-(1H-imidazol-2-yl)vinyl]phenyl}pyridine (6.3 g, 26 mmol) in methanol (200 mL) was stirred under an atmosphere of hydrogen overnight. The reaction mixture was filtered through Celite, acidified with hydrogen chloride (1 M in diethyl ether) and concentrated in vacuo to afford 2-{4-[2-(1H-imidazol-2-yl)ethyl]phenyl}-pyridine, which was used without further purification.

Step C: Sodium carbonate (8.0 g, 75.3 mmol) followed by iodine (13.4 g, 52.7 mmol) were added to a solution of 2-{4-]2-(1H-imidazol-2-yl)ethyl]phenyl}pyridine (6.3 g, 25.1 mmol) in dioxane/water (1:1) (200 mL). After stirring in the dark at rt overnight, ethyl acetate (ca. 500 mL) was added and the mixture was washed with 10% aqueous sodium thiosulfate solution. The product was extracted with ethyl acetate, and the combined extracts were washed with brine, dried over sodium sulfate and concentrated to afford 2-{4-[2-(4,5-diiodo-1H-imidazol-2-yl)ethyl]phenyl}pyridine, which was used in the next step without further purification.

Step D: A solution of 2-{4-[2-(4,5-diiodo-1H-imidazol-2-yl)ethyl]phenyl}pyridine (11.2 g, 22.4 mmol) and sodium sulfite (3.1 g, 24.7 mmol) in ethanol (200 mL) and water (200 mL) was heated at 100° C. for 2 days. The reaction mixture was concentrated to half its original volume and partitioned between ethyl acetate and water. The organic phase was separated and concentrated in vacuo to afford 2-{4-[2-(4-iodo-1H-imidazol-2-yl)ethyl]phenyl}pyridine, which was used without further purification.

Step E: Sodium hydride (384 mg, 16 mmol) was added to a solution of 2-{4-[2-(4-iodo-1H-imidazol-2-yl)ethyl]phenyl}pyridine (5 g, 13.3 mmol) in dimethylformamide (100 mL) at 0° C. After stirring at 0° C. for 1 hr, dimethylsulfamoyl chloride (2.15 mL, 20 mmol) was added. After stirring at rt overnight, the reaction mixture was poured into water and extracted with ethyl acetate. The extracts were washed with brine, dried (sodium sulfate) and concentrated to give a residue. Chromatography of the residue over silica gel eluting with 0-20% acetone methylene chloride afforded 4-iodo-N,N-dimethyl-2-[2-(4-pyridin-2-ylphenyl)ethyl]-1H-imidazole-1-sulfonamide.

Step F: 1-Chloro-N,N,2-trimethyl-1-propenylamine (332 mg, 2.5 mmol) was added to a solution of 1-(trifluoromethyl)cyclobutanecarboxylic acid (418 mg, 2.5 mmol) in methylene chloride (3 mL) and the reaction left to stir at rt for 1 h to afford a acyl chloride solution. Ethylmagnesium bromide (3 M in diethyl ether) (0.46 mL, 1.4 mmol) was added to a solution of 4-iodo-N,N-dimethyl-2-[2-(4-pyridin-2-ylphenyl)-1H-imidazole-1-sulfonamide (600 mg, 1.2 mmol) in methylene chloride (12 mL) at rt. After stirring at rt for 30 min, CuCN-2LiCl (1 M in THF; 1.37 mL, 1.37 mmol) was added followed by the above acyl chloride solution, and the reaction was stirred for 2 hr. The reaction mixture was diluted with methylene chloride and poured into half saturated aqueous ammonium chloride. The aqueous phase was extracted with methylene chloride, and the extracts were dried (sodium sulfate) and concentrated in vacuo. Chromatography of the resulting residue over silica gel eluting with 40-100% ethyl acetate/hexane afforded N,N-dimethyl-2-[2-(4-pyridin-2-ylphenyl)ethyl]-4-{[1-(trifluoromethyl)-cyclobutyl]carbonyl}-1H-imidazole-1-sulfonamide.

Step G: Sodium borohydride (8 mg, 0.21 mmol) was added to a solution of N,N-dimethyl-2-[2-(4-pyridin-2-ylphenyl)ethyl]-4-{[1-(trifluoromethyl)cyclobutyl]carbonyl}-1H-imidazole-1-sulfonamide (106 mg, 0.21 mmol) in methanol (3 mL) at 0° C. followed by 1 drop of water. The resulting solution was stirred at rt for 1 hr. The reaction mixture was partially concentrated and partitioned between 1N aqueous sodium hydroxide and ethyl acetate. The organic phase was washed with brine, dried (sodium sulfate) and concentrated to give a residue. Chromatography of the residue over silica gel eluting with 40-100% ethyl acetate/hexane afforded 4-{hydroxy[1-(trifluoromethyl)cyclobutyl]methyl}-N,N-dimethyl-2-[2-(4-pyridin-2-ylphenyl)ethyl]-1H-imidazole-1-sulfonamide.

Step H: 1,1'-Thiocarbonyldiimidazole (15 mg, 0.08 mmol) and catalytic DMAP were added to a solution of 4-{hydroxy[1-(trifluoromethyl)cyclobutyl]methyl}-N,N-dimethyl-2-[2-(4-pyridin-2-ylphenyl)ethyl]-1H-imidazole-1-sulfonamide (21 mg, 0.04 mmol) in methylene chloride (1 mL). After stirring at rt for 24 hr, the reaction mixture was concentrated in vacuo to give a residue. Chromatography of the residue over silica gel (eluting with 20-100% ethyl acetate/hexane) afforded O-{{1-[(dimethylamino)sulfonyl]-2-[2-(4-pyridin-2-ylphenyl)ethyl]-1H-imidazol-4-yl}[1-(trifluoromethyl)cyclobutyl]methyl}1H-imidazole-1-carbothioate.

Step I: Tributyltin hydride (8 mg, 0.03 mmol) in toluene (0.1 mL) was added to a solution of O-{{1-[(dimethylamino)sulfonyl]-2-[2-(4-pyridin-2-ylphenyl)ethyl]-1H-imidazol-4-yl}[1-(trifluoromethyl)-cyclobutyl]methyl}1H-imidazole-1-carbothioate (12 mg, 0.02 mmol) and ADEN (1 mg, 0.005 mmol) in refluxing toluene (0.4 mL) dropwise over 2 minutes. After stirring at 110° C. for 10 minutes, the volatiles were removed in vacuo to give a residue. Chromatography of the residue over silica gel eluting with 20-80% ethyl acetate/hexane afforded N,N-dimethyl-2-[2-(4-pyridin-2-ylphenyl)ethyl]-4-{[1-(trifluoro-methyl)cyclobutyl]methyl}-1H-imidazole-1-sulfonamide.

Step J: A solution of N,N-dimethyl-2-[2-(4-pyridin-2-ylphenyl)ethyl]-4-{[1-(trifluoromethyl)cyclobutyl]-methyl}-1H-imidazole-1-sulfonamide (5 mg, 0.01 mmol) in THF (0.5 mL) and 2 M HCl (0.5 mL) was heated at 70° C. for 4 hr. The volatiles were removed, the resulting residue was basified with 1 N NaOH and the product extracted with ethyl acetate. The combined phases were washed with brine, dried (sodium sulfate) and concentrated to afford the title compound. LC-MS: m/e 386 (M+H).

EXAMPLE 242

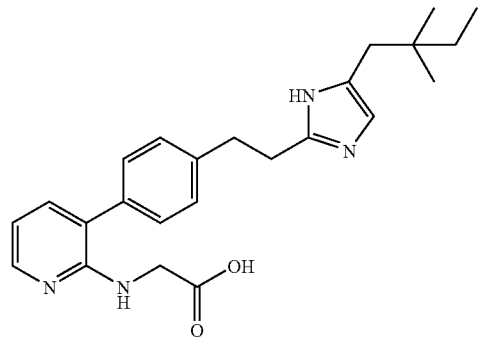

2-[3-(4-{2-[5-(2,2-Dimethylbutyl)-1H-imidazol-2-yl]ethyl}phenyl)pyridin-2-ylamino]acetic acid Step A: 2-[3-(4-{2-[4-(2,2-Dimethylbutyl)-1-trityl-1H-imidazol-2-yl]ethyl}phenyl)pyridin-2-ylamino]acetic acid methyl ester was prepared following the procedure described for Example 196 by substituting 2-bromothiophene with (3-bromopyridin-2-ylamino)acetic acid methyl ester (*J. Org. Chem.* 1990, 55, 3143). The crude product was purified by flash column chromatography (silica gel) eluting with 0-50% ethyl acetate in hexanes to give 2-[3-(4-{2-[4-(2,2-Dimethylbutyl)-1-trityl-1H-imidazol-2-yl]ethyl}phenyl)pyridin-2-ylamino]acetic acid methyl ester.

Step B: 2-[3-(4-{2-[4-(2,2-Dimethylbutyl)-1-trityl-1H-imidazol-2-yl]ethyl}phenyl)pyridin-2-ylamino]acetic acid methyl ester (20 mg, 0.03 mmol) was refluxed in a mixture of toluene (2 mL) and 6 M HCl (2 mL) for 1 h. Upon cooling, the aqueous phase was separated, washed with toluene and concentrated to give the title compound as the HCl salt. $^1$H NMR (500 MHz, DMSO-d$_6$) δ 14.2 (br, 2H), 7.99 (dd, J=6.1, 1.5 Hz, 1H), 7.71 (br, 1H), 7.38 (m, 4H), 7.27 (s, 1H), 6.69 (br, 1H), 4.20 (s, 2H), 3.25 (t, J=7.5 Hz, 2H), 3.15 (t, J=7.5 Hz, 2H), 2.43 (s, 2H), 1.19 (q, J=7.6 Hz, 2H), 0.80 (m, 9H; LC-MS: m/e 407 (M+H).

EXAMPLE 243

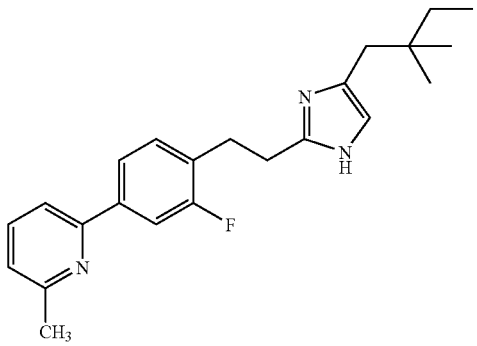

2-(4-{2-[5-(2,2-Dimethylbutyl)-1H-imidazol-2-yl]ethyl)-3-fluorophenyl)-6-methylpyridine The title compound was prepared from intermediate 12 and 2-bromo-6-methylpyridine according to procedure described for Example 196. The crude product was purified by silica gel chromatography eluting with methylene chloride/methanol/concentrated ammonium hydroxide (200:10:1) to give the title compound, which was converted to the HCl salt using 2M HCl in diethyl ether. $^1$H NMR (500 MHz, CD$_3$OD) δ 8.48 (t, J=8.0 Hz, 1H), 8.06 (d, J=8.0 Hz, 1H), 7.87 (d, J=7.8 Hz, 1H), 7.71-7.77 (m, 2H), 7.57 (t, J=7.6 Hz, 1H), 7.18 (s, 1H), 3.26-3.35 (m, 4H), 2.91 (s, 3H), 2.53 (s, 2H), 1.25 (q, J=7.3 Hz, 2H), 0.86-0.92 (m, 9H); LC-MS: m/e 366 (M+H).

EXAMPLE 244

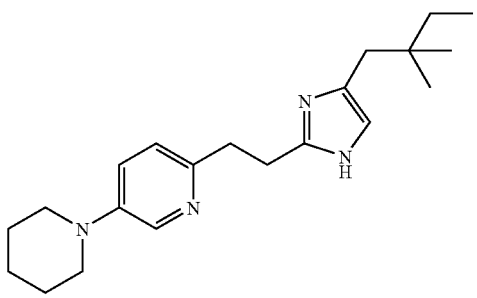

2-(4-{2-[5-(2,2-Dimethylbutyl)-1H-imidazol-2-yl]ethyl}-3-fluorophenyl)-6-methylpyridine The title compound was prepared from intermediate 13 and piperidine following the procedure described for Example 224. The crude product was purified by flash column chromatography (silica gel) eluting with 1-10% MeOH/NH$_4$OH (10:1) in methylene chloride to give the title compound, which was converted to the HCl salt with 1M HCl in diethyl ether. $^1$H NMR (500 MHz, CD$_3$OD) δ 8.24 (s, 1H), 8.01 (s, 1H), 7.65 (d, J=9.1 Hz, 1H), 7.22 (s, 1H), 3.49-3.40 (m, 8H), 2.56 (s, 2H), 1.71 (m, 6H), 1.31-1.26 (m, 2H), 0.92-0.87 (m, 9H); LC-MS: m/e 341 (M+H).

EXAMPLE 245

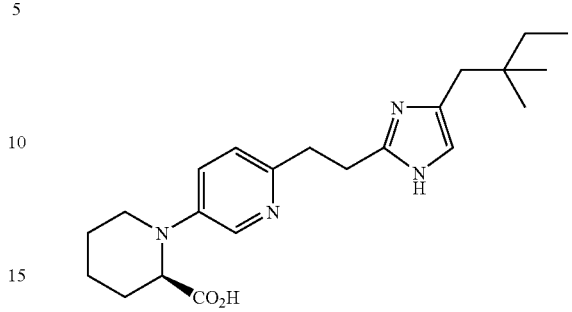

(R)-6'-{2-[5-(2,2-Dimethylbutyl)-1H-imidazol-2-yl]ethyl}-3,4,5,6-tetrahydro-2H-[1,3']bipyridinyl-2-carboxylic acid The title compound was prepared from intermediate 13 and D-pipecolinic acid following the procedure described for Example 225. The crude product was purified by flash column chromatography (silica gel) eluting with 0-20% MeOH/NH$_4$OH (10:1) in methylene chloride to give the title compound, which was converted to the HCl salt with 1M HCl in diethyl ether. $^1$H NMR (500 MHz, CD$_3$OD) δ 8.26 (s, 1H), 8.03-8.01 (d, J=9.1 Hz, 1H), 7.67-7.65 (d, J=9.1 Hz, 1H), 7.22 (s, 1H), 3.76-3.74 (m, 1H), 3.45-3.41 (m, 4H), 3.19-3.14 (m, 1H), 2.56 (s, 2H), 2.43-2.40 (m, 1H), 2.02 (s, 1H), 1.94-1.87 (m, 2H), 1.81-1.77 (m, 1H), 1.69-1.64 (m, 1H), 1.46-1.40 (m, 1H), 1.31-1.27 (q, J=7.6 Hz, 2H), 0.92-0.87 (m, 9H); LC-MS: m/e 385 (M+H).

EXAMPLE 246

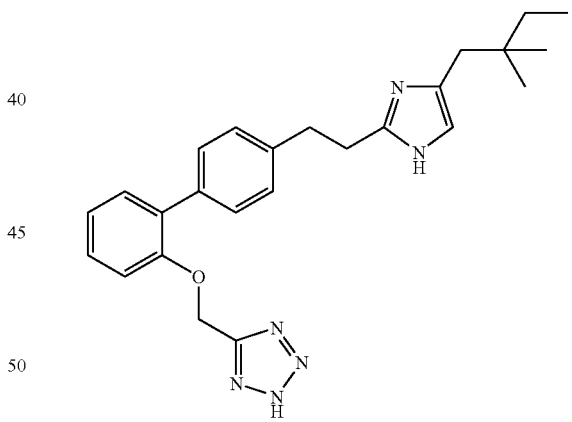

5-(4'-{2-[4-(2,2-Dimethylbutyl)-1H-imidazol-2-yl]ethyl}biphenyl-2-yloxymethyl)-1H-tetrazole Step A: (4'-{2-[4-(2,2-Dimethylbutyl)-1-trityl-1H-imidazol-2-yl]ethyl}biphenyl-2-yloxy)acetonitrile was prepared following the procedure described for Example 196 by substituting 2-bromothiophene with 2-iodophenoxyacetonitrile. The crude product was purified by flash column chromatography on silica gel eluting with 0-40% ethyl acetate in hexanes to give (4'-{2-[4-(2,2-Dimethylbutyl)-1-trityl-1H-imidazol-2-yl]ethyl}biphenyl-2-yloxy)acetonitrile.

Step B: (4'-{2-[4-(2,2-Dimethylbutyl)-1-trityl-1H-imidazol-2-yl]ethyl}biphenyl-2-yloxy)acetonitrile (151 mg, 0.24 mmol), sodium azide (140 mg, 2.14 mmol) and ammonium chloride (102 mg, 1.71 mmol) in DMF (3 mL) were heated at 100° C. for 24 h under nitrogen.

Upon cooling, the reaction mixture was partitioned between brine and ethyl acetate. The organic layer was separated, dried over sodium sulfate and concentrated to give a residue. The residue was purified by flash column chromatography on silica gel eluting with 0-20% methanol/ammonium hydroxide (10:1) in methylene chloride to provide the title compound. $^1$H NMR (300 MHz, CD$_3$OD) δ 7.38 (d, J=8.1 Hz, 2H), 7.24 (m, 3H), 7.00 (m, 4H), 5.20 (s, 2H), 3.20 (t, J=7.1 Hz, 2H), 3.04 (t, J=7.0 Hz, 2H), 2.46 (s, 2H), 1.20 (q, J=7.6 Hz, 2H), 0.82 (m, 9H); LC-MS: m/e 431 (M+H).

EXAMPLE 247

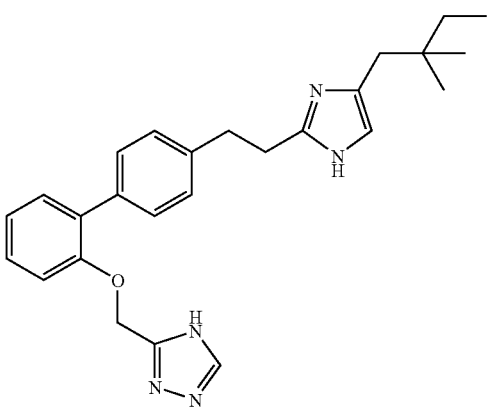

3-(4'-{2-[4-(2,2-Dimethylbutyl)-1H-imidazol-2-yl] ethyl}biphenyl-2-yloxymethyl)-4H-[1,2,4]triazole Step A: To a solution of (4'-{2-[4-(2,2-dimethylbutyl)-1-trityl-1H-imidazol-2-yl]ethyl}biphenyl-2-yloxy)acetonitrile (Example 225, Step A, 225 mg, 0.36 mmol) in anhydrous methanol (5 mL) was added potassium tert-butoxide (44 mg, 0.43 mmol) under nitrogen. The reaction was brought to reflux and then allowed to cool to rt for 2 h. Formic hydrazide (107 mg, 1.79 mmol) was added and the reaction was heated at reflux for 16 hours. The resulting mixture was cooled and concentrated to give a residue. The residue was purified by flash column chromatography on silica gel eluting with 0-10% methanol/ammonium hydroxide (10:1) in methylene chloride to provide 3-(4'-{2-[4-(2,2-dimethylbutyl)-1-trityl-1H-imidazol-2-yl]ethyl}biphenyl-2-yloxymethyl)-4H-[1,2, 4]triazole.

Step B: 3-(4'-{2-[4-(2,2-Dimethylbutyl)-1-trityl-1H-imidazol-2-yl]ethyl}biphenyl-2-yloxymethyl)-4H-[1,2,4]triazole was converted to the title compound by treatment with TFA at 60° C. for 30 minutes. The crude product was purified by flash column chromatography on silica gel eluting with 0-20% methanol/ammonium hydroxide (10:1) in methylene chloride to afford the title compound. $^1$H NMR (300 MHz, CD$_3$OD) δ 8.30 (s, 1H), 7.38 (d, J=8.2 Hz, 2H), 7.28 (m, 2H), 7.12 (m, 4H), 6.57 (s, 1H), 5.11 (s, 2H), 2.96 (m, 4H), 2.38 (s, 2H), 1.22 (m, 2H), 0.84 (s, 9H); LC-MS: m/e (M+H).

EXAMPLE 248

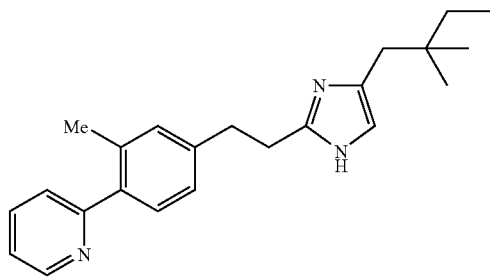

2-(4-{2-[4-(2,2-Dimethylbutyl)-1H-imidazol-2-yl] ethyl}-2-methylphenyl)pyridine

The title compound was prepared from intermediate 20 with 2-bromopyridine following the procedure described for Example 196. The crude product was purified by flash column chromatography on silica gel eluting with 0-5% methanol/ammonium hydroxide mixture in methylene chloride to give the title compound, which was converted to the TFA salt using TFA. $^1$NMR (300 MHz, CDCl$_3$) δ 8.79 (s, 1H), 8.55-8.50 (t, J=7.7 Hz, 1H), 7.95-7.93 (d, J=7.7 Hz, 2H), 7.22-7.19 (d, J=7.6 Hz, 1H), 6.98-6.92 (m, 2H), 6.78 (s, 1H), 3.21-3.19 (m, 2H), 3.06-3.04 (m, 2H), 2.45 (s, 2H), 2.21 (s, 3H), 1.24-1.16 (m, 2H), 0.83-0.79 (m, 9H); LC-MS: m/e 348 (M+H).

EXAMPLE 249

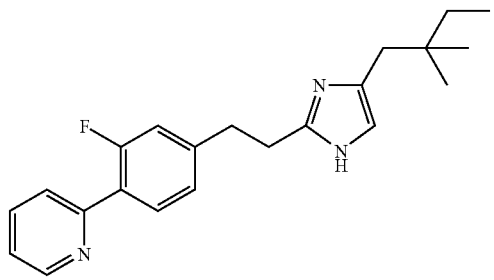

2-(4-{2-[4-(2,2-Dimethylbutyl)-1H-imidazol-2-yl] ethyl}-2-fluorolphenyl)pyridine The title compound was prepared from intermediate 19 with 2-bromopyridine following the procedure described for Example 196. The crude product was purified by flash column chromatography on silica gel eluting with 0-5% methanol/ammonium hydroxide mixture in methylene chloride to give the title compound, which was converted to the HCl salt with 1M HCl in diethyl ether. $^1$H NMR (300 MHz, CD3OD) δ 8.91 (d, J=5.4 Hz, 1H), 8.68 (t, J=7.5 Hz, 1H), 8.26 (d, J=8.0 Hz, 1H), 8.07 (t, J=6.7 Hz, 1H), 7.81 (t, J=7.6 Hz, 1H), 7.33-7.37 (m, 2H), 7.19 (s, 1H), 3.27-3.40 (m, 4H), 2.54 (s, 2H), 1.26 (q, J=7.5 Hz, 2H), 0.86-0.91 (m, 9H); LC-MS: m/e 352 (M+H).

EXAMPLE 250

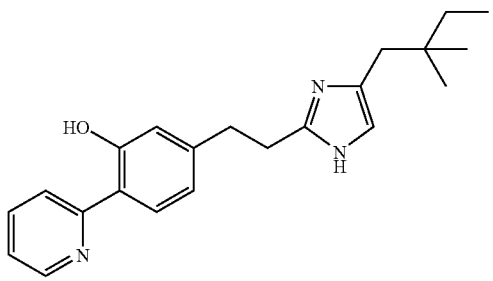

2-(4-{2-[4-(2,2-Dimethylbutyl)-1H-imidazol-2-yl]ethyl}-2-hydroxyphenyl)pyridine

Step A: 2-(4-{2-[4-(2,2-Dimethylbutyl)-1-trityl-1H-imidazol-2-yl]ethyl}-2-methoxyphenyl)pyridine was prepared from intermediate 21 with 2-bromopyridine following the procedure described for Example 196. The crude product was purified by flash column chromatography on silica gel eluting with 0-50% ethyl acetate in hexanes to give the title compound.

Step B: A solution of 2-(4-{2-[4-(2,2-Dimethylbutyl)-1-trityl-1H-imidazol-2-yl]ethyl}-2-methoxyphenyl)pyridine (110 mg, 0.19 mmol) in 30% HBr in acetic acid (5 mL) was heated at reflux in a sealed tube for 6 hours. Upon cooling, the volatiles were removed, and the resulting residue was purified by flash column chromatography on silica gel eluting with 0-5% methanol/ammonium hydroxide mixture in methylene chloride to give the title compound, which was converted to the HCl salt with 1M HCl in diethyl ether. $^1$H NMR (500 MHz, CD$_3$OD) δ 8.75-8.73 (δ, J=5.8 Hz, 1H) 8.57-8.54 (t, J=7.6 Hz, 1H), 8.35-8.32 (d, J=8.3 Hz, 1H), 7.92-7.88 (t, J=6.6 Hz, 1H), 7.75-7.72 (d, J=8.4 Hz, 1H), 7.17 (s, 1H), 6.92-6.90 (m, 2H), 3.40-3.30 (t, 2H, masked by solvent), 3.17-3.12 (t, J=7.0 Hz, 2H), 2.52 (s, 2H), 1.28-1.21 (q, J=7.7 Hz, 2H), 0.89-0.82 (m, 9H); LC-MS: m/e 350 (M+H).

EXAMPLE 251

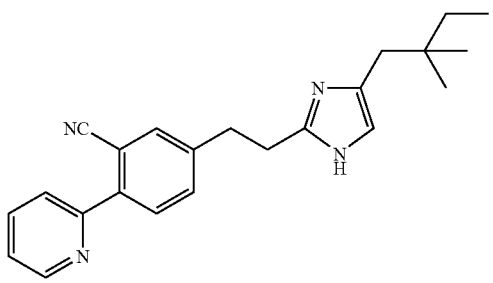

2-(4-{2-[4-(2,2-Dimethylbutyl)-1H-imidazol-2-yl]ethyl}-2-cyanophenyl)pyridine

The title compound was prepared from intermediate 22 and intermediate 3 following the procedure described in Example 1. The crude product was purified by flash column chromatography on silica gel eluting with 0-5% methanol in methylene chloride to give the title compound. $^1$H NMR (300 MHz, CDCl$_3$) δ 8.76-8.74 (d, J=4.9 Hz, 1H), 7.86-7.80 (m, 1H), 7.76-7.71 (m, 2H), 7.55 (s, 1H), 7.61-7.55 (d, J=8.0 Hz, 1H), 7.37-7.33 (m, 1H), 6.65 (s, 1H), 3.15-3.13 (m, 2H), 3.04-3.01 (m, 2H), 2.41 (s, 2H), 1.34-1.19 (m, 2H), 0.94-0.83 (m, 9H); LC-MS: m/e 359 (M+H).

EXAMPLE 252

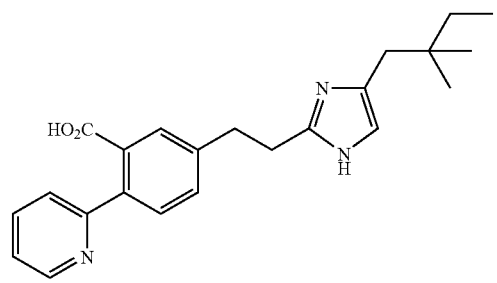

5-{2-[4-(2,2-dimethylbutyl)-1H-imidazol-2-yl]ethyl}-2-pyridin-2-ylbenzoic acid

A mixture of 2-(4-{2-[4-(2,2-dimethylbutyl)-1H-imidazol-2-yl]ethyl}-2-cyanophenyl)pyridine (30 mg, 0.08 mmol) and 6N HCl (10 mL) was heated at reflux for 3 h. Upon cooling, the volatiles were removed, and the resulting residue was purified by flash column chromatography on silica gel eluting with 0-10% methanol/ammonium hydroxide mixture in methylene chloride the title compound, which was converted to the potassium salt with KOH (1 eq) in methanol. NMR (500 MHz, CD$_3$OD) δ 8.53-8.51 (d, J=4.5 Hz, 1H), 7.81-7.77 (m, 1H), 7.63-7.61 (d, J=7.9 Hz, 1H), 7.49 (s, 1H), 7.43-7.42 (d, J=7.8 Hz, 1H), 7.33-7.30 (m, 1H), 7.13-7.11 (m, 1H), 6.96 (s, 1H), 3.22-3.19 (t, J=7.5 Hz, 2H), 3.10-3.07 (t, J=7.2 Hz, 2H), 2.44 (s, 2H), 1.23-1.16 (m, 2H), 0.85-0.82 (t, J=7.4 Hz, 3H), 0.79 (s, 6H); LC-MS: m/e 378 (M+H).

BIOLOGICAL ASSAYS

A. Bombesin Receptor Subtype 3 (BRS3) Binding Assays

Human embryonic kidney (HEK 293) cells expressing human BRS-3 were cultured to confluence and harvested by aspirating the culture medium and rinsing twice with 1×PBS without Mg$^{++}$ and Ca$^{++}$. Cellstriper Solution (Cellgrow #25-056-C1, 3 mL) was added to each T-175 flask until all cells dissociated and then an additional 15 mL 1×PBS without Mg$^{++}$ and Ca$^{++}$ were added to each flask. Dissociated cells were collected by centrifuging at 1000 rpm for 10 minutes. Cell pellets were resuspended and homogenized at 4° C. using a Polytron homogenizer (setting 40, 20 stokes) in approximately 10 mL membrane preparation buffer (10 mM Tris pH 7.4, 0.01 mM Pefabloc, 10 µM phosphoramidon and 40 µg/mL Bacitracin) per T175 flask. After centrifugation at 2200 rpm (1000×g) for 10 minutes at 4° C., the supernatant was transferred to a clean centrifuge tube and spun at 18,000 rpm (38,742×g) for 15 minutes. at 4° C. Membranes were resuspended in the above membrane preparation buffer (1 mL/T-175 flask), homogenized, aliquoted, quickly frozen in liquid nitrogen and stored at −80° C.

For the [$^{125}$I][D-Tyr$^6$,β-Ala$^{11}$,Phe$^{13}$,Nle$^{14}$)-Bombesin(6-14), "[$^{125}$I]-dY-peptide", radioligand assay the specific binding of [$^{125}$I]-dY-peptide to human BRS3 was measured by filtration assay in 96-well plate format. The receptor membrane (2 µg/well) in binding buffer (50 mM Tris pH 7.4, 5 mM MgCl$_2$, 0.1% BSA and protease inhibitor cocktail) was mixed with compound in DMSO (1% final concentration) and 30 pM [$^{125}$I]-dY-peptide. After incubation for 1-2 hours at room temperature, membrane-bound [$^{125}$I]-dY-peptide was separated from free [$^{125}$I]-dY-peptide by filtering through GF/C filters presoaked in 1% PEI solution. The filters were washed five times with ice-cold washing buffer (1×PBS without Mg$^{++}$ and Ca$^{++}$). The radioactivity was determined by adding 30 µl of microscintillant/well after each plate was dried at room temperature overnight or placed at 50° C. for 1 hr.

The radioligand, [$^3$H]-1-{4-[(4,5-difluoro-2-hydroxycarbonylphenyl)phenyl])-2-(4-cyclohexylmethyl-1H-imidazol-2-yl)ethane, was used for binding to receptor membranes generated with BRS3 from other species and was also utilized for the human receptor. Cell membranes (5 to 20 µg/well) were added to binding buffer (25 mM Tris pH 7.4, 10 mM MgCl$_2$, 2 mM EDTA and protease I cocktail) containing compound in DMSO (1% final concentration) and 660 pM [$^3$H]-biphenyl. After incubation for 1-2 hours at room temperature, membrane bound [$^3$H]-biphenyl was separated from free radiologand by filtering through GF/C filters presoaked in 1% PEI solution. The filters were washed five times with ice-cold washing buffer (50 mM Tris pH 7.4, 10 mM MgCl$_2$, 2.5 mM EDTA and 0.02% Triton X-100). The radioactivity was determined by adding 30 µl of microscintillant/well after each plate was dried at room temperature overnight or placed at 50° C. for 1 hr.

A Packard Top Count was used to read the filter plates. The data in % inhibition of binding was plotted vs. the log molar concentration of receptor ligand (compound). The IC$_{50}$ was reported as the inflection point of the resulting sigmoidal curve. The maximum inhibition observed at the highest compound concentration tested was reported for compounds which did not generate a curve.

The binding assays for the rat and mouse Bombesin Receptor Subtype 3 (BRS3) were performed in a similar fashion.

B. Cell Culture of Human, Rat and Mouse BRS3 Expressing Cell Lines

An NFATCHO cell line stably expressing human BRS3 cDNA was generated using standard cell biology techniques and used to prepare receptor membranes for the human "[$^{125}$I]-dY-peptide binding assay. The cell line was cultured in T175 flasks in Iscove's Modified Dulbecco's Medium with L-glutamine and 25 mM HEPES buffer (Gibco #12440-046) supplemented with 10% FBS (cat #SH30070.03, Hyclone, Logan, Utah), 1×HT Supplement (0.1 mM Sodium Hypoxanthine and 16 µM Thymidine Gibco #11067-030), 2 mM L-glutamine (Gibco #25030-081), 100 units/mL Pennicillin-G and 100 µg/mL Streptomycin (Gibco #15140-122) and 1 mg/mL Geneticin (Gibco #10131-027).

HEK293/AEQ cell lines stably expressing either human, rat or mouse BRS3 cDNA were generated using standard cell biology techniques and were used for all functional assays and to prepare membranes for the rat BRS3 binding assay. The cell lines were routinely cultured in T75 or T175 flasks in Dulbecco's Modified Eagle Medium (Gibco #11965-084) supplemented with 10% FBS, 25 mM HEPES buffer solution (Gibco #15630-080), 0.5 mg/mL Geneticin and 50 µg/mL Hygromycin B (Boehringer Mannheim #14937400).

Transient transfection of mouse BRS3 cDNA, as well as BRS3 cDNA from other species, in the HEK293AEQ cell line was achieved using the Lipofectamine transfection method following the recommended protocol (Invitrogen Lipofectamine 2000 #11668-027). The transfected cells were used to prepare membranes for the [$^3$H]-biphenyl binding assay and for the functional assays. The cells were maintained in culture under the same conditions used for the human and rat stable BRS3 HEK293AEQ cell lines.

All cells were grown as attached monolayers to approximately 90% confluency in tissue culture flasks under the appropriate media in an incubator at 37° C. with 5% CO$_2$. Cells were passed 1:3 to 1:5 twice a week depending on the rate of growth.

C. BRS3 Functional Assays

1) Aequorin Bioluminescent Assay to Measure Intracellular Ca$^{++}$

The apoaequorin containing HEK293AEQ cell lines expressing BRS3 were first charged with coelenterazine (Molecular Probes #C-14260) by rinsing confluent T75 flasks with 12 mL Hams F-12 media (Gibco #11765-054) containing 300 mM glutathione and 0.1% FBS. The same media (8 mL) containing 20 µM coelenterzine was added to the cells and incubated at 37° C. for 1 hr. The media was aspirated and the flasks rinsed with 6 mL ECB buffer (140 mM NaCl, 20 mM KCl, 20 mM HEPES, 5 mM glucose, 1 mM MgCl, 1 mM CaCl, 0.1 mg/mL BSA, pH 7.4). The cells were dissociated with a rubber-tipped scraper in 6 mL of fresh ECB buffer and collected by centrifugation at 2500 rpm for 5 minutes. The cell pellets were resuspended in ECB buffer to a concentration of 200,000 cells/mL and were either used right away or quickly frozen in liquid nitrogen for storage at −80° C. for up to six weeks.

The Aequorin assay itself was performed in 96-well format using a Wallac Microbeta luminometer equipped with microinjector module. Compounds in DMSO (0.5% final concentration) were titrated in the plates at 2× concentration in a volume of 0.1 mL ECB buffer. The cells (20,000 per well) were then injected in 0.1 mL ECB buffer and the bioluminescence monitored for 30 seconds. Alternatively, total bioluminescence was determined over 10 minutes. The bioluminescent readings were plotted vs. the log molar concentration of receptor ligand (compound). The EC$_{50}$ for activation was reported as the inflection point of the resulting sigmoidal curve.

2) Inositol Phosphate SPA Assay (IP) to Measure IP3 Accumulation

The IP functional assay was performed in 96-well format. The BRS3 expressing HEK293AEQ cells were plated on poly-D-lysine plates (~25,000 cells/0.15 mL) and kept in culture for 24 hours. The media from each well was aspirated and the cells were washed with PBS without Mg$^{++}$ and Ca$^{++}$. Inositol labeling media consisting of Inositol-free DMEM media (ICN #1642954) supplemented with 10% FBS, 1×HT Supplement, 2 mM glutamine, 70 mM HEPES buffer solution and 0.02% BSA to which $^3$H-myo-inositol (NEN #NET114A 1 mCi/mL, 25 Ci/mmol) was added so that there was 1 µCi $^3$H-myo-inositol in 150 µL media per well. After 18 hours of labeling, 5 µl 300 mM LiCl was added to each well, mixed, and incubated for 20 minutes at 37° C. Compound (1.5 µl of 100× compound in DMSO) was added and incubated for an additional 60 minutes at 37° C. The labeled media was aspirated, and the reaction terminated by lysing the cells with the addition of 60 µl 10 mM formic acid for 60 minutes at room temperature. A 20 µl aliquot of the lysate was transferred from each well to a clear-bottom Opti-plate which contained 70 µL RNA binding YSi SPA-beads (Amersham RPNQ0013) that had been suspended in 10% glycerol at 1 mg beads/70 µl of solution. After mixing, the plates were left at room temperature for 2 hours and were then counted using a Wallac Microbeta luminometer. The data in cpm (counts per minute) as plotted vs. the log molar concentration of receptor ligand (compound). The EC$_{50}$ for activation was reported as the inflection point of the resulting sigmoidal curve.

D. In-Vivo Overnight Food Intake and Body Weight in C57 Obese Male Mice

Methods: Male C57 mice were made obese by maintenance on a high fat diet (45-60% kcal from fat), such as Research Diets RD12492, starting at 6 weeks of age. Obese mice, approximately 20-52 weeks old and weighing approximately 45-62 g, were individually housed and acclimated for several days prior to testing. On the day of study, mice were orally dosed (n=6-8/group) with either vehicle only (10% Tween-water) or BRS-3 agonists (various doses). A known CB1R inverse agonist, AM251 (3 mg/kg), was used as the positive control for inter- and intra-experimental control. BRS-3 agonists were dosed approximately 60 minutes prior to the onset of the dark cycle. Overnight food intake and body weight were measured and analyzed. All data are presented as mean±SEM. Statistical significance was calculated using Student's t-test with differences considered significant when 2-tailed p<0.05.

Compounds useful in the present invention decrease overnight food intake by at least 10% and/or decrease body weight overnight by at least 1% relative to placebo.

E. In-Vivo Chronic Administration on Body Weight in C57 Obese Male Mice

Methods: Male C57 mice were made obese by maintenance on a high fat diet (45-60% kcal from fat), such as Research Diets RD12492, starting at 6 weeks of age. Obese mice, approximately 20-52 weeks old and weighing approximately 45-62 g, were individually housed and acclimated for several days prior to testing. During the study, mice were orally dosed (n7-9/group) with either vehicle only (10% Tween-water) or BRS-3 agonists (various doses). A known anorectic agent, dexfenfluramine (10-15 mg/kg) was used as the positive control for inter- and intra-experimental control. Two doses (PO) of BRS-3 agonist were administered each day for 14 days. The first dose was given approximately 60 minutes prior to the onset of the dark cycle and the second, 5 hours after the first dose. A single dose of dexfenfluramine was given approximately 60 minutes prior to the onset of the dark cycle and vehicle was dosed for the second dose, 5 hours after the first dose. Daily food intake and body weight were measured and analyzed. All data are presented as mean±SEM. Statistical significance was calculated using Student's t-test with differences considered significant when 2-tailed p<0.05.

Compounds useful in the present invention, by day 14, decrease cumulative food intake by at least 10% and/or decrease body weight by at least 2% relative to placebo.

The compounds of the present invention, including the compounds in Examples 1-252, were tested and found to bind to the bombesin subtype 3 receptor with $IC_{50}$ values less than 10 µM, and to agonize the bombesin subtype 3 receptor with $EC_{50}$ values less than 10 µM. Preferred compounds of the present invention, including the compounds in Examples 1-252, were tested and found to bind to the bombesin subtype 3 receptor with $IC_{50}$ values less than 1 µM, and to agonize the bombesin subtype 3 receptor with $EC_{50}$ values less than 1 µM.

| BRS-3 Receptor Binding Activity for Selected Compounds | |
|---|---|
| Example No. | BRS-3 binding $IC_{50}$ (nM) |
| 26 | 117 |
| 94 | 20 |
| 1 | 38 |
| 240 | 116 |

| BRS-3 Receptor Binding Activity for Selected Compounds | |
|---|---|
| Example No. | BRS-3 binding $IC_{50}$ (nM) |
| 98 | 20 |
| 206 | 19 |
| 205 | 33 |
| 246 | 5.3 |
| 221 | 4.8 |
| 110 | 6.3 |
| 225 | 18 |
| 227 | 2.8 |
| 226 | 18 |
| 237 | 15 |
| 236 | 25 |

EXAMPLES OF PHARMACEUTICAL COMPOSITIONS

As a specific embodiment of an oral composition of a composition of the present invention, 5 mg of Example 1 is formulated with sufficient finely divided lactose to provide a total amount of 580 to 590 mg to fill a size O hard gelatin capsule.

As another specific embodiment of an oral composition of a compound of the present invention, 2.5 mg of Example 1 is formulated with sufficient finely divided lactose to provide a total amount of 580 to 590 mg to fill a size O hard gelatin capsule.

While the invention has been described and illustrated in reference to certain preferred embodiments thereof, those skilled in the art will appreciate that various changes, modifications and substitutions can be made therein without departing from the spirit and scope of the invention. For example, effective dosages other than the preferred doses as set forth hereinabove may be applicable as a consequence of variations in the responsiveness of the subject or mammal being treated for severity of bone disorders caused by resorption, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the practices of the present invention. It is intended, therefore, that the invention be limited only by the scope of the claims which follow and that such claims be interpreted as broadly as is reasonable.

What is claimed is:

1. A compound of formula I:

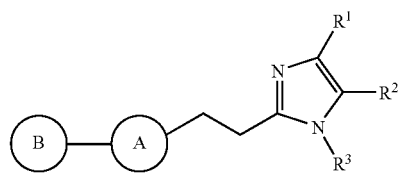

or a pharmaceutically acceptable salt thereof; wherein
A is

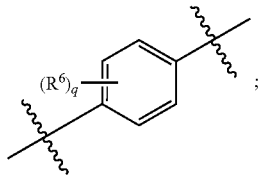

B is a mono- or bicyclic ring selected from the group consisting of:
(1) —$C_{3-8}$cycloalkyl,
(2) —$C_{3-8}$cycloalkenyl,
(3) —$C_{2-8}$heterocycloalkyl,
(4) —$C_{2-8}$heterocycloalkenyl,
(5) -aryl, and
(6) -heteroaryl,
wherein cycloalkyl, cycloalkenyl, heterocycloalkyl, heterocycloalkenyl, aryl, and heteroaryl are unsubstituted or substituted with 0 to 4 substituents selected from $R^5$;
$R^1$ and $R^2$ are each independently selected from the group consisting of:
(1) —$(CH_2)_4F$,
(2) —$CH_2F$,
(3) Br,
(4) Cl,
(5) I,
(6) —$(CH_2)_{0-4}OH$,
(7) —$(CH_2)_2C(CH_3)_2OH$,
(8) —$(CH_2)_2CN$,
(9) —$CH_2C(CH_2CH_3)_2CN$,
(10) —$(CH_2)_2CF_3$,
(11) —$(CH_2)_{2-3}CCl_3$,
(12) —$(CH_2)_{0-4}CH_3$,
(13) —$CH(CH_3)CH_2CH_3$,
(14) —$CH_2CH(CH_3)CH_2CH_3$,
(15) —$CH_2C(CH_3)_2CH_2CH_3$,
(16) —$CH_2C(CH_3)(CH_2CH_3)CH_2CH_3$,
(17) —$(CH_2)_{1-2}CH(CH_3)_2$,
(18) —$(CH_2)_{1-2}CH(CH_2CH_3)_2$,
(19) —$(CH_2)_{1-2}C(CH_3)_3$,
(20) —$CH(CH_3)_3$,
(21) —$CH_2C(CH_2CH_3)_2CH_2CH_3$,
(22) —$CH_2C(CH_2F)_2CH_2CH_3$,
(23) —$CH=C(CH_3)_2$,
(24) —$CH=CH_2$,
(25) —$CH_2C(CH_3)_2CH_2CH=CH_2$,
(26) —$CH_2C(CH_3)_2CH_2CH=CHCH_3$,
(27) —$CH_2C(CH_2CH_3)_2CH=CH_2$,
(28) —$(CH_2)_3OCH_2$phenyl,
(29) —$(CH_2)_{0-2}$cyclopropyl,
(30) —$(CH_2)_{0-2}$cyclobutyl,
(31) —$(CH_2)_{0-2}$cyclopentyl,
(32) —$(CH_2)_{0-2}$cyclohexyl,
(33) —$(CH_2)_{0-2}$cycloheptyl,
(34) —$(CH_2)_{0-2}$cyclooctyl,
(35) —$(CH_2)_{0-2}$adamantane,
(36) —$(CH_2)_{0-1}$cyclopentene,
(37) —$(CH_2)_{0-1}$cyclohexene,
(38) —$CH_2$tetrahydrofuran,
(39) —$CH_2$tetrahydropyran,
(40) —$(CH_2)_{1-2}$phenyl,
(41) —$CH_2$naphthalene,
(42) benzocyclobutene,
(43) —$CH_2$benzodioxole,
(44) —$(CH_2)_{0-1}$pyridine,
(45) —$(CH_2)_3$thiophene,
(46) —$C(CH_3)_2CO_2CH_3$,
(47) —$CH_2C(CH_3)_2C(O)CH_2CH_3$,
(48) —$C(O)C(CH_3)_3$,
(49) —$CH_2C(CH_3)_2CH_2CO_2CH_3$, and
(50) —$CH_2$cyclopentyl,
provided that $R^1$ and $R^2$ are not both hydrogen, wherein alkyl, alkenyl, alkynyl, cycloalkyl, heterocycloalkyl, aryl, heteroaryl, and $(CH_2)_n$ are unsubstituted or substituted with 1 to 5 substituents selected from $R^6$, and wherein two $R^6$ substituents together with the atom to which they are attached may form a 3-6 membered cycloalkyl or cycloalkenyl ring containing 0 to 3 heteroatoms independently selected from oxygen, sulfur, and $NR^7$, wherein the 3-6 membered cycloalkyl or cycloalkenyl ring is unsubstituted or substituted with 1 to 5 substituents selected from $R^6$;
$R^3$ is selected from the group consisting of:
(1) hydrogen,
(2) —$C_{1-6}$alkyl, and
(3) —$COC_{1-6}$alkyl;
$R^4$ is selected from the group consisting of:
(1) —$C_{1-6}$alkyl,
(2) —$(CH_2)_n$halogen,
(3) —$(CH_2)_nOR^8$,
(4) —$(CH_2)_nCN$,
(5) —$(CH_2)_nCF_3$,
(6) —$(CH_2)_nCO_2R^7$,
(7) —$(CH_2)_nN(R^8)_2$,
(8) —$(CH_2)_nNO_2$,
(9) —$(CH_2)_nNR^7COC_{1-6}$alkyl,
(10) —$(CH_2)_nNR^7CO_2C_{1-6}$alkyl,
(11) —$(CH_2)_nNR^7SO_2C_{1-6}$alkyl, and
(12) —$(CH_2)_nSO_{0-2}C_{1-6}$alkyl,
wherein alkyl is substituted with 1 to 3 halogens;
$R^5$ is selected from the group consisting of:
(1) —$(CH_2)_n$halogen,
(2) —$C_{1-6}$alkyl,
(3) —$C_{2-6}$alkenyl,
(4) —$(CH_2)_nC_{3-8}$cycloalkyl,
(5) —$(CH_2)_n$heterocycloalkyl,
(6) oxo,
(7) —$(CH_2)_nR^8$,
(8) —$(CH_2)_nCN$,
(9) —$(CH_2)_nCOR^7$,
(10) —$(CH_2)_nCO_2R^8$,
(11) —$(CH_2)_nCONR^7N(R^7)_2$,
(12) —$(CH_2)_nO(CH_2)_nCO_2R^7$,
(13) —$(CH_2)_nNO_2$,
(14) —$(CH_2)_nCON(R^7)_2$,
(15) —$(CH_2)_nN(R^8)_2$,
(16) —$(CH_2)_nNR^7(CH_2)_nCO_2R^7$,
(17) —$(CH_2)_nNR^7COC_{1-6}$alkyl,
(18) —$(CH_2)_nSO_2N(R^7)_2$,
(19) —$(CH_2)_nNR^7SO_2C_{1-6}$alkyl,
(20) —$(CH_2)_nSO_{0-2}R^8$,
(21) —$(CH_2)_nOP(O)_2OH$,
(22) —CH=N—OH,
(23) —$(CH_2)_n$aryl,
(24) —$(CH_2)_n$heteroaryl, and
(25) —$(CH_2)_nO(CH_2)_n$heteroaryl,
wherein alkyl, alkenyl, cycloalkyl, heterocycloalkyl, aryl, heteroaryl, and —$(CH_2)_n$ are unsubstituted or substituted with 1 to 3 halogens;

$R^6$ is independently selected from the group consisting of:
(1) halogen,
(2) —OH,
(3) oxo,
(4) —CN,
(5) —CCl$_3$,
(6) —CF$_3$,
(7) —CHF$_2$,
(8) —CH$_2$F,
(9) —SO$_2$C$_{1-6}$alkyl,
(10) —COC$_{1-8}$alkyl,
(11) —CO$_2$C$_{1-8}$alkyl,
(12) —CO$_2$H,
(13) —C$_{1-8}$alkyl, and
(14) —C$_{1-8}$alkoxy,
wherein alkyl and alkoxy are unsubstituted or substituted with 1 to 4 substituents selected from —C$_{1-6}$alkyl and halogen, and wherein the —C$_{1-6}$alkyl substituent is unsubstituted or substituted with 1 to 3 halogens;

$R^7$ is selected from the group consisting of:
(1) hydrogen, and
(2) —C$_{1-6}$alkyl,
wherein alkyl is unsubstituted or substituted with 1 to 3 substituents selected from halogen and —OH;

$R^8$ is selected from the group consisting of:
(1) hydrogen,
(2) —C$_{1-6}$alkyl,
(3) —C$_{3-8}$cycloalkyl,
(4) —C$_{2-7}$heterocycloalkyl,
(5) —(CH$_2$)$_m$phenyl, and
(6) —(CH$_2$)$_m$heteroaryl,
wherein alkyl, cycloalkyl, and heterocycloalkyl are unsubstituted or substituted with 1 to 3 halogens or —OH, and wherein phenyl and heteroaryl are unsubstituted or substituted with 1 to 3 halogens;

each n is independently 0, 1, 2, 3, 4, or 5;
each m is independently 1, 2, 3 or 4; and
q is 0, 1, 2, 3 or 4.

2. The compound of claim 1 wherein B is a mono- or bicyclic ring selected from the group consisting of: —C$_{3-8}$cycloalkyl, —C$_{2-8}$heterocycloalkyl, —C$_{2-8}$heterocycloalkenyl, -aryl, and -heteroaryl, wherein cycloalkyl, heterocycloalkyl, heterocycloalkenyl, aryl, and heteroaryl are unsubstituted or substituted with 0 to 4 substituents selected from $R^5$; or a pharmaceutically acceptable salt thereof.

3. The compound of claim 1 wherein B is a ring selected from the group consisting of: cyclohexyl, piperidine, tetrahydropyrazolopyridine, oxodihydropyridine, tetrahydropyrazine, phenyl, pyrazole, imidazole, pyrazine, pyridazine, pyridine, pyrimidine, thiazole, isothiazole, thiadiazole, triazole, thiene, indazole, isoquinoline, triazolopyridine, pyrrolopyridine, imidazopyrazine, and pyrazolopyridine, wherein the ring is unsubstituted or substituted with 0 to 4 substituents selected from $R^5$; or a pharmaceutically acceptable salt thereof.

4. The compound of claim 1 wherein A is phenyl, wherein phenyl is unsubstituted or substituted with 0 to 4 substituents selected from $R^4$; or a pharmaceutically acceptable salt thereof.

5. The compound of claim 1 wherein A is unsubstituted phenyl; or a pharmaceutically acceptable salt thereof.

6. The compound of claim 1 wherein $R^2$ and $R^3$ are hydrogen; or a pharmaceutically acceptable salt thereof.

7. The compound of claim 1 wherein $R^5$ is selected from the group consisting of: —(CH$_2$)$_n$halogen, —C$_{1-6}$alkyl, —C$_{2-6}$alkenyl, oxo, —(CH$_2$)$_n$OR$^8$, —CN, —COR$^7$, —(CH$_2$)$_n$CO$_2$R$^8$, —(CH$_2$)$_n$O(CH$_2$)$_n$CO$_2$R$^7$, —NO$_2$, —(CH$_2$)$_n$N(R$^8$)$_2$, —NH(CH$_2$)$_n$CO$_2$R$^7$, —NHCOC$_{1-6}$alkyl, —SO$_2$N(R$^7$)$_2$, —CH=N—OH, —(CH$_2$)$_n$heteroaryl, and —(CH$_2$)$_n$O(CH$_2$)$_n$heteroaryl, wherein alkyl, alkenyl, heteroaryl, and —(CH$_2$)$_n$ are unsubstituted or substituted with 1 to 3 halogens; or a pharmaceutically acceptable salt thereof.

8. The compound of claim 1 of formula IV:

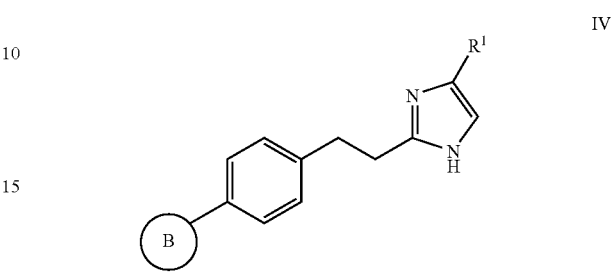

IV or a pharmaceutically acceptable salt thereof; wherein
B is selected from the group consisting of:
(1) —C$_{3-8}$cycloalkyl,
(2) -aryl, and
(3) -heteroaryl,
wherein cycloalkyl, aryl, and heteroaryl are unsubstituted or substituted with 0 to 4 substituents selected from $R^5$;

$R^5$ is selected from the group consisting of:
(1) halogen,
(2) —C$_{1-6}$alkyl,
(3) —(CH$_2$)$_n$O(CH$_2$)$_n$heteroaryl, and
(4) —(CH$_2$)$_n$CO$_2$H;

$R^6$ is —C$_{1-6}$alkyl, wherein alkyl is unsubstituted or substituted with 1 to 4 substituents selected from —C$_{1-6}$alkyl and halogen, and wherein the —C$_{1-6}$alkyl substituent is unsubstituted or substituted with 1 to 3 halogens; and
each n is independently 0, 1, 2, 3 or 4.

9. The compound of claim 1 selected from the group consisting of:

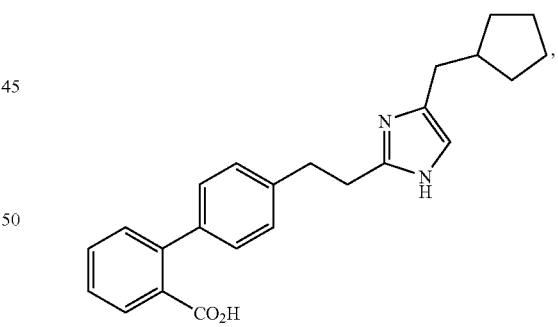

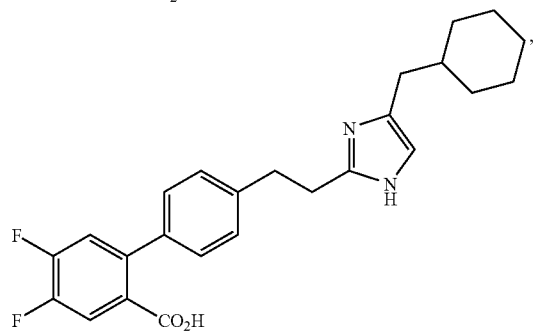

139
-continued
140
-continued
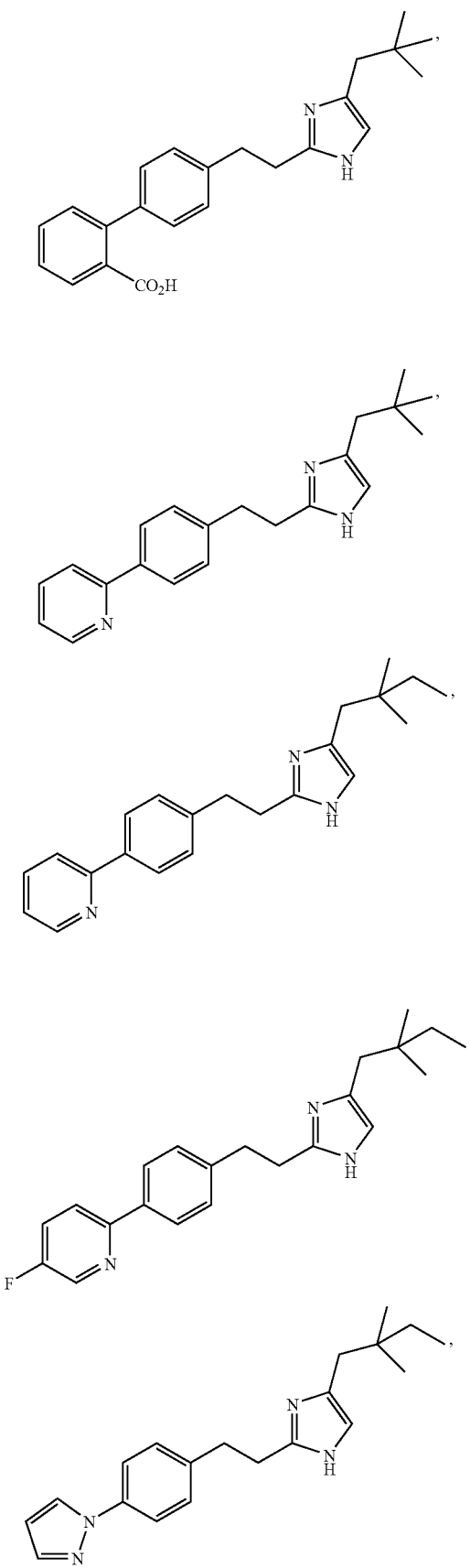
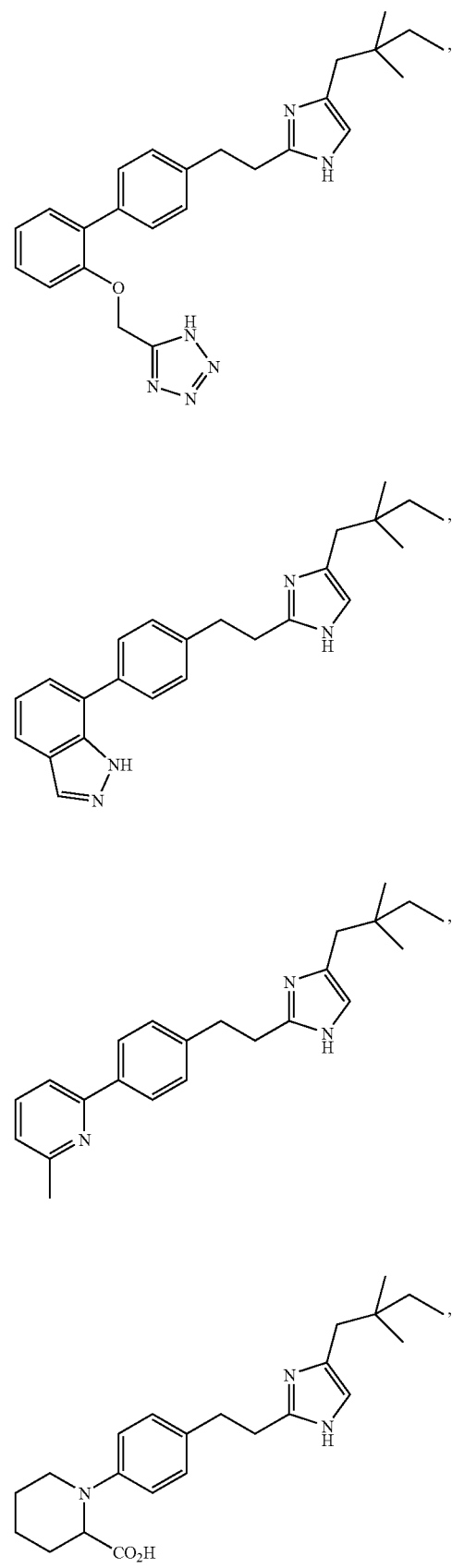

-continued

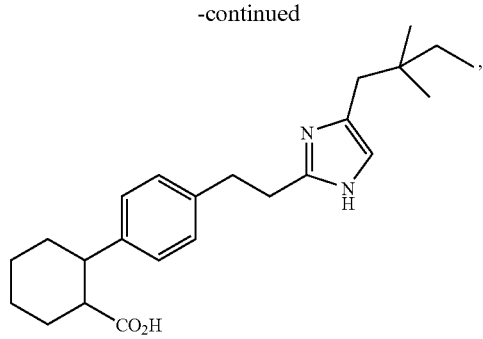

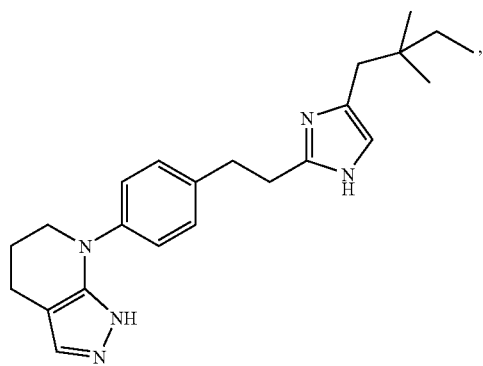

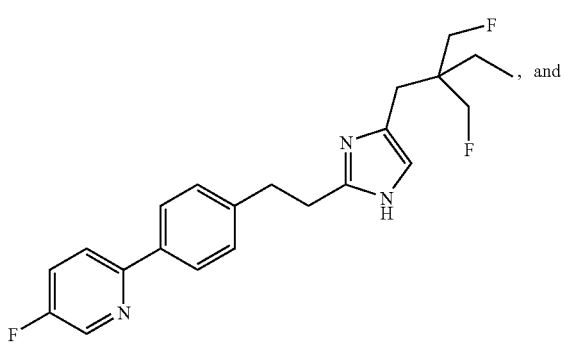, and

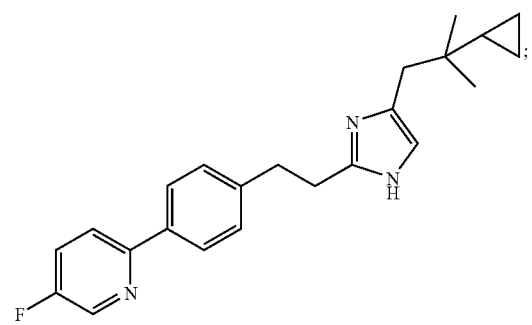

or a pharmaceutically acceptable salt thereof.

10. The compound of claim 9 which is:

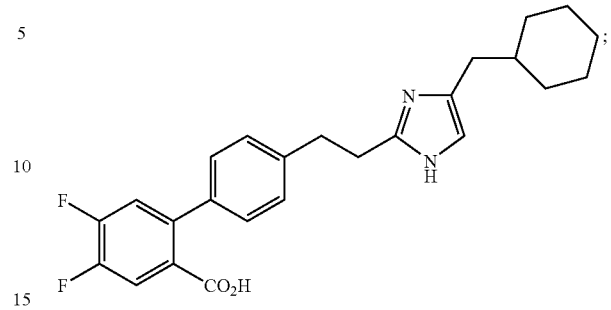

or a pharmaceutically acceptable salt thereof.

11. The compound of claim 9 which is:

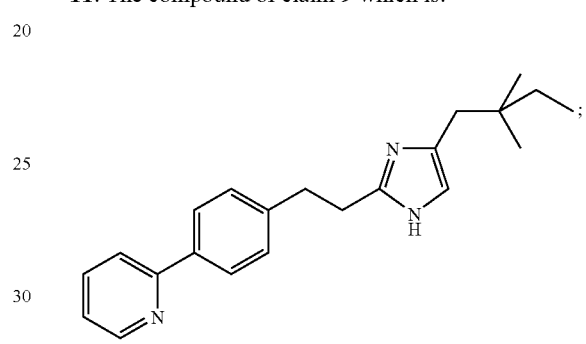

or a pharmaceutically acceptable salt thereof.

12. The compound of claim 9 which is:

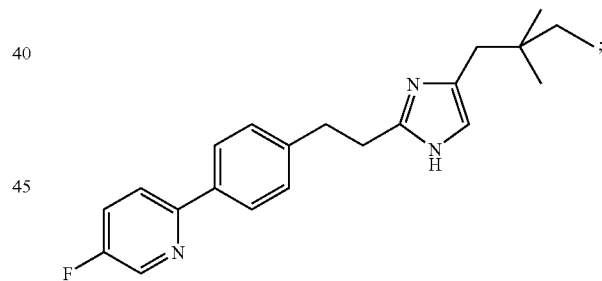

or a pharmaceutically acceptable salt thereof.

13. The compound of claim 9 which is:

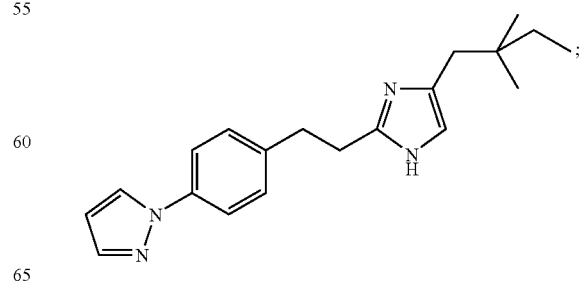

or a pharmaceutically acceptable salt thereof.

14. The compound of claim 9 which is:
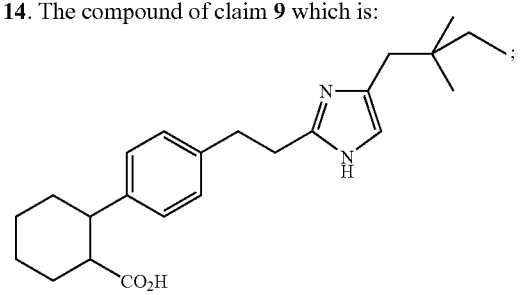
or a pharmaceutically acceptable salt thereof.
15. A composition which comprises a compound of claim 1, or a pharmaceutically acceptable salt thereof, and a pharmaceutically acceptable carrier.
* * * * *